(12) United States Patent
Liu et al.

(10) Patent No.: US 11,958,914 B2
(45) Date of Patent: *Apr. 16, 2024

(54) CAR-T CELLS TARGETING GLIOMA STEM CELLS FOR THE TREATMENT OF GLIOBLASTOMA MULTIFORME

(71) Applicant: H. Lee Moffitt Cancer Center and Research Institute, Inc., Tampa, FL (US)

(72) Inventors: James Liu, Lutz, FL (US); Daniel Abate-Daga, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/811,945

(22) Filed: Jul. 12, 2022

(65) Prior Publication Data
US 2023/0038996 A1    Feb. 9, 2023

Related U.S. Application Data

(63) Continuation of application No. 17/212,320, filed on Mar. 25, 2021, now Pat. No. 11,384,118, which is a continuation-in-part of application No. PCT/US2019/053793, filed on Sep. 30, 2019.

(60) Provisional application No. 62/739,579, filed on Oct. 1, 2018.

(51) Int. Cl.
| | |
|---|---|
| *A61K 35/00* | (2006.01) |
| *A61K 35/17* | (2015.01) |
| *C07K 7/06* | (2006.01) |
| *C07K 16/28* | (2006.01) |

(52) U.S. Cl.
CPC .............. *C07K 7/06* (2013.01); *A61K 35/17* (2013.01); *C07K 16/2818* (2013.01); *C07K 16/2827* (2013.01)

(58) Field of Classification Search
CPC .. C07K 7/06; C07K 16/2818; C07K 16/2827; A61K 35/17
See application file for complete search history.

(56) References Cited

U.S. PATENT DOCUMENTS

2017/0281766 A1* 10/2017 Wiltzius ........... C07K 14/70575

OTHER PUBLICATIONS

Abate-Daga, Daniel, et al., "A Novel Chimeric Antigen Receptor Against Prostate Stem Cell Antigen Mediates Tumor Destruction in a Humanized Mouse Model of Pancreatic Cancer," Human Gene Therapy, vol. 25 (2014), pp. 1003-1012.
Abate-Daga, Daniel, et al., "CAR models: next-generation CAR modifications for enhanced T-cell function," Molecular Therapy—Oncolytics, vol. 3 (2016) (7 pages).
Bao, Shideng, et al., "Glioma stem cells promote radioresistance by preferential activation of the DNA damage response," Nature, vol. 444 (2006), pp. 756-760.
Brown, Christine E., et al., "Stem-like Tumor-Initiating Cells Isolated from IL13Ra2 Expressing Gliomas are Targeted and Killed by IL13-Zetakine-Redirected T Cells," Clinical Cancer Research, vol. 18, No. 8 (2012), pp. 2199-2209.
Brown, Christine E., et al., "Regression of Glioblastoma after Chimeric Antigen Receptor T-Cell Therapy," The New England Journal of Medicine, vol. 375, No. 26 (2016), pp. 2561-2569.
Chatalic, Kristell L.S., et al., "Radiopeptides for Imaging and Therapy: A Radiant Future," Journal of Nuclear Medicine, vol. 56 (2015), pp. 1809-1812.
Cordier, Dominik, et al., "Neoadjuvant targeting of glioblastoma multiforme with radiolabeled DOTAGA-substance P-results from a phase I study," Journal Neurooncology, vol. 100 (2010), pp. 129-136.
Cui, Yanna, et al., "Dual-Targeting Magnetic PLGA Nanoparticles for Codelivery of Paclitaxel and Curcumin for Brain Tumor Therapy," ACS Applied Materials Interfaces, vol. 8 (2016), pp. 32159-32169.
Davies, D. C., et al., "Blood-brain barrier breakdown in septic encephalopathy and brain tumours," J. Anat., vol. 200 (2002), pp. 639-646.
Fauriat, C., et al., "Impaired activating receptor expression pattern in natural killer cells from patients with multiple myeloma," Leukemia, vol. 20 (2006), pp. 732-733.
Fesnak, Andrew D., et al., "Engineered T cells: the promise and challenges of cancer immunotherapy," Nature, vol. 16 (2016), pp. 566-581.
Godfrey, James, et al., "The role of natural killer cells in immunity against multiple myeloma," Leukemia & Lymphoma, vol. 53, No. 9 (2012), pp. 1666-1676.
Hu, Yifang, et al., "ELDA: Extreme limiting dilution analysis for comparing depleted and enriched populations in stem cell and other assays," Journal of Immunological Methods, vol. 347 (2009), pp. 70-78.
Huang, Ping, et al., "Endothelial Expression of TNF Receptor-1 Generates a Proapoptotic Signal Inhibited by Integrin a6B1 in Glioblastoma," Molecular and Cellular Pathobiology, Cancer Research, vol. 72, No. 6 (2012), pp. 1428-1437.
Mai, C., et al., "Chimeric receptors with 4-1BB signaling capacity provoke potent cytotoxicity against acute lymphoblastic leukemia," Leukemia, vol. 18 (2004), pp. 676-684.

(Continued)

*Primary Examiner* — Jeanette M Lieb
(74) *Attorney, Agent, or Firm* — Thomas | Horstemeyer, LLP

(57) ABSTRACT

Disclosed are compositions and methods for targeted treatment of glioblastoma multiforme (GBM). In particular, chimeric antigen receptor (CAR) polypeptides are disclosed that can be used with adoptive cell transfer to target and kill Glioblastoma Stem Cells (GSCs). Also disclosed are immune effector cells, such as T cells or Natural Killer (NK) cells, that are engineered to express these CARs. Therefore, also disclosed are methods of providing an anti-tumor immunity in a subject with Glioblastoma Stem Cells (GSCs) that involves adoptive transfer of the disclosed immune effector cells engineered to express the disclosed CARs.

14 Claims, 18 Drawing Sheets
Specification includes a Sequence Listing.

(56) References Cited

OTHER PUBLICATIONS

Xu, Jinshu, et al., "Eya1 Interacts with Six2 and Myc to Regulate Expansion of the Nephron Progenitor Pool during Nephrogenesis," Developmental Cell, vol. 31 (2014), pp. 434-447.
Jin, Xun, et al., "Targeting glioma stem cells through combined BMI1 and EZH2 inhibition," Nature Medicine, vol. 23, No. 11 (2017), pp. 1352-1361.
Kim, S-H, et al., "The LIM-only transcription factor LMO2 determines tumorigenic and angiogenic traints in glioma stem cells," Cedll Death and Differentiation, vol. 22 (2015), pp. 1517-1525.
Liu, JK, et al., "Phage display discovery of novel molecular targets in glioblastoma-initiating cells," Cell Death and Differentiation, vol. 21 (2014), pp. 1325-1339.
Maher, John, et al., "Human T-lymphocyte cytotoxicity and proliferation directed by a single chimeric TCRs/CD28 receptor," Nature Biotechnology, vol. 20 (2002), pp. 70-75.
Morgan, Richard A., Case Report of a Serious Adverse Event Following the Administration of T Cells Transduced With a Chimeric Antigen Receptor Recognizing ERBB2, Molecular Therapy, vol. 18, No. 4 (2010), pp. 843-851.
Morshed, Rarmin A., et al., "Cell-Penetrating Peptide-Modified Gold Nanoparticles for the Delivery of Doxorubicin to Brain Metastatic Breast Cancer," Mol. Pharmaceutics, vol. 13 (2016), pp. 1843-1854.
Narni-Mancinelli, Emilie, et al., "The 'T-cell-ness' of NK cells: unexpected similarities between NK cells and T cells," International Immunology, vol. 23, No. 7 (2011), pp. 427-431.
Neelapu, S. S., et al., "Axicabtagene Ciloleucel CAR T-Cell Therapy in Refractory Large B-Cell Lymphoma," The New England Journal of Medicine, vol. 377 (2017), pp. 2531-2544.
Ohto, Hiromi, et al., "Cooperation of Six and Eya in Activation of Their Target Genes through Nuclear Translocation of Eya," Molecular and Cellular Biology, vol. 19, No. 10 (1999), pp. 6815-6824.
O'Rourke, Donald M., et al., "A single doese of peripherally infused EGFRvIII-directed CAR T cells mediates antigen loss and induces adaptive resistance in patients with recurrent glioblastoma," Sci. Transl. Med., vol. 9 (2017) (15 pages).
Ostertag, Derek, et al., "Brain tumor eradication and prolonged survival from intratumoral conversion of 5-fluorocytosine to 5-fluorouracil using a nonlytic retroviral replicating vector," Neuro-Oncology, vol. 14, No. 2 (2012), pp. 145-159.
Pandey, RN, et al., "The Eyes Absent phosphatase-transactivator proteins promote proliferation, transformation, migration, and invasion of tumor cells," Oncogene, vol. 29 (2010), pp. 3715-3722.

Porter, David L., et al., "Chimeric Antigen Receptor-Modified T Cells in Chronic Lymphoid Leukemia," The New England Journal of Medicine, vol. 365 (2011), pp. 725-733.
Puchalski, Ralph B., et al., "An anatomic transcriptional atlas of human glioblastoma," Science, vol. 360 (2018), pp. 660-663.
Rayapureddi, Jayanagendra P., et al., "Eyes absent represents a class of protein tyrosine phosphatases," Nature, vol. 426 (2003), pp. 295-298.
Ricci-Vitiani, Lucia, et al., "Tumour vascularization via endothelial differentiation of glioblastoma stem-like cells," Nature, vol. 468 (2010), pp. 824-828.
Rosenberg, Steven A., et al., "Use of Tumor-Infiltrating Lymphocytes and Interleukin-2 in the Immunotherapy of Patients with Metastatic Melanoma," The New England Journal of Medicine, vol. 319, No. 25 (1988), pp. 1676-1680.
Sampson, John H., et al., "Poor drug distribution as a possible explanation for the results of the Precise trial," J. Neurosurg., vol. 113 (2010), pp. 301-309.
Sandmann, Thomas, et al., "Patients with Proneural Glioblastoma May Derive Overall Survival Benefit from the Addition of Bevacizumab to First-Line Radiotherapy and Temozolomie: Restrospective Analysis of the AVAglio Trial," Journal of Clinical Oncology, vol. 33, No. 25 (2015), pp. 2735-2744.
Stummer, Walter, et al., "Counterbalancing risks and gains from extended resections in malignant glioma surgery: a supplemental analysis from the randomized 5-aminolevulinic acid glioma resection study," Journal of Neurosurgery, vol. 114 (2011), pp. 613-623.
Stupp, Roger, et al., "Radiotherapy plus Concomitant and Adjuvant Temozolomide for Glioblastoma," The New England Journal of Medicine, vol. 351, No. 10 (2005), pp. 987-996.
Tadjuidje, Emmanuel, et al., "The Eyes Absent Proteins in Development and Disease," Cell Mol. Life Science, vol. 70, No. 11 (2013), pp. 1987-1913.
Weller, Michael, et al., "European Association for Neuro-Oncology (EANO) guideline on the diagnosis and treatment of adult astrocytic and oligodendroglial gliomas," Lancet Onocology, vol. 18 (2017), pp. 315-329.
Woof, Jenny M., et al., "Human Antibody-FC Receptor Interactions Illuminated by Crystal Structures," Nature Reviews, vol. 4 (2004) (11 pages).
Wu, Kongming, et al., "EYA1 Phosphatase Function Is Essential to Drive Breast Cancer Cell Proliferation through Cyclin D1," Cancer Research, vol. 73, No. 14 (2013), pp. 4488-4499.
Yin, D., et al., "Convection-enhanced delivery improves distribution and efficacy of tumor-selective retroviral replicating vectors in a rodent brain tumor model," Cancer Gene Therapy, vol. 20 (2013), pp. 336-341.

* cited by examiner

CAR-T CELLS TARGETING GLIOMA STEM CELLS FOR THE TREATMENT OF GLIOBLASTOMA MULTIFORME

CROSS-REFERENCE TO RELATED APPLICATIONS

This application is a continuation of U.S. patent application Ser. No. 17/212,320, filed Mar. 25, 2021, which claims priority of continuation-in-part of International Application No. PCT/US2019/053793, filed Sep. 30, 2019, which claims benefit of U.S. Provisional Application No. 62/739,579, filed Oct. 1, 2018, which is hereby incorporated herein by reference in its entirety.

SEQUENCE LISTING

This application contains a sequence listing filed in electronic form as a WIPO Standard ST.26 file entitled "320803-1831 Sequence Listing.xml" created on Jul. 12, 2022. The content of the sequence listing is incorporated herein in its entirety.

BACKGROUND

Glioblastoma multiforme (GBM) remains an incurable condition, typically associated with high mortality and morbidity (Stupp R, et al. N Engl J Med. 2005 352(10):987-96). Recent advances in the field of cancer immunotherapy have brought renewed hope for a cure of otherwise deadly diseases, with major breakthroughs achieved in the treatment of hematological malignancies (Neelapu SS, et al. N Engl J Med. 2017 377(26):2531-44). Moreover, a case report showed evidence of the therapeutic potential of an anti-IL13RA2 zetakine product, which induced complete regression of multifocal GBM in a patient who have failed multiple courses of standard and experimental therapies (Brown CE, et al. N Engl J Med. 2016 375(26):2561-9). Unfortunately, other single-target immunotherapies against GBM have shown modest therapeutic benefit, due to antigen escape associated with heterogeneity in tumor antigen expression (O'Rourke DM, et al. Sci Transl Med. 2017 9(399)).

SUMMARY

Disclosed herein are peptides that preferentially bind Glioblastoma Stem Cells (GSCs). These peptides were used to construct chimeric antigen receptor (CAR) polypeptides for use in CAR-T cells that can be used to treat glioblastoma multiforme (GBM).

Therefore, disclosed herein are chimeric antigen receptor (CAR) polypeptides that can be used with adoptive cell transfer to target and kill GSCs. The disclosed CAR polypeptides contain in an ectodomain a GSC-binding agent disclosed herein that can bind antigens on GSCs. Also disclosed is an immune effector cell genetically modified to express the disclosed CAR polypeptide.

Also disclosed are chimeric costimulatory receptor (CCR or switch receptor) polypeptides that can be used with adoptive cell transfer to target and kill GSCs. CCRs mimic costimulatory signals, but unlike CARs, do not provide a T cell activation signal. Their purpose is to provide costimulation, e.g. a CD28-like signal, in the absence of the natural costimulatory ligand on the antigen-presenting cell. CCRs can be used in conjunction with a TCR or a CAR to augment T cell reactivity against dual-antigen expressing T cells, reinforcing T cell activation in the absence of natural costimulatory ligands and in antigen-dependent fashion. The disclosed CCR polypeptides contain in an ectodomain a GSC-binding agent disclosed herein that can bind antigens on GSCs. Also disclosed is an immune effector cell genetically modified to express the disclosed CCR polypeptide.

The GSC-binding agent is in some embodiments a natural or synthetic polypeptide comprising one or more GSC-binding peptides that bind antigens on GSCs. In some embodiments, the GSC-binding peptide comprises the amino acid sequence SSQPFWS (SEQ ID NO:1, VAV), AWEFYFP (SEQ ID NO:2, EYA), AWTITFP (SEQ ID NO:3, Peptide #1), AWTWTLP (SEQ ID NO:4, Peptide #2), EWLFSMP (SEQ ID NO:5, Peptide #3), GWFYTFP (SEQ ID NO:6, Peptide #4), or NWYWVYP (SEQ ID NO:7, Peptide #5), QYRPTHS (SEQ ID NO:29), LSKKLPV (SEQ ID NO:30), EPFTIGR (SEQ ID NO:31), or NTQPPTT (SEQ ID NO:32).

In some embodiments, the GSC-binding agent contains 2, 3, 4, 5, or 6 GSC-binding peptides, each optionally separated by a linker. Suitable linkers for CARs are known in the art. In some embodiments, the linker comprises the amino acid sequence GGGGSGGGGSGGGGS (SEQ ID NO:8), GGGGSGGGGSGGGGSGGGGS (SEQ ID NO:9), GST-SGSGKPGSGEGSTKG (218 linker, SEQ ID NO:10), PRGASKSGSASQTGSAPGS (SEQ ID NO:11), GTAAAGAGAAGGAAAGAAG (SEQ ID NO:12), GTSGSSGSGSGGSGSGGG (SEQ ID NO:13), or GKPGSGKPGSGKPGSGKPGS (SEQ ID NO:14).

Therefore, in some embodiments, the GSC-binding agent comprises an amino acid sequence: SSQPFWS-GGGGSGGGGSGGGGS-AWEFYFP-GST-SGSGKPGSGEGSTKG (SEQ ID NO:15).

Therefore, in some embodiments, the GSC-binding agent is encoded by the nucleic acid sequence:

```
                                     (SEQ ID NO: 16)
tagactgctcgagccgccaccatggttctgctggt caccagcctgctgctgtgcgagctgccccacccccg cctttctgctgatccccAGTAGCCAGCCATTCTGG

AGCGGTGGGGGGGATCAGGCGGCGGCGGGAGTGG

GGGGGGTGGATCAGCGTGGGAGTTTTACTTTCCAG

GCTCCACATCTGGTAGTGGTAAACCCGGATCAGGT

GAGGGAAGCACAAAAGGTgcggccgcattcgtgcc ggtcttcc.
```

Therefore, in some embodiments, the GSC-binding agent comprises an amino acid sequence: AWEFYFP-GGGGSGGGGSGGGGS-SSQPFWS-GST-SGSGKPGSGEGSTKG (SEQ ID NO:17).

Therefore, in some embodiments, the GSC-binding agent is encoded by the nucleic acid sequence:

```
                                     (SEQ ID NO: 18)
tagactgctcgagccgccaccatggttctgctggt caccagcctgctgctgtgcgagctgccccacccccg cctttctgctgatccccGCATGGGAGTTTTACTTT

CCCGGTGGAGGTGGGTCIGGTGGGGGGGAAGCGG
```

-continued
```
TGGAGGTGGTAGCTCTAGCCAACCTTTCTGGAGTG

GGAGTACGAGTGGGTCCGGCAAGCCAGGCTCTGGC

GAAGGATCAACTAAAGGTgcggccgcattcgtgcc ggtcttcc.
```

Therefore, in some embodiments, the GSC-binding agent comprises an amino acid sequence: AWTITFP-GGGGSGGGGSGGGGS-SSQPFWS-GST-SGSGKPGSGEGSTKG (SEQ ID NO:19).

Therefore, in some embodiments, the GSC-binding agent is encoded by the nucleic acid sequence:

```
                                      (SEQ ID NO: 20)
tagactgctcgagccgccaccatggttctgctggt caccagcctgctgctgtgcgagctgccccacccccg cctttctgctgatccccGCCTGGACGATTACGTTC

CCTGGTGGCGGAGGTTCTGGCGGTGGAGGAAGTGG

TGGTGGCGGCAGCAGTTCCCAACCTTTCTGGTCAG

GTTCCACGAGTGGAAGCGGCAAACCGGGCAGTGGC

GAAGGGAGTACGAAGGGAgcggccgcattcgtgcc ggtcttcc.
```

Therefore, in some embodiments, the GSC-binding agent comprises an amino acid sequence: AWTWTLP-GGGGSGGGGSGGGGS-SSQPFWS-GST-SGSGKPGSGEGSTKG (SEQ ID NO:21).

Therefore, in some embodiments, the GSC-binding agent is encoded by the nucleic acid sequence:

```
                                      (SEQ ID NO: 22)
tagactgctcgagccgccaccatggttctgctggt caccagcctgctgctgtgcgagctgccccacccccg cctttctgctgatccccGCTTGGACATGGACCCTT

CCCGGAGGTGGTGGCTCTGGGGGGGCGGGTCAGG

TGGAGGCGGTTCTAGTAGTCAACCGTTTTGGTCCG

GCAGTACCTCCGGGAGTGGCAAACCCGGCAGTGGT

GAAGGTTCCACGAAAGGAgcggccgcattcgtgcc ggtcttcc.
```

Therefore, in some embodiments, the GSC-binding agent comprises an amino acid sequence: EWLFSMP-GGGGSGGGGSGGGGS-SSQPFWS-GST-SGSGKPGSGEGSTKG (SEQ ID NO:23).

Therefore, in some embodiments, the GSC-binding agent is encoded by the nucleic acid sequence:

```
                                      (SEQ ID NO: 24)
tagactgctcgagccgccaccatggttctgctggt caccagcctgctgctgtgcgagctgccccacccccg cctttctgctgatccccGAGTGGCTGTTTTCCATG

CCAGGCGGAGGGGGCAGCGGAGGGGGCGGCAGTGG
```

-continued
```
CGGAGGGGGCTCATCCTCACAACCTTTTTGGAGTG

GATCAACATCTGGGTCTGGGAAGCCTGGATCTGGT

GAGGGATCAACCAAGGGGgcggccgcattcgtgcc ggtcttcc.
```

Therefore, in some embodiments, the GSC-binding agent comprises an amino acid sequence: GWFYTFP-GGGGSGGGGSGGGGS-SSQPFWS-GST-SGSGKPGSGEGSTKG (SEQ ID NO:25).

Therefore, in some embodiments, the GSC-binding agent is encoded by the nucleic acid sequence:

```
                                      (SEQ ID NO: 26)
tagactgctcgagccgccaccatggttctgctggt caccagcctgctgctgtgcgagctgccccacccccg cctttctgctgatccccGGTTGGTTTTACACCTTC

CCTGGTGGAGGAGGCTCCGGCGGGGCGGTTCTGG

TGGCGGGGGCTCCTCTAGTCAACCATTCTGGTCAG

GAAGCACGTCAGGGAGCGGAAAACCGGGAAGCGGG

GAGGGGTCCACCAAAGGGgcggccgcattcgtgcc ggtcttcc.
```

Therefore, in some embodiments, the GSC-binding agent comprises an amino acid sequence: NWYWVYP-GGGGSGGGGSGGGGS-SSQPFWS-GST-SGSGKPGSGEGSTKG (SEQ ID NO:27).

Therefore, in some embodiments, the GSC-binding agent is encoded by the nucleic acid sequence:

```
                                      (SEQ ID NO: 28)
tagactgctcgagccgccaccatggttctgctggt caccagcctgctgctgtgcgagctgccccacccccg cctttctgctgatccccAACTGGTATTGGGTCTAC

CCCGGCGGTGGCGGCTCTGGTGGCGGTGGCTCAGG

TGGAGGCGGTAGCTCTTCACAACCATTCTGGAGCG

GGTCTACGTCTGGTAGCGGTAAACCAGGGTCCGGT

GAGGGGAGTACGAAGGGGgcggccgcattcgtgcc ggtcttcc.
```

In some embodiments, the disclosed CAR polypeptide is defined by the formula:

SP—GBP—HG—TM—CSR—ISD; or

SP—GBP—HG—TM—ISD—CSR wherein "SP" represents a signal peptide,
wherein "GBP" represents a GSC-binding peptide,
wherein "HG" represents and optional hinge domain,
wherein "TM" represents a transmembrane domain,
wherein "CSR" represents a co-stimulatory signaling region,
wherein "ISD" represents an intracellular signaling domain, and
wherein "-" represents a bivalent linker.

Also disclosed is a chimeric costimulatory receptor (CCR), which mimics costimulatory signals, but unlike CARs, do not provide a T cell activation signal.

Therefore, in some embodiments, the disclosed CCR polypeptide is defined by the formula:

SP-GBP—HG—TM—CSR.

In some of these embodiments, the costimulatory signaling region comprises the cytoplasmic domain of a CD28. In some of these embodiments, the hinge domain comprises a CD8 hinge domain. In some of these embodiments, the transmembrane domain transmembrane a CD8 hinge domain.

The disclosed polypeptides can also contain a transmembrane domain and an endodomain optinally capable of activating an immune effector cell. For example, the endodomain can contain one or more co-stimulatory signaling regions and optionally a signaling domain.

In some embodiments, the intracellular signaling domain is a CD3 zeta (CD3ζ) signaling domain. In some embodiments, the costimulatory signaling region comprises the cytoplasmic domain of CD28, 4-1BB, or a combination thereof. In some cases, the costimulatory signaling region contains 1, 2, 3, or 4 cytoplasmic domains of one or more intracellular signaling and/or costimulatory molecules. In some embodiments, the co-stimulatory signaling region contains one or more mutations in the cytoplasmic domains of CD28 and/or 4-1 BB that enhance signaling.

In some embodiments, the CAR polypeptide contains an incomplete endodomain. For example, the CAR polypeptide can contain only an intracellular signaling domain or a co-stimulatory domain, but not both. In these embodiments, the immune effector cell is not activated unless it and a second CAR polypeptide, CCR, or endogenous T-cell receptor that contains the missing domain both bind their respective antigens. Therefore, in some embodiments, the CAR polypeptide contains a CD3 zeta (CD3ζ) signaling domain but does not contain a costimulatory signaling region (CSR). In other embodiments, a CCR polypeptide contains the cytoplasmic domain of CD28, 4-1 BB, or a combination thereof, but does not contain a CD3 zeta (CD3ζ) signaling domain (SD).

In some embodiments, the disclosed CAR/CCR is used in combination with a CAR/CCR that specifically binds another antigen. A dual CAR/CCR can be engineered such that one extracellular antigen binding domain is connected to the intracellular costimulatory domain and a second, distinct extracellular antigen binding domain is connected to the intracellular stimulatory domain.

Also disclosed are isolated nucleic acid sequences encoding the disclosed CAR/CCR polypeptides, vectors comprising these isolated nucleic acids, and cells containing these vectors. For example, the cell can be an immune effector cell selected from the group consisting of an alpha-beta T cells, a gamma-delta T cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, and a regulatory T cell.

In some embodiments, the cell exhibits an anti-tumor immunity when the antigen binding domain of the CAR/CCR binds to antigens on GSCs.

Also disclosed is a method of providing an anti-tumor immunity in a subject with glioblastoma multiforme (GBM) that involves administering to the subject an effective amount of an immune effector cell genetically modified with a disclosed GSC-specific CAR/CCR.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
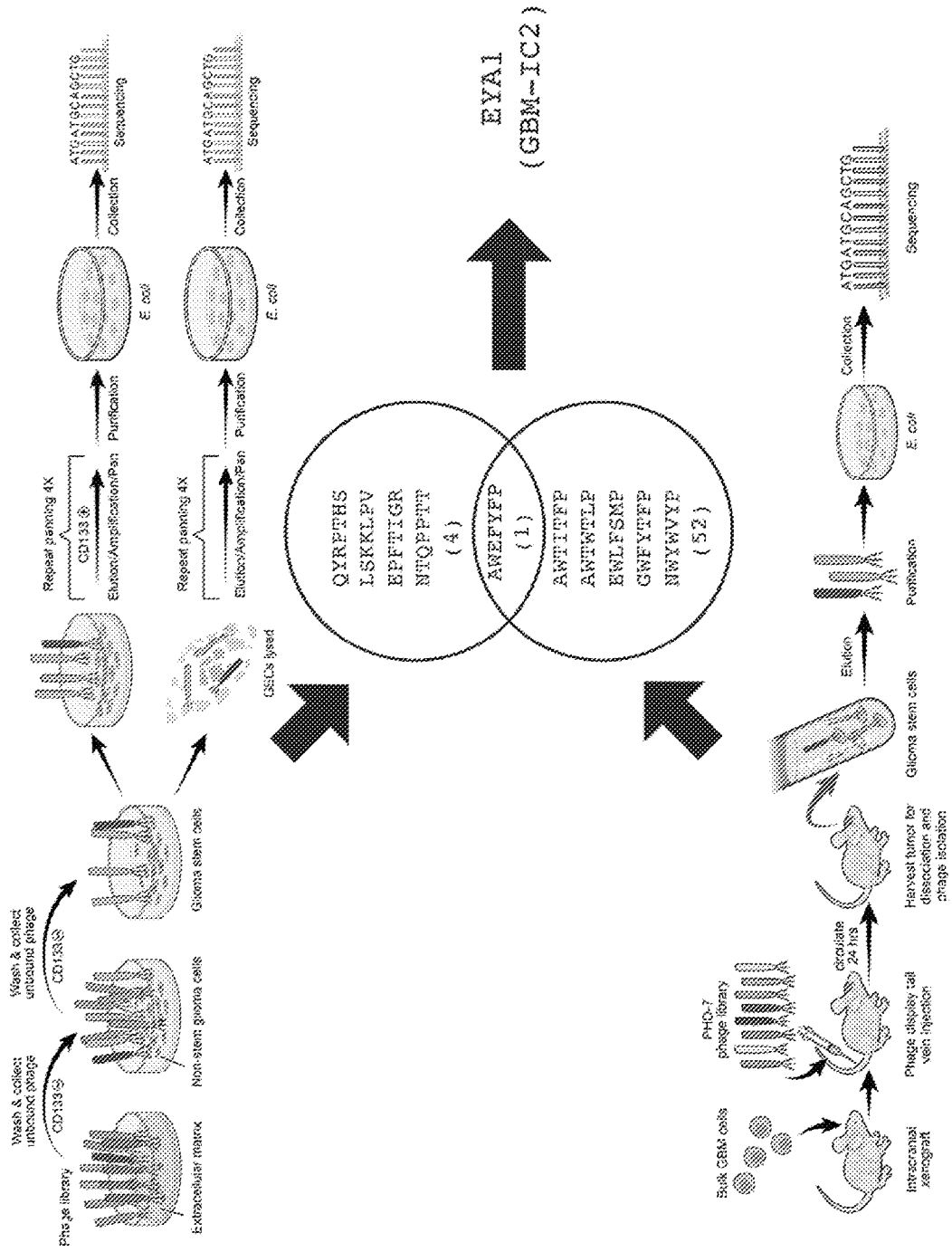
FIG. 1. GSC targeting peptide isolated through phage display biopanning. Phage display biopanning was performed to isolate 7-amino acid length peptides that demonstrate a specific binding affinity against GSCs. In vitro bipoanning was performed by negative selection against extracellular matrix and DGCs, following by four rounds of biopanning against GSCs. In vivo biopanning was performed to select for peptides tumor targeting peptides with the potential to cross the blood brain barrier. 53 peptide sequences were obtained from the in vitro screening and 5 unique peptides sequences were obtained through the in vivo screen. Amongst the peptides recovered from the in vitro screen, 6 peptide sequences were recovered several different clones (sequences shown in figure: AWEFYFP (SEQ ID NO:2), QYRPTHS (SEQ ID NO:29), LSKKLPV (SEQ ID NO:30), EPFTIGR (SEQ ID NO:31), NTQPPTT (SEQ ID NO:32), AWTITFP (SEQ ID NO:3), AWTWTLP (SEQ ID NO:4), EWLFSMP (SEQ ID NO:5), GWFYTFP (SEQ ID NO:6), NWYWVYP (SEQ ID NO:7)). One of the sequences matched a sequence recovered from the in vivo screen (GBM-IC2). A BLAST search correlated GBM-IC2 with the protein EYA1 (FIG. 1A). Evaluation of EYA1 in the TCGA Database demonstrated an increased expression of EYA1 in the proneural GBM subtype as well as the G-CIMP positive GBM. Survival data from TCGA indicated that in non-G-CIMP tumors, there is a correlation with decreased overall survival in EYA1 high expression patients (FIG. 1B). Using the Ivy Glioblastoma Atlas Project (Ivy GAP) database, EYA1 expression is shown to be increased in the infiltrating aspect of GBM tumors demonstrating an association of EYA1 in tumor proliferation and invasion (FIG. 1C).

Disclosed herein are chimeric antigen receptors (CAR) that can specifically recognize Glioblastoma Stem Cells (GSCs) in glioblastoma multiforme (GBM). Also disclosed are immune effector cells, such as T cells or Natural Killer (NK) cells, that are engineered to express these CARs. Therefore, also disclosed are methods for providing an anti-tumor immunity in a subject with GBM that involves adoptive transfer of the disclosed immune effector cells engineered to express the disclosed GSC-specific CARs.

GSC-specific chimeric antigen receptors (CAR) The disclosed CAR is generally made up of three domains: an ectodomain, a transmembrane domain, and an endodomain. The ectodomain comprises the GSC-binding region and is responsible for antigen recognition. It also optionally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain an intracellular signaling domain (ISD) and optionally a co-stimulatory signaling region (CSR).

A "signaling domain (SD)" generally contains immunoreceptor tyrosine-based activation motifs (ITAMs) that activate a signaling cascade when the ITAM is phosphorylated. The term "co-stimulatory signaling region (CSR)" refers to intracellular signaling domains from costimulatory protein receptors, such as CD28, 41BB, and ICOS, that are able to enhance T-cell activation by T-cell receptors.

In some embodiments, the endodomain contains an SD or a CSR, but not both. In these embodiments, an immune effector cell containing the disclosed CAR is only activated if another CAR (or a T-cell receptor) containing the missing domain also binds its respective antigen.

In some embodiments, the disclosed CAR is defined by the formula:

SP—GBP—HG—TM—CSR—ISD; or

SP—GBP—HG—TM—ISD—CSR wherein "SP" represents a signal peptide,
wherein "GBP" represents a GSC-binding peptide,
wherein "HG" represents and optional hinge domain,
wherein "TM" represents a transmembrane domain,
wherein "CSR" represents a co-stimulatory signaling region,
wherein "ISD" represents an intracellular signaling domain, and
wherein "-" represents a bivalent linker.

Additional CAR constructs are described, for example, in Fresnak AD, et al. Engineered T cells: the promise and challenges of cancer immunotherapy. Nat Rev Cancer. 2016 Aug 23;16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

TRUCKs (T cells redirected for universal cytokine killing) co-express a chimeric antigen receptor (CAR) and an antitumor cytokine. Cytokine expression may be constitutive or induced by T cell activation. Targeted by CAR specificity, localized production of pro-inflammatory cytokines recruits endogenous immune cells to tumor sites and may potentiate an antitumor response.

Universal, allogeneic CAR T cells are engineered to no longer express endogenous T cell receptor (TCR) and/or major histocompatibility complex (MHC) molecules, thereby preventing graft-versus-host disease (GVHD) or rejection, respectively.

Self-driving CARs co-express a CAR and a chemokine receptor, which binds to a tumor ligand, thereby enhancing tumor homing.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

Marked CAR T cells express a CAR plus a tumor epitope to which an existing monoclonal antibody agent binds. In the setting of intolerable adverse effects, administration of the monoclonal antibody clears the CAR T cells and alleviates symptoms with no additional off-tumor effects.

A tandem CAR (TanCAR) T cell expresses a single CAR consisting of two linked single-chain variable fragments (scFvs) that have different affinities fused to intracellular co-stimulatory domain(s) and a CD3ζ domain. TanCAR T cell activation is achieved only when target cells co-express both targets.

A dual CAR T cell expresses two separate CARs with different ligand binding targets; one CAR includes only the CD3ζ domain and the other CAR includes only the co-stimulatory domain(s). Dual CAR T cell activation requires co-expression of both targets on the tumor.

A safety CAR (sCAR) consists of an extracellular domain fused to an intracellular inhibitory domain. sCAR T cells co-expressing a standard CAR become activated only when encountering target cells that possess the standard CAR target but lack the sCAR target.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from CD8, CD3ζ, CD3δ, CD3γ, CD3ε, CD32 (Fc gamma RIIa), DAP10, DAP12, CD79a, CD79b, FcγRIγ, FcγRIIIγ, FcεRIβ (FCERIB), and FcεRIγ (FCERIG).

In particular embodiments, the intracellular signaling domain is derived from CD3 zeta (CD3ζ) (TCR zeta, GenBank accno. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3ζ chain, which is the primary transmitter of signals from endogenous TCRs. Second-generation CARs add intracellular signaling domains from various costimulatory protein receptors (e.g., CD28, 41 BB, ICOS) to the endodomain of the CAR to provide additional signals to the T cell. Preclinical studies have indicated that the second generation of CAR designs improves the antitumor activity of T cells. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3ζ signaling domain by itself or combined with any other desired cytoplasmic domain(s) useful in the context of the CAR of the invention. For example, the cytoplasmic domain of the CAR can comprise a CD3ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD83, CD8, CD4, b2c, CD80, CD86, DAP10, DAP12, MyD88, BTNL3, and NKG2D. Thus, while the CAR is exemplified primarily with CD28 as the co-stimulatory signaling element, other costimulatory elements can be used alone or in combination with other co-stimulatory signaling elements.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety (e.g., GSC-binding domain) and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

Tables 1, 2, and 3 below provide some example combinations of GSC-binding domain (GBD), co-stimulatory signaling regions, and intracellular signaling domain that can occur in the disclosed CARs.

TABLE 1

First Generation CARs

| | Signal Domain |
|---|---|
| GBD | CD8 |
| GBD | CD3ζ |
| GBD | CD3δ |
| GBD | CD3γ |
| GBD | CD3ε |
| GBD | FcγRI-γ |
| GBD | FcγRIII-γ |
| GBD | FcεRIβ |
| GBD | FcεRIγ |
| GBD | DAP10 |
| GBD | DAP12 |
| GBD | CD32 |
| GBD | CD79a |

TABLE 2

Second Generation CARs

| | Co-stimulatory Signal | | Signal Domain | | Co-stimulatory Signal | | Signal Domain |
|---|---|---|---|---|---|---|---|
| GBD | CD28 | | CD8 | GBD | CD80 | | FcεRIβ |
| GBD | CD28 | | CD3ζ | GBD | CD80 | | FcεRIγ |
| GBD | CD28 | | CD3δ | GBD | CD80 | | DAP10 |
| GBD | CD28 | | CD3γ | GBD | CD80 | | DAP12 |
| GBD | CD28 | | CD3ε | GBD | CD80 | | CD32 |
| GBD | CD28 | | FcγRI-γ | GBD | CD80 | | CD79a |
| GBD | CD28 | | FcγRIII-γ | GBD | CD80 | | CD79b |
| GBD | CD28 | | FcεRIβ | GBD | CD86 | | CD8 |
| GBD | CD28 | | FcεRIγ | GBD | CD86 | | CD3ζ |
| GBD | CD28 | | DAP10 | GBD | CD86 | | CD3δ |
| GBD | CD28 | | DAP12 | GBD | CD86 | | CD3γ |
| GBD | CD28 | | CD32 | GBD | CD86 | | CD3ε |
| GBD | CD28 | | CD79a | GBD | CD86 | | FcγRI-γ |
| GBD | CD28 | | CD79b | GBD | CD86 | | FcγRIII-γ |
| GBD | CD8 | | CD8 | GBD | CD86 | | FcεRIβ |
| GBD | CD8 | | CD3ζ | GBD | CD86 | | FcεRIγ |
| GBD | CD8 | | CD3δ | GBD | CD86 | | DAP10 |
| GBD | CD8 | | CD3γ | GBD | CD86 | | DAP12 |
| GBD | CD8 | | CD3ε | GBD | CD86 | | CD32 |
| GBD | CD8 | | FcγRI-γ | GBD | CD86 | | CD79a |
| GBD | CD8 | | FcγRIII-γ | GBD | CD86 | | CD79b |
| GBD | CD8 | | FcεRIβ | GBD | OX40 | | CD8 |
| GBD | CD8 | | FcεRIγ | GBD | OX40 | | CD3ζ |

TABLE 2-continued

Second Generation CARs

| | Co-stimulatory Signal | | Signal Domain | | Co-stimulatory Signal | | Signal Domain |
|---|---|---|---|---|---|---|---|
| GBD | CD8 | | DAP10 | GBD | OX40 | | CD3δ |
| GBD | CD8 | | DAP12 | GBD | OX40 | | CD3γ |
| GBD | CD8 | | CD32 | GBD | OX40 | | CD3ε |
| GBD | CD8 | | CD79a | GBD | OX40 | | FcγRI-γ |
| GBD | CD8 | | CD79b | GBD | OX40 | | FcγRIII-γ |
| GBD | CD4 | | CD8 | GBD | OX40 | | FcεRIβ |
| GBD | CD4 | | CD3ζ | GBD | OX40 | | FcεRIγ |
| GBD | CD4 | | CD3δ | GBD | OX40 | | DAP10 |
| GBD | CD4 | | CD3γ | GBD | OX40 | | DAP12 |
| GBD | CD4 | | CD3ε | GBD | OX40 | | CD32 |
| GBD | CD4 | | FcγRI-γ | GBD | OX40 | | CD79a |
| GBD | CD4 | | FcγRIII-γ | GBD | OX40 | | CD79b |
| GBD | CD4 | | FcεRIβ | GBD | DAP10 | | CD8 |
| GBD | CD4 | | FcεRIγ | GBD | DAP10 | | CD3ζ |
| GBD | CD4 | | DAP10 | GBD | DAP10 | | CD3δ |
| GBD | CD4 | | DAP12 | GBD | DAP10 | | CD3γ |
| GBD | CD4 | | CD32 | GBD | DAP10 | | CD3ε |
| GBD | CD4 | | CD79a | GBD | DAP10 | | FcγRI-γ |
| GBD | CD4 | | CD79b | GBD | DAP10 | | FcγRIII-γ |
| GBD | b2c | | CD8 | GBD | DAP10 | | FcεRIβ |
| GBD | b2c | | CD3ζ | GBD | DAP10 | | FcεRIγ |
| GBD | b2c | | CD3δ | GBD | DAP10 | | DAP10 |
| GBD | b2c | | CD3γ | GBD | DAP10 | | DAP12 |
| GBD |ب2c | | CD3ε | GBD | DAP10 | | CD32 |
| GBD | b2c | | FcγRI-γ | GBD | DAP10 | | CD79a |
| GBD | b2c | | FcγRIII-γ | GBD | DAP10 | | CD79b |
| GBD | b2c | | FcεRIβ | GBD | DAP12 | | CD8 |
| GBD | b2c | | FcεRIγ | GBD | DAP12 | | CD3ζ |
| GBD | b2c | | DAP10 | GBD | DAP12 | | CD3δ |
| GBD | b2c | | DAP12 | GBD | DAP12 | | CD3γ |
| GBD | b2c | | CD32 | GBD | DAP12 | | CD3ε |
| GBD | b2c | | CD79a | GBD | DAP12 | | FcγRI-γ |
| GBD | b2c | | CD79b | GBD | DAP12 | | FcγRIII-γ |
| GBD | CD137/41BB | | CD8 | GBD | DAP12 | | FcεRIβ |
| GBD | CD137/41BB | | CD3ζ | GBD | DAP12 | | FcεRIγ |
| GBD | CD137/41BB | | CD3δ | GBD | DAP12 | | DAP10 |
| GBD | CD137/41BB | | CD3γ | GBD | DAP12 | | DAP12 |
| GBD | CD137/41BB | | CD3ε | GBD | DAP12 | | CD32 |
| GBD | CD137/41BB | | FcγRI-γ | GBD | DAP12 | | CD79a |
| GBD | CD137/41BB | | FcγRIII-γ | GBD | DAP12 | | CD79b |
| GBD | CD137/41BB | | FcεRIβ | GBD | MyD88 | | CD8 |
| GBD | CD137/41BB | | FcεRIγ | GBD | MyD88 | | CD3ζ |
| GBD | CD137/41BB | | DAP10 | GBD | MyD88 | | CD3δ |
| GBD | CD137/41BB | | DAP12 | GBD | MyD88 | | CD3γ |
| GBD | CD137/41BB | | CD32 | GBD | MyD88 | | CD3ε |
| GBD | CD137/41BB | | CD79a | GBD | MyD88 | | FcγRI-γ |
| GBD | CD137/41BB | | CD79b | GBD | MyD88 | | FcγRIII-γ |
| GBD | ICOS | | CD8 | GBD | MyD88 | | FcεRIβ |
| GBD | ICOS | | CD3ζ | GBD | MyD88 | | FcεRIγ |
| GBD | ICOS | | CD3δ | GBD | MyD88 | | DAP10 |
| GBD | ICOS | | CD3γ | GBD | MyD88 | | DAP12 |
| GBD | ICOS | | CD3ε | GBD | MyD88 | | CD32 |
| GBD | ICOS | | FcγRI-γ | GBD | MyD88 | | CD79a |
| GBD | ICOS | | FcγRIII-γ | GBD | MyD88 | | CD79b |
| GBD | ICOS | | FcεRIβ | GBD | CD7 | | CD8 |
| GBD | ICOS | | FcεRIγ | GBD | CD7 | | CD3ζ |
| GBD | ICOS | | DAP10 | GBD | CD7 | | CD3δ |
| GBD | ICOS | | DAP12 | GBD | CD7 | | CD3γ |
| GBD | ICOS | | CD32 | GBD | CD7 | | CD3ε |
| GBD | ICOS | | CD79a | GBD | CD7 | | FcγRI-γ |
| GBD | ICOS | | CD79b | GBD | CD7 | | FcγRIII-γ |
| GBD | CD27 | | CD8 | GBD | CD7 | | FcεRIβ |
| GBD | CD27 | | CD3ζ | GBD | CD7 | | FcεRIγ |
| GBD | CD27 | | CD3δ | GBD | CD7 | | DAP10 |
| GBD | CD27 | | CD3γ | GBD | CD7 | | DAP12 |
| GBD | CD27 | | CD3ε | GBD | CD7 | | CD32 |
| GBD | CD27 | | FcγRI-γ | GBD | CD7 | | CD79a |
| GBD | CD27 | | FcγRIII-γ | GBD | CD7 | | CD79b |
| GBD | CD27 | | FcεRIβ | GBD | BTNL3 | | CD8 |
| GBD | CD27 | | FcεRIγ | GBD | BTNL3 | | CD3ζ |
| GBD | CD27 | | DAP10 | GBD | BTNL3 | | CD3δ |
| GBD | CD27 | | DAP12 | GBD | BTNL3 | | CD3γ |
| GBD | CD27 | | CD32 | GBD | BTNL3 | | CD3ε |
| GBD | CD27 | | CD79a | GBD | BTNL3 | | FcγRI-γ |
| GBD | CD27 | | CD79b | GBD | BTNL3 | | FcγRIII-γ |

TABLE 2-continued

Second Generation CARs

| | Co-stimulatory Signal | Signal Domain | | Co-stimulatory Signal | Signal Domain |
|---|---|---|---|---|---|
| GBD | CD28δ | CD8 | GBD | BTNL3 | FcεRIβ |
| GBD | CD28δ | CD3ζ | GBD | BTNL3 | FcεRIγ |
| GBD | CD28δ | CD3δ | GBD | BTNL3 | DAP10 |
| GBD | CD28δ | CD3γ | GBD | BTNL3 | DAP12 |
| GBD | CD28δ | CD3ε | GBD | BTNL3 | CD32 |
| GBD | CD28δ | FcγRI-γ | GBD | BTNL3 | CD79a |
| GBD | CD28δ | FcγRIII-γ | GBD | BTNL3 | CD79b |
| GBD | CD28δ | FcεRIβ | GBD | NKG2D | CD8 |
| GBD | CD28δ | FcεRIγ | GBD | NKG2D | CD3ζ |
| GBD | CD28δ | DAP10 | GBD | NKG2D | CD3δ |
| GBD | CD28δ | DAP12 | GBD | NKG2D | CD3γ |
| GBD | CD28δ | CD32 | GBD | NKG2D | CD3ε |
| GBD | CD28δ | CD79a | GBD | NKG2D | FcγRI-γ |
| GBD | CD28δ | CD79b | GBD | NKG2D | FcγRIII-γ |
| GBD | CD80 | CD8 | GBD | NKG2D | FcεRIβ |
| GBD | CD80 | CD3ζ | GBD | NKG2D | FcεRIγ |
| GBD | CD80 | CD3δ | GBD | NKG2D | DAP10 |
| GBD | CD80 | CD3γ | GBD | NKG2D | DAP12 |
| GBD | CD80 | CD3ε | GBD | NKG2D | CD32 |
| GBD | CD80 | FcγRI-γ | GBD | NKG2D | CD79a |
| GBD | CD80 | FcγRIII-γ | GBD | NKG2D | CD79b |

TABLE 3

Third Generation CARs

| | Co-stimulatory Signal | Co-stimulatory Signal | Signal Domain |
|---|---|---|---|
| GBD | CD28 | CD28 | CD8 |
| GBD | CD28 | CD28 | CD3ζ |
| GBD | CD28 | CD28 | CD3δ |
| GBD | CD28 | CD28 | CD3γ |
| GBD | CD28 | CD28 | CD3ε |
| GBD | CD28 | CD28 | FcγRI-γ |
| GBD | CD28 | CD28 | FcγRIII-γ |
| GBD | CD28 | CD28 | FcεRIβ |
| GBD | CD28 | CD28 | FcεRIγ |
| GBD | CD28 | CD28 | DAP10 |
| GBD | CD28 | CD28 | DAP12 |
| GBD | CD28 | CD28 | CD32 |
| GBD | CD28 | CD28 | CD79a |
| GBD | CD28 | CD28 | CD79b |
| GBD | CD28 | CD28 | CD8 |
| GBD | CD28 | CD28 | CD3ζ |
| GBD | CD28 | CD8 | CD3δ |
| GBD | CD28 | CD8 | CD3γ |
| GBD | CD28 | CD8 | CD3ε |
| GBD | CD28 | CD8 | FcγRI-γ |
| GBD | CD28 | CD8 | FcγRIII-γ |
| GBD | CD28 | CD8 | FcεRIβ |
| GBD | CD28 | CD8 | FcεRIγ |
| GBD | CD28 | CD8 | DAP10 |
| GBD | CD28 | CD8 | DAP12 |
| GBD | CD28 | CD8 | CD32 |
| GBD | CD28 | CD8 | CD79a |
| GBD | CD28 | CD8 | CD79b |
| GBD | CD28 | CD4 | CD8 |
| GBD | CD28 | CD4 | CD3ζ |
| GBD | CD28 | CD4 | CD3δ |
| GBD | CD28 | CD4 | CD3γ |
| GBD | CD28 | CD4 | CD3ε |
| GBD | CD28 | CD4 | FcγRI-γ |
| GBD | CD28 | CD4 | FcγRIII-γ |
| GBD | CD28 | CD4 | FcεRIβ |
| GBD | CD28 | CD4 | FcεRIγ |
| GBD | CD28 | CD4 | DAP10 |
| GBD | CD28 | CD4 | DAP12 |
| GBD | CD28 | CD4 | CD32 |
| GBD | CD28 | CD4 | CD79a |
| GBD | CD28 | CD4 | CD79b |
| GBD | CD28 | b2c | CD8 |

TABLE 3-continued

Third Generation CARs

| | Co-stimulatory Signal | Co-stimulatory Signal | Signal Domain |
|---|---|---|---|
| GBD | CD28 | b2c | CD3ζ |
| GBD | CD28 | b2c | CD3δ |
| GBD | CD28 | b2c | CD3γ |
| GBD | CD28 | b2c | CD3ε |
| GBD | CD28 | b2c | FcγRI-γ |
| GBD | CD28 | b2c | FcγRIII-γ |
| GBD | CD28 | b2c | FcεRIβ |
| GBD | CD28 | b2c | FcεRIγ |
| GBD | CD28 | b2c | DAP10 |
| GBD | CD28 | b2c | DAP12 |
| GBD | CD28 | b2c | CD32 |
| GBD | CD28 | b2c | CD79a |
| GBD | CD28 | b2c | CD79b |
| GBD | CD28 | CD137/41BB | CD8 |
| GBD | CD28 | CD137/41BB | CD3ζ |
| GBD | CD28 | CD137/41BB | CD3δ |
| GBD | CD28 | CD137/41BB | CD3γ |
| GBD | CD28 | CD137/41BB | CD3ε |
| GBD | CD28 | CD137/41BB | FcγRI-γ |
| GBD | CD28 | CD137/41BB | FcγRIII-γ |
| GBD | CD28 | CD137/41BB | FcεRIβ |
| GBD | CD28 | CD137/41BB | FcεRIγ |
| GBD | CD28 | CD137/41BB | DAP10 |
| GBD | CD28 | CD137/41BB | DAP12 |
| GBD | CD28 | CD137/41BB | CD32 |
| GBD | CD28 | CD137/41BB | CD79a |
| GBD | CD28 | CD137/41BB | CD79b |
| GBD | CD28 | ICOS | CD8 |
| GBD | CD28 | ICOS | CD3ζ |
| GBD | CD28 | ICOS | CD3δ |
| GBD | CD28 | ICOS | CD3γ |
| GBD | CD28 | ICOS | CD3ε |
| GBD | CD28 | ICOS | FcγRI-γ |
| GBD | CD28 | ICOS | FcγRIII-γ |
| GBD | CD28 | ICOS | FcεRIβ |
| GBD | CD28 | ICOS | FcεRIγ |
| GBD | CD28 | ICOS | DAP10 |
| GBD | CD28 | ICOS | DAP12 |
| GBD | CD28 | ICOS | CD32 |
| GBD | CD28 | ICOS | CD79a |
| GBD | CD28 | ICOS | CD79b |
| GBD | CD28 | CD27 | CD8 |
| GBD | CD28 | CD27 | CD3ζ |
| GBD | CD28 | CD27 | CD3δ |
| GBD | CD28 | CD27 | CD3γ |
| GBD | CD28 | CD27 | CD3ε |
| GBD | CD28 | CD27 | FcγRI-γ |
| GBD | CD28 | CD27 | FcγRIII-γ |
| GBD | CD28 | CD27 | FcεRIβ |
| GBD | CD28 | CD27 | FcεRIγ |
| GBD | CD28 | CD27 | DAP10 |
| GBD | CD28 | CD27 | DAP12 |
| GBD | CD28 | CD27 | CD32 |
| GBD | CD28 | CD27 | CD79a |
| GBD | CD28 | CD27 | CD79b |
| GBD | CD28 | CD28δ | CD8 |
| GBD | CD28 | CD28δ | CD3ζ |
| GBD | CD28 | CD28δ | CD3δ |
| GBD | CD28 | CD28δ | CD3γ |
| GBD | CD28 | CD28δ | CD3ε |
| GBD | CD28 | CD28δ | FcγRI-γ |
| GBD | CD28 | CD28δ | FcγRIII-γ |
| GBD | CD28 | CD28δ | FcεRIβ |
| GBD | CD28 | CD28δ | FcεRIγ |
| GBD | CD28 | CD28δ | DAP10 |
| GBD | CD28 | CD28δ | DAP12 |
| GBD | CD28 | CD28δ | CD32 |
| GBD | CD28 | CD28δ | CD79a |
| GBD | CD28 | CD28δ | CD79b |
| GBD | CD28 | CD80 | CD8 |
| GBD | CD28 | CD80 | CD3ζ |
| GBD | CD28 | CD80 | CD3δ |
| GBD | CD28 | CD80 | CD3γ |
| GBD | CD28 | CD80 | CD3ε |
| GBD | CD28 | CD80 | FcγRI-γ |

TABLE 3-continued

Third Generation CARs

| Co-stimulatory Signal | Co-stimulatory Signal | Signal Domain |
|---|---|---|
| GBD | CD28 | CD80 | FcγRIII-γ |
| GBD | CD28 | CD80 | FcεRIβ |
| GBD | CD28 | CD80 | FcεRIγ |
| GBD | CD28 | CD80 | DAP10 |
| GBD | CD28 | CD80 | DAP12 |
| GBD | CD28 | CD80 | CD32 |
| GBD | CD28 | CD80 | CD79a |
| GBD | CD28 | CD80 | CD79b |
| GBD | CD28 | CD86 | CD8 |
| GBD | CD28 | CD86 | CD3ζ |
| GBD | CD28 | CD86 | CD3δ |
| GBD | CD28 | CD86 | CD3γ |
| GBD | CD28 | CD86 | CD3ε |
| GBD | CD28 | CD86 | FcγRI-γ |
| GBD | CD28 | CD86 | FcγRIII-γ |
| GBD | CD28 | CD86 | FcεRIβ |
| GBD | CD28 | CD86 | FcεRIγ |
| GBD | CD28 | CD86 | DAP10 |
| GBD | CD28 | CD86 | DAP12 |
| GBD | CD28 | CD86 | CD32 |
| GBD | CD28 | CD86 | CD79a |
| GBD | CD28 | CD86 | CD79b |
| GBD | CD28 | OX40 | CD8 |
| GBD | CD28 | OX40 | CD3ζ |
| GBD | CD28 | OX40 | CD3δ |
| GBD | CD28 | OX40 | CD3γ |
| GBD | CD28 | OX40 | CD3ε |
| GBD | CD28 | OX40 | FcγRI-γ |
| GBD | CD28 | OX40 | FcγRIII-γ |
| GBD | CD28 | OX40 | FcεRIβ |
| GBD | CD28 | OX40 | FcεRIγ |
| GBD | CD28 | OX40 | DAP10 |
| GBD | CD28 | OX40 | DAP12 |
| GBD | CD28 | OX40 | CD32 |
| GBD | CD28 | OX40 | CD79a |
| GBD | CD28 | OX40 | CD79b |
| GBD | CD28 | DAP10 | CD8 |
| GBD | CD28 | DAP10 | CD3ζ |
| GBD | CD28 | DAP10 | CD3δ |
| GBD | CD28 | DAP10 | CD3γ |
| GBD | CD28 | DAP10 | CD3ε |
| GBD | CD28 | DAP10 | FcγRI-γ |
| GBD | CD28 | DAP10 | FcγRIII-γ |
| GBD | CD28 | DAP10 | FcεRIβ |
| GBD | CD28 | DAP10 | FcεRIγ |
| GBD | CD28 | DAP10 | DAP10 |
| GBD | CD28 | DAP10 | DAP12 |
| GBD | CD28 | DAP10 | CD32 |
| GBD | CD28 | DAP10 | CD79a |
| GBD | CD28 | DAP10 | CD79b |
| GBD | CD28 | DAP12 | CD8 |
| GBD | CD28 | DAP12 | CD3ζ |
| GBD | CD28 | DAP12 | CD3δ |
| GBD | CD28 | DAP12 | CD3γ |
| GBD | CD28 | DAP12 | CD3ε |
| GBD | CD28 | DAP12 | FcγRI-γ |
| GBD | CD28 | DAP12 | FcγRIII-γ |
| GBD | CD28 | DAP12 | FcεRIβ |
| GBD | CD28 | DAP12 | FcεRIγ |
| GBD | CD28 | DAP12 | DAP10 |
| GBD | CD28 | DAP12 | DAP12 |
| GBD | CD28 | DAP12 | CD32 |
| GBD | CD28 | DAP12 | CD79a |
| GBD | CD28 | DAP12 | CD79b |
| GBD | CD28 | MyD88 | CD8 |
| GBD | CD28 | MyD88 | CD3ζ |
| GBD | CD28 | MyD88 | CD3δ |
| GBD | CD28 | MyD88 | CD3γ |
| GBD | CD28 | MyD88 | CD3ε |
| GBD | CD28 | MyD88 | FcγRI-γ |
| GBD | CD28 | MyD88 | FcγRIII-γ |
| GBD | CD28 | MyD88 | FcεRIβ |
| GBD | CD28 | MyD88 | FcεRIγ |
| GBD | CD28 | MyD88 | DAP10 |
| GBD | CD28 | MyD88 | DAP12 |
| GBD | CD28 | MyD88 | CD32 |
| GBD | CD28 | MyD88 | CD79a |
| GBD | CD28 | MyD88 | CD79b |
| GBD | CD28 | CD7 | CD8 |
| GBD | CD28 | CD7 | CD3ζ |
| GBD | CD28 | CD7 | CD3δ |
| GBD | CD28 | CD7 | CD3γ |
| GBD | CD28 | CD7 | CD3ε |
| GBD | CD28 | CD7 | FcγRI-γ |
| GBD | CD28 | CD7 | FcγRIII-γ |
| GBD | CD28 | CD7 | FcεRIβ |
| GBD | CD28 | CD7 | FcεRIγ |
| GBD | CD28 | CD7 | DAP10 |
| GBD | CD28 | CD7 | DAP12 |
| GBD | CD28 | CD7 | CD32 |
| GBD | CD28 | CD7 | CD79a |
| GBD | CD28 | CD7 | CD79b |
| GBD | CD28 | BTNL3 | CD8 |
| GBD | CD28 | BTNL3 | CD3ζ |
| GBD | CD28 | BTNL3 | CD3δ |
| GBD | CD28 | BTNL3 | CD3γ |
| GBD | CD28 | BTNL3 | CD3ε |
| GBD | CD28 | BTNL3 | FcγRI-γ |
| GBD | CD28 | BTNL3 | FcγRIII-γ |
| GBD | CD28 | BTNL3 | FcεRIβ |
| GBD | CD28 | BTNL3 | FcεRIγ |
| GBD | CD28 | BTNL3 | DAP10 |
| GBD | CD28 | BTNL3 | DAP12 |
| GBD | CD28 | BTNL3 | CD32 |
| GBD | CD28 | BTNL3 | CD79a |
| GBD | CD28 | BTNL3 | CD79b |
| GBD | CD28 | NKG2D | CD8 |
| GBD | CD28 | NKG2D | CD3ζ |
| GBD | CD28 | NKG2D | CD3δ |
| GBD | CD28 | NKG2D | CD3γ |
| GBD | CD28 | NKG2D | CD3ε |
| GBD | CD28 | NKG2D | FcγRI-γ |
| GBD | CD28 | NKG2D | FcγRIII-γ |
| GBD | CD28 | NKG2D | FcεRIβ |
| GBD | CD28 | NKG2D | FcεRIγ |
| GBD | CD28 | NKG2D | DAP10 |
| GBD | CD28 | NKG2D | DAP12 |
| GBD | CD28 | NKG2D | CD32 |
| GBD | CD28 | NKG2D | CD79a |
| GBD | CD28 | NKG2D | CD79b |
| GBD | CD8 | CD28 | CD8 |
| GBD | CD8 | CD28 | CD3ζ |
| GBD | CD8 | CD28 | CD3δ |
| GBD | CD8 | CD28 | CD3γ |
| GBD | CD8 | CD28 | CD3ε |
| GBD | CD8 | CD28 | FcγRI-γ |
| GBD | CD8 | CD28 | FcγRIII-γ |
| GBD | CD8 | CD28 | FcεRIβ |
| GBD | CD8 | CD28 | FcεRIγ |
| GBD | CD8 | CD28 | DAP10 |
| GBD | CD8 | CD28 | DAP12 |
| GBD | CD8 | CD28 | CD32 |
| GBD | CD8 | CD28 | CD79a |
| GBD | CD8 | CD28 | CD79b |
| GBD | CD8 | CD8 | CD8 |
| GBD | CD8 | CD8 | CD3ζ |
| GBD | CD8 | CD8 | CD3δ |
| GBD | CD8 | CD8 | CD3γ |
| GBD | CD8 | CD8 | CD3ε |
| GBD | CD8 | CD8 | FcγRI-γ |
| GBD | CD8 | CD8 | FcγRIII-γ |
| GBD | CD8 | CD8 | FcεRIβ |
| GBD | CD8 | CD8 | FcεRIγ |
| GBD | CD8 | CD8 | DAP10 |
| GBD | CD8 | CD8 | DAP12 |
| GBD | CD8 | CD8 | CD32 |
| GBD | CD8 | CD8 | CD79a |
| GBD | CD8 | CD8 | CD79b |
| GBD | CD8 | CD4 | CD8 |
| GBD | CD8 | CD4 | CD3ζ |

TABLE 3-continued

Third Generation CARs

| | Co-stimulatory Signal | Co-stimulatory Signal | Signal Domain |
|---|---|---|---|
| GBD | CD8 | CD4 | CD3δ |
| GBD | CD8 | CD4 | CD3γ |
| GBD | CD8 | CD4 | CD3ε |
| GBD | CD8 | CD4 | FcγRI-γ |
| GBD | CD8 | CD4 | FcγRIII-γ |
| GBD | CD8 | CD4 | FcεRIβ |
| GBD | CD8 | CD4 | FcεRIγ |
| GBD | CD8 | CD4 | DAP10 |
| GBD | CD8 | CD4 | DAP12 |
| GBD | CD8 | CD4 | CD32 |
| GBD | CD8 | CD4 | CD79a |
| GBD | CD8 | CD4 | CD79b |
| GBD | CD8 | b2c | CD8 |
| GBD | CD8 | b2c | CD3ζ |
| GBD | CD8 | b2c | CD3δ |
| GBD | CD8 | b2c | CD3γ |
| GBD | CD8 | b2c | CD3ε |
| GBD | CD8 | b2c | FcγRI-γ |
| GBD | CD8 | b2c | FcγRIII-γ |
| GBD | CD8 | b2c | FcεRIβ |
| GBD | CD8 | b2c | FcεRIγ |
| GBD | CD8 | b2c | DAP10 |
| GBD | CD8 | b2c | DAP12 |
| GBD | CD8 | b2c | CD32 |
| GBD | CD8 | b2c | CD79a |
| GBD | CD8 | b2c | CD79b |
| GBD | CD8 | CD137/41BB | CD8 |
| GBD | CD8 | CD137/41BB | CD3ζ |
| GBD | CD8 | CD137/41BB | CD3δ |
| GBD | CD8 | CD137/41BB | CD3γ |
| GBD | CD8 | CD137/41BB | CD3ε |
| GBD | CD8 | CD137/41BB | FcγRI-γ |
| GBD | CD8 | CD137/41BB | FcγRIII-γ |
| GBD | CD8 | CD137/41BB | FcεRIβ |
| GBD | CD8 | CD137/41BB | FcεRIγ |
| GBD | CD8 | CD137/41BB | DAP10 |
| GBD | CD8 | CD137/41BB | DAP12 |
| GBD | CD8 | CD137/41BB | CD32 |
| GBD | CD8 | CD137/41BB | CD79a |
| GBD | CD8 | CD137/41BB | CD79b |
| GBD | CD8 | ICOS | CD8 |
| GBD | CD8 | ICOS | CD3ζ |
| GBD | CD8 | ICOS | CD3δ |
| GBD | CD8 | ICOS | CD3γ |
| GBD | CD8 | ICOS | CD3ε |
| GBD | CD8 | ICOS | FcγRI-γ |
| GBD | CD8 | ICOS | FcγRIII-γ |
| GBD | CD8 | ICOS | FcεRIβ |
| GBD | CD8 | ICOS | FcεRIγ |
| GBD | CD8 | ICOS | DAP10 |
| GBD | CD8 | ICOS | DAP12 |
| GBD | CD8 | ICOS | CD32 |
| GBD | CD8 | ICOS | CD79a |
| GBD | CD8 | ICOS | CD79b |
| GBD | CD8 | CD27 | CD8 |
| GBD | CD8 | CD27 | CD3ζ |
| GBD | CD8 | CD27 | CD3δ |
| GBD | CD8 | CD27 | CD3γ |
| GBD | CD8 | CD27 | CD3ε |
| GBD | CD8 | CD27 | FcγRI-γ |
| GBD | CD8 | CD27 | FcγRIII-γ |
| GBD | CD8 | CD27 | FcεRIβ |
| GBD | CD8 | CD27 | FcεRIγ |
| GBD | CD8 | CD27 | DAP10 |
| GBD | CD8 | CD27 | DAP12 |
| GBD | CD8 | CD27 | CD32 |
| GBD | CD8 | CD27 | CD79a |
| GBD | CD8 | CD27 | CD79b |
| GBD | CD8 | CD28δ | CD8 |
| GBD | CD8 | CD28δ | CD3ζ |
| GBD | CD8 | CD28δ | CD3δ |
| GBD | CD8 | CD28δ | CD3γ |
| GBD | CD8 | CD28δ | CD3ε |
| GBD | CD8 | CD28δ | FcγRI-γ |
| GBD | CD8 | CD28δ | FcγRIII-γ |
| GBD | CD8 | CD28δ | FcεRIβ |
| GBD | CD8 | CD28δ | FcεRIγ |
| GBD | CD8 | CD28δ | DAP10 |
| GBD | CD8 | CD28δ | DAP12 |
| GBD | CD8 | CD28δ | CD32 |
| GBD | CD8 | CD28δ | CD79a |
| GBD | CD8 | CD28δ | CD79b |
| GBD | CD8 | CD80 | CD8 |
| GBD | CD8 | CD80 | CD3ζ |
| GBD | CD8 | CD80 | CD3δ |
| GBD | CD8 | CD80 | CD3γ |
| GBD | CD8 | CD80 | CD3ε |
| GBD | CD8 | CD80 | FcγRI-γ |
| GBD | CD8 | CD80 | FcγRIII-γ |
| GBD | CD8 | CD80 | FcεRIβ |
| GBD | CD8 | CD80 | FcεRIγ |
| GBD | CD8 | CD80 | DAP10 |
| GBD | CD8 | CD80 | DAP12 |
| GBD | CD8 | CD80 | CD32 |
| GBD | CD8 | CD80 | CD79a |
| GBD | CD8 | CD80 | CD79b |
| GBD | CD8 | CD86 | CD8 |
| GBD | CD8 | CD86 | CD3ζ |
| GBD | CD8 | CD86 | CD3δ |
| GBD | CD8 | CD86 | CD3γ |
| GBD | CD8 | CD86 | CD3ε |
| GBD | CD8 | CD86 | FcγRI-γ |
| GBD | CD8 | CD86 | FcγRIII-γ |
| GBD | CD8 | CD86 | FcεRIβ |
| GBD | CD8 | CD86 | FcεRIγ |
| GBD | CD8 | CD86 | DAP10 |
| GBD | CD8 | CD86 | DAP12 |
| GBD | CD8 | CD86 | CD32 |
| GBD | CD8 | CD86 | CD79a |
| GBD | CD8 | CD86 | CD79b |
| GBD | CD8 | OX40 | CD8 |
| GBD | CD8 | OX40 | CD3ζ |
| GBD | CD8 | OX40 | CD3δ |
| GBD | CD8 | OX40 | CD3γ |
| GBD | CD8 | OX40 | CD3ε |
| GBD | CD8 | OX40 | FcγRI-γ |
| GBD | CD8 | OX40 | FcγRIII-γ |
| GBD | CD8 | OX40 | FcεRIβ |
| GBD | CD8 | OX40 | FcεRIγ |
| GBD | CD8 | OX40 | DAP10 |
| GBD | CD8 | OX40 | DAP12 |
| GBD | CD8 | OX40 | CD32 |
| GBD | CD8 | OX40 | CD79a |
| GBD | CD8 | OX40 | CD79b |
| GBD | CD8 | DAP10 | CD8 |
| GBD | CD8 | DAP10 | CD3ζ |
| GBD | CD8 | DAP10 | CD3δ |
| GBD | CD8 | DAP10 | CD3γ |
| GBD | CD8 | DAP10 | CD3ε |
| GBD | CD8 | DAP10 | FcγRI-γ |
| GBD | CD8 | DAP10 | FcγRIII-γ |
| GBD | CD8 | DAP10 | FcεRIβ |
| GBD | CD8 | DAP10 | FcεRIγ |
| GBD | CD8 | DAP10 | DAP10 |
| GBD | CD8 | DAP10 | DAP12 |
| GBD | CD8 | DAP10 | CD32 |
| GBD | CD8 | DAP10 | CD79a |
| GBD | CD8 | DAP10 | CD79b |
| GBD | CD8 | DAP12 | CD8 |
| GBD | CD8 | DAP12 | CD3ζ |
| GBD | CD8 | DAP12 | CD3δ |
| GBD | CD8 | DAP12 | CD3γ |
| GBD | CD8 | DAP12 | CD3ε |
| GBD | CD8 | DAP12 | FcγRI-γ |
| GBD | CD8 | DAP12 | FcγRIII-γ |
| GBD | CD8 | DAP12 | FcεRIβ |
| GBD | CD8 | DAP12 | FcεRIγ |
| GBD | CD8 | DAP12 | DAP10 |
| GBD | CD8 | DAP12 | DAP12 |
| GBD | CD8 | DAP12 | CD32 |

TABLE 3-continued

Third Generation CARs

| Co-stimulatory Signal | Co-stimulatory Signal | Signal Domain |
|---|---|---|
| GBD | CD8 | DAP12 | CD79a |
| GBD | CD8 | DAP12 | CD79b |
| GBD | CD8 | MyD88 | CD8 |
| GBD | CD8 | MyD88 | CD3ζ |
| GBD | CD8 | MyD88 | CD3δ |
| GBD | CD8 | MyD88 | CD3γ |
| GBD | CD8 | MyD88 | CD3ε |
| GBD | CD8 | MyD88 | FcγRI-γ |
| GBD | CD8 | MyD88 | FcγRIII-γ |
| GBD | CD8 | MyD88 | FcεRIβ |
| GBD | CD8 | MyD88 | FcεRIγ |
| GBD | CD8 | MyD88 | DAP10 |
| GBD | CD8 | MyD88 | DAP12 |
| GBD | CD8 | MyD88 | CD32 |
| GBD | CD8 | MyD88 | CD79a |
| GBD | CD8 | MyD88 | CD79b |
| GBD | CD8 | CD7 | CD8 |
| GBD | CD8 | CD7 | CD3ζ |
| GBD | CD8 | CD7 | CD3δ |
| GBD | CD8 | CD7 | CD3γ |
| GBD | CD8 | CD7 | CD3ε |
| GBD | CD8 | CD7 | FcγRI-γ |
| GBD | CD8 | CD7 | FcγRIII-γ |
| GBD | CD8 | CD7 | FcεRIβ |
| GBD | CD8 | CD7 | FcεRIγ |
| GBD | CD8 | CD7 | DAP10 |
| GBD | CD8 | CD7 | DAP12 |
| GBD | CD8 | CD7 | CD32 |
| GBD | CD8 | CD7 | CD79a |
| GBD | CD8 | CD7 | CD79b |
| GBD | CD8 | BTNL3 | CD8 |
| GBD | CD8 | BTNL3 | CD3ζ |
| GBD | CD8 | BTNL3 | CD3δ |
| GBD | CD8 | BTNL3 | CD3γ |
| GBD | CD8 | BTNL3 | CD3ε |
| GBD | CD8 | BTNL3 | FcγRI-γ |
| GBD | CD8 | BTNL3 | FcγRIII-γ |
| GBD | CD8 | BTNL3 | FcεRIβ |
| GBD | CD8 | BTNL3 | FcεRIγ |
| GBD | CD8 | BTNL3 | DAP10 |
| GBD | CD8 | BTNL3 | DAP12 |
| GBD | CD8 | BTNL3 | CD32 |
| GBD | CD8 | BTNL3 | CD79a |
| GBD | CD8 | BTNL3 | CD79b |
| GBD | CD8 | NKG2D | CD8 |
| GBD | CD8 | NKG2D | CD3ζ |
| GBD | CD8 | NKG2D | CD3δ |
| GBD | CD8 | NKG2D | CD3γ |
| GBD | CD8 | NKG2D | CD3ε |
| GBD | CD8 | NKG2D | FcγRI-γ |
| GBD | CD8 | NKG2D | FcγRIII-γ |
| GBD | CD8 | NKG2D | FcεRIβ |
| GBD | CD8 | NKG2D | FcεRIγ |
| GBD | CD8 | NKG2D | DAP10 |
| GBD | CD8 | NKG2D | DAP12 |
| GBD | CD8 | NKG2D | CD32 |
| GBD | CD8 | NKG2D | CD79a |
| GBD | CD8 | NKG2D | CD79b |
| GBD | CD4 | CD28 | CD8 |
| GBD | CD4 | CD28 | CD3ζ |
| GBD | CD4 | CD28 | CD3δ |
| GBD | CD4 | CD28 | CD3γ |
| GBD | CD4 | CD28 | CD3ε |
| GBD | CD4 | CD28 | FcγRI-γ |
| GBD | CD4 | CD28 | FcγRIII-γ |
| GBD | CD4 | CD28 | FcεRIβ |
| GBD | CD4 | CD28 | FcεRIγ |
| GBD | CD4 | CD28 | DAP10 |
| GBD | CD4 | CD28 | DAP12 |
| GBD | CD4 | CD28 | CD32 |
| GBD | CD4 | CD28 | CD79a |
| GBD | CD4 | CD28 | CD79b |
| GBD | CD4 | CD8 | CD8 |
| GBD | CD4 | CD8 | CD3ζ |
| GBD | CD4 | CD8 | CD3δ |
| GBD | CD4 | CD8 | CD3γ |
| GBD | CD4 | CD8 | CD3ε |
| GBD | CD4 | CD8 | FcγRI-γ |
| GBD | CD4 | CD8 | FcγRIII-γ |
| GBD | CD4 | CD8 | FcεRIβ |
| GBD | CD4 | CD8 | FcεRIγ |
| GBD | CD4 | CD8 | DAP10 |
| GBD | CD4 | CD8 | DAP12 |
| GBD | CD4 | CD8 | CD32 |
| GBD | CD4 | CD8 | CD79a |
| GBD | CD4 | CD8 | CD79b |
| GBD | CD4 | CD4 | CD8 |
| GBD | CD4 | CD4 | CD3ζ |
| GBD | CD4 | CD4 | CD3δ |
| GBD | CD4 | CD4 | CD3γ |
| GBD | CD4 | CD4 | CD3ε |
| GBD | CD4 | CD4 | FcγRI-γ |
| GBD | CD4 | CD4 | FcγRIII-γ |
| GBD | CD4 | CD4 | FcεRIβ |
| GBD | CD4 | CD4 | FcεRIγ |
| GBD | CD4 | CD4 | DAP10 |
| GBD | CD4 | CD4 | DAP12 |
| GBD | CD4 | CD4 | CD32 |
| GBD | CD4 | CD4 | CD79a |
| GBD | CD4 | CD4 | CD79b |
| GBD | CD4 | b2c | CD8 |
| GBD | CD4 | b2c | CD3ζ |
| GBD | CD4 | b2c | CD3δ |
| GBD | CD4 | b2c | CD3γ |
| GBD | CD4 | b2c | CD3ε |
| GBD | CD4 | b2c | FcγRI-γ |
| GBD | CD4 | b2c | FcγRIII-γ |
| GBD | CD4 | b2c | FcεRIβ |
| GBD | CD4 | b2c | FcεRIγ |
| GBD | CD4 | b2c | DAP10 |
| GBD | CD4 | b2c | DAP12 |
| GBD | CD4 | b2c | CD32 |
| GBD | CD4 | b2c | CD79a |
| GBD | CD4 | b2c | CD79b |
| GBD | CD4 | CD137/41BB | CD8 |
| GBD | CD4 | CD137/41BB | CD3ζ |
| GBD | CD4 | CD137/41BB | CD3δ |
| GBD | CD4 | CD137/41BB | CD3γ |
| GBD | CD4 | CD137/41BB | CD3ε |
| GBD | CD4 | CD137/41BB | FcγRI-γ |
| GBD | CD4 | CD137/41BB | FcγRIII-γ |
| GBD | CD4 | CD137/41BB | FcεRIβ |
| GBD | CD4 | CD137/41BB | FcεRIγ |
| GBD | CD4 | CD137/41BB | DAP10 |
| GBD | CD4 | CD137/41BB | DAP12 |
| GBD | CD4 | CD137/41BB | CD32 |
| GBD | CD4 | CD137/41BB | CD79a |
| GBD | CD4 | CD137/41BB | CD79b |
| GBD | CD4 | ICOS | CD8 |
| GBD | CD4 | ICOS | CD3ζ |
| GBD | CD4 | ICOS | CD3δ |
| GBD | CD4 | ICOS | CD3γ |
| GBD | CD4 | ICOS | CD3ε |
| GBD | CD4 | ICOS | FcγRI-γ |
| GBD | CD4 | ICOS | FcγRIII-γ |
| GBD | CD4 | ICOS | FcεRIβ |
| GBD | CD4 | ICOS | FcεRIγ |
| GBD | CD4 | ICOS | DAP10 |
| GBD | CD4 | ICOS | DAP12 |
| GBD | CD4 | ICOS | CD32 |
| GBD | CD4 | ICOS | CD79a |
| GBD | CD4 | ICOS | CD79b |
| GBD | CD4 | CD27 | CD8 |
| GBD | CD4 | CD27 | CD3ζ |
| GBD | CD4 | CD27 | CD3δ |
| GBD | CD4 | CD27 | CD3γ |
| GBD | CD4 | CD27 | CD3ε |
| GBD | CD4 | CD27 | FcγRI-γ |
| GBD | CD4 | CD27 | FcγRIII-γ |
| GBD | CD4 | CD27 | FcεRIβ |

TABLE 3-continued

Third Generation CARs

| | Co-stimulatory Signal | Co-stimulatory Signal | Signal Domain |
|---|---|---|---|
| GBD | CD4 | CD27 | FcεRIγ |
| GBD | CD4 | CD27 | DAP10 |
| GBD | CD4 | CD27 | DAP12 |
| GBD | CD4 | CD27 | CD32 |
| GBD | CD4 | CD27 | CD79a |
| GBD | CD4 | CD27 | CD79b |
| GBD | CD4 | CD28δ | CD8 |
| GBD | CD4 | CD28δ | CD3ζ |
| GBD | CD4 | CD28δ | CD3δ |
| GBD | CD4 | CD28δ | CD3γ |
| GBD | CD4 | CD28δ | CD3ε |
| GBD | CD4 | CD28δ | FcγRI-γ |
| GBD | CD4 | CD28δ | FcγRIII-γ |
| GBD | CD4 | CD28δ | FcεRIβ |
| GBD | CD4 | CD28δ | FcεRIγ |
| GBD | CD4 | CD28δ | DAP10 |
| GBD | CD4 | CD28δ | DAP12 |
| GBD | CD4 | CD28δ | CD32 |
| GBD | CD4 | CD28δ | CD79a |
| GBD | CD4 | CD28δ | CD79b |
| GBD | CD4 | CD80 | CD8 |
| GBD | CD4 | CD80 | CD3ζ |
| GBD | CD4 | CD80 | CD3δ |
| GBD | CD4 | CD80 | CD3γ |
| GBD | CD4 | CD80 | CD3ε |
| GBD | CD4 | CD80 | FcγRI-γ |
| GBD | CD4 | CD80 | FcγRIII-γ |
| GBD | CD4 | CD80 | FcεRIβ |
| GBD | CD4 | CD80 | FcεRIγ |
| GBD | CD4 | CD80 | DAP10 |
| GBD | CD4 | CD80 | DAP12 |
| GBD | CD4 | CD80 | CD32 |
| GBD | CD4 | CD80 | CD79a |
| GBD | CD4 | CD80 | CD79b |
| GBD | CD4 | CD86 | CD8 |
| GBD | CD4 | CD86 | CD3ζ |
| GBD | CD4 | CD86 | CD3δ |
| GBD | CD4 | CD86 | CD3γ |
| GBD | CD4 | CD86 | CD3ε |
| GBD | CD4 | CD86 | FcγRI-γ |
| GBD | CD4 | CD86 | FcγRIII-γ |
| GBD | CD4 | CD86 | FcεRIβ |
| GBD | CD4 | CD86 | FcεRIγ |
| GBD | CD4 | CD86 | DAP10 |
| GBD | CD4 | CD86 | DAP12 |
| GBD | CD4 | CD86 | CD32 |
| GBD | CD4 | CD86 | CD79a |
| GBD | CD4 | CD86 | CD79b |
| GBD | CD4 | OX40 | CD8 |
| GBD | CD4 | OX40 | CD3ζ |
| GBD | CD4 | OX40 | CD3δ |
| GBD | CD4 | OX40 | CD3γ |
| GBD | CD4 | OX40 | CD3ε |
| GBD | CD4 | OX40 | FcγRI-γ |
| GBD | CD4 | OX40 | FcγRIII-γ |
| GBD | CD4 | OX40 | FcεRIβ |
| GBD | CD4 | OX40 | FcεRIγ |
| GBD | CD4 | OX40 | DAP10 |
| GBD | CD4 | OX40 | DAP12 |
| GBD | CD4 | OX40 | CD32 |
| GBD | CD4 | OX40 | CD79a |
| GBD | CD4 | OX40 | CD79b |
| GBD | CD4 | DAP10 | CD8 |
| GBD | CD4 | DAP10 | CD3ζ |
| GBD | CD4 | DAP10 | CD3δ |
| GBD | CD4 | DAP10 | CD3γ |
| GBD | CD4 | DAP10 | CD3ε |
| GBD | CD4 | DAP10 | FcγRI-γ |
| GBD | CD4 | DAP10 | FcγRIII-γ |
| GBD | CD4 | DAP10 | FcεRIβ |
| GBD | CD4 | DAP10 | FcεRIγ |
| GBD | CD4 | DAP10 | DAP10 |
| GBD | CD4 | DAP10 | DAP12 |
| GBD | CD4 | DAP10 | CD32 |
| GBD | CD4 | DAP10 | CD79a |
| GBD | CD4 | DAP10 | CD79b |
| GBD | CD4 | DAP12 | CD8 |
| GBD | CD4 | DAP12 | CD3ζ |
| GBD | CD4 | DAP12 | CD3δ |
| GBD | CD4 | DAP12 | CD3γ |
| GBD | CD4 | DAP12 | CD3ε |
| GBD | CD4 | DAP12 | FcγRI-γ |
| GBD | CD4 | DAP12 | FcγRIII-γ |
| GBD | CD4 | DAP12 | FcεRIβ |
| GBD | CD4 | DAP12 | FcεRIγ |
| GBD | CD4 | DAP12 | DAP10 |
| GBD | CD4 | DAP12 | DAP12 |
| GBD | CD4 | DAP12 | CD32 |
| GBD | CD4 | DAP12 | CD79a |
| GBD | CD4 | DAP12 | CD79b |
| GBD | CD4 | MyD88 | CD8 |
| GBD | CD4 | MyD88 | CD3ζ |
| GBD | CD4 | MyD88 | CD3δ |
| GBD | CD4 | MyD88 | CD3γ |
| GBD | CD4 | MyD88 | CD3ε |
| GBD | CD4 | MyD88 | FcγRI-γ |
| GBD | CD4 | MyD88 | FcγRIII-γ |
| GBD | CD4 | MyD88 | FcεRIβ |
| GBD | CD4 | MyD88 | FcεRIγ |
| GBD | CD4 | MyD88 | DAP10 |
| GBD | CD4 | MyD88 | DAP12 |
| GBD | CD4 | MyD88 | CD32 |
| GBD | CD4 | MyD88 | CD79a |
| GBD | CD4 | MyD88 | CD79b |
| GBD | CD4 | CD7 | CD8 |
| GBD | CD4 | CD7 | CD3ζ |
| GBD | CD4 | CD7 | CD3δ |
| GBD | CD4 | CD7 | CD3γ |
| GBD | CD4 | CD7 | CD3ε |
| GBD | CD4 | CD7 | FcγRI-γ |
| GBD | CD4 | CD7 | FcγRIII-γ |
| GBD | CD4 | CD7 | FcεRIβ |
| GBD | CD4 | CD7 | FcεRIγ |
| GBD | CD4 | CD7 | DAP10 |
| GBD | CD4 | CD7 | DAP12 |
| GBD | CD4 | CD7 | CD32 |
| GBD | CD4 | CD7 | CD79a |
| GBD | CD4 | CD7 | CD79b |
| GBD | CD4 | BTNL3 | CD8 |
| GBD | CD4 | BTNL3 | CD3ζ |
| GBD | CD4 | BTNL3 | CD3δ |
| GBD | CD4 | BTNL3 | CD3γ |
| GBD | CD4 | BTNL3 | CD3ε |
| GBD | CD4 | BTNL3 | FcγRI-γ |
| GBD | CD4 | BTNL3 | FcγRIII-γ |
| GBD | CD4 | BTNL3 | FcεRIβ |
| GBD | CD4 | BTNL3 | FcεRIγ |
| GBD | CD4 | BTNL3 | DAP10 |
| GBD | CD4 | BTNL3 | DAP12 |
| GBD | CD4 | BTNL3 | CD32 |
| GBD | CD4 | BTNL3 | CD79a |
| GBD | CD4 | BTNL3 | CD79b |
| GBD | CD4 | NKG2D | CD8 |
| GBD | CD4 | NKG2D | CD3ζ |
| GBD | CD4 | NKG2D | CD3δ |
| GBD | CD4 | NKG2D | CD3γ |
| GBD | CD4 | NKG2D | CD3ε |
| GBD | CD4 | NKG2D | FcγRI-γ |
| GBD | CD4 | NKG2D | FcγRIII-γ |
| GBD | CD4 | NKG2D | FcεRIβ |
| GBD | CD4 | NKG2D | FcεRIγ |
| GBD | CD4 | NKG2D | DAP10 |
| GBD | CD4 | NKG2D | DAP12 |
| GBD | CD4 | NKG2D | CD32 |
| GBD | CD4 | NKG2D | CD79a |
| GBD | CD4 | NKG2D | CD79b |
| GBD | b2c | CD28 | CD8 |
| GBD | b2c | CD28 | CD3ζ |
| GBD | b2c | CD28 | CD3δ |
| GBD | b2c | CD28 | CD3γ |

TABLE 3-continued

Third Generation CARs

| | Co-stimulatory Signal | Co-stimulatory Signal | Signal Domain |
|---|---|---|---|
| GBD | b2c | CD28 | CD3ε |
| GBD | b2c | CD28 | FcγRI-γ |
| GBD | b2c | CD28 | FcγRIII-γ |
| GBD | b2c | CD28 | FcεRIβ |
| GBD | b2c | CD28 | FcεRIγ |
| GBD | b2c | CD28 | DAP10 |
| GBD | b2c | CD28 | DAP12 |
| GBD | b2c | CD28 | CD32 |
| GBD | b2c | CD28 | CD79a |
| GBD | b2c | CD28 | CD79b |
| GBD | b2c | CD8 | CD8 |
| GBD | b2c | CD8 | CD3ζ |
| GBD | b2c | CD8 | CD3δ |
| GBD | b2c | CD8 | CD3γ |
| GBD | b2c | CD8 | CD3ε |
| GBD | b2c | CD8 | FcγRI-γ |
| GBD | b2c | CD8 | FcγRIII-γ |
| GBD | b2c | CD8 | FcεRIβ |
| GBD | b2c | CD8 | FcεRIγ |
| GBD | b2c | CD8 | DAP10 |
| GBD | b2c | CD8 | DAP12 |
| GBD | b2c | CD8 | CD32 |
| GBD | b2c | CD8 | CD79a |
| GBD | b2c | CD8 | CD79b |
| GBD | b2c | CD4 | CD8 |
| GBD | b2c | CD4 | CD3ζ |
| GBD | b2c | CD4 | CD3δ |
| GBD | b2c | CD4 | CD3γ |
| GBD | b2c | CD4 | CD3ε |
| GBD | b2c | CD4 | FcγRI-γ |
| GBD | b2c | CD4 | FcγRIII-γ |
| GBD | b2c | CD4 | FcεRIβ |
| GBD | b2c | CD4 | FcεRIγ |
| GBD | b2c | CD4 | DAP10 |
| GBD | b2c | CD4 | DAP12 |
| GBD | b2c | CD4 | CD32 |
| GBD | b2c | CD4 | CD79a |
| GBD | b2c | CD4 | CD79b |
| GBD | b2c | b2c | CD8 |
| GBD | b2c | b2c | CD3ζ |
| GBD | b2c | b2c | CD3δ |
| GBD | b2c | b2c | CD3γ |
| GBD | b2c | b2c | CD3ε |
| GBD | b2c | b2c | FcγRI-γ |
| GBD | b2c | b2c | FcγRIII-γ |
| GBD | b2c | b2c | FcεRIβ |
| GBD | b2c | b2c | FcεRIγ |
| GBD | b2c | b2c | DAP10 |
| GBD | b2c | b2c | DAP12 |
| GBD | b2c | b2c | CD32 |
| GBD | b2c | b2c | CD79a |
| GBD | b2c | b2c | CD79b |
| GBD | b2c | CD137/41BB | CD8 |
| GBD | b2c | CD137/41BB | CD3ζ |
| GBD | b2c | CD137/41BB | CD3δ |
| GBD | b2c | CD137/41BB | CD3γ |
| GBD | b2c | CD137/41BB | CD3ε |
| GBD | b2c | CD137/41BB | FcγRI-γ |
| GBD | b2c | CD137/41BB | FcγRIII-γ |
| GBD | b2c | CD137/41BB | FcεRIβ |
| GBD | b2c | CD137/41BB | FcεRIγ |
| GBD | b2c | CD137/41BB | DAP10 |
| GBD | b2c | CD137/41BB | DAP12 |
| GBD | b2c | CD137/41BB | CD32 |
| GBD | b2c | CD137/41BB | CD79a |
| GBD | b2c | CD137/41BB | CD79b |
| GBD | b2c | ICOS | CD8 |
| GBD | b2c | ICOS | CD3ζ |
| GBD | b2c | ICOS | CD3δ |
| GBD | b2c | ICOS | CD3γ |
| GBD | b2c | ICOS | CD3ε |
| GBD | b2c | ICOS | FcγRI-γ |
| GBD | b2c | ICOS | FcγRIII-γ |
| GBD | b2c | ICOS | FcεRIβ |
| GBD | b2c | ICOS | FcεRIγ |
| GBD | b2c | ICOS | DAP10 |
| GBD | b2c | ICOS | DAP12 |
| GBD | b2c | ICOS | CD32 |
| GBD | b2c | ICOS | CD79a |
| GBD | b2c | ICOS | CD79b |
| GBD | b2c | CD27 | CD8 |
| GBD | b2c | CD27 | CD3ζ |
| GBD | b2c | CD27 | CD3δ |
| GBD | b2c | CD27 | CD3γ |
| GBD | b2c | CD27 | CD3ε |
| GBD | b2c | CD27 | FcγRI-γ |
| GBD | b2c | CD27 | FcγRIII-γ |
| GBD | b2c | CD27 | FcεRIβ |
| GBD | b2c | CD27 | FcεRIγ |
| GBD | b2c | CD27 | DAP10 |
| GBD | b2c | CD27 | DAP12 |
| GBD | b2c | CD27 | CD32 |
| GBD | b2c | CD27 | CD79a |
| GBD | b2c | CD27 | CD79b |
| GBD | b2c | CD28δ | CD8 |
| GBD | b2c | CD28δ | CD3ζ |
| GBD | b2c | CD28δ | CD3δ |
| GBD | b2c | CD28δ | CD3γ |
| GBD | b2c | CD28δ | CD3ε |
| GBD | b2c | CD28δ | FcγRI-γ |
| GBD | b2c | CD28δ | FcγRIII-γ |
| GBD | b2c | CD28δ | FcεRIβ |
| GBD | b2c | CD28δ | FcεRIγ |
| GBD | b2c | CD28δ | DAP10 |
| GBD | b2c | CD28δ | DAP12 |
| GBD | b2c | CD28δ | CD32 |
| GBD | b2c | CD28δ | CD79a |
| GBD | b2c | CD28δ | CD79b |
| GBD | b2c | CD80 | CD8 |
| GBD | b2c | CD80 | CD3ζ |
| GBD | b2c | CD80 | CD3δ |
| GBD | b2c | CD80 | CD3γ |
| GBD | b2c | CD80 | CD3ε |
| GBD | b2c | CD80 | FcγRI-γ |
| GBD | b2c | CD80 | FcγRIII-γ |
| GBD | b2c | CD80 | FcεRIβ |
| GBD | b2c | CD80 | FcεRIγ |
| GBD | b2c | CD80 | DAP10 |
| GBD | b2c | CD80 | DAP12 |
| GBD | b2c | CD80 | CD32 |
| GBD | b2c | CD80 | CD79a |
| GBD | b2c | CD80 | CD79b |
| GBD | b2c | CD86 | CD8 |
| GBD | b2c | CD86 | CD3ζ |
| GBD | b2c | CD86 | CD3δ |
| GBD | b2c | CD86 | CD3γ |
| GBD | b2c | CD86 | CD3ε |
| GBD | b2c | CD86 | FcγRI-γ |
| GBD | b2c | CD86 | FcγRIII-γ |
| GBD | b2c | CD86 | FcεRIβ |
| GBD | b2c | CD86 | FcεRIγ |
| GBD | b2c | CD86 | DAP10 |
| GBD | b2c | CD86 | DAP12 |
| GBD | b2c | CD86 | CD32 |
| GBD | b2c | CD86 | CD79a |
| GBD | b2c | CD86 | CD79b |
| GBD | b2c | OX40 | CD8 |
| GBD | b2c | OX40 | CD3ζ |
| GBD | b2c | OX40 | CD3δ |
| GBD | b2c | OX40 | CD3γ |
| GBD | b2c | OX40 | CD3ε |
| GBD | b2c | OX40 | FcγRI-γ |
| GBD | b2c | OX40 | FcγRIII-γ |
| GBD | b2c | OX40 | FcεRIβ |
| GBD | b2c | OX40 | FcεRIγ |
| GBD | b2c | OX40 | DAP10 |
| GBD | b2c | OX40 | DAP12 |
| GBD | b2c | OX40 | CD32 |
| GBD | b2c | OX40 | CD79a |
| GBD | b2c | OX40 | CD79b |

TABLE 3-continued

Third Generation CARs

| Co-stimulatory Signal | Co-stimulatory Signal | Signal Domain |
|---|---|---|
| GBD | b2c | DAP10 | CD8 |
| GBD | b2c | DAP10 | CD3ζ |
| GBD | b2c | DAP10 | CD3δ |
| GBD | b2c | DAP10 | CD3γ |
| GBD | b2c | DAP10 | CD3ε |
| GBD | b2c | DAP10 | FcγRI-γ |
| GBD | b2c | DAP10 | FcγRIII-γ |
| GBD | b2c | DAP10 | FcεRIβ |
| GBD | b2c | DAP10 | FcεRIγ |
| GBD | b2c | DAP10 | DAP10 |
| GBD | b2c | DAP10 | DAP12 |
| GBD | b2c | DAP10 | CD32 |
| GBD | b2c | DAP10 | CD79a |
| GBD | b2c | DAP10 | CD79b |
| GBD | b2c | DAP12 | CD8 |
| GBD | b2c | DAP12 | CD3ζ |
| GBD | b2c | DAP12 | CD3δ |
| GBD | b2c | DAP12 | CD3γ |
| GBD | b2c | DAP12 | CD3ε |
| GBD | b2c | DAP12 | FcγRI-γ |
| GBD | b2c | DAP12 | FcγRIII-γ |
| GBD | b2c | DAP12 | FcεRIβ |
| GBD | b2c | DAP12 | FcεRIγ |
| GBD | b2c | DAP12 | DAP10 |
| GBD | b2c | DAP12 | DAP12 |
| GBD | b2c | DAP12 | CD32 |
| GBD | b2c | DAP12 | CD79a |
| GBD | b2c | DAP12 | CD79b |
| GBD | b2c | MyD88 | CD8 |
| GBD | b2c | MyD88 | CD3ζ |
| GBD | b2c | MyD88 | CD3δ |
| GBD | b2c | MyD88 | CD3γ |
| GBD | b2c | MyD88 | CD3ε |
| GBD | b2c | MyD88 | FcγRI-γ |
| GBD | b2c | MyD88 | FcγRIII-γ |
| GBD | b2c | MyD88 | FcεRIβ |
| GBD | b2c | MyD88 | FcεRIγ |
| GBD | b2c | MyD88 | DAP10 |
| GBD | b2c | MyD88 | DAP12 |
| GBD | b2c | MyD88 | CD32 |
| GBD | b2c | MyD88 | CD79a |
| GBD | b2c | MyD88 | CD79b |
| GBD | b2c | CD7 | CD8 |
| GBD | b2c | CD7 | CD3ζ |
| GBD | b2c | CD7 | CD3δ |
| GBD | b2c | CD7 | CD3γ |
| GBD | b2c | CD7 | CD3ε |
| GBD | b2c | CD7 | FcγRI-γ |
| GBD | b2c | CD7 | FcγRIII-γ |
| GBD | b2c | CD7 | FcεRIβ |
| GBD | b2c | CD7 | FcεRIγ |
| GBD | b2c | CD7 | DAP10 |
| GBD | b2c | CD7 | DAP12 |
| GBD | b2c | CD7 | CD32 |
| GBD | b2c | CD7 | CD79a |
| GBD | b2c | CD7 | CD79b |
| GBD | b2c | BTNL3 | CD8 |
| GBD | b2c | BTNL3 | CD3ζ |
| GBD | b2c | BTNL3 | CD3δ |
| GBD | b2c | BTNL3 | CD3γ |
| GBD | b2c | BTNL3 | CD3ε |
| GBD | b2c | BTNL3 | FcγRI-γ |
| GBD | b2c | BTNL3 | FcγRIII-γ |
| GBD | b2c | BTNL3 | FcεRIβ |
| GBD | b2c | BTNL3 | FcεRIγ |
| GBD | b2c | BTNL3 | DAP10 |
| GBD | b2c | BTNL3 | DAP12 |
| GBD | b2c | BTNL3 | CD32 |
| GBD | b2c | BTNL3 | CD79a |
| GBD | b2c | BTNL3 | CD79b |
| GBD | b2c | NKG2D | CD8 |
| GBD | b2c | NKG2D | CD3ζ |
| GBD | b2c | NKG2D | CD3δ |
| GBD | b2c | NKG2D | CD3γ |
| GBD | b2c | NKG2D | CD3ε |
| GBD | b2c | NKG2D | FcγRI-γ |
| GBD | b2c | NKG2D | FcγRIII-γ |
| GBD | b2c | NKG2D | FcεRIβ |
| GBD | b2c | NKG2D | FcεRIγ |
| GBD | b2c | NKG2D | DAP10 |
| GBD | b2c | NKG2D | DAP12 |
| GBD | b2c | NKG2D | CD32 |
| GBD | b2c | NKG2D | CD79a |
| GBD | b2c | NKG2D | CD79b |
| GBD | CD137/41BB | CD28 | CD8 |
| GBD | CD137/41BB | CD28 | CD3ζ |
| GBD | CD137/41BB | CD28 | CD3δ |
| GBD | CD137/41BB | CD28 | CD3γ |
| GBD | CD137/41BB | CD28 | CD3ε |
| GBD | CD137/41BB | CD28 | FcγRI-γ |
| GBD | CD137/41BB | CD28 | FcγRIII-γ |
| GBD | CD137/41BB | CD28 | FcεRIβ |
| GBD | CD137/41BB | CD28 | FcεRIγ |
| GBD | CD137/41BB | CD28 | DAP10 |
| GBD | CD137/41BB | CD28 | DAP12 |
| GBD | CD137/41BB | CD28 | CD32 |
| GBD | CD137/41BB | CD28 | CD79a |
| GBD | CD137/41BB | CD28 | CD79b |
| GBD | CD137/41BB | CD8 | CD8 |
| GBD | CD137/41BB | CD8 | CD3ζ |
| GBD | CD137/41BB | CD8 | CD3δ |
| GBD | CD137/41BB | CD8 | CD3γ |
| GBD | CD137/41BB | CD8 | CD3ε |
| GBD | CD137/41BB | CD8 | FcγRI-γ |
| GBD | CD137/41BB | CD8 | FcγRIII-γ |
| GBD | CD137/41BB | CD8 | FcεRIβ |
| GBD | CD137/41BB | CD8 | FcεRIγ |
| GBD | CD137/41BB | CD8 | DAP10 |
| GBD | CD137/41BB | CD8 | DAP12 |
| GBD | CD137/41BB | CD8 | CD32 |
| GBD | CD137/41BB | CD8 | CD79a |
| GBD | CD137/41BB | CD8 | CD79b |
| GBD | CD137/41BB | CD4 | CD8 |
| GBD | CD137/41BB | CD4 | CD3ζ |
| GBD | CD137/41BB | CD4 | CD3δ |
| GBD | CD137/41BB | CD4 | CD3γ |
| GBD | CD137/41BB | CD4 | CD3ε |
| GBD | CD137/41BB | CD4 | FcγRI-γ |
| GBD | CD137/41BB | CD4 | FcγRIII-γ |
| GBD | CD137/41BB | CD4 | FcεRIβ |
| GBD | CD137/41BB | CD4 | FcεRIγ |
| GBD | CD137/41BB | CD4 | DAP10 |
| GBD | CD137/41BB | CD4 | DAP12 |
| GBD | CD137/41BB | CD4 | CD32 |
| GBD | CD137/41BB | CD4 | CD79a |
| GBD | CD137/41BB | CD4 | CD79b |
| GBD | CD137/41BB | b2c | CD8 |
| GBD | CD137/41BB | b2c | CD3ζ |
| GBD | CD137/41BB | b2c | CD3δ |
| GBD | CD137/41BB | b2c | CD3γ |
| GBD | CD137/41BB | b2c | CD3ε |
| GBD | CD137/41BB | b2c | FcγRI-γ |
| GBD | CD137/41BB | b2c | FcγRIII-γ |
| GBD | CD137/41BB | b2c | FcεRIβ |
| GBD | CD137/41BB | b2c | FcεRIγ |
| GBD | CD137/41BB | b2c | DAP10 |
| GBD | CD137/41BB | b2c | DAP12 |
| GBD | CD137/41BB | b2c | CD32 |
| GBD | CD137/41BB | b2c | CD79a |
| GBD | CD137/41BB | b2c | CD79b |
| GBD | CD137/41BB | CD137/41BB | CD8 |
| GBD | CD137/41BB | CD137/41BB | CD3ζ |
| GBD | CD137/41BB | CD137/41BB | CD3δ |
| GBD | CD137/41BB | CD137/41BB | CD3γ |
| GBD | CD137/41BB | CD137/41BB | CD3ε |
| GBD | CD137/41BB | CD137/41BB | FcγRI-γ |
| GBD | CD137/41BB | CD137/41BB | FcγRIII-γ |
| GBD | CD137/41BB | CD137/41BB | FcεRIβ |
| GBD | CD137/41BB | CD137/41BB | FcεRIγ |
| GBD | CD137/41BB | CD137/41BB | DAP10 |

TABLE 3-continued

Third Generation CARs

| Co-stimulatory Signal | Co-stimulatory Signal | Signal Domain |
|---|---|---|
| GBD | CD137/41BB | CD137/41BB | DAP12 |
| GBD | CD137/41BB | CD137/41BB | CD32 |
| GBD | CD137/41BB | CD137/41BB | CD79a |
| GBD | CD137/41BB | CD137/41BB | CD79b |
| GBD | CD137/41BB | ICOS | CD8 |
| GBD | CD137/41BB | ICOS | CD3ζ |
| GBD | CD137/41BB | ICOS | CD3δ |
| GBD | CD137/41BB | ICOS | CD3γ |
| GBD | CD137/41BB | ICOS | CD3ε |
| GBD | CD137/41BB | ICOS | FcγRI-γ |
| GBD | CD137/41BB | ICOS | FcγRIII-γ |
| GBD | CD137/41BB | ICOS | FcεRIβ |
| GBD | CD137/41BB | ICOS | FcεRIγ |
| GBD | CD137/41BB | ICOS | DAP10 |
| GBD | CD137/41BB | ICOS | DAP12 |
| GBD | CD137/41BB | ICOS | CD32 |
| GBD | CD137/41BB | ICOS | CD79a |
| GBD | CD137/41BB | ICOS | CD79b |
| GBD | CD137/41BB | CD27 | CD8 |
| GBD | CD137/41BB | CD27 | CD3ζ |
| GBD | CD137/41BB | CD27 | CD3δ |
| GBD | CD137/41BB | CD27 | CD3γ |
| GBD | CD137/41BB | CD27 | CD3ε |
| GBD | CD137/41BB | CD27 | FcγRI-γ |
| GBD | CD137/41BB | CD27 | FcγRIII-γ |
| GBD | CD137/41BB | CD27 | FcεRIβ |
| GBD | CD137/41BB | CD27 | FcεRIγ |
| GBD | CD137/41BB | CD27 | DAP10 |
| GBD | CD137/41BB | CD27 | DAP12 |
| GBD | CD137/41BB | CD27 | CD32 |
| GBD | CD137/41BB | CD27 | CD79a |
| GBD | CD137/41BB | CD27 | CD79b |
| GBD | CD137/41BB | CD28δ | CD8 |
| GBD | CD137/41BB | CD28δ | CD3ζ |
| GBD | CD137/41BB | CD28δ | CD3δ |
| GBD | CD137/41BB | CD28δ | CD3γ |
| GBD | CD137/41BB | CD28δ | CD3ε |
| GBD | CD137/41BB | CD28δ | FcγRI-γ |
| GBD | CD137/41BB | CD28δ | FcγRIII-γ |
| GBD | CD137/41BB | CD28δ | FcεRIβ |
| GBD | CD137/41BB | CD28δ | FcεRIγ |
| GBD | CD137/41BB | CD28δ | DAP10 |
| GBD | CD137/41BB | CD28δ | DAP12 |
| GBD | CD137/41BB | CD28δ | CD32 |
| GBD | CD137/41BB | CD28δ | CD79a |
| GBD | CD137/41BB | CD28δ | CD79b |
| GBD | CD137/41BB | CD80 | CD8 |
| GBD | CD137/41BB | CD80 | CD3ζ |
| GBD | CD137/41BB | CD80 | CD3δ |
| GBD | CD137/41BB | CD80 | CD3γ |
| GBD | CD137/41BB | CD80 | CD3ε |
| GBD | CD137/41BB | CD80 | FcγRI-γ |
| GBD | CD137/41BB | CD80 | FcγRIII-γ |
| GBD | CD137/41BB | CD80 | FcεRIβ |
| GBD | CD137/41BB | CD80 | FcεRIγ |
| GBD | CD137/41BB | CD80 | DAP10 |
| GBD | CD137/41BB | CD80 | DAP12 |
| GBD | CD137/41BB | CD80 | CD32 |
| GBD | CD137/41BB | CD80 | CD79a |
| GBD | CD137/41BB | CD80 | CD79b |
| GBD | CD137/41BB | CD86 | CD8 |
| GBD | CD137/41BB | CD86 | CD3ζ |
| GBD | CD137/41BB | CD86 | CD3δ |
| GBD | CD137/41BB | CD86 | CD3γ |
| GBD | CD137/41BB | CD86 | CD3ε |
| GBD | CD137/41BB | CD86 | FcγRI-γ |
| GBD | CD137/41BB | CD86 | FcγRIII-γ |
| GBD | CD137/41BB | CD86 | FcεRIβ |
| GBD | CD137/41BB | CD86 | FcεRIγ |
| GBD | CD137/41BB | CD86 | DAP10 |
| GBD | CD137/41BB | CD86 | DAP12 |
| GBD | CD137/41BB | CD86 | CD32 |
| GBD | CD137/41BB | CD86 | CD79a |
| GBD | CD137/41BB | CD86 | CD79b |
| GBD | CD137/41BB | OX40 | CD8 |
| GBD | CD137/41BB | OX40 | CD3ζ |
| GBD | CD137/41BB | OX40 | CD3δ |
| GBD | CD137/41BB | OX40 | CD3γ |
| GBD | CD137/41BB | OX40 | CD3ε |
| GBD | CD137/41BB | OX40 | FcγRI-γ |
| GBD | CD137/41BB | OX40 | FcγRIII-γ |
| GBD | CD137/41BB | OX40 | FcεRIβ |
| GBD | CD137/41BB | OX40 | FcεRIγ |
| GBD | CD137/41BB | OX40 | DAP10 |
| GBD | CD137/41BB | OX40 | DAP12 |
| GBD | CD137/41BB | OX40 | CD32 |
| GBD | CD137/41BB | OX40 | CD79a |
| GBD | CD137/41BB | OX40 | CD79b |
| GBD | CD137/41BB | DAP10 | CD8 |
| GBD | CD137/41BB | DAP10 | CD3ζ |
| GBD | CD137/41BB | DAP10 | CD3δ |
| GBD | CD137/41BB | DAP10 | CD3γ |
| GBD | CD137/41BB | DAP10 | CD3ε |
| GBD | CD137/41BB | DAP10 | FcγRI-γ |
| GBD | CD137/41BB | DAP10 | FcγRIII-γ |
| GBD | CD137/41BB | DAP10 | FcεRIβ |
| GBD | CD137/41BB | DAP10 | FcεRIγ |
| GBD | CD137/41BB | DAP10 | DAP10 |
| GBD | CD137/41BB | DAP10 | DAP12 |
| GBD | CD137/41BB | DAP10 | CD32 |
| GBD | CD137/41BB | DAP10 | CD79a |
| GBD | CD137/41BB | DAP10 | CD79b |
| GBD | CD137/41BB | DAP12 | CD8 |
| GBD | CD137/41BB | DAP12 | CD3ζ |
| GBD | CD137/41BB | DAP12 | CD3δ |
| GBD | CD137/41BB | DAP12 | CD3γ |
| GBD | CD137/41BB | DAP12 | CD3ε |
| GBD | CD137/41BB | DAP12 | FcγRI-γ |
| GBD | CD137/41BB | DAP12 | FcγRIII-γ |
| GBD | CD137/41BB | DAP12 | FcεRIβ |
| GBD | CD137/41BB | DAP12 | FcεRIγ |
| GBD | CD137/41BB | DAP12 | DAP10 |
| GBD | CD137/41BB | DAP12 | DAP12 |
| GBD | CD137/41BB | DAP12 | CD32 |
| GBD | CD137/41BB | DAP12 | CD79a |
| GBD | CD137/41BB | DAP12 | CD79b |
| GBD | CD137/41BB | MyD88 | CD8 |
| GBD | CD137/41BB | MyD88 | CD3ζ |
| GBD | CD137/41BB | MyD88 | CD3δ |
| GBD | CD137/41BB | MyD88 | CD3γ |
| GBD | CD137/41BB | MyD88 | CD3ε |
| GBD | CD137/41BB | MyD88 | FcγRI-γ |
| GBD | CD137/41BB | MyD88 | FcγRIII-γ |
| GBD | CD137/41BB | MyD88 | FcεRIβ |
| GBD | CD137/41BB | MyD88 | FcεRIγ |
| GBD | CD137/41BB | MyD88 | DAP10 |
| GBD | CD137/41BB | MyD88 | DAP12 |
| GBD | CD137/41BB | MyD88 | CD32 |
| GBD | CD137/41BB | MyD88 | CD79a |
| GBD | CD137/41BB | MyD88 | CD79b |
| GBD | CD137/41BB | CD7 | CD8 |
| GBD | CD137/41BB | CD7 | CD3ζ |
| GBD | CD137/41BB | CD7 | CD3δ |
| GBD | CD137/41BB | CD7 | CD3γ |
| GBD | CD137/41BB | CD7 | CD3ε |
| GBD | CD137/41BB | CD7 | FcγRI-γ |
| GBD | CD137/41BB | CD7 | FcγRIII-γ |
| GBD | CD137/41BB | CD7 | FcεRIβ |
| GBD | CD137/41BB | CD7 | FcεRIγ |
| GBD | CD137/41BB | CD7 | DAP10 |
| GBD | CD137/41BB | CD7 | DAP12 |
| GBD | CD137/41BB | CD7 | CD32 |
| GBD | CD137/41BB | CD7 | CD79a |
| GBD | CD137/41BB | CD7 | CD79b |
| GBD | CD137/41BB | BTNL3 | CD8 |
| GBD | CD137/41BB | BTNL3 | CD3ζ |
| GBD | CD137/41BB | BTNL3 | CD3δ |
| GBD | CD137/41BB | BTNL3 | CD3γ |
| GBD | CD137/41BB | BTNL3 | CD3ε |
| GBD | CD137/41BB | BTNL3 | FcγRI-γ |

TABLE 3-continued

| Third Generation CARs | | |
|---|---|---|
| Co-stimulatory Signal | Co-stimulatory Signal | Signal Domain |
| GBD | CD137/41BB | BTNL3 | FcγRIII-γ |
| GBD | CD137/41BB | BTNL3 | FcεRIβ |
| GBD | CD137/41BB | BTNL3 | FcεRIγ |
| GBD | CD137/41BB | BTNL3 | DAP10 |
| GBD | CD137/41BB | BTNL3 | DAP12 |
| GBD | CD137/41BB | BTNL3 | CD32 |
| GBD | CD137/41BB | BTNL3 | CD79a |
| GBD | CD137/41BB | BTNL3 | CD79b |
| GBD | CD137/41BB | NKG2D | CD8 |
| GBD | CD137/41BB | NKG2D | CD3ζ |
| GBD | CD137/41BB | NKG2D | CD3δ |
| GBD | CD137/41BB | NKG2D | CD3γ |
| GBD | CD137/41BB | NKG2D | CD3ε |
| GBD | CD137/41BB | NKG2D | FcγRI-γ |
| GBD | CD137/41BB | NKG2D | FcγRIII-γ |
| GBD | CD137/41BB | NKG2D | FcεRIβ |
| GBD | CD137/41BB | NKG2D | FcεRIγ |
| GBD | CD137/41BB | NKG2D | DAP10 |
| GBD | CD137/41BB | NKG2D | DAP12 |
| GBD | CD137/41BB | NKG2D | CD32 |
| GBD | CD137/41BB | NKG2D | CD79a |
| GBD | CD137/41BB | NKG2D | CD79b |
| GBD | ICOS | CD28 | CD8 |
| GBD | ICOS | CD28 | CD3ζ |
| GBD | ICOS | CD28 | CD3δ |
| GBD | ICOS | CD28 | CD3γ |
| GBD | ICOS | CD28 | CD3ε |
| GBD | ICOS | CD28 | FcγRI-γ |
| GBD | ICOS | CD28 | FcγRIII-γ |
| GBD | ICOS | CD28 | FcεRIβ |
| GBD | ICOS | CD28 | FcεRIγ |
| GBD | ICOS | CD28 | DAP10 |
| GBD | ICOS | CD28 | DAP12 |
| GBD | ICOS | CD28 | CD32 |
| GBD | ICOS | CD28 | CD79a |
| GBD | ICOS | CD28 | CD79b |
| GBD | ICOS | CD8 | CD8 |
| GBD | ICOS | CD8 | CD3ζ |
| GBD | ICOS | CD8 | CD3δ |
| GBD | ICOS | CD8 | CD3γ |
| GBD | ICOS | CD8 | CD3ε |
| GBD | ICOS | CD8 | FcγRI-γ |
| GBD | ICOS | CD8 | FcγRIII-γ |
| GBD | ICOS | CD8 | FcεRIβ |
| GBD | ICOS | CD8 | FcεRIγ |
| GBD | ICOS | CD8 | DAP10 |
| GBD | ICOS | CD8 | DAP12 |
| GBD | ICOS | CD8 | CD32 |
| GBD | ICOS | CD8 | CD79a |
| GBD | ICOS | CD8 | CD79b |
| GBD | ICOS | CD4 | CD8 |
| GBD | ICOS | CD4 | CD3ζ |
| GBD | ICOS | CD4 | CD3δ |
| GBD | ICOS | CD4 | CD3γ |
| GBD | ICOS | CD4 | CD3ε |
| GBD | ICOS | CD4 | FcγRI-γ |
| GBD | ICOS | CD4 | FcγRIII-γ |
| GBD | ICOS | CD4 | FcεRIβ |
| GBD | ICOS | CD4 | FcεRIγ |
| GBD | ICOS | CD4 | DAP10 |
| GBD | ICOS | CD4 | DAP12 |
| GBD | ICOS | CD4 | CD32 |
| GBD | ICOS | CD4 | CD79a |
| GBD | ICOS | CD4 | CD79b |
| GBD | ICOS | b2c | CD8 |
| GBD | ICOS | b2c | CD3ζ |
| GBD | ICOS | b2c | CD3δ |
| GBD | ICOS | b2c | CD3γ |
| GBD | ICOS | b2c | CD3ε |
| GBD | ICOS | b2c | FcγRI-γ |
| GBD | ICOS | b2c | FcγRIII-γ |
| GBD | ICOS | b2c | FcεRIβ |
| GBD | ICOS | b2c | FcεRIγ |
| GBD | ICOS | b2c | DAP10 |
| GBD | ICOS | b2c | DAP12 |
| GBD | ICOS | b2c | CD32 |
| GBD | ICOS | b2c | CD79a |
| GBD | ICOS | b2c | CD79b |
| GBD | ICOS | CD137/41BB | CD8 |
| GBD | ICOS | CD137/41BB | CD3ζ |
| GBD | ICOS | CD137/41BB | CD3δ |
| GBD | ICOS | CD137/41BB | CD3γ |
| GBD | ICOS | CD137/41BB | CD3ε |
| GBD | ICOS | CD137/41BB | FcγRI-γ |
| GBD | ICOS | CD137/41BB | FcγRIII-γ |
| GBD | ICOS | CD137/41BB | FcεRIβ |
| GBD | ICOS | CD137/41BB | FcεRIγ |
| GBD | ICOS | CD137/41BB | DAP10 |
| GBD | ICOS | CD137/41BB | DAP12 |
| GBD | ICOS | CD137/41BB | CD32 |
| GBD | ICOS | CD137/41BB | CD79a |
| GBD | ICOS | CD137/41BB | CD79b |
| GBD | ICOS | ICOS | CD8 |
| GBD | ICOS | ICOS | CD3ζ |
| GBD | ICOS | ICOS | CD3δ |
| GBD | ICOS | ICOS | CD3γ |
| GBD | ICOS | ICOS | CD3ε |
| GBD | ICOS | ICOS | FcγRI-γ |
| GBD | ICOS | ICOS | FcγRIII-γ |
| GBD | ICOS | ICOS | FcεRIβ |
| GBD | ICOS | ICOS | FcεRIγ |
| GBD | ICOS | ICOS | DAP10 |
| GBD | ICOS | ICOS | DAP12 |
| GBD | ICOS | ICOS | CD32 |
| GBD | ICOS | ICOS | CD79a |
| GBD | ICOS | ICOS | CD79b |
| GBD | ICOS | CD27 | CD8 |
| GBD | ICOS | CD27 | CD3ζ |
| GBD | ICOS | CD27 | CD3δ |
| GBD | ICOS | CD27 | CD3γ |
| GBD | ICOS | CD27 | CD3ε |
| GBD | ICOS | CD27 | FcγRI-γ |
| GBD | ICOS | CD27 | FcγRIII-γ |
| GBD | ICOS | CD27 | FcεRIβ |
| GBD | ICOS | CD27 | FcεRIγ |
| GBD | ICOS | CD27 | DAP10 |
| GBD | ICOS | CD27 | DAP12 |
| GBD | ICOS | CD27 | CD32 |
| GBD | ICOS | CD27 | CD79a |
| GBD | ICOS | CD27 | CD79b |
| GBD | ICOS | CD28δ | CD8 |
| GBD | ICOS | CD28δ | CD3ζ |
| GBD | ICOS | CD28δ | CD3δ |
| GBD | ICOS | CD28δ | CD3γ |
| GBD | ICOS | CD28δ | CD3ε |
| GBD | ICOS | CD28δ | FcγRI-γ |
| GBD | ICOS | CD28δ | FcγRIII-γ |
| GBD | ICOS | CD28δ | FcεRIβ |
| GBD | ICOS | CD28δ | FcεRIγ |
| GBD | ICOS | CD28δ | DAP10 |
| GBD | ICOS | CD28δ | DAP12 |
| GBD | ICOS | CD28δ | CD32 |
| GBD | ICOS | CD28δ | CD79a |
| GBD | ICOS | CD28δ | CD79b |
| GBD | ICOS | CD80 | CD8 |
| GBD | ICOS | CD80 | CD3ζ |
| GBD | ICOS | CD80 | CD3δ |
| GBD | ICOS | CD80 | CD3γ |
| GBD | ICOS | CD80 | CD3ε |
| GBD | ICOS | CD80 | FcγRI-γ |
| GBD | ICOS | CD80 | FcγRIII-γ |
| GBD | ICOS | CD80 | FcεRIβ |
| GBD | ICOS | CD80 | FcεRIγ |
| GBD | ICOS | CD80 | DAP10 |
| GBD | ICOS | CD80 | DAP12 |
| GBD | ICOS | CD80 | CD32 |
| GBD | ICOS | CD80 | CD79a |
| GBD | ICOS | CD80 | CD79b |
| GBD | ICOS | CD86 | CD8 |
| GBD | ICOS | CD86 | CD3ζ |

TABLE 3-continued

Third Generation CARs

| | Co-stimulatory Signal | Co-stimulatory Signal | Signal Domain |
|---|---|---|---|
| GBD | ICOS | CD86 | CD3δ |
| GBD | ICOS | CD86 | CD3γ |
| GBD | ICOS | CD86 | CD3ε |
| GBD | ICOS | CD86 | FcγRI-γ |
| GBD | ICOS | CD86 | FcγRIII-γ |
| GBD | ICOS | CD86 | FcεRIβ |
| GBD | ICOS | CD86 | FcεRIγ |
| GBD | ICOS | CD86 | DAP10 |
| GBD | ICOS | CD86 | DAP12 |
| GBD | ICOS | CD86 | CD32 |
| GBD | ICOS | CD86 | CD79a |
| GBD | ICOS | CD86 | CD79b |
| GBD | ICOS | OX40 | CD8 |
| GBD | ICOS | OX40 | CD3ζ |
| GBD | ICOS | OX40 | CD3δ |
| GBD | ICOS | OX40 | CD3γ |
| GBD | ICOS | OX40 | CD3ε |
| GBD | ICOS | OX40 | FcγRI-γ |
| GBD | ICOS | OX40 | FcγRIII-γ |
| GBD | ICOS | OX40 | FcεRIβ |
| GBD | ICOS | OX40 | FcεRIγ |
| GBD | ICOS | OX40 | DAP10 |
| GBD | ICOS | OX40 | DAP12 |
| GBD | ICOS | OX40 | CD32 |
| GBD | ICOS | OX40 | CD79a |
| GBD | ICOS | OX40 | CD79b |
| GBD | ICOS | DAP10 | CD8 |
| GBD | ICOS | DAP10 | CD3ζ |
| GBD | ICOS | DAP10 | CD3δ |
| GBD | ICOS | DAP10 | CD3γ |
| GBD | ICOS | DAP10 | CD3ε |
| GBD | ICOS | DAP10 | FcγRI-γ |
| GBD | ICOS | DAP10 | FcγRIII-γ |
| GBD | ICOS | DAP10 | FcεRIβ |
| GBD | ICOS | DAP10 | FcεRIγ |
| GBD | ICOS | DAP10 | DAP10 |
| GBD | ICOS | DAP10 | DAP12 |
| GBD | ICOS | DAP10 | CD32 |
| GBD | ICOS | DAP10 | CD79a |
| GBD | ICOS | DAP10 | CD79b |
| GBD | ICOS | DAP12 | CD8 |
| GBD | ICOS | DAP12 | CD3ζ |
| GBD | ICOS | DAP12 | CD3δ |
| GBD | ICOS | DAP12 | CD3γ |
| GBD | ICOS | DAP12 | CD3ε |
| GBD | ICOS | DAP12 | FcγRI-γ |
| GBD | ICOS | DAP12 | FcγRIII-γ |
| GBD | ICOS | DAP12 | FcεRIβ |
| GBD | ICOS | DAP12 | FcεRIγ |
| GBD | ICOS | DAP12 | DAP10 |
| GBD | ICOS | DAP12 | DAP12 |
| GBD | ICOS | DAP12 | CD32 |
| GBD | ICOS | DAP12 | CD79a |
| GBD | ICOS | DAP12 | CD79b |
| GBD | ICOS | MyD88 | CD8 |
| GBD | ICOS | MyD88 | CD3ζ |
| GBD | ICOS | MyD88 | CD3δ |
| GBD | ICOS | MyD88 | CD3γ |
| GBD | ICOS | MyD88 | CD3ε |
| GBD | ICOS | MyD88 | FcγRI-γ |
| GBD | ICOS | MyD88 | FcγRIII-γ |
| GBD | ICOS | MyD88 | FcεRIβ |
| GBD | ICOS | MyD88 | FcεRIγ |
| GBD | ICOS | MyD88 | DAP10 |
| GBD | ICOS | MyD88 | DAP12 |
| GBD | ICOS | MyD88 | CD32 |
| GBD | ICOS | MyD88 | CD79a |
| GBD | ICOS | MyD88 | CD79b |
| GBD | ICOS | CD7 | CD8 |
| GBD | ICOS | CD7 | CD3ζ |
| GBD | ICOS | CD7 | CD3δ |
| GBD | ICOS | CD7 | CD3γ |
| GBD | ICOS | CD7 | CD3ε |
| GBD | ICOS | CD7 | FcγRI-γ |
| GBD | ICOS | CD7 | FcγRIII-γ |
| GBD | ICOS | CD7 | FcεRIβ |
| GBD | ICOS | CD7 | FcεRIγ |
| GBD | ICOS | CD7 | DAP10 |
| GBD | ICOS | CD7 | DAP12 |
| GBD | ICOS | CD7 | CD32 |
| GBD | ICOS | CD7 | CD79a |
| GBD | ICOS | CD7 | CD79b |
| GBD | ICOS | BTNL3 | CD8 |
| GBD | ICOS | BTNL3 | CD3ζ |
| GBD | ICOS | BTNL3 | CD3δ |
| GBD | ICOS | BTNL3 | CD3γ |
| GBD | ICOS | BTNL3 | CD3ε |
| GBD | ICOS | BTNL3 | FcγRI-γ |
| GBD | ICOS | BTNL3 | FcγRIII-γ |
| GBD | ICOS | BTNL3 | FcεRIβ |
| GBD | ICOS | BTNL3 | FcεRIγ |
| GBD | ICOS | BTNL3 | DAP10 |
| GBD | ICOS | BTNL3 | DAP12 |
| GBD | ICOS | BTNL3 | CD32 |
| GBD | ICOS | BTNL3 | CD79a |
| GBD | ICOS | BTNL3 | CD79b |
| GBD | ICOS | NKG2D | CD8 |
| GBD | ICOS | NKG2D | CD3ζ |
| GBD | ICOS | NKG2D | CD3δ |
| GBD | ICOS | NKG2D | CD3γ |
| GBD | ICOS | NKG2D | CD3ε |
| GBD | ICOS | NKG2D | FcγRI-γ |
| GBD | ICOS | NKG2D | FcγRIII-γ |
| GBD | ICOS | NKG2D | FcεRIβ |
| GBD | ICOS | NKG2D | FcεRIγ |
| GBD | ICOS | NKG2D | DAP10 |
| GBD | ICOS | NKG2D | DAP12 |
| GBD | ICOS | NKG2D | CD32 |
| GBD | ICOS | NKG2D | CD79a |
| GBD | ICOS | NKG2D | CD79b |
| GBD | CD27 | CD28 | CD8 |
| GBD | CD27 | CD28 | CD3ζ |
| GBD | CD27 | CD28 | CD3δ |
| GBD | CD27 | CD28 | CD3γ |
| GBD | CD27 | CD28 | CD3ε |
| GBD | CD27 | CD28 | FcγRI-γ |
| GBD | CD27 | CD28 | FcγRIII-γ |
| GBD | CD27 | CD28 | FcεRIβ |
| GBD | CD27 | CD28 | FcεRIγ |
| GBD | CD27 | CD28 | DAP10 |
| GBD | CD27 | CD28 | DAP12 |
| GBD | CD27 | CD28 | CD32 |
| GBD | CD27 | CD28 | CD79a |
| GBD | CD27 | CD28 | CD79b |
| GBD | CD27 | CD8 | CD8 |
| GBD | CD27 | CD8 | CD3ζ |
| GBD | CD27 | CD8 | CD3δ |
| GBD | CD27 | CD8 | CD3γ |
| GBD | CD27 | CD8 | CD3ε |
| GBD | CD27 | CD8 | FcγRI-γ |
| GBD | CD27 | CD8 | FcγRIII-γ |
| GBD | CD27 | CD8 | FcεRIβ |
| GBD | CD27 | CD8 | FcεRIγ |
| GBD | CD27 | CD8 | DAP10 |
| GBD | CD27 | CD8 | DAP12 |
| GBD | CD27 | CD8 | CD32 |
| GBD | CD27 | CD8 | CD79a |
| GBD | CD27 | CD8 | CD79b |
| GBD | CD27 | CD4 | CD8 |
| GBD | CD27 | CD4 | CD3ζ |
| GBD | CD27 | CD4 | CD3δ |
| GBD | CD27 | CD4 | CD3γ |
| GBD | CD27 | CD4 | CD3ε |
| GBD | CD27 | CD4 | FcγRI-γ |
| GBD | CD27 | CD4 | FcγRIII-γ |
| GBD | CD27 | CD4 | FcεRIβ |
| GBD | CD27 | CD4 | FcεRIγ |
| GBD | CD27 | CD4 | DAP10 |
| GBD | CD27 | CD4 | DAP12 |
| GBD | CD27 | CD4 | CD32 |

TABLE 3-continued

Third Generation CARs

| | Co-stimulatory Signal | Co-stimulatory Signal | Signal Domain |
|---|---|---|---|
| GBD | CD27 | CD4 | CD79a |
| GBD | CD27 | CD4 | CD79b |
| GBD | CD27 | b2c | CD8 |
| GBD | CD27 | b2c | CD3ζ |
| GBD | CD27 | b2c | CD3δ |
| GBD | CD27 | b2c | CD3γ |
| GBD | CD27 | b2c | CD3ε |
| GBD | CD27 | b2c | FcγRI-γ |
| GBD | CD27 | b2c | FcγRIII-γ |
| GBD | CD27 | b2c | FcεRIβ |
| GBD | CD27 | b2c | FcεRIγ |
| GBD | CD27 | b2c | DAP10 |
| GBD | CD27 | b2c | DAP12 |
| GBD | CD27 | b2c | CD32 |
| GBD | CD27 | b2c | CD79a |
| GBD | CD27 | b2c | CD79b |
| GBD | CD27 | CD137/41BB | CD8 |
| GBD | CD27 | CD137/41BB | CD3ζ |
| GBD | CD27 | CD137/41BB | CD3δ |
| GBD | CD27 | CD137/41BB | CD3γ |
| GBD | CD27 | CD137/41BB | CD3ε |
| GBD | CD27 | CD137/41BB | FcγRI-γ |
| GBD | CD27 | CD137/41BB | FcγRIII-γ |
| GBD | CD27 | CD137/41BB | FcεRIβ |
| GBD | CD27 | CD137/41BB | FcεRIγ |
| GBD | CD27 | CD137/41BB | DAP10 |
| GBD | CD27 | CD137/41BB | DAP12 |
| GBD | CD27 | CD137/41BB | CD32 |
| GBD | CD27 | CD137/41BB | CD79a |
| GBD | CD27 | CD137/41BB | CD79b |
| GBD | CD27 | ICOS | CD8 |
| GBD | CD27 | ICOS | CD3ζ |
| GBD | CD27 | ICOS | CD3δ |
| GBD | CD27 | ICOS | CD3γ |
| GBD | CD27 | ICOS | CD3ε |
| GBD | CD27 | ICOS | FcγRI-γ |
| GBD | CD27 | ICOS | FcγRIII-γ |
| GBD | CD27 | ICOS | FcεRIβ |
| GBD | CD27 | ICOS | FcεRIγ |
| GBD | CD27 | ICOS | DAP10 |
| GBD | CD27 | ICOS | DAP12 |
| GBD | CD27 | ICOS | CD32 |
| GBD | CD27 | ICOS | CD79a |
| GBD | CD27 | ICOS | CD79b |
| GBD | CD27 | CD27 | CD8 |
| GBD | CD27 | CD27 | CD3ζ |
| GBD | CD27 | CD27 | CD3δ |
| GBD | CD27 | CD27 | CD3γ |
| GBD | CD27 | CD27 | CD3ε |
| GBD | CD27 | CD27 | FcγRI-γ |
| GBD | CD27 | CD27 | FcγRIII-γ |
| GBD | CD27 | CD27 | FcεRIβ |
| GBD | CD27 | CD27 | FcεRIγ |
| GBD | CD27 | CD27 | DAP10 |
| GBD | CD27 | CD27 | DAP12 |
| GBD | CD27 | CD27 | CD32 |
| GBD | CD27 | CD27 | CD79a |
| GBD | CD27 | CD27 | CD79b |
| GBD | CD27 | CD28δ | CD8 |
| GBD | CD27 | CD28δ | CD3ζ |
| GBD | CD27 | CD28δ | CD3δ |
| GBD | CD27 | CD28δ | CD3γ |
| GBD | CD27 | CD28δ | CD3ε |
| GBD | CD27 | CD28δ | FcγRI-γ |
| GBD | CD27 | CD28δ | FcγRIII-γ |
| GBD | CD27 | CD28δ | FcεRIβ |
| GBD | CD27 | CD28δ | FcεRIγ |
| GBD | CD27 | CD28δ | DAP10 |
| GBD | CD27 | CD28δ | DAP12 |
| GBD | CD27 | CD28δ | CD32 |
| GBD | CD27 | CD28δ | CD79a |
| GBD | CD27 | CD28δ | CD79b |
| GBD | CD27 | CD80 | CD8 |
| GBD | CD27 | CD80 | CD3ζ |
| GBD | CD27 | CD80 | CD3δ |
| GBD | CD27 | CD80 | CD3γ |
| GBD | CD27 | CD80 | CD3ε |
| GBD | CD27 | CD80 | FcγRI-γ |
| GBD | CD27 | CD80 | FcγRIII-γ |
| GBD | CD27 | CD80 | FcεRIβ |
| GBD | CD27 | CD80 | FcεRIγ |
| GBD | CD27 | CD80 | DAP10 |
| GBD | CD27 | CD80 | DAP12 |
| GBD | CD27 | CD80 | CD32 |
| GBD | CD27 | CD80 | CD79a |
| GBD | CD27 | CD80 | CD79b |
| GBD | CD27 | CD86 | CD8 |
| GBD | CD27 | CD86 | CD3ζ |
| GBD | CD27 | CD86 | CD3δ |
| GBD | CD27 | CD86 | CD3γ |
| GBD | CD27 | CD86 | CD3ε |
| GBD | CD27 | CD86 | FcγRI-γ |
| GBD | CD27 | CD86 | FcγRIII-γ |
| GBD | CD27 | CD86 | FcεRIβ |
| GBD | CD27 | CD86 | FcεRIγ |
| GBD | CD27 | CD86 | DAP10 |
| GBD | CD27 | CD86 | DAP12 |
| GBD | CD27 | CD86 | CD32 |
| GBD | CD27 | CD86 | CD79a |
| GBD | CD27 | CD86 | CD79b |
| GBD | CD27 | OX40 | CD8 |
| GBD | CD27 | OX40 | CD3ζ |
| GBD | CD27 | OX40 | CD3δ |
| GBD | CD27 | OX40 | CD3γ |
| GBD | CD27 | OX40 | CD3ε |
| GBD | CD27 | OX40 | FcγRI-γ |
| GBD | CD27 | OX40 | FcγRIII-γ |
| GBD | CD27 | OX40 | FcεRIβ |
| GBD | CD27 | OX40 | FcεRIγ |
| GBD | CD27 | OX40 | DAP10 |
| GBD | CD27 | OX40 | DAP12 |
| GBD | CD27 | OX40 | CD32 |
| GBD | CD27 | OX40 | CD79a |
| GBD | CD27 | OX40 | CD79b |
| GBD | CD27 | DAP10 | CD8 |
| GBD | CD27 | DAP10 | CD3ζ |
| GBD | CD27 | DAP10 | CD3δ |
| GBD | CD27 | DAP10 | CD3γ |
| GBD | CD27 | DAP10 | CD3ε |
| GBD | CD27 | DAP10 | FcγRI-γ |
| GBD | CD27 | DAP10 | FcγRIII-γ |
| GBD | CD27 | DAP10 | FcεRIβ |
| GBD | CD27 | DAP10 | FcεRIγ |
| GBD | CD27 | DAP10 | DAP10 |
| GBD | CD27 | DAP10 | DAP12 |
| GBD | CD27 | DAP10 | CD32 |
| GBD | CD27 | DAP10 | CD79a |
| GBD | CD27 | DAP10 | CD79b |
| GBD | CD27 | DAP12 | CD8 |
| GBD | CD27 | DAP12 | CD3ζ |
| GBD | CD27 | DAP12 | CD3δ |
| GBD | CD27 | DAP12 | CD3γ |
| GBD | CD27 | DAP12 | CD3ε |
| GBD | CD27 | DAP12 | FcγRI-γ |
| GBD | CD27 | DAP12 | FcγRIII-γ |
| GBD | CD27 | DAP12 | FcεRIβ |
| GBD | CD27 | DAP12 | FcεRIγ |
| GBD | CD27 | DAP12 | DAP10 |
| GBD | CD27 | DAP12 | DAP12 |
| GBD | CD27 | DAP12 | CD32 |
| GBD | CD27 | DAP12 | CD79a |
| GBD | CD27 | DAP12 | CD79b |
| GBD | CD27 | MyD88 | CD8 |
| GBD | CD27 | MyD88 | CD3ζ |
| GBD | CD27 | MyD88 | CD3δ |
| GBD | CD27 | MyD88 | CD3γ |
| GBD | CD27 | MyD88 | CD3ε |
| GBD | CD27 | MyD88 | FcγRI-γ |
| GBD | CD27 | MyD88 | FcγRIII-γ |
| GBD | CD27 | MyD88 | FcεRIβ |

TABLE 3-continued

Third Generation CARs

| | Co-stimulatory Signal | Co-stimulatory Signal | Signal Domain |
|---|---|---|---|
| GBD | CD27 | MyD88 | FcεRIγ |
| GBD | CD27 | MyD88 | DAP10 |
| GBD | CD27 | MyD88 | DAP12 |
| GBD | CD27 | MyD88 | CD32 |
| GBD | CD27 | MyD88 | CD79a |
| GBD | CD27 | MyD88 | CD79b |
| GBD | CD27 | CD7 | CD8 |
| GBD | CD27 | CD7 | CD3ζ |
| GBD | CD27 | CD7 | CD3δ |
| GBD | CD27 | CD7 | CD3γ |
| GBD | CD27 | CD7 | CD3ε |
| GBD | CD27 | CD7 | FcγRI-γ |
| GBD | CD27 | CD7 | FcγRIII-γ |
| GBD | CD27 | CD7 | FcεRIβ |
| GBD | CD27 | CD7 | FcεRIγ |
| GBD | CD27 | CD7 | DAP10 |
| GBD | CD27 | CD7 | DAP12 |
| GBD | CD27 | CD7 | CD32 |
| GBD | CD27 | CD7 | CD79a |
| GBD | CD27 | CD7 | CD79b |
| GBD | CD27 | BTNL3 | CD8 |
| GBD | CD27 | BTNL3 | CD3ζ |
| GBD | CD27 | BTNL3 | CD3δ |
| GBD | CD27 | BTNL3 | CD3γ |
| GBD | CD27 | BTNL3 | CD3ε |
| GBD | CD27 | BTNL3 | FcγRI-γ |
| GBD | CD27 | BTNL3 | FcγRIII-γ |
| GBD | CD27 | BTNL3 | FcεRIβ |
| GBD | CD27 | BTNL3 | FcεRIγ |
| GBD | CD27 | BTNL3 | DAP10 |
| GBD | CD27 | BTNL3 | DAP12 |
| GBD | CD27 | BTNL3 | CD32 |
| GBD | CD27 | BTNL3 | CD79a |
| GBD | CD27 | BTNL3 | CD79b |
| GBD | CD27 | NKG2D | CD8 |
| GBD | CD27 | NKG2D | CD3ζ |
| GBD | CD27 | NKG2D | CD3δ |
| GBD | CD27 | NKG2D | CD3γ |
| GBD | CD27 | NKG2D | CD3ε |
| GBD | CD27 | NKG2D | FcγRI-γ |
| GBD | CD27 | NKG2D | FcγRIII-γ |
| GBD | CD27 | NKG2D | FcεRIβ |
| GBD | CD27 | NKG2D | FcεRIγ |
| GBD | CD27 | NKG2D | DAP10 |
| GBD | CD27 | NKG2D | DAP12 |
| GBD | CD27 | NKG2D | CD32 |
| GBD | CD27 | NKG2D | CD79a |
| GBD | CD27 | NKG2D | CD79b |
| GBD | CD28δ | CD28 | CD8 |
| GBD | CD28δ | CD28 | CD3ζ |
| GBD | CD28δ | CD28 | CD3δ |
| GBD | CD28δ | CD28 | CD3γ |
| GBD | CD28δ | CD28 | CD3ε |
| GBD | CD28δ | CD28 | FcγRI-γ |
| GBD | CD28δ | CD28 | FcγRIII-γ |
| GBD | CD28δ | CD28 | FcεRIβ |
| GBD | CD28δ | CD28 | FcεRIγ |
| GBD | CD28δ | CD28 | DAP10 |
| GBD | CD28δ | CD28 | DAP12 |
| GBD | CD28δ | CD28 | CD32 |
| GBD | CD28δ | CD28 | CD79a |
| GBD | CD28δ | CD28 | CD79b |
| GBD | CD28δ | CD8 | CD8 |
| GBD | CD28δ | CD8 | CD3ζ |
| GBD | CD28δ | CD8 | CD3δ |
| GBD | CD28δ | CD8 | CD3γ |
| GBD | CD28δ | CD8 | CD3ε |
| GBD | CD28δ | CD8 | FcγRI-γ |
| GBD | CD28δ | CD8 | FcγRIII-γ |
| GBD | CD28δ | CD8 | FcεRIβ |
| GBD | CD28δ | CD8 | FcεRIγ |
| GBD | CD28δ | CD8 | DAP10 |
| GBD | CD28δ | CD8 | DAP12 |
| GBD | CD28δ | CD8 | CD32 |
| GBD | CD28δ | CD8 | CD79a |
| GBD | CD28δ | CD8 | CD79b |
| GBD | CD28δ | CD4 | CD8 |
| GBD | CD28δ | CD4 | CD3ζ |
| GBD | CD28δ | CD4 | CD3δ |
| GBD | CD28δ | CD4 | CD3γ |
| GBD | CD28δ | CD4 | CD3ε |
| GBD | CD28δ | CD4 | FcγRI-γ |
| GBD | CD28δ | CD4 | FcγRIII-γ |
| GBD | CD28δ | CD4 | FcεRIβ |
| GBD | CD28δ | CD4 | FcεRIγ |
| GBD | CD28δ | CD4 | DAP10 |
| GBD | CD28δ | CD4 | DAP12 |
| GBD | CD28δ | CD4 | CD32 |
| GBD | CD28δ | CD4 | CD79a |
| GBD | CD28δ | CD4 | CD79b |
| GBD | CD28δ | b2c | CD8 |
| GBD | CD28δ | b2c | CD3ζ |
| GBD | CD28δ | b2c | CD3δ |
| GBD | CD28δ | b2c | CD3γ |
| GBD | CD28δ | b2c | CD3ε |
| GBD | CD28δ | b2c | FcγRI-γ |
| GBD | CD28δ | b2c | FcγRIII-γ |
| GBD | CD28δ | b2c | FcεRIβ |
| GBD | CD28δ | b2c | FcεRIγ |
| GBD | CD28δ | b2c | DAP10 |
| GBD | CD28δ | b2c | DAP12 |
| GBD | CD28δ | b2c | CD32 |
| GBD | CD28δ | b2c | CD79a |
| GBD | CD28δ | b2c | CD79b |
| GBD | CD28δ | CD137/41BB | CD8 |
| GBD | CD28δ | CD137/41BB | CD3ζ |
| GBD | CD28δ | CD137/41BB | CD3δ |
| GBD | CD28δ | CD137/41BB | CD3γ |
| GBD | CD28δ | CD137/41BB | CD3ε |
| GBD | CD28δ | CD137/41BB | FcγRI-γ |
| GBD | CD28δ | CD137/41BB | FcγRIII-γ |
| GBD | CD28δ | CD137/41BB | FcεRIβ |
| GBD | CD28δ | CD137/41BB | FcεRIγ |
| GBD | CD28δ | CD137/41BB | DAP10 |
| GBD | CD28δ | CD137/41BB | DAP12 |
| GBD | CD28δ | CD137/41BB | CD32 |
| GBD | CD28δ | CD137/41BB | CD79a |
| GBD | CD28δ | CD137/41BB | CD79b |
| GBD | CD28δ | ICOS | CD8 |
| GBD | CD28δ | ICOS | CD3ζ |
| GBD | CD28δ | ICOS | CD3δ |
| GBD | CD28δ | ICOS | CD3γ |
| GBD | CD28δ | ICOS | CD3ε |
| GBD | CD28δ | ICOS | FcγRI-γ |
| GBD | CD28δ | ICOS | FcγRIII-γ |
| GBD | CD28δ | ICOS | FcεRIβ |
| GBD | CD28δ | ICOS | FcεRIγ |
| GBD | CD28δ | ICOS | DAP10 |
| GBD | CD28δ | ICOS | DAP12 |
| GBD | CD28δ | ICOS | CD32 |
| GBD | CD28δ | ICOS | CD79a |
| GBD | CD28δ | ICOS | CD79b |
| GBD | CD28δ | CD27 | CD8 |
| GBD | CD28δ | CD27 | CD3ζ |
| GBD | CD28δ | CD27 | CD3δ |
| GBD | CD28δ | CD27 | CD3γ |
| GBD | CD28δ | CD27 | CD3ε |
| GBD | CD28δ | CD27 | FcγRI-γ |
| GBD | CD28δ | CD27 | FcγRIII-γ |
| GBD | CD28δ | CD27 | FcεRIβ |
| GBD | CD28δ | CD27 | FcεRIγ |
| GBD | CD28δ | CD27 | DAP10 |
| GBD | CD28δ | CD27 | DAP12 |
| GBD | CD28δ | CD27 | CD32 |
| GBD | CD28δ | CD27 | CD79a |
| GBD | CD28δ | CD27 | CD79b |
| GBD | CD28δ | CD28δ | CD8 |
| GBD | CD28δ | CD28δ | CD3ζ |
| GBD | CD28δ | CD28δ | CD3δ |
| GBD | CD28δ | CD28δ | CD3γ |

TABLE 3-continued

Third Generation CARs

| | Co-stimulatory Signal | Co-stimulatory Signal | Signal Domain |
|---|---|---|---|
| GBD | CD28δ | CD28δ | CD3ε |
| GBD | CD28δ | CD28δ | FcγRI-γ |
| GBD | CD28δ | CD28δ | FcγRIII-γ |
| GBD | CD28δ | CD28δ | FcεRIβ |
| GBD | CD28δ | CD28δ | FcεRIγ |
| GBD | CD28δ | CD28δ | DAP10 |
| GBD | CD28δ | CD28δ | DAP12 |
| GBD | CD28δ | CD28δ | CD32 |
| GBD | CD28δ | CD28δ | CD79a |
| GBD | CD28δ | CD28δ | CD79b |
| GBD | CD28δ | CD80 | CD8 |
| GBD | CD28δ | CD80 | CD3ζ |
| GBD | CD28δ | CD80 | CD3δ |
| GBD | CD28δ | CD80 | CD3γ |
| GBD | CD28δ | CD80 | CD3ε |
| GBD | CD28δ | CD80 | FcγRI-γ |
| GBD | CD28δ | CD80 | FcγRIII-γ |
| GBD | CD28δ | CD80 | FcεRIβ |
| GBD | CD28δ | CD80 | FcεRIγ |
| GBD | CD28δ | CD80 | DAP10 |
| GBD | CD28δ | CD80 | DAP12 |
| GBD | CD28δ | CD80 | CD32 |
| GBD | CD28δ | CD80 | CD79a |
| GBD | CD28δ | CD80 | CD79b |
| GBD | CD28δ | CD86 | CD8 |
| GBD | CD28δ | CD86 | CD3ζ |
| GBD | CD28δ | CD86 | CD3δ |
| GBD | CD28δ | CD86 | CD3γ |
| GBD | CD28δ | CD86 | CD3ε |
| GBD | CD28δ | CD86 | FcγRI-γ |
| GBD | CD28δ | CD86 | FcγRIII-γ |
| GBD | CD28δ | CD86 | FcεRIβ |
| GBD | CD28δ | CD86 | FcεRIγ |
| GBD | CD28δ | CD86 | DAP10 |
| GBD | CD28δ | CD86 | DAP12 |
| GBD | CD28δ | CD86 | CD32 |
| GBD | CD28δ | CD86 | CD79a |
| GBD | CD28δ | CD86 | CD79b |
| GBD | CD28δ | OX40 | CD8 |
| GBD | CD28δ | OX40 | CD3ζ |
| GBD | CD28δ | OX40 | CD3δ |
| GBD | CD28δ | OX40 | CD3γ |
| GBD | CD28δ | OX40 | CD3ε |
| GBD | CD28δ | OX40 | FcγRI-γ |
| GBD | CD28δ | OX40 | FcγRIII-γ |
| GBD | CD28δ | OX40 | FcεRIβ |
| GBD | CD28δ | OX40 | FcεRIγ |
| GBD | CD28δ | OX40 | DAP10 |
| GBD | CD28δ | OX40 | DAP12 |
| GBD | CD28δ | OX40 | CD32 |
| GBD | CD28δ | OX40 | CD79a |
| GBD | CD28δ | OX40 | CD79b |
| GBD | CD28δ | DAP10 | CD8 |
| GBD | CD28δ | DAP10 | CD3ζ |
| GBD | CD28δ | DAP10 | CD3δ |
| GBD | CD28δ | DAP10 | CD3γ |
| GBD | CD28δ | DAP10 | CD3ε |
| GBD | CD28δ | DAP10 | FcγRI-γ |
| GBD | CD28δ | DAP10 | FcγRIII-γ |
| GBD | CD28δ | DAP10 | FcεRIβ |
| GBD | CD28δ | DAP10 | FcεRIγ |
| GBD | CD28δ | DAP10 | DAP10 |
| GBD | CD28δ | DAP10 | DAP12 |
| GBD | CD28δ | DAP10 | CD32 |
| GBD | CD28δ | DAP10 | CD79a |
| GBD | CD28δ | DAP10 | CD79b |
| GBD | CD28δ | DAP12 | CD8 |
| GBD | CD28δ | DAP12 | CD3ζ |
| GBD | CD28δ | DAP12 | CD3δ |
| GBD | CD28δ | DAP12 | CD3γ |
| GBD | CD28δ | DAP12 | CD3ε |
| GBD | CD28δ | DAP12 | FcγRI-γ |
| GBD | CD28δ | DAP12 | FcγRIII-γ |
| GBD | CD28δ | DAP12 | FcεRIβ |
| GBD | CD28δ | DAP12 | FcεRIγ |
| GBD | CD28δ | DAP12 | DAP10 |
| GBD | CD28δ | DAP12 | DAP12 |
| GBD | CD28δ | DAP12 | CD32 |
| GBD | CD28δ | DAP12 | CD79a |
| GBD | CD28δ | DAP12 | CD79b |
| GBD | CD28δ | MyD88 | CD8 |
| GBD | CD28δ | MyD88 | CD3ζ |
| GBD | CD28δ | MyD88 | CD3δ |
| GBD | CD28δ | MyD88 | CD3γ |
| GBD | CD28δ | MyD88 | CD3ε |
| GBD | CD28δ | MyD88 | FcγRI-γ |
| GBD | CD28δ | MyD88 | FcγRIII-γ |
| GBD | CD28δ | MyD88 | FcεRIβ |
| GBD | CD28δ | MyD88 | FcεRIγ |
| GBD | CD28δ | MyD88 | DAP10 |
| GBD | CD28δ | MyD88 | DAP12 |
| GBD | CD28δ | MyD88 | CD32 |
| GBD | CD28δ | MyD88 | CD79a |
| GBD | CD28δ | MyD88 | CD79b |
| GBD | CD28δ | CD7 | CD8 |
| GBD | CD28δ | CD7 | CD3ζ |
| GBD | CD28δ | CD7 | CD3δ |
| GBD | CD28δ | CD7 | CD3γ |
| GBD | CD28δ | CD7 | CD3ε |
| GBD | CD28δ | CD7 | FcγRI-γ |
| GBD | CD28δ | CD7 | FcγRIII-γ |
| GBD | CD28δ | CD7 | FcεRIβ |
| GBD | CD28δ | CD7 | FcεRIγ |
| GBD | CD28δ | CD7 | DAP10 |
| GBD | CD28δ | CD7 | DAP12 |
| GBD | CD28δ | CD7 | CD32 |
| GBD | CD28δ | CD7 | CD79a |
| GBD | CD28δ | CD7 | CD79b |
| GBD | CD28δ | BTNL3 | CD8 |
| GBD | CD28δ | BTNL3 | CD3ζ |
| GBD | CD28δ | BTNL3 | CD3δ |
| GBD | CD28δ | BTNL3 | CD3γ |
| GBD | CD28δ | BTNL3 | CD3ε |
| GBD | CD28δ | BTNL3 | FcγRI-γ |
| GBD | CD28δ | BTNL3 | FcγRIII-γ |
| GBD | CD28δ | BTNL3 | FcεRIβ |
| GBD | CD28δ | BTNL3 | FcεRIγ |
| GBD | CD28δ | BTNL3 | DAP10 |
| GBD | CD28δ | BTNL3 | DAP12 |
| GBD | CD28δ | BTNL3 | CD32 |
| GBD | CD28δ | BTNL3 | CD79a |
| GBD | CD28δ | BTNL3 | CD79b |
| GBD | CD28δ | NKG2D | CD8 |
| GBD | CD28δ | NKG2D | CD3ζ |
| GBD | CD28δ | NKG2D | CD3δ |
| GBD | CD28δ | NKG2D | CD3γ |
| GBD | CD28δ | NKG2D | CD3ε |
| GBD | CD28δ | NKG2D | FcγRI-γ |
| GBD | CD28δ | NKG2D | FcγRIII-γ |
| GBD | CD28δ | NKG2D | FcεRIβ |
| GBD | CD28δ | NKG2D | FcεRIγ |
| GBD | CD28δ | NKG2D | DAP10 |
| GBD | CD28δ | NKG2D | DAP12 |
| GBD | CD28δ | NKG2D | CD32 |
| GBD | CD28δ | NKG2D | CD79a |
| GBD | CD28δ | NKG2D | CD79b |
| GBD | CD80 | CD28 | CD8 |
| GBD | CD80 | CD28 | CD3ζ |
| GBD | CD80 | CD28 | CD3δ |
| GBD | CD80 | CD28 | CD3γ |
| GBD | CD80 | CD28 | CD3ε |
| GBD | CD80 | CD28 | FcγRI-γ |
| GBD | CD80 | CD28 | FcγRIII-γ |
| GBD | CD80 | CD28 | FcεRIβ |
| GBD | CD80 | CD28 | FcεRIγ |
| GBD | CD80 | CD28 | DAP10 |
| GBD | CD80 | CD28 | DAP12 |
| GBD | CD80 | CD28 | CD32 |
| GBD | CD80 | CD28 | CD79a |
| GBD | CD80 | CD28 | CD79b |

TABLE 3-continued

Third Generation CARs

| Co-stimulatory Signal | Co-stimulatory Signal | Signal Domain |
|---|---|---|
| GBD CD80 | CD8 | CD8 |
| GBD CD80 | CD8 | CD3ζ |
| GBD CD80 | CD8 | CD3δ |
| GBD CD80 | CD8 | CD3γ |
| GBD CD80 | CD8 | CD3ε |
| GBD CD80 | CD8 | FcγRI-γ |
| GBD CD80 | CD8 | FcγRIII-γ |
| GBD CD80 | CD8 | FcεRIβ |
| GBD CD80 | CD8 | FcεRIγ |
| GBD CD80 | CD8 | DAP10 |
| GBD CD80 | CD8 | DAP12 |
| GBD CD80 | CD8 | CD32 |
| GBD CD80 | CD8 | CD79a |
| GBD CD80 | CD8 | CD79b |
| GBD CD80 | CD4 | CD8 |
| GBD CD80 | CD4 | CD3ζ |
| GBD CD80 | CD4 | CD3δ |
| GBD CD80 | CD4 | CD3γ |
| GBD CD80 | CD4 | CD3ε |
| GBD CD80 | CD4 | FcγRI-γ |
| GBD CD80 | CD4 | FcγRIII-γ |
| GBD CD80 | CD4 | FcεRIβ |
| GBD CD80 | CD4 | FcεRIγ |
| GBD CD80 | CD4 | DAP10 |
| GBD CD80 | CD4 | DAP12 |
| GBD CD80 | CD4 | CD32 |
| GBD CD80 | CD4 | CD79a |
| GBD CD80 | CD4 | CD79b |
| GBD CD80 | b2c | CD8 |
| GBD CD80 | b2c | CD3ζ |
| GBD CD80 | b2c | CD3δ |
| GBD CD80 | b2c | CD3γ |
| GBD CD80 | b2c | CD3ε |
| GBD CD80 | b2c | FcγRI-γ |
| GBD CD80 | b2c | FcγRIII-γ |
| GBD CD80 | b2c | FcεRIβ |
| GBD CD80 | b2c | FcεRIγ |
| GBD CD80 | b2c | DAP10 |
| GBD CD80 | b2c | DAP12 |
| GBD CD80 | b2c | CD32 |
| GBD CD80 | b2c | CD79a |
| GBD CD80 | b2c | CD79b |
| GBD CD80 | CD137/41BB | CD8 |
| GBD CD80 | CD137/41BB | CD3ζ |
| GBD CD80 | CD137/41BB | CD3δ |
| GBD CD80 | CD137/41BB | CD3γ |
| GBD CD80 | CD137/41BB | CD3ε |
| GBD CD80 | CD137/41BB | FcγRI-γ |
| GBD CD80 | CD137/41BB | FcγRIII-γ |
| GBD CD80 | CD137/41BB | FcεRIβ |
| GBD CD80 | CD137/41BB | FcεRIγ |
| GBD CD80 | CD137/41BB | DAP10 |
| GBD CD80 | CD137/41BB | DAP12 |
| GBD CD80 | CD137/41BB | CD32 |
| GBD CD80 | CD137/41BB | CD79a |
| GBD CD80 | CD137/41BB | CD79b |
| GBD CD80 | ICOS | CD8 |
| GBD CD80 | ICOS | CD3ζ |
| GBD CD80 | ICOS | CD3δ |
| GBD CD80 | ICOS | CD3γ |
| GBD CD80 | ICOS | CD3ε |
| GBD CD80 | ICOS | FcγRI-γ |
| GBD CD80 | ICOS | FcγRIII-γ |
| GBD CD80 | ICOS | FcεRIβ |
| GBD CD80 | ICOS | FcεRIγ |
| GBD CD80 | ICOS | DAP10 |
| GBD CD80 | ICOS | DAP12 |
| GBD CD80 | ICOS | CD32 |
| GBD CD80 | ICOS | CD79a |
| GBD CD80 | ICOS | CD79b |
| GBD CD80 | CD27 | CD8 |
| GBD CD80 | CD27 | CD3ζ |
| GBD CD80 | CD27 | CD3δ |
| GBD CD80 | CD27 | CD3γ |
| GBD CD80 | CD27 | CD3ε |
| GBD CD80 | CD27 | FcγRI-γ |
| GBD CD80 | CD27 | FcγRIII-γ |
| GBD CD80 | CD27 | FcεRIβ |
| GBD CD80 | CD27 | FcεRIγ |
| GBD CD80 | CD27 | DAP10 |
| GBD CD80 | CD27 | DAP12 |
| GBD CD80 | CD27 | CD32 |
| GBD CD80 | CD27 | CD79a |
| GBD CD80 | CD27 | CD79b |
| GBD CD80 | CD28δ | CD8 |
| GBD CD80 | CD28δ | CD3ζ |
| GBD CD80 | CD28δ | CD3δ |
| GBD CD80 | CD28δ | CD3γ |
| GBD CD80 | CD28δ | CD3ε |
| GBD CD80 | CD28δ | FcγRI-γ |
| GBD CD80 | CD28δ | FcγRIII-γ |
| GBD CD80 | CD28δ | FcεRIβ |
| GBD CD80 | CD28δ | FcεRIγ |
| GBD CD80 | CD28δ | DAP10 |
| GBD CD80 | CD28δ | DAP12 |
| GBD CD80 | CD28δ | CD32 |
| GBD CD80 | CD28δ | CD79a |
| GBD CD80 | CD28δ | CD79b |
| GBD CD80 | CD80 | CD8 |
| GBD CD80 | CD80 | CD3ζ |
| GBD CD80 | CD80 | CD3δ |
| GBD CD80 | CD80 | CD3γ |
| GBD CD80 | CD80 | CD3ε |
| GBD CD80 | CD80 | FcγRI-γ |
| GBD CD80 | CD80 | FcγRIII-γ |
| GBD CD80 | CD80 | FcεRIβ |
| GBD CD80 | CD80 | FcεRIγ |
| GBD CD80 | CD80 | DAP10 |
| GBD CD80 | CD80 | DAP12 |
| GBD CD80 | CD80 | CD32 |
| GBD CD80 | CD80 | CD79a |
| GBD CD80 | CD80 | CD79b |
| GBD CD80 | CD86 | CD8 |
| GBD CD80 | CD86 | CD3ζ |
| GBD CD80 | CD86 | CD3δ |
| GBD CD80 | CD86 | CD3γ |
| GBD CD80 | CD86 | CD3ε |
| GBD CD80 | CD86 | FcγRI-γ |
| GBD CD80 | CD86 | FcγRIII-γ |
| GBD CD80 | CD86 | FcεRIβ |
| GBD CD80 | CD86 | FcεRIγ |
| GBD CD80 | CD86 | DAP10 |
| GBD CD80 | CD86 | DAP12 |
| GBD CD80 | CD86 | CD32 |
| GBD CD80 | CD86 | CD79a |
| GBD CD80 | CD86 | CD79b |
| GBD CD80 | OX40 | CD8 |
| GBD CD80 | OX40 | CD3ζ |
| GBD CD80 | OX40 | CD3δ |
| GBD CD80 | OX40 | CD3γ |
| GBD CD80 | OX40 | CD3ε |
| GBD CD80 | OX40 | FcγRI-γ |
| GBD CD80 | OX40 | FcγRIII-γ |
| GBD CD80 | OX40 | FcεRIβ |
| GBD CD80 | OX40 | FcεRIγ |
| GBD CD80 | OX40 | DAP10 |
| GBD CD80 | OX40 | DAP12 |
| GBD CD80 | OX40 | CD32 |
| GBD CD80 | OX40 | CD79a |
| GBD CD80 | OX40 | CD79b |
| GBD CD80 | DAP10 | CD8 |
| GBD CD80 | DAP10 | CD3ζ |
| GBD CD80 | DAP10 | CD3δ |
| GBD CD80 | DAP10 | CD3γ |
| GBD CD80 | DAP10 | CD3ε |
| GBD CD80 | DAP10 | FcγRI-γ |
| GBD CD80 | DAP10 | FcγRIII-γ |
| GBD CD80 | DAP10 | FcεRIβ |
| GBD CD80 | DAP10 | FcεRIγ |
| GBD CD80 | DAP10 | DAP10 |

TABLE 3-continued

Third Generation CARs

| | Co-stimulatory Signal | Co-stimulatory Signal | Signal Domain |
|---|---|---|---|
| GBD | CD80 | DAP10 | DAP12 |
| GBD | CD80 | DAP10 | CD32 |
| GBD | CD80 | DAP10 | CD79a |
| GBD | CD80 | DAP10 | CD79b |
| GBD | CD80 | DAP12 | CD8 |
| GBD | CD80 | DAP12 | CD3ζ |
| GBD | CD80 | DAP12 | CD3δ |
| GBD | CD80 | DAP12 | CD3γ |
| GBD | CD80 | DAP12 | CD3ε |
| GBD | CD80 | DAP12 | FcγRI-γ |
| GBD | CD80 | DAP12 | FcγRIII-γ |
| GBD | CD80 | DAP12 | FcεRIβ |
| GBD | CD80 | DAP12 | FcεRIγ |
| GBD | CD80 | DAP12 | DAP10 |
| GBD | CD80 | DAP12 | DAP12 |
| GBD | CD80 | DAP12 | CD32 |
| GBD | CD80 | DAP12 | CD79a |
| GBD | CD80 | DAP12 | CD79b |
| GBD | CD80 | MyD88 | CD8 |
| GBD | CD80 | MyD88 | CD3ζ |
| GBD | CD80 | MyD88 | CD3δ |
| GBD | CD80 | MyD88 | CD3γ |
| GBD | CD80 | MyD88 | CD3ε |
| GBD | CD80 | MyD88 | FcγRI-γ |
| GBD | CD80 | MyD88 | FcγRIII-γ |
| GBD | CD80 | MyD88 | FcεRIβ |
| GBD | CD80 | MyD88 | FcεRIγ |
| GBD | CD80 | MyD88 | DAP10 |
| GBD | CD80 | MyD88 | DAP12 |
| GBD | CD80 | MyD88 | CD32 |
| GBD | CD80 | MyD88 | CD79a |
| GBD | CD80 | MyD88 | CD79b |
| GBD | CD80 | CD7 | CD8 |
| GBD | CD80 | CD7 | CD3ζ |
| GBD | CD80 | CD7 | CD3δ |
| GBD | CD80 | CD7 | CD3γ |
| GBD | CD80 | CD7 | CD3ε |
| GBD | CD80 | CD7 | FcγRI-γ |
| GBD | CD80 | CD7 | FcγRIII-γ |
| GBD | CD80 | CD7 | FcεRIβ |
| GBD | CD80 | CD7 | FcεRIγ |
| GBD | CD80 | CD7 | DAP10 |
| GBD | CD80 | CD7 | DAP12 |
| GBD | CD80 | CD7 | CD32 |
| GBD | CD80 | CD7 | CD79a |
| GBD | CD80 | CD7 | CD79b |
| GBD | CD80 | BTNL3 | CD8 |
| GBD | CD80 | BTNL3 | CD3ζ |
| GBD | CD80 | BTNL3 | CD3δ |
| GBD | CD80 | BTNL3 | CD3γ |
| GBD | CD80 | BTNL3 | CD3ε |
| GBD | CD80 | BTNL3 | FcγRI-γ |
| GBD | CD80 | BTNL3 | FcγRIII-γ |
| GBD | CD80 | BTNL3 | FcεRIβ |
| GBD | CD80 | BTNL3 | FcεRIγ |
| GBD | CD80 | BTNL3 | DAP10 |
| GBD | CD80 | BTNL3 | DAP12 |
| GBD | CD80 | BTNL3 | CD32 |
| GBD | CD80 | BTNL3 | CD79a |
| GBD | CD80 | BTNL3 | CD79b |
| GBD | CD80 | NKG2D | CD8 |
| GBD | CD80 | NKG2D | CD3ζ |
| GBD | CD80 | NKG2D | CD3δ |
| GBD | CD80 | NKG2D | CD3γ |
| GBD | CD80 | NKG2D | CD3ε |
| GBD | CD80 | NKG2D | FcγRI-γ |
| GBD | CD80 | NKG2D | FcγRIII-γ |
| GBD | CD80 | NKG2D | FcεRIβ |
| GBD | CD80 | NKG2D | FcεRIγ |
| GBD | CD80 | NKG2D | DAP10 |
| GBD | CD80 | NKG2D | DAP12 |
| GBD | CD80 | NKG2D | CD32 |
| GBD | CD80 | NKG2D | CD79a |
| GBD | CD80 | NKG2D | CD79b |
| GBD | CD86 | CD28 | CD8 |
| GBD | CD86 | CD28 | CD3ζ |
| GBD | CD86 | CD28 | CD3δ |
| GBD | CD86 | CD28 | CD3γ |
| GBD | CD86 | CD28 | CD3ε |
| GBD | CD86 | CD28 | FcγRI-γ |
| GBD | CD86 | CD28 | FcγRIII-γ |
| GBD | CD86 | CD28 | FcεRIβ |
| GBD | CD86 | CD28 | FcεRIγ |
| GBD | CD86 | CD28 | DAP10 |
| GBD | CD86 | CD28 | DAP12 |
| GBD | CD86 | CD28 | CD32 |
| GBD | CD86 | CD28 | CD79a |
| GBD | CD86 | CD28 | CD79b |
| GBD | CD86 | CD8 | CD8 |
| GBD | CD86 | CD8 | CD3ζ |
| GBD | CD86 | CD8 | CD3δ |
| GBD | CD86 | CD8 | CD3γ |
| GBD | CD86 | CD8 | CD3ε |
| GBD | CD86 | CD8 | FcγRI-γ |
| GBD | CD86 | CD8 | FcγRIII-γ |
| GBD | CD86 | CD8 | FcεRIβ |
| GBD | CD86 | CD8 | FcεRIγ |
| GBD | CD86 | CD8 | DAP10 |
| GBD | CD86 | CD8 | DAP12 |
| GBD | CD86 | CD8 | CD32 |
| GBD | CD86 | CD8 | CD79a |
| GBD | CD86 | CD8 | CD79b |
| GBD | CD86 | CD4 | CD8 |
| GBD | CD86 | CD4 | CD3ζ |
| GBD | CD86 | CD4 | CD3δ |
| GBD | CD86 | CD4 | CD3γ |
| GBD | CD86 | CD4 | CD3ε |
| GBD | CD86 | CD4 | FcγRI-γ |
| GBD | CD86 | CD4 | FcγRIII-γ |
| GBD | CD86 | CD4 | FcεRIβ |
| GBD | CD86 | CD4 | FcεRIγ |
| GBD | CD86 | CD4 | DAP10 |
| GBD | CD86 | CD4 | DAP12 |
| GBD | CD86 | CD4 | CD32 |
| GBD | CD86 | CD4 | CD79a |
| GBD | CD86 | CD4 | CD79b |
| GBD | CD86 | b2c | CD8 |
| GBD | 0D86 | b2c | CD3ζ |
| GBD | 0D86 | b2c | CD3δ |
| GBD | CD86 | b2c | CD3γ |
| GBD | CD86 | b2c | CD3ε |
| GBD | CD86 | b2c | FcγRI-γ |
| GBD | CD86 | b2c | FcγRIII-γ |
| GBD | CD86 | b2c | FcεRIβ |
| GBD | CD86 | b2c | FcεRIγ |
| GBD | CD86 | b2c | DAP10 |
| GBD | CD86 | b2c | DAP12 |
| GBD | CD86 | b2c | CD32 |
| GBD | CD86 | b2c | CD79a |
| GBD | CD86 | b2c | CD79b |
| GBD | CD86 | CD137/41BB | CD8 |
| GBD | CD86 | CD137/41BB | CD3ζ |
| GBD | CD86 | CD137/41BB | CD3δ |
| GBD | CD86 | CD137/41BB | CD3γ |
| GBD | CD86 | CD137/41BB | CD3ε |
| GBD | CD86 | CD137/41BB | FcγRI-γ |
| GBD | CD86 | CD137/41BB | FcγRIII-γ |
| GBD | CD86 | CD137/41BB | FcεRIβ |
| GBD | CD86 | CD137/41BB | FcεRIγ |
| GBD | CD86 | CD137/41BB | DAP10 |
| GBD | CD86 | CD137/41BB | DAP12 |
| GBD | CD86 | CD137/41BB | CD32 |
| GBD | CD86 | CD137/41BB | CD79a |
| GBD | CD86 | CD137/41BB | CD79b |
| GBD | CD86 | ICOS | CD8 |
| GBD | CD86 | ICOS | CD3ζ |
| GBD | CD86 | ICOS | CD3δ |
| GBD | CD86 | ICOS | CD3γ |
| GBD | CD86 | ICOS | CD3ε |
| GBD | CD86 | ICOS | FcγRI-γ |

TABLE 3-continued

Third Generation CARs

| | Co-stimulatory Signal | Co-stimulatory Signal | Signal Domain |
|---|---|---|---|
| GBD | CD86 | ICOS | FcγRIII-γ |
| GBD | CD86 | ICOS | FcεRIβ |
| GBD | CD86 | ICOS | FcεRIγ |
| GBD | CD86 | ICOS | DAP10 |
| GBD | CD86 | ICOS | DAP12 |
| GBD | CD86 | ICOS | CD32 |
| GBD | CD86 | ICOS | CD79a |
| GBD | CD86 | ICOS | CD79b |
| GBD | CD86 | CD27 | CD8 |
| GBD | CD86 | CD27 | CD3ζ |
| GBD | CD86 | CD27 | CD3δ |
| GBD | CD86 | CD27 | CD3γ |
| GBD | CD86 | CD27 | CD3ε |
| GBD | CD86 | CD27 | FcγRI-γ |
| GBD | CD86 | CD27 | FcγRIII-γ |
| GBD | CD86 | CD27 | FcεRIβ |
| GBD | CD86 | CD27 | FcεRIγ |
| GBD | CD86 | CD27 | DAP10 |
| GBD | CD86 | CD27 | DAP12 |
| GBD | CD86 | CD27 | CD32 |
| GBD | CD86 | CD27 | CD79a |
| GBD | CD86 | CD27 | CD79b |
| GBD | CD86 | CD28δ | CD8 |
| GBD | CD86 | CD28δ | CD3ζ |
| GBD | CD86 | CD28δ | CD3δ |
| GBD | CD86 | CD28δ | CD3γ |
| GBD | CD86 | CD28δ | CD3ε |
| GBD | CD86 | CD28δ | FcγRI-γ |
| GBD | CD86 | CD28δ | FcγRIII-γ |
| GBD | CD86 | CD28δ | FcεRIβ |
| GBD | CD86 | CD28δ | FcεRIγ |
| GBD | CD86 | CD28δ | DAP10 |
| GBD | CD86 | CD28δ | DAP12 |
| GBD | CD86 | CD28δ | CD32 |
| GBD | CD86 | CD28δ | CD79a |
| GBD | CD86 | CD28δ | CD79b |
| GBD | CD86 | CD80 | CD8 |
| GBD | CD86 | CD80 | CD3ζ |
| GBD | CD86 | CD80 | CD3δ |
| GBD | CD86 | CD80 | CD3γ |
| GBD | CD86 | CD80 | CD3ε |
| GBD | CD86 | CD80 | FcγRI-γ |
| GBD | CD86 | CD80 | FcγRIII-γ |
| GBD | CD86 | CD80 | FcεRIβ |
| GBD | CD86 | CD80 | FcεRIγ |
| GBD | CD86 | CD80 | DAP10 |
| GBD | CD86 | CD80 | DAP12 |
| GBD | CD86 | CD80 | CD32 |
| GBD | CD86 | CD80 | CD79a |
| GBD | CD86 | CD80 | CD79b |
| GBD | CD86 | CD86 | CD8 |
| GBD | CD86 | CD86 | CD3ζ |
| GBD | CD86 | CD86 | CD3δ |
| GBD | CD86 | CD86 | CD3γ |
| GBD | CD86 | CD86 | CD3ε |
| GBD | CD86 | CD86 | FcγRI-γ |
| GBD | CD86 | CD86 | FcγRIII-γ |
| GBD | CD86 | CD86 | FcεRIβ |
| GBD | CD86 | CD86 | FcεRIγ |
| GBD | CD86 | CD86 | DAP10 |
| GBD | CD86 | CD86 | DAP12 |
| GBD | CD86 | CD86 | CD32 |
| GBD | CD86 | CD86 | CD79a |
| GBD | CD86 | CD86 | CD79b |
| GBD | CD86 | OX40 | CD8 |
| GBD | CD86 | OX40 | CD3ζ |
| GBD | CD86 | OX40 | CD3δ |
| GBD | CD86 | OX40 | CD3γ |
| GBD | CD86 | OX40 | CD3ε |
| GBD | CD86 | OX40 | FcγRI-γ |
| GBD | CD86 | OX40 | FcγRIII-γ |
| GBD | CD86 | OX40 | FcεRIβ |
| GBD | CD86 | OX40 | FcεRIγ |
| GBD | CD86 | OX40 | DAP10 |
| GBD | CD86 | OX40 | DAP12 |
| GBD | CD86 | OX40 | CD32 |
| GBD | CD86 | OX40 | CD79a |
| GBD | CD86 | OX40 | CD79b |
| GBD | CD86 | DAP10 | CD8 |
| GBD | CD86 | DAP10 | CD3ζ |
| GBD | CD86 | DAP10 | CD3δ |
| GBD | CD86 | DAP10 | CD3γ |
| GBD | CD86 | DAP10 | CD3ε |
| GBD | CD86 | DAP10 | FcγRI-γ |
| GBD | CD86 | DAP10 | FcγRIII-γ |
| GBD | CD86 | DAP10 | FcεRIβ |
| GBD | 0D86 | DAP10 | FcεRIγ |
| GBD | 0D86 | DAP10 | DAP10 |
| GBD | CD86 | DAP10 | DAP12 |
| GBD | CD86 | DAP10 | CD32 |
| GBD | CD86 | DAP10 | CD79a |
| GBD | CD86 | DAP10 | CD79b |
| GBD | CD86 | DAP12 | CD8 |
| GBD | CD86 | DAP12 | CD3ζ |
| GBD | CD86 | DAP12 | CD3δ |
| GBD | CD86 | DAP12 | CD3γ |
| GBD | CD86 | DAP12 | CD3ε |
| GBD | CD86 | DAP12 | FcγRI-γ |
| GBD | CD86 | DAP12 | FcγRIII-γ |
| GBD | CD86 | DAP12 | FcεRIβ |
| GBD | CD86 | DAP12 | FcεRIγ |
| GBD | CD86 | DAP12 | DAP10 |
| GBD | CD86 | DAP12 | DAP12 |
| GBD | CD86 | DAP12 | CD32 |
| GBD | CD86 | DAP12 | CD79a |
| GBD | CD86 | DAP12 | CD79b |
| GBD | CD86 | MyD88 | CD8 |
| GBD | CD86 | MyD88 | CD3ζ |
| GBD | CD86 | MyD88 | CD3δ |
| GBD | CD86 | MyD88 | CD3γ |
| GBD | CD86 | MyD88 | CD3ε |
| GBD | CD86 | MyD88 | FcγRI-γ |
| GBD | CD86 | MyD88 | FcγRIII-γ |
| GBD | CD86 | MyD88 | FcεRIβ |
| GBD | CD86 | MyD88 | FcεRIγ |
| GBD | CD86 | MyD88 | DAP10 |
| GBD | CD86 | MyD88 | DAP12 |
| GBD | CD86 | MyD88 | CD32 |
| GBD | CD86 | MyD88 | CD79a |
| GBD | CD86 | MyD88 | CD79b |
| GBD | CD86 | CD7 | CD8 |
| GBD | CD86 | CD7 | CD3ζ |
| GBD | CD86 | CD7 | CD3δ |
| GBD | CD86 | CD7 | CD3γ |
| GBD | CD86 | CD7 | CD3ε |
| GBD | CD86 | CD7 | FcγRI-γ |
| GBD | CD86 | CD7 | FcγRIII-γ |
| GBD | CD86 | CD7 | FcεRIβ |
| GBD | CD86 | CD7 | FcεRIγ |
| GBD | CD86 | CD7 | DAP10 |
| GBD | CD86 | CD7 | DAP12 |
| GBD | CD86 | CD7 | CD32 |
| GBD | CD86 | CD7 | CD79a |
| GBD | CD86 | CD7 | CD79b |
| GBD | CD86 | BTNL3 | CD8 |
| GBD | CD86 | BTNL3 | CD3ζ |
| GBD | CD86 | BTNL3 | CD3δ |
| GBD | CD86 | BTNL3 | CD3γ |
| GBD | CD86 | BTNL3 | CD3ε |
| GBD | CD86 | BTNL3 | FcγRI-γ |
| GBD | CD86 | BTNL3 | FcγRIII-γ |
| GBD | CD86 | BTNL3 | FcεRIβ |
| GBD | CD86 | BTNL3 | FcεRIγ |
| GBD | CD86 | BTNL3 | DAP10 |
| GBD | CD86 | BTNL3 | DAP12 |
| GBD | CD86 | BTNL3 | CD32 |
| GBD | CD86 | BTNL3 | CD79a |
| GBD | CD86 | BTNL3 | CD79b |
| GBD | CD86 | NKG2D | CD8 |
| GBD | CD86 | NKG2D | CD3ζ |

TABLE 3-continued

| | Third Generation CARs | | |
|---|---|---|---|
| | Co-stimulatory Signal | Co-stimulatory Signal | Signal Domain |
| GBD | CD86 | NKG2D | CD3δ |
| GBD | CD86 | NKG2D | CD3γ |
| GBD | CD86 | NKG2D | CD3ε |
| GBD | CD86 | NKG2D | FcγRI-γ |
| GBD | CD86 | NKG2D | FcγRIII-γ |
| GBD | CD86 | NKG2D | FcεRIβ |
| GBD | CD86 | NKG2D | FcεRIγ |
| GBD | CD86 | NKG2D | DAP10 |
| GBD | CD86 | NKG2D | DAP12 |
| GBD | CD86 | NKG2D | CD32 |
| GBD | CD86 | NKG2D | CD79a |
| GBD | CD86 | NKG2D | CD79b |
| GBD | OX40 | CD28 | CD8 |
| GBD | OX40 | CD28 | CD3ζ |
| GBD | OX40 | CD28 | CD3δ |
| GBD | OX40 | CD28 | CD3γ |
| GBD | OX40 | CD28 | CD3ε |
| GBD | OX40 | CD28 | FcγRI-γ |
| GBD | OX40 | CD28 | FcγRIII-γ |
| GBD | OX40 | CD28 | FcεRIβ |
| GBD | OX40 | CD28 | FcεRIγ |
| GBD | OX40 | CD28 | DAP10 |
| GBD | OX40 | CD28 | DAP12 |
| GBD | OX40 | CD28 | CD32 |
| GBD | OX40 | CD28 | CD79a |
| GBD | OX40 | CD28 | CD79b |
| GBD | OX40 | CD8 | CD8 |
| GBD | OX40 | CD8 | CD3ζ |
| GBD | OX40 | CD8 | CD3δ |
| GBD | OX40 | CD8 | CD3γ |
| GBD | OX40 | CD8 | CD3ε |
| GBD | OX40 | CD8 | FcγRI-γ |
| GBD | OX40 | CD8 | FcγRIII-γ |
| GBD | OX40 | CD8 | FcεRIβ |
| GBD | OX40 | CD8 | FcεRIγ |
| GBD | OX40 | CD8 | DAP10 |
| GBD | OX40 | CD8 | DAP12 |
| GBD | OX40 | CD8 | CD32 |
| GBD | OX40 | CD8 | CD79a |
| GBD | OX40 | CD8 | CD79b |
| GBD | OX40 | CD4 | CD8 |
| GBD | OX40 | CD4 | CD3ζ |
| GBD | OX40 | CD4 | CD3δ |
| GBD | OX40 | CD4 | CD3γ |
| GBD | OX40 | CD4 | CD3ε |
| GBD | OX40 | CD4 | FcγRI-γ |
| GBD | OX40 | CD4 | FcγRIII-γ |
| GBD | OX40 | CD4 | FcεRIβ |
| GBD | OX40 | CD4 | FcεRIγ |
| GBD | OX40 | CD4 | DAP10 |
| GBD | OX40 | CD4 | DAP12 |
| GBD | OX40 | CD4 | CD32 |
| GBD | OX40 | CD4 | CD79a |
| GBD | OX40 | CD4 | CD79b |
| GBD | OX40 | b2c | CD8 |
| GBD | OX40 | b2c | CD3ζ |
| GBD | OX40 | b2c | CD3δ |
| GBD | OX40 | b2c | CD3γ |
| GBD | OX40 | b2c | CD3ε |
| GBD | OX40 | b2c | FcγRI-γ |
| GBD | OX40 | b2c | FcγRIII-γ |
| GBD | OX40 | b2c | FcεRIβ |
| GBD | OX40 | b2c | FcεRIγ |
| GBD | OX40 | b2c | DAP10 |
| GBD | OX40 | b2c | DAP12 |
| GBD | OX40 | b2c | CD32 |
| GBD | OX40 | b2c | CD79a |
| GBD | OX40 | b2c | CD79b |
| GBD | OX40 | CD137/41BB | CD8 |
| GBD | OX40 | CD137/41BB | CD3ζ |
| GBD | OX40 | CD137/41BB | CD3δ |
| GBD | OX40 | CD137/41BB | CD3γ |
| GBD | OX40 | CD137/41BB | CD3ε |
| GBD | OX40 | CD137/41BB | FcγRI-γ |
| GBD | OX40 | CD137/41BB | FcγRIII-γ |
| GBD | OX40 | CD137/41BB | FcεRIβ |
| GBD | OX40 | CD137/41BB | FcεRIγ |
| GBD | OX40 | CD137/41BB | DAP10 |
| GBD | OX40 | CD137/41BB | DAP12 |
| GBD | OX40 | CD137/41BB | CD32 |
| GBD | OX40 | CD137/41BB | CD79a |
| GBD | OX40 | CD137/41BB | CD79b |
| GBD | OX40 | ICOS | CD8 |
| GBD | OX40 | ICOS | CD3ζ |
| GBD | OX40 | ICOS | CD3δ |
| GBD | OX40 | ICOS | CD3γ |
| GBD | OX40 | ICOS | CD3ε |
| GBD | OX40 | ICOS | FcγRI-γ |
| GBD | OX40 | ICOS | FcγRIII-γ |
| GBD | OX40 | ICOS | FcεRIβ |
| GBD | OX40 | ICOS | FcεRIγ |
| GBD | OX40 | ICOS | DAP10 |
| GBD | OX40 | ICOS | DAP12 |
| GBD | OX40 | ICOS | CD32 |
| GBD | OX40 | ICOS | CD79a |
| GBD | OX40 | ICOS | CD79b |
| GBD | OX40 | CD27 | CD8 |
| GBD | OX40 | CD27 | CD3ζ |
| GBD | OX40 | CD27 | CD3δ |
| GBD | OX40 | CD27 | CD3γ |
| GBD | OX40 | CD27 | CD3ε |
| GBD | OX40 | CD27 | FcγRI-γ |
| GBD | OX40 | CD27 | FcγRIII-γ |
| GBD | OX40 | CD27 | FcεRIβ |
| GBD | OX40 | CD27 | FcεRIγ |
| GBD | OX40 | CD27 | DAP10 |
| GBD | OX40 | CD27 | DAP12 |
| GBD | OX40 | CD27 | CD32 |
| GBD | OX40 | CD27 | CD79a |
| GBD | OX40 | CD27 | CD79b |
| GBD | OX40 | CD28δ | CD8 |
| GBD | OX40 | CD28δ | CD3ζ |
| GBD | OX40 | CD28δ | CD3δ |
| GBD | OX40 | CD28δ | CD3γ |
| GBD | OX40 | CD28δ | CD3ε |
| GBD | OX40 | CD28δ | FcγRI-γ |
| GBD | OX40 | CD28δ | FcγRIII-γ |
| GBD | OX40 | CD28δ | FcεRIβ |
| GBD | OX40 | CD28δ | FcεRIγ |
| GBD | OX40 | CD28δ | DAP10 |
| GBD | OX40 | CD28δ | DAP12 |
| GBD | OX40 | CD28δ | CD32 |
| GBD | OX40 | CD28δ | CD79a |
| GBD | OX40 | CD28δ | CD79b |
| GBD | OX40 | CD80 | CD8 |
| GBD | OX40 | CD80 | CD3ζ |
| GBD | OX40 | CD80 | CD3δ |
| GBD | OX40 | CD80 | CD3γ |
| GBD | OX40 | CD80 | CD3ε |
| GBD | OX40 | CD80 | FcγRI-γ |
| GBD | OX40 | CD80 | FcγRIII-γ |
| GBD | OX40 | CD80 | FcεRIβ |
| GBD | OX40 | CD80 | FcεRIγ |
| GBD | OX40 | CD80 | DAP10 |
| GBD | OX40 | CD80 | DAP12 |
| GBD | OX40 | CD80 | CD32 |
| GBD | OX40 | CD80 | CD79a |
| GBD | OX40 | CD80 | CD79b |
| GBD | OX40 | CD86 | CD8 |
| GBD | OX40 | CD86 | CD3ζ |
| GBD | OX40 | CD86 | CD3δ |
| GBD | OX40 | CD86 | CD3γ |
| GBD | OX40 | CD86 | CD3ε |
| GBD | OX40 | CD86 | FcγRI-γ |
| GBD | OX40 | CD86 | FcγRIII-γ |
| GBD | OX40 | CD86 | FcεRIβ |
| GBD | OX40 | CD86 | FcεRIγ |
| GBD | OX40 | CD86 | DAP10 |
| GBD | OX40 | CD86 | DAP12 |
| GBD | OX40 | CD86 | CD32 |

TABLE 3-continued

Third Generation CARs

| | Co-stimulatory Signal | Co-stimulatory Signal | Signal Domain |
|---|---|---|---|
| GBD | OX40 | CD86 | CD79a |
| GBD | OX40 | CD86 | CD79b |
| GBD | OX40 | OX40 | CD8 |
| GBD | OX40 | OX40 | CD3ζ |
| GBD | OX40 | OX40 | CD3δ |
| GBD | OX40 | OX40 | CD3γ |
| GBD | OX40 | OX40 | CD3ε |
| GBD | OX40 | OX40 | FcγRI-γ |
| GBD | OX40 | OX40 | FcγRIII-γ |
| GBD | OX40 | OX40 | FcεRIβ |
| GBD | OX40 | OX40 | FcεRIγ |
| GBD | OX40 | OX40 | DAP10 |
| GBD | OX40 | OX40 | DAP12 |
| GBD | OX40 | OX40 | CD32 |
| GBD | OX40 | OX40 | CD79a |
| GBD | OX40 | OX40 | CD79b |
| GBD | OX40 | DAP10 | CD8 |
| GBD | OX40 | DAP10 | CD3ζ |
| GBD | OX40 | DAP10 | CD3δ |
| GBD | OX40 | DAP10 | CD3γ |
| GBD | OX40 | DAP10 | CD3ε |
| GBD | OX40 | DAP10 | FcγRI-γ |
| GBD | OX40 | DAP10 | FcγRIII-γ |
| GBD | OX40 | DAP10 | FcεRIβ |
| GBD | OX40 | DAP10 | FcεRIγ |
| GBD | OX40 | DAP10 | DAP10 |
| GBD | OX40 | DAP10 | DAP12 |
| GBD | OX40 | DAP10 | CD32 |
| GBD | OX40 | DAP10 | CD79a |
| GBD | OX40 | DAP10 | CD79b |
| GBD | OX40 | DAP12 | CD8 |
| GBD | OX40 | DAP12 | CD3ζ |
| GBD | OX40 | DAP12 | CD3δ |
| GBD | OX40 | DAP12 | CD3γ |
| GBD | OX40 | DAP12 | CD3ε |
| GBD | OX40 | DAP12 | FcγRI-γ |
| GBD | OX40 | DAP12 | FcγRIII-γ |
| GBD | OX40 | DAP12 | FcεRIβ |
| GBD | OX40 | DAP12 | FcεRIγ |
| GBD | OX40 | DAP12 | DAP10 |
| GBD | OX40 | DAP12 | DAP12 |
| GBD | OX40 | DAP12 | CD32 |
| GBD | OX40 | DAP12 | CD79a |
| GBD | OX40 | DAP12 | CD79b |
| GBD | OX40 | MyD88 | CD8 |
| GBD | OX40 | MyD88 | CD3ζ |
| GBD | OX40 | MyD88 | CD3δ |
| GBD | OX40 | MyD88 | CD3γ |
| GBD | OX40 | MyD88 | CD3ε |
| GBD | OX40 | MyD88 | FcγRI-γ |
| GBD | OX40 | MyD88 | FcγRIII-γ |
| GBD | OX40 | MyD88 | FcεRIβ |
| GBD | OX40 | MyD88 | FcεRIγ |
| GBD | OX40 | MyD88 | DAP10 |
| GBD | OX40 | MyD88 | DAP12 |
| GBD | OX40 | MyD88 | CD32 |
| GBD | OX40 | MyD88 | CD79a |
| GBD | OX40 | MyD88 | CD79b |
| GBD | OX40 | CD7 | CD8 |
| GBD | OX40 | CD7 | CD3ζ |
| GBD | OX40 | CD7 | CD3δ |
| GBD | OX40 | CD7 | CD3γ |
| GBD | OX40 | CD7 | CD3ε |
| GBD | OX40 | CD7 | FcγRI-γ |
| GBD | OX40 | CD7 | FcγRIII-γ |
| GBD | OX40 | CD7 | FcεRIβ |
| GBD | OX40 | CD7 | FcεRIγ |
| GBD | OX40 | CD7 | DAP10 |
| GBD | OX40 | CD7 | DAP12 |
| GBD | OX40 | CD7 | CD32 |
| GBD | OX40 | CD7 | CD79a |
| GBD | OX40 | CD7 | CD79b |
| GBD | OX40 | BTNL3 | CD8 |
| GBD | OX40 | BTNL3 | CD3ζ |
| GBD | OX40 | BTNL3 | CD3δ |
| GBD | OX40 | BTNL3 | CD3γ |
| GBD | OX40 | BTNL3 | CD3ε |
| GBD | OX40 | BTNL3 | FcγRI-γ |
| GBD | OX40 | BTNL3 | FcγRIII-γ |
| GBD | OX40 | BTNL3 | FcεRIβ |
| GBD | OX40 | BTNL3 | FcεRIγ |
| GBD | OX40 | BTNL3 | DAP10 |
| GBD | OX40 | BTNL3 | DAP12 |
| GBD | OX40 | BTNL3 | CD32 |
| GBD | OX40 | BTNL3 | CD79a |
| GBD | OX40 | BTNL3 | CD79b |
| GBD | OX40 | NKG2D | CD8 |
| GBD | OX40 | NKG2D | CD3ζ |
| GBD | OX40 | NKG2D | CD3δ |
| GBD | OX40 | NKG2D | CD3γ |
| GBD | OX40 | NKG2D | CD3ε |
| GBD | OX40 | NKG2D | FcγRI-γ |
| GBD | OX40 | NKG2D | FcγRIII-γ |
| GBD | OX40 | NKG2D | FcεRIβ |
| GBD | OX40 | NKG2D | FcεRIγ |
| GBD | OX40 | NKG2D | DAP10 |
| GBD | OX40 | NKG2D | DAP12 |
| GBD | OX40 | NKG2D | CD32 |
| GBD | OX40 | NKG2D | CD79a |
| GBD | OX40 | NKG2D | CD79b |
| GBD | DAP10 | CD28 | CD8 |
| GBD | DAP10 | CD28 | CD3ζ |
| GBD | DAP10 | CD28 | CD3δ |
| GBD | DAP10 | CD28 | CD3γ |
| GBD | DAP10 | CD28 | CD3ε |
| GBD | DAP10 | CD28 | FcγRI-γ |
| GBD | DAP10 | CD28 | FcγRIII-γ |
| GBD | DAP10 | CD28 | FcεRIβ |
| GBD | DAP10 | CD28 | FcεRIγ |
| GBD | DAP10 | CD28 | DAP10 |
| GBD | DAP10 | CD28 | DAP12 |
| GBD | DAP10 | CD28 | CD32 |
| GBD | DAP10 | CD28 | CD79a |
| GBD | DAP10 | CD28 | CD79b |
| GBD | DAP10 | CD8 | CD8 |
| GBD | DAP10 | CD8 | CD3ζ |
| GBD | DAP10 | CD8 | CD3δ |
| GBD | DAP10 | CD8 | CD3γ |
| GBD | DAP10 | CD8 | CD3ε |
| GBD | DAP10 | CD8 | FcγRI-γ |
| GBD | DAP10 | CD8 | FcγRIII-γ |
| GBD | DAP10 | CD8 | FcεRIβ |
| GBD | DAP10 | CD8 | FcεRIγ |
| GBD | DAP10 | CD8 | DAP10 |
| GBD | DAP10 | CD8 | DAP12 |
| GBD | DAP10 | CD8 | CD32 |
| GBD | DAP10 | CD8 | CD79a |
| GBD | DAP10 | CD8 | CD79b |
| GBD | DAP10 | CD4 | CD8 |
| GBD | DAP10 | CD4 | CD3ζ |
| GBD | DAP10 | CD4 | CD3δ |
| GBD | DAP10 | CD4 | CD3γ |
| GBD | DAP10 | CD4 | CD3ε |
| GBD | DAP10 | CD4 | FcγRI-γ |
| GBD | DAP10 | CD4 | FcγRIII-γ |
| GBD | DAP10 | CD4 | FcεRIβ |
| GBD | DAP10 | CD4 | FcεRIγ |
| GBD | DAP10 | CD4 | DAP10 |
| GBD | DAP10 | CD4 | DAP12 |
| GBD | DAP10 | CD4 | CD32 |
| GBD | DAP10 | CD4 | CD79a |
| GBD | DAP10 | CD4 | CD79b |
| GBD | DAP10 | b2c | CD8 |
| GBD | DAP10 | b2c | CD3ζ |
| GBD | DAP10 | b2c | CD3δ |
| GBD | DAP10 | b2c | CD3γ |
| GBD | DAP10 | b2c | CD3ε |
| GBD | DAP10 | b2c | FcγRI-γ |
| GBD | DAP10 | b2c | FcγRIII-γ |
| GBD | DAP10 | b2c | FcεRIβ |

TABLE 3-continued

Third Generation CARs

| | Co-stimulatory Signal | Co-stimulatory Signal | Signal Domain |
|---|---|---|---|
| GBD | DAP10 | b2c | FcεRIγ |
| GBD | DAP10 | b2c | DAP10 |
| GBD | DAP10 | b2c | DAP12 |
| GBD | DAP10 | b2c | CD32 |
| GBD | DAP10 | b2c | CD79a |
| GBD | DAP10 | b2c | CD79b |
| GBD | DAP10 | CD137/41BB | CD8 |
| GBD | DAP10 | CD137/41BB | CD3ζ |
| GBD | DAP10 | CD137/41BB | CD3δ |
| GBD | DAP10 | CD137/41BB | CD3γ |
| GBD | DAP10 | CD137/41BB | CD3ε |
| GBD | DAP10 | CD137/41BB | FcγRI-γ |
| GBD | DAP10 | CD137/41BB | FcγRIII-γ |
| GBD | DAP10 | CD137/41BB | FcεRIβ |
| GBD | DAP10 | CD137/41BB | FcεRIγ |
| GBD | DAP10 | CD137/41BB | DAP10 |
| GBD | DAP10 | CD137/41BB | DAP12 |
| GBD | DAP10 | CD137/41BB | CD32 |
| GBD | DAP10 | CD137/41BB | CD79a |
| GBD | DAP10 | CD137/41BB | CD79b |
| GBD | DAP10 | ICOS | CD8 |
| GBD | DAP10 | ICOS | CD3ζ |
| GBD | DAP10 | ICOS | CD3δ |
| GBD | DAP10 | ICOS | CD3γ |
| GBD | DAP10 | ICOS | CD3ε |
| GBD | DAP10 | ICOS | FcγRI-γ |
| GBD | DAP10 | ICOS | FcγRIII-γ |
| GBD | DAP10 | ICOS | FcεRIβ |
| GBD | DAP10 | ICOS | FcεRIγ |
| GBD | DAP10 | ICOS | DAP10 |
| GBD | DAP10 | ICOS | DAP12 |
| GBD | DAP10 | ICOS | CD32 |
| GBD | DAP10 | ICOS | CD79a |
| GBD | DAP10 | ICOS | CD79b |
| GBD | DAP10 | CD27 | CD8 |
| GBD | DAP10 | CD27 | CD3ζ |
| GBD | DAP10 | CD27 | CD3δ |
| GBD | DAP10 | CD27 | CD3γ |
| GBD | DAP10 | CD27 | CD3ε |
| GBD | DAP10 | CD27 | FcγRI-γ |
| GBD | DAP10 | CD27 | FcγRIII-γ |
| GBD | DAP10 | CD27 | FcεRIβ |
| GBD | DAP10 | CD27 | FcεRIγ |
| GBD | DAP10 | CD27 | DAP10 |
| GBD | DAP10 | CD27 | DAP12 |
| GBD | DAP10 | CD27 | CD32 |
| GBD | DAP10 | CD27 | CD79a |
| GBD | DAP10 | CD27 | CD79b |
| GBD | DAP10 | CD28δ | CD8 |
| GBD | DAP10 | CD28δ | CD3ζ |
| GBD | DAP10 | CD28δ | CD3δ |
| GBD | DAP10 | CD28δ | CD3γ |
| GBD | DAP10 | CD28δ | CD3ε |
| GBD | DAP10 | CD28δ | FcγRI-γ |
| GBD | DAP10 | CD28δ | FcγRIII-γ |
| GBD | DAP10 | CD28δ | FcεRIβ |
| GBD | DAP10 | CD28δ | FcεRIγ |
| GBD | DAP10 | CD28δ | DAP10 |
| GBD | DAP10 | CD28δ | DAP12 |
| GBD | DAP10 | CD28δ | CD32 |
| GBD | DAP10 | CD28δ | CD79a |
| GBD | DAP10 | CD28δ | CD79b |
| GBD | DAP10 | CD80 | CD8 |
| GBD | DAP10 | CD80 | CD3ζ |
| GBD | DAP10 | CD80 | CD3δ |
| GBD | DAP10 | CD80 | CD3γ |
| GBD | DAP10 | CD80 | CD3ε |
| GBD | DAP10 | CD80 | FcγRI-γ |
| GBD | DAP10 | CD80 | FcγRIII-γ |
| GBD | DAP10 | CD80 | FcεRIβ |
| GBD | DAP10 | CD80 | FcεRIγ |
| GBD | DAP10 | CD80 | DAP10 |
| GBD | DAP10 | CD80 | DAP12 |
| GBD | DAP10 | CD80 | CD32 |
| GBD | DAP10 | CD80 | CD79a |
| GBD | DAP10 | CD80 | CD79b |
| GBD | DAP10 | CD86 | CD8 |
| GBD | DAP10 | CD86 | CD3ζ |
| GBD | DAP10 | CD86 | CD3δ |
| GBD | DAP10 | CD86 | CD3γ |
| GBD | DAP10 | CD86 | CD3ε |
| GBD | DAP10 | CD86 | FcγRI-γ |
| GBD | DAP10 | CD86 | FcγRIII-γ |
| GBD | DAP10 | CD86 | FcεRIβ |
| GBD | DAP10 | CD86 | FcεRIγ |
| GBD | DAP10 | CD86 | DAP10 |
| GBD | DAP10 | CD86 | DAP12 |
| GBD | DAP10 | CD86 | CD32 |
| GBD | DAP10 | CD86 | CD79a |
| GBD | DAP10 | CD86 | CD79b |
| GBD | DAP10 | OX40 | CD8 |
| GBD | DAP10 | OX40 | CD3ζ |
| GBD | DAP10 | OX40 | CD3δ |
| GBD | DAP10 | OX40 | CD3γ |
| GBD | DAP10 | OX40 | CD3ε |
| GBD | DAP10 | OX40 | FcγRI-γ |
| GBD | DAP10 | OX40 | FcγRIII-γ |
| GBD | DAP10 | OX40 | FcεRIβ |
| GBD | DAP10 | OX40 | FcεRIγ |
| GBD | DAP10 | OX40 | DAP10 |
| GBD | DAP10 | OX40 | DAP12 |
| GBD | DAP10 | OX40 | CD32 |
| GBD | DAP10 | OX40 | CD79a |
| GBD | DAP10 | OX40 | CD79b |
| GBD | DAP10 | DAP10 | CD8 |
| GBD | DAP10 | DAP10 | CD3ζ |
| GBD | DAP10 | DAP10 | CD3δ |
| GBD | DAP10 | DAP10 | CD3γ |
| GBD | DAP10 | DAP10 | CD3ε |
| GBD | DAP10 | DAP10 | FcγRI-γ |
| GBD | DAP10 | DAP10 | FcγRIII-γ |
| GBD | DAP10 | DAP10 | FcεRIβ |
| GBD | DAP10 | DAP10 | FcεRIγ |
| GBD | DAP10 | DAP10 | DAP10 |
| GBD | DAP10 | DAP10 | DAP12 |
| GBD | DAP10 | DAP10 | CD32 |
| GBD | DAP10 | DAP10 | CD79a |
| GBD | DAP10 | DAP10 | CD79b |
| GBD | DAP10 | DAP12 | CD8 |
| GBD | DAP10 | DAP12 | CD3ζ |
| GBD | DAP10 | DAP12 | CD3δ |
| GBD | DAP10 | DAP12 | CD3γ |
| GBD | DAP10 | DAP12 | CD3ε |
| GBD | DAP10 | DAP12 | FcγRI-γ |
| GBD | DAP10 | DAP12 | FcγRIII-γ |
| GBD | DAP10 | DAP12 | FcεRIβ |
| GBD | DAP10 | DAP12 | FcεRIγ |
| GBD | DAP10 | DAP12 | DAP10 |
| GBD | DAP10 | DAP12 | DAP12 |
| GBD | DAP10 | DAP12 | CD32 |
| GBD | DAP10 | DAP12 | CD79a |
| GBD | DAP10 | DAP12 | CD79b |
| GBD | DAP10 | MyD88 | CD8 |
| GBD | DAP10 | MyD88 | CD3ζ |
| GBD | DAP10 | MyD88 | CD3δ |
| GBD | DAP10 | MyD88 | CD3γ |
| GBD | DAP10 | MyD88 | CD3ε |
| GBD | DAP10 | MyD88 | FcγRI-γ |
| GBD | DAP10 | MyD88 | FcγRIII-γ |
| GBD | DAP10 | MyD88 | FcεRIβ |
| GBD | DAP10 | MyD88 | FcεRIγ |
| GBD | DAP10 | MyD88 | DAP10 |
| GBD | DAP10 | MyD88 | DAP12 |
| GBD | DAP10 | MyD88 | CD32 |
| GBD | DAP10 | MyD88 | CD79a |
| GBD | DAP10 | MyD88 | CD79b |
| GBD | DAP10 | CD7 | CD8 |
| GBD | DAP10 | CD7 | CD3ζ |
| GBD | DAP10 | CD7 | CD3δ |
| GBD | DAP10 | CD7 | CD3γ |

TABLE 3-continued

Third Generation CARs

| | Co-stimulatory Signal | Co-stimulatory Signal | Signal Domain |
|---|---|---|---|
| GBD | DAP10 | CD7 | CD3ε |
| GBD | DAP10 | CD7 | FcγRI-γ |
| GBD | DAP10 | CD7 | FcγRIII-γ |
| GBD | DAP10 | CD7 | FcεRIβ |
| GBD | DAP10 | CD7 | FcεRIγ |
| GBD | DAP10 | CD7 | DAP10 |
| GBD | DAP10 | CD7 | DAP12 |
| GBD | DAP10 | CD7 | CD32 |
| GBD | DAP10 | CD7 | CD79a |
| GBD | DAP10 | CD7 | CD79b |
| GBD | DAP10 | BTNL3 | CD8 |
| GBD | DAP10 | BTNL3 | CD3ζ |
| GBD | DAP10 | BTNL3 | CD3δ |
| GBD | DAP10 | BTNL3 | CD3γ |
| GBD | DAP10 | BTNL3 | CD3ε |
| GBD | DAP10 | BTNL3 | FcγRI-γ |
| GBD | DAP10 | BTNL3 | FcγRIII-γ |
| GBD | DAP10 | BTNL3 | FcεRIβ |
| GBD | DAP10 | BTNL3 | FcεRIγ |
| GBD | DAP10 | BTNL3 | DAP10 |
| GBD | DAP10 | BTNL3 | DAP12 |
| GBD | DAP10 | BTNL3 | CD32 |
| GBD | DAP10 | BTNL3 | CD79a |
| GBD | DAP10 | BTNL3 | CD79b |
| GBD | DAP10 | NKG2D | CD8 |
| GBD | DAP10 | NKG2D | CD3ζ |
| GBD | DAP10 | NKG2D | CD3δ |
| GBD | DAP10 | NKG2D | CD3γ |
| GBD | DAP10 | NKG2D | CD3ε |
| GBD | DAP10 | NKG2D | FcγRI-γ |
| GBD | DAP10 | NKG2D | FcγRIII-γ |
| GBD | DAP10 | NKG2D | FcεRIβ |
| GBD | DAP10 | NKG2D | FcεRIγ |
| GBD | DAP10 | NKG2D | DAP10 |
| GBD | DAP10 | NKG2D | DAP12 |
| GBD | DAP10 | NKG2D | CD32 |
| GBD | DAP10 | NKG2D | CD79a |
| GBD | DAP10 | NKG2D | CD79b |
| GBD | DAP12 | CD28 | CD8 |
| GBD | DAP12 | CD28 | CD3ζ |
| GBD | DAP12 | CD28 | CD3δ |
| GBD | DAP12 | CD28 | CD3γ |
| GBD | DAP12 | CD28 | CD3ε |
| GBD | DAP12 | CD28 | FcγRI-γ |
| GBD | DAP12 | CD28 | FcγRIII-γ |
| GBD | DAP12 | CD28 | FcεRIβ |
| GBD | DAP12 | CD28 | FcεRIγ |
| GBD | DAP12 | CD28 | DAP10 |
| GBD | DAP12 | CD28 | DAP12 |
| GBD | DAP12 | CD28 | CD32 |
| GBD | DAP12 | CD28 | CD79a |
| GBD | DAP12 | CD28 | CD79b |
| GBD | DAP12 | CD8 | CD8 |
| GBD | DAP12 | CD8 | CD3ζ |
| GBD | DAP12 | CD8 | CD3δ |
| GBD | DAP12 | CD8 | CD3γ |
| GBD | DAP12 | CD8 | CD3ε |
| GBD | DAP12 | CD8 | FcγRI-γ |
| GBD | DAP12 | CD8 | FcγRIII-γ |
| GBD | DAP12 | CD8 | FcεRIβ |
| GBD | DAP12 | CD8 | FcεRIγ |
| GBD | DAP12 | CD8 | DAP10 |
| GBD | DAP12 | CD8 | DAP12 |
| GBD | DAP12 | CD8 | CD32 |
| GBD | DAP12 | CD8 | CD79a |
| GBD | DAP12 | CD8 | CD79b |
| GBD | DAP12 | CD4 | CD8 |
| GBD | DAP12 | CD4 | CD3ζ |
| GBD | DAP12 | CD4 | CD3δ |
| GBD | DAP12 | CD4 | CD3γ |
| GBD | DAP12 | CD4 | CD3ε |
| GBD | DAP12 | CD4 | FcγRI-γ |
| GBD | DAP12 | CD4 | FcγRIII-γ |
| GBD | DAP12 | CD4 | FcεRIβ |
| GBD | DAP12 | CD4 | FcεRIγ |
| GBD | DAP12 | CD4 | DAP10 |
| GBD | DAP12 | CD4 | DAP12 |
| GBD | DAP12 | CD4 | CD32 |
| GBD | DAP12 | CD4 | CD79a |
| GBD | DAP12 | CD4 | CD79b |
| GBD | DAP12 | b2c | CD8 |
| GBD | DAP12 | b2c | CD3ζ |
| GBD | DAP12 | b2c | CD3δ |
| GBD | DAP12 | b2c | CD3γ |
| GBD | DAP12 | b2c | CD3ε |
| GBD | DAP12 | b2c | FcγRI-γ |
| GBD | DAP12 | b2c | FcγRIII-γ |
| GBD | DAP12 | b2c | FcεRIβ |
| GBD | DAP12 | b2c | FcεRIγ |
| GBD | DAP12 | b2c | DAP10 |
| GBD | DAP12 | b2c | DAP12 |
| GBD | DAP12 | b2c | CD32 |
| GBD | DAP12 | b2c | CD79a |
| GBD | DAP12 | b2c | CD79b |
| GBD | DAP12 | CD137/41BB | CD8 |
| GBD | DAP12 | CD137/41BB | CD3ζ |
| GBD | DAP12 | CD137/41BB | CD3δ |
| GBD | DAP12 | CD137/41BB | CD3γ |
| GBD | DAP12 | CD137/41BB | CD3ε |
| GBD | DAP12 | CD137/41BB | FcγRI-γ |
| GBD | DAP12 | CD137/41BB | FcγRIII-γ |
| GBD | DAP12 | CD137/41BB | FcεRIβ |
| GBD | DAP12 | CD137/41BB | FcεRIγ |
| GBD | DAP12 | CD137/41BB | DAP10 |
| GBD | DAP12 | CD137/41BB | DAP12 |
| GBD | DAP12 | CD137/41BB | CD32 |
| GBD | DAP12 | CD137/41BB | CD79a |
| GBD | DAP12 | CD137/41BB | CD79b |
| GBD | DAP12 | ICOS | CD8 |
| GBD | DAP12 | ICOS | CD3ζ |
| GBD | DAP12 | ICOS | CD3δ |
| GBD | DAP12 | ICOS | CD3γ |
| GBD | DAP12 | ICOS | CD3ε |
| GBD | DAP12 | ICOS | FcγRI-γ |
| GBD | DAP12 | ICOS | FcγRIII-γ |
| GBD | DAP12 | ICOS | FcεRIβ |
| GBD | DAP12 | ICOS | FcεRIγ |
| GBD | DAP12 | ICOS | DAP10 |
| GBD | DAP12 | ICOS | DAP12 |
| GBD | DAP12 | ICOS | CD32 |
| GBD | DAP12 | ICOS | CD79a |
| GBD | DAP12 | ICOS | CD79b |
| GBD | DAP12 | CD27 | CD8 |
| GBD | DAP12 | CD27 | CD3ζ |
| GBD | DAP12 | CD27 | CD3δ |
| GBD | DAP12 | CD27 | CD3γ |
| GBD | DAP12 | CD27 | CD3ε |
| GBD | DAP12 | CD27 | FcγRI-γ |
| GBD | DAP12 | CD27 | FcγRIII-γ |
| GBD | DAP12 | CD27 | FcεRIβ |
| GBD | DAP12 | CD27 | FcεRIγ |
| GBD | DAP12 | CD27 | DAP10 |
| GBD | DAP12 | CD27 | DAP12 |
| GBD | DAP12 | CD27 | CD32 |
| GBD | DAP12 | CD27 | CD79a |
| GBD | DAP12 | CD27 | CD79b |
| GBD | DAP12 | CD28δ | CD8 |
| GBD | DAP12 | CD28δ | CD3ζ |
| GBD | DAP12 | CD28δ | CD3δ |
| GBD | DAP12 | CD28δ | CD3γ |
| GBD | DAP12 | CD28δ | CD3ε |
| GBD | DAP12 | CD28δ | FcγRI-γ |
| GBD | DAP12 | CD28δ | FcγRIII-γ |
| GBD | DAP12 | CD28δ | FcεRIβ |
| GBD | DAP12 | CD28δ | FcεRIγ |
| GBD | DAP12 | CD28δ | DAP10 |
| GBD | DAP12 | CD28δ | DAP12 |
| GBD | DAP12 | CD28δ | CD32 |
| GBD | DAP12 | CD28δ | CD79a |
| GBD | DAP12 | CD28δ | CD79b |

TABLE 3-continued

Third Generation CARs

| | Co-stimulatory Signal | Co-stimulatory Signal | Signal Domain |
|---|---|---|---|
| GBD | DAP12 | CD80 | CD8 |
| GBD | DAP12 | CD80 | CD3ζ |
| GBD | DAP12 | CD80 | CD3δ |
| GBD | DAP12 | CD80 | CD3γ |
| GBD | DAP12 | CD80 | CD3ε |
| GBD | DAP12 | CD80 | FcγRI-γ |
| GBD | DAP12 | CD80 | FcγRIII-γ |
| GBD | DAP12 | CD80 | FcεRIβ |
| GBD | DAP12 | CD80 | FcεRIγ |
| GBD | DAP12 | CD80 | DAP10 |
| GBD | DAP12 | CD80 | DAP12 |
| GBD | DAP12 | CD80 | CD32 |
| GBD | DAP12 | CD80 | CD79a |
| GBD | DAP12 | CD80 | CD79b |
| GBD | DAP12 | CD86 | CD8 |
| GBD | DAP12 | CD86 | CD3ζ |
| GBD | DAP12 | CD86 | CD3δ |
| GBD | DAP12 | CD86 | CD3γ |
| GBD | DAP12 | CD86 | CD3ε |
| GBD | DAP12 | CD86 | FcγRI-γ |
| GBD | DAP12 | CD86 | FcγRIII-γ |
| GBD | DAP12 | CD86 | FcεRIβ |
| GBD | DAP12 | CD86 | FcεRIγ |
| GBD | DAP12 | CD86 | DAP10 |
| GBD | DAP12 | CD86 | DAP12 |
| GBD | DAP12 | CD86 | CD32 |
| GBD | DAP12 | CD86 | CD79a |
| GBD | DAP12 | CD86 | CD79b |
| GBD | DAP12 | OX40 | CD8 |
| GBD | DAP12 | OX40 | CD3ζ |
| GBD | DAP12 | OX40 | CD3δ |
| GBD | DAP12 | OX40 | CD3γ |
| GBD | DAP12 | OX40 | CD3ε |
| GBD | DAP12 | OX40 | FcγRI-γ |
| GBD | DAP12 | OX40 | FcγRIII-γ |
| GBD | DAP12 | OX40 | FcεRIβ |
| GBD | DAP12 | OX40 | FcεRIγ |
| GBD | DAP12 | OX40 | DAP10 |
| GBD | DAP12 | OX40 | DAP12 |
| GBD | DAP12 | OX40 | CD32 |
| GBD | DAP12 | OX40 | CD79a |
| GBD | DAP12 | OX40 | CD79b |
| GBD | DAP12 | DAP10 | CD8 |
| GBD | DAP12 | DAP10 | CD3ζ |
| GBD | DAP12 | DAP10 | CD3δ |
| GBD | DAP12 | DAP10 | CD3γ |
| GBD | DAP12 | DAP10 | CD3ε |
| GBD | DAP12 | DAP10 | FcγRI-γ |
| GBD | DAP12 | DAP10 | FcγRIII-γ |
| GBD | DAP12 | DAP10 | FcεRIβ |
| GBD | DAP12 | DAP10 | FcεRIγ |
| GBD | DAP12 | DAP10 | DAP10 |
| GBD | DAP12 | DAP10 | DAP12 |
| GBD | DAP12 | DAP10 | CD32 |
| GBD | DAP12 | DAP10 | CD79a |
| GBD | DAP12 | DAP10 | CD79b |
| GBD | DAP12 | DAP12 | CD8 |
| GBD | DAP12 | DAP12 | CD3ζ |
| GBD | DAP12 | DAP12 | CD3δ |
| GBD | DAP12 | DAP12 | CD3γ |
| GBD | DAP12 | DAP12 | CD3ε |
| GBD | DAP12 | DAP12 | FcγRI-γ |
| GBD | DAP12 | DAP12 | FcγRIII-γ |
| GBD | DAP12 | DAP12 | FcεRIβ |
| GBD | DAP12 | DAP12 | FcεRIγ |
| GBD | DAP12 | DAP12 | DAP10 |
| GBD | DAP12 | DAP12 | DAP12 |
| GBD | DAP12 | DAP12 | CD32 |
| GBD | DAP12 | DAP12 | CD79a |
| GBD | DAP12 | DAP12 | CD79b |
| GBD | DAP12 | MyD88 | CD8 |
| GBD | DAP12 | MyD88 | CD3ζ |
| GBD | DAP12 | MyD88 | CD3δ |
| GBD | DAP12 | MyD88 | CD3γ |
| GBD | DAP12 | MyD88 | CD3ε |
| GBD | DAP12 | MyD88 | FcγRI-γ |
| GBD | DAP12 | MyD88 | FcγRIII-γ |
| GBD | DAP12 | MyD88 | FcεRIβ |
| GBD | DAP12 | MyD88 | FcεRIγ |
| GBD | DAP12 | MyD88 | DAP10 |
| GBD | DAP12 | MyD88 | DAP12 |
| GBD | DAP12 | MyD88 | CD32 |
| GBD | DAP12 | MyD88 | CD79a |
| GBD | DAP12 | MyD88 | CD79b |
| GBD | DAP12 | CD7 | CD8 |
| GBD | DAP12 | CD7 | CD3ζ |
| GBD | DAP12 | CD7 | CD3δ |
| GBD | DAP12 | CD7 | CD3γ |
| GBD | DAP12 | CD7 | CD3ε |
| GBD | DAP12 | CD7 | FcγRI-γ |
| GBD | DAP12 | CD7 | FcγRIII-γ |
| GBD | DAP12 | CD7 | FcεRIβ |
| GBD | DAP12 | CD7 | FcεRIγ |
| GBD | DAP12 | CD7 | DAP10 |
| GBD | DAP12 | CD7 | DAP12 |
| GBD | DAP12 | CD7 | CD32 |
| GBD | DAP12 | CD7 | CD79a |
| GBD | DAP12 | CD7 | CD79b |
| GBD | DAP12 | BTNL3 | CD8 |
| GBD | DAP12 | BTNL3 | CD3ζ |
| GBD | DAP12 | BTNL3 | CD3δ |
| GBD | DAP12 | BTNL3 | CD3γ |
| GBD | DAP12 | BTNL3 | CD3ε |
| GBD | DAP12 | BTNL3 | FcγRI-γ |
| GBD | DAP12 | BTNL3 | FcγRIII-γ |
| GBD | DAP12 | BTNL3 | FcεRIβ |
| GBD | DAP12 | BTNL3 | FcεRIγ |
| GBD | DAP12 | BTNL3 | DAP10 |
| GBD | DAP12 | BTNL3 | DAP12 |
| GBD | DAP12 | BTNL3 | CD32 |
| GBD | DAP12 | BTNL3 | CD79a |
| GBD | DAP12 | BTNL3 | CD79b |
| GBD | DAP12 | NKG2D | CD8 |
| GBD | DAP12 | NKG2D | CD3ζ |
| GBD | DAP12 | NKG2D | CD3δ |
| GBD | DAP12 | NKG2D | CD3γ |
| GBD | DAP12 | NKG2D | CD3ε |
| GBD | DAP12 | NKG2D | FcγRI-γ |
| GBD | DAP12 | NKG2D | FcγRIII-γ |
| GBD | DAP12 | NKG2D | FcεRIβ |
| GBD | DAP12 | NKG2D | FcεRIγ |
| GBD | DAP12 | NKG2D | DAP10 |
| GBD | DAP12 | NKG2D | DAP12 |
| GBD | DAP12 | NKG2D | CD32 |
| GBD | DAP12 | NKG2D | CD79a |
| GBD | DAP12 | NKG2D | CD79b |
| GBD | MyD88 | CD28 | CD8 |
| GBD | MyD88 | CD28 | CD3ζ |
| GBD | MyD88 | CD28 | CD3δ |
| GBD | MyD88 | CD28 | CD3γ |
| GBD | MyD88 | CD28 | CD3ε |
| GBD | MyD88 | CD28 | FcγRI-γ |
| GBD | MyD88 | CD28 | FcγRIII-γ |
| GBD | MyD88 | CD28 | FcεRIβ |
| GBD | MyD88 | CD28 | FcεRIγ |
| GBD | MyD88 | CD28 | DAP10 |
| GBD | MyD88 | CD28 | DAP12 |
| GBD | MyD88 | CD28 | CD32 |
| GBD | MyD88 | CD28 | CD79a |
| GBD | MyD88 | CD28 | CD79b |
| GBD | MyD88 | CD8 | CD8 |
| GBD | MyD88 | CD8 | CD3ζ |
| GBD | MyD88 | CD8 | CD3δ |
| GBD | MyD88 | CD8 | CD3γ |
| GBD | MyD88 | CD8 | CD3ε |
| GBD | MyD88 | CD8 | FcγRI-γ |
| GBD | MyD88 | CD8 | FcγRIII-γ |
| GBD | MyD88 | CD8 | FcεRIβ |
| GBD | MyD88 | CD8 | FcεRIγ |
| GBD | MyD88 | CD8 | DAP10 |

TABLE 3-continued

Third Generation CARs

| | Co-stimulatory Signal | Co-stimulatory Signal | Signal Domain |
|---|---|---|---|
| GBD | MyD88 | CD8 | DAP12 |
| GBD | MyD88 | CD8 | CD32 |
| GBD | MyD88 | CD8 | CD79a |
| GBD | MyD88 | CD8 | CD79b |
| GBD | MyD88 | CD4 | CD8 |
| GBD | MyD88 | CD4 | CD3ζ |
| GBD | MyD88 | CD4 | CD3δ |
| GBD | MyD88 | CD4 | CD3γ |
| GBD | MyD88 | CD4 | CD3ε |
| GBD | MyD88 | CD4 | FcγRI-γ |
| GBD | MyD88 | CD4 | FcγRIII-γ |
| GBD | MyD88 | CD4 | FcεRIβ |
| GBD | MyD88 | CD4 | FcεRIγ |
| GBD | MyD88 | CD4 | DAP10 |
| GBD | MyD88 | CD4 | DAP12 |
| GBD | MyD88 | CD4 | CD32 |
| GBD | MyD88 | CD4 | CD79a |
| GBD | MyD88 | CD4 | CD79b |
| GBD | MyD88 | b2c | CD8 |
| GBD | MyD88 | b2c | CD3ζ |
| GBD | MyD88 | b2c | CD3δ |
| GBD | MyD88 | b2c | CD3γ |
| GBD | MyD88 | b2c | CD3ε |
| GBD | MyD88 | b2c | FcγRI-γ |
| GBD | MyD88 | b2c | FcγRIII-γ |
| GBD | MyD88 | b2c | FcεRIβ |
| GBD | MyD88 | b2c | FcεRIγ |
| GBD | MyD88 | b2c | DAP10 |
| GBD | MyD88 | b2c | DAP12 |
| GBD | MyD88 | b2c | CD32 |
| GBD | MyD88 | b2c | CD79a |
| GBD | MyD88 | b2c | CD79b |
| GBD | MyD88 | CD137/41BB | CD8 |
| GBD | MyD88 | CD137/41BB | CD3ζ |
| GBD | MyD88 | CD137/41BB | CD3δ |
| GBD | MyD88 | CD137/41BB | CD3γ |
| GBD | MyD88 | CD137/41BB | CD3ε |
| GBD | MyD88 | CD137/41BB | FcγRI-γ |
| GBD | MyD88 | CD137/41BB | FcγRIII-γ |
| GBD | MyD88 | CD137/41BB | FcεRIβ |
| GBD | MyD88 | CD137/41BB | FcεRIγ |
| GBD | MyD88 | CD137/41BB | DAP10 |
| GBD | MyD88 | CD137/41BB | DAP12 |
| GBD | MyD88 | CD137/41BB | CD32 |
| GBD | MyD88 | CD137/41BB | CD79a |
| GBD | MyD88 | CD137/41BB | CD79b |
| GBD | MyD88 | ICOS | CD8 |
| GBD | MyD88 | ICOS | CD3ζ |
| GBD | MyD88 | ICOS | CD3δ |
| GBD | MyD88 | ICOS | CD3γ |
| GBD | MyD88 | ICOS | CD3ε |
| GBD | MyD88 | ICOS | FcγRI-γ |
| GBD | MyD88 | ICOS | FcγRIII-γ |
| GBD | MyD88 | ICOS | FcεRIβ |
| GBD | MyD88 | ICOS | FcεRIγ |
| GBD | MyD88 | ICOS | DAP10 |
| GBD | MyD88 | ICOS | DAP12 |
| GBD | MyD88 | ICOS | CD32 |
| GBD | MyD88 | ICOS | CD79a |
| GBD | MyD88 | ICOS | CD79b |
| GBD | MyD88 | CD27 | CD8 |
| GBD | MyD88 | CD27 | CD3ζ |
| GBD | MyD88 | CD27 | CD3δ |
| GBD | MyD88 | CD27 | CD3γ |
| GBD | MyD88 | CD27 | CD3ε |
| GBD | MyD88 | CD27 | FcγRI-γ |
| GBD | MyD88 | CD27 | FcγRIII-γ |
| GBD | MyD88 | CD27 | FcεRIβ |
| GBD | MyD88 | CD27 | FcεRIγ |
| GBD | MyD88 | CD27 | DAP10 |
| GBD | MyD88 | CD27 | DAP12 |
| GBD | MyD88 | CD27 | CD32 |
| GBD | MyD88 | CD27 | CD79a |
| GBD | MyD88 | CD27 | CD79b |
| GBD | MyD88 | CD28δ | CD8 |
| GBD | MyD88 | CD28δ | CD3ζ |
| GBD | MyD88 | CD28δ | CD3δ |
| GBD | MyD88 | CD28δ | CD3γ |
| GBD | MyD88 | CD28δ | CD3ε |
| GBD | MyD88 | CD28δ | FcγRI-γ |
| GBD | MyD88 | CD28δ | FcγRIII-γ |
| GBD | MyD88 | CD28δ | FcεRIβ |
| GBD | MyD88 | CD28δ | FcεRIγ |
| GBD | MyD88 | CD28δ | DAP10 |
| GBD | MyD88 | CD28δ | DAP12 |
| GBD | MyD88 | CD28δ | CD32 |
| GBD | MyD88 | CD28δ | CD79a |
| GBD | MyD88 | CD28δ | CD79b |
| GBD | MyD88 | CD80 | CD8 |
| GBD | MyD88 | CD80 | CD3ζ |
| GBD | MyD88 | CD80 | CD3δ |
| GBD | MyD88 | CD80 | CD3γ |
| GBD | MyD88 | CD80 | CD3ε |
| GBD | MyD88 | CD80 | FcγRI-γ |
| GBD | MyD88 | CD80 | FcγRIII-γ |
| GBD | MyD88 | CD80 | FcεRIβ |
| GBD | MyD88 | CD80 | FcεRIγ |
| GBD | MyD88 | CD80 | DAP10 |
| GBD | MyD88 | CD80 | DAP12 |
| GBD | MyD88 | CD80 | CD32 |
| GBD | MyD88 | CD80 | CD79a |
| GBD | MyD88 | CD80 | CD79b |
| GBD | MyD88 | CD86 | CD8 |
| GBD | MyD88 | CD86 | CD3ζ |
| GBD | MyD88 | CD86 | CD3δ |
| GBD | MyD88 | CD86 | CD3γ |
| GBD | MyD88 | CD86 | CD3ε |
| GBD | MyD88 | CD86 | FcγRI-γ |
| GBD | MyD88 | CD86 | FcγRIII-γ |
| GBD | MyD88 | CD86 | FcεRIβ |
| GBD | MyD88 | CD86 | FcεRIγ |
| GBD | MyD88 | CD86 | DAP10 |
| GBD | MyD88 | CD86 | DAP12 |
| GBD | MyD88 | CD86 | CD32 |
| GBD | MyD88 | CD86 | CD79a |
| GBD | MyD88 | CD86 | CD79b |
| GBD | MyD88 | OX40 | CD8 |
| GBD | MyD88 | OX40 | CD3ζ |
| GBD | MyD88 | OX40 | CD3δ |
| GBD | MyD88 | OX40 | CD3γ |
| GBD | MyD88 | OX40 | CD3ε |
| GBD | MyD88 | OX40 | FcγRI-γ |
| GBD | MyD88 | OX40 | FcγRIII-γ |
| GBD | MyD88 | OX40 | FcεRIβ |
| GBD | MyD88 | OX40 | FcεRIγ |
| GBD | MyD88 | OX40 | DAP10 |
| GBD | MyD88 | OX40 | DAP12 |
| GBD | MyD88 | OX40 | CD32 |
| GBD | MyD88 | OX40 | CD79a |
| GBD | MyD88 | OX40 | CD79b |
| GBD | MyD88 | DAP10 | CD8 |
| GBD | MyD88 | DAP10 | CD3ζ |
| GBD | MyD88 | DAP10 | CD3δ |
| GBD | MyD88 | DAP10 | CD3γ |
| GBD | MyD88 | DAP10 | CD3ε |
| GBD | MyD88 | DAP10 | FcγRI-γ |
| GBD | MyD88 | DAP10 | FcγRIII-γ |
| GBD | MyD88 | DAP10 | FcεRIβ |
| GBD | MyD88 | DAP10 | FcεRIγ |
| GBD | MyD88 | DAP10 | DAP10 |
| GBD | MyD88 | DAP10 | DAP12 |
| GBD | MyD88 | DAP10 | CD32 |
| GBD | MyD88 | DAP10 | CD79a |
| GBD | MyD88 | DAP10 | CD79b |
| GBD | MyD88 | DAP12 | CD8 |
| GBD | MyD88 | DAP12 | CD3ζ |
| GBD | MyD88 | DAP12 | CD3δ |
| GBD | MyD88 | DAP12 | CD3γ |
| GBD | MyD88 | DAP12 | CD3ε |
| GBD | MyD88 | DAP12 | FcγRI-γ |

TABLE 3-continued

Third Generation CARs

| | Co-stimulatory Signal | Co-stimulatory Signal | Signal Domain |
|---|---|---|---|
| GBD | MyD88 | DAP12 | FcγRIII-γ |
| GBD | MyD88 | DAP12 | FcεRIβ |
| GBD | MyD88 | DAP12 | FcεRIγ |
| GBD | MyD88 | DAP12 | DAP10 |
| GBD | MyD88 | DAP12 | DAP12 |
| GBD | MyD88 | DAP12 | CD32 |
| GBD | MyD88 | DAP12 | CD79a |
| GBD | MyD88 | DAP12 | CD79b |
| GBD | MyD88 | MyD88 | CD8 |
| GBD | MyD88 | MyD88 | CD3ζ |
| GBD | MyD88 | MyD88 | CD3δ |
| GBD | MyD88 | MyD88 | CD3γ |
| GBD | MyD88 | MyD88 | CD3ε |
| GBD | MyD88 | MyD88 | FcγRI-γ |
| GBD | MyD88 | MyD88 | FcγRIII-γ |
| GBD | MyD88 | MyD88 | FcεRIβ |
| GBD | MyD88 | MyD88 | FcεRIγ |
| GBD | MyD88 | MyD88 | DAP10 |
| GBD | MyD88 | MyD88 | DAP12 |
| GBD | MyD88 | MyD88 | CD32 |
| GBD | MyD88 | MyD88 | CD79a |
| GBD | MyD88 | MyD88 | CD79b |
| GBD | MyD88 | CD7 | CD8 |
| GBD | MyD88 | CD7 | CD3ζ |
| GBD | MyD88 | CD7 | CD3δ |
| GBD | MyD88 | CD7 | CD3γ |
| GBD | MyD88 | CD7 | CD3ε |
| GBD | MyD88 | CD7 | FcγRI-γ |
| GBD | MyD88 | CD7 | FcγRIII-γ |
| GBD | MyD88 | CD7 | FcεRIβ |
| GBD | MyD88 | CD7 | FcεRIγ |
| GBD | MyD88 | CD7 | DAP10 |
| GBD | MyD88 | CD7 | DAP12 |
| GBD | MyD88 | CD7 | CD32 |
| GBD | MyD88 | CD7 | CD79a |
| GBD | MyD88 | CD7 | CD79b |
| GBD | MyD88 | BTNL3 | CD8 |
| GBD | MyD88 | BTNL3 | CD3ζ |
| GBD | MyD88 | BTNL3 | CD3δ |
| GBD | MyD88 | BTNL3 | CD3γ |
| GBD | MyD88 | BTNL3 | CD3ε |
| GBD | MyD88 | BTNL3 | FcγRI-γ |
| GBD | MyD88 | BTNL3 | FcγRIII-γ |
| GBD | MyD88 | BTNL3 | FcεRIβ |
| GBD | MyD88 | BTNL3 | FcεRIγ |
| GBD | MyD88 | BTNL3 | DAP10 |
| GBD | MyD88 | BTNL3 | DAP12 |
| GBD | MyD88 | BTNL3 | CD32 |
| GBD | MyD88 | BTNL3 | CD79a |
| GBD | MyD88 | BTNL3 | CD79b |
| GBD | MyD88 | NKG2D | CD8 |
| GBD | MyD88 | NKG2D | CD3ζ |
| GBD | MyD88 | NKG2D | CD3δ |
| GBD | MyD88 | NKG2D | CD3γ |
| GBD | MyD88 | NKG2D | CD3ε |
| GBD | MyD88 | NKG2D | FcγRI-γ |
| GBD | MyD88 | NKG2D | FcγRIII-γ |
| GBD | MyD88 | NKG2D | FcεRIβ |
| GBD | MyD88 | NKG2D | FcεRIγ |
| GBD | MyD88 | NKG2D | DAP10 |
| GBD | MyD88 | NKG2D | DAP12 |
| GBD | MyD88 | NKG2D | CD32 |
| GBD | MyD88 | NKG2D | CD79a |
| GBD | MyD88 | NKG2D | CD79b |
| GBD | CD7 | CD28 | CD8 |
| GBD | CD7 | CD28 | CD3ζ |
| GBD | CD7 | CD28 | CD3δ |
| GBD | CD7 | CD28 | CD3γ |
| GBD | CD7 | CD28 | CD3ε |
| GBD | CD7 | CD28 | FcγRI-γ |
| GBD | CD7 | CD28 | FcγRIII-γ |
| GBD | CD7 | CD28 | FcεRIβ |
| GBD | CD7 | CD28 | FcεRIγ |
| GBD | CD7 | CD28 | DAP10 |
| GBD | CD7 | CD28 | DAP12 |
| GBD | CD7 | CD28 | CD32 |
| GBD | CD7 | CD28 | CD79a |
| GBD | CD7 | CD28 | CD79b |
| GBD | CD7 | CD8 | CD8 |
| GBD | CD7 | CD8 | CD3ζ |
| GBD | CD7 | CD8 | CD3δ |
| GBD | CD7 | CD8 | CD3γ |
| GBD | CD7 | CD8 | CD3ε |
| GBD | CD7 | CD8 | FcγRI-γ |
| GBD | CD7 | CD8 | FcγRIII-γ |
| GBD | CD7 | CD8 | FcεRIβ |
| GBD | CD7 | CD8 | FcεRIγ |
| GBD | CD7 | CD8 | DAP10 |
| GBD | CD7 | CD8 | DAP12 |
| GBD | CD7 | CD8 | CD32 |
| GBD | CD7 | CD8 | CD79a |
| GBD | CD7 | CD8 | CD79b |
| GBD | CD7 | CD4 | CD8 |
| GBD | CD7 | CD4 | CD3ζ |
| GBD | CD7 | CD4 | CD3δ |
| GBD | CD7 | CD4 | CD3γ |
| GBD | CD7 | CD4 | CD3ε |
| GBD | CD7 | CD4 | FcγRI-γ |
| GBD | CD7 | CD4 | FcγRIII-γ |
| GBD | CD7 | CD4 | FcεRIβ |
| GBD | CD7 | CD4 | FcεRIγ |
| GBD | CD7 | CD4 | DAP10 |
| GBD | CD7 | CD4 | DAP12 |
| GBD | CD7 | CD4 | CD32 |
| GBD | CD7 | CD4 | CD79a |
| GBD | CD7 | CD4 | CD79b |
| GBD | CD7 | b2c | CD8 |
| GBD | CD7 | b2c | CD3ζ |
| GBD | CD7 | b2c | CD3δ |
| GBD | CD7 | b2c | CD3γ |
| GBD | CD7 | b2c | CD3ε |
| GBD | CD7 | b2c | FcγRI-γ |
| GBD | CD7 | b2c | FcγRIII-γ |
| GBD | CD7 | b2c | FcεRIβ |
| GBD | CD7 | b2c | FcεRIγ |
| GBD | CD7 | b2c | DAP10 |
| GBD | CD7 | b2c | DAP12 |
| GBD | CD7 | b2c | CD32 |
| GBD | CD7 | b2c | CD79a |
| GBD | CD7 | b2c | CD79b |
| GBD | CD7 | CD137/41BB | CD8 |
| GBD | CD7 | CD137/41BB | CD3ζ |
| GBD | CD7 | CD137/41BB | CD3δ |
| GBD | CD7 | CD137/41BB | CD3γ |
| GBD | CD7 | CD137/41BB | CD3ε |
| GBD | CD7 | CD137/41BB | FcγRI-γ |
| GBD | CD7 | CD137/41BB | FcγRIII-γ |
| GBD | CD7 | CD137/41BB | FcεRIβ |
| GBD | CD7 | CD137/41BB | FcεRIγ |
| GBD | CD7 | CD137/41BB | DAP10 |
| GBD | CD7 | CD137/41BB | DAP12 |
| GBD | CD7 | CD137/41BB | CD32 |
| GBD | CD7 | CD137/41BB | CD79a |
| GBD | CD7 | CD137/41BB | CD79b |
| GBD | CD7 | ICOS | CD8 |
| GBD | CD7 | ICOS | CD3ζ |
| GBD | CD7 | ICOS | CD3δ |
| GBD | CD7 | ICOS | CD3γ |
| GBD | CD7 | ICOS | CD3ε |
| GBD | CD7 | ICOS | FcγRI-γ |
| GBD | CD7 | ICOS | FcγRIII-γ |
| GBD | CD7 | ICOS | FcεRIβ |
| GBD | CD7 | ICOS | FcεRIγ |
| GBD | CD7 | ICOS | DAP10 |
| GBD | CD7 | ICOS | DAP12 |
| GBD | CD7 | ICOS | CD32 |
| GBD | CD7 | ICOS | CD79a |
| GBD | CD7 | ICOS | CD79b |
| GBD | CD7 | CD27 | CD8 |
| GBD | CD7 | CD27 | CD3ζ |

TABLE 3-continued

Third Generation CARs

| Co-stimulatory Signal | Co-stimulatory Signal | Signal Domain |
|---|---|---|
| GBD | CD7 | CD27 | CD3δ |
| GBD | CD7 | CD27 | CD3γ |
| GBD | CD7 | CD27 | CD3ε |
| GBD | CD7 | CD27 | FcγRI-γ |
| GBD | CD7 | CD27 | FcγRIII-γ |
| GBD | CD7 | CD27 | FcεRIβ |
| GBD | CD7 | CD27 | FcεRIγ |
| GBD | CD7 | CD27 | DAP10 |
| GBD | CD7 | CD27 | DAP12 |
| GBD | CD7 | CD27 | CD32 |
| GBD | CD7 | CD27 | CD79a |
| GBD | CD7 | CD27 | CD79b |
| GBD | CD7 | CD28δ | CD8 |
| GBD | CD7 | CD28δ | CD3ζ |
| GBD | CD7 | CD28δ | CD3δ |
| GBD | CD7 | CD28δ | CD3γ |
| GBD | CD7 | CD28δ | CD3ε |
| GBD | CD7 | CD28δ | FcγRI-γ |
| GBD | CD7 | CD28δ | FcγRIII-γ |
| GBD | CD7 | CD28δ | FcεRIβ |
| GBD | CD7 | CD28δ | FcεRIγ |
| GBD | CD7 | CD28δ | DAP10 |
| GBD | CD7 | CD28δ | DAP12 |
| GBD | CD7 | CD28δ | CD32 |
| GBD | CD7 | CD28δ | CD79a |
| GBD | CD7 | CD28δ | CD79b |
| GBD | CD7 | CD80 | CD8 |
| GBD | CD7 | CD80 | CD3ζ |
| GBD | CD7 | CD80 | CD3δ |
| GBD | CD7 | CD80 | CD3γ |
| GBD | CD7 | CD80 | CD3ε |
| GBD | CD7 | CD80 | FcγRI-γ |
| GBD | CD7 | CD80 | FcγRIII-γ |
| GBD | CD7 | CD80 | FcεRIβ |
| GBD | CD7 | CD80 | FcεRIγ |
| GBD | CD7 | CD80 | DAP10 |
| GBD | CD7 | CD80 | DAP12 |
| GBD | CD7 | CD80 | CD32 |
| GBD | CD7 | CD80 | CD79a |
| GBD | CD7 | CD80 | CD79b |
| GBD | CD7 | CD86 | CD8 |
| GBD | CD7 | CD86 | CD3ζ |
| GBD | CD7 | CD86 | CD3δ |
| GBD | CD7 | CD86 | CD3γ |
| GBD | CD7 | CD86 | CD3ε |
| GBD | CD7 | CD86 | FcγRI-γ |
| GBD | CD7 | CD86 | FcγRIII-γ |
| GBD | CD7 | CD86 | FcεRIβ |
| GBD | CD7 | CD86 | FcεRIγ |
| GBD | CD7 | CD86 | DAP10 |
| GBD | CD7 | CD86 | DAP12 |
| GBD | CD7 | CD86 | CD32 |
| GBD | CD7 | CD86 | CD79a |
| GBD | CD7 | CD86 | CD79b |
| GBD | CD7 | OX40 | CD8 |
| GBD | CD7 | OX40 | CD3ζ |
| GBD | CD7 | OX40 | CD3δ |
| GBD | CD7 | OX40 | CD3γ |
| GBD | CD7 | OX40 | CD3ε |
| GBD | CD7 | OX40 | FcγRI-γ |
| GBD | CD7 | OX40 | FcγRIII-γ |
| GBD | CD7 | OX40 | FcεRIβ |
| GBD | CD7 | OX40 | FcεRIγ |
| GBD | CD7 | OX40 | DAP10 |
| GBD | CD7 | OX40 | DAP12 |
| GBD | CD7 | OX40 | CD32 |
| GBD | CD7 | OX40 | CD79a |
| GBD | CD7 | OX40 | CD79b |
| GBD | CD7 | DAP10 | CD8 |
| GBD | CD7 | DAP10 | CD3ζ |
| GBD | CD7 | DAP10 | CD3δ |
| GBD | CD7 | DAP10 | CD3γ |
| GBD | CD7 | DAP10 | CD3ε |
| GBD | CD7 | DAP10 | FcγRI-γ |
| GBD | CD7 | DAP10 | FcγRIII-γ |
| GBD | CD7 | DAP10 | FcεRIβ |
| GBD | CD7 | DAP10 | FcεRIγ |
| GBD | CD7 | DAP10 | DAP10 |
| GBD | CD7 | DAP10 | DAP12 |
| GBD | CD7 | DAP10 | CD32 |
| GBD | CD7 | DAP10 | CD79a |
| GBD | CD7 | DAP10 | CD79b |
| GBD | CD7 | DAP12 | CD8 |
| GBD | CD7 | DAP12 | CD3ζ |
| GBD | CD7 | DAP12 | CD3δ |
| GBD | CD7 | DAP12 | CD3γ |
| GBD | CD7 | DAP12 | CD3ε |
| GBD | CD7 | DAP12 | FcγRI-γ |
| GBD | CD7 | DAP12 | FcγRIII-γ |
| GBD | CD7 | DAP12 | FcεRIβ |
| GBD | CD7 | DAP12 | FcεRIγ |
| GBD | CD7 | DAP12 | DAP10 |
| GBD | CD7 | DAP12 | DAP12 |
| GBD | CD7 | DAP12 | CD32 |
| GBD | CD7 | DAP12 | CD79a |
| GBD | CD7 | DAP12 | CD79b |
| GBD | CD7 | MyD88 | CD8 |
| GBD | CD7 | MyD88 | CD3ζ |
| GBD | CD7 | MyD88 | CD3δ |
| GBD | CD7 | MyD88 | CD3γ |
| GBD | CD7 | MyD88 | CD3ε |
| GBD | CD7 | MyD88 | FcγRI-γ |
| GBD | CD7 | MyD88 | FcγRIII-γ |
| GBD | CD7 | MyD88 | FcεRIβ |
| GBD | CD7 | MyD88 | FcεRIγ |
| GBD | CD7 | MyD88 | DAP10 |
| GBD | CD7 | MyD88 | DAP12 |
| GBD | CD7 | MyD88 | CD32 |
| GBD | CD7 | MyD88 | CD79a |
| GBD | CD7 | MyD88 | CD79b |
| GBD | CD7 | CD7 | CD8 |
| GBD | CD7 | CD7 | CD3ζ |
| GBD | CD7 | CD7 | CD3δ |
| GBD | CD7 | CD7 | CD3γ |
| GBD | CD7 | CD7 | CD3ε |
| GBD | CD7 | CD7 | FcγRI-γ |
| GBD | CD7 | CD7 | FcγRIII-γ |
| GBD | CD7 | CD7 | FcεRIβ |
| GBD | CD7 | CD7 | FcεRIγ |
| GBD | CD7 | CD7 | DAP10 |
| GBD | CD7 | CD7 | DAP12 |
| GBD | CD7 | CD7 | CD32 |
| GBD | CD7 | CD7 | CD79a |
| GBD | CD7 | CD7 | CD79b |
| GBD | CD7 | BTNL3 | CD8 |
| GBD | CD7 | BTNL3 | CD3ζ |
| GBD | CD7 | BTNL3 | CD3δ |
| GBD | CD7 | BTNL3 | CD3γ |
| GBD | CD7 | BTNL3 | CD3ε |
| GBD | CD7 | BTNL3 | FcγRI-γ |
| GBD | CD7 | BTNL3 | FcγRIII-γ |
| GBD | CD7 | BTNL3 | FcεRIβ |
| GBD | CD7 | BTNL3 | FcεRIγ |
| GBD | CD7 | BTNL3 | DAP10 |
| GBD | CD7 | BTNL3 | DAP12 |
| GBD | CD7 | BTNL3 | CD32 |
| GBD | CD7 | BTNL3 | CD79a |
| GBD | CD7 | BTNL3 | CD79b |
| GBD | CD7 | NKG2D | CD8 |
| GBD | CD7 | NKG2D | CD3ζ |
| GBD | CD7 | NKG2D | CD3δ |
| GBD | CD7 | NKG2D | CD3γ |
| GBD | CD7 | NKG2D | CD3ε |
| GBD | CD7 | NKG2D | FcγRI-γ |
| GBD | CD7 | NKG2D | FcγRIII-γ |
| GBD | CD7 | NKG2D | FcεRIβ |
| GBD | CD7 | NKG2D | FcεRIγ |
| GBD | CD7 | NKG2D | DAP10 |
| GBD | CD7 | NKG2D | DAP12 |
| GBD | CD7 | NKG2D | CD32 |

TABLE 3-continued

Third Generation CARs

| | Co-stimulatory Signal | Co-stimulatory Signal | Signal Domain |
|---|---|---|---|
| GBD | CD7 | NKG2D | CD79a |
| GBD | CD7 | NKG2D | CD79b |
| GBD | BTNL3 | CD28 | CD8 |
| GBD | BTNL3 | CD28 | CD3ζ |
| GBD | BTNL3 | CD28 | CD3δ |
| GBD | BTNL3 | CD28 | CD3γ |
| GBD | BTNL3 | CD28 | CD3ε |
| GBD | BTNL3 | CD28 | FcγRI-γ |
| GBD | BTNL3 | CD28 | FcγRIII-γ |
| GBD | BTNL3 | CD28 | FcεRIβ |
| GBD | BTNL3 | CD28 | FcεRIγ |
| GBD | BTNL3 | CD28 | DAP10 |
| GBD | BTNL3 | CD28 | DAP12 |
| GBD | BTNL3 | CD28 | CD32 |
| GBD | BTNL3 | CD28 | CD79a |
| GBD | BTNL3 | CD28 | CD79b |
| GBD | BTNL3 | CD8 | CD8 |
| GBD | BTNL3 | CD8 | CD3ζ |
| GBD | BTNL3 | CD8 | CD3δ |
| GBD | BTNL3 | CD8 | CD3γ |
| GBD | BTNL3 | CD8 | CD3ε |
| GBD | BTNL3 | CD8 | FcγRI-γ |
| GBD | BTNL3 | CD8 | FcγRIII-γ |
| GBD | BTNL3 | CD8 | FcεRIβ |
| GBD | BTNL3 | CD8 | FcεRIγ |
| GBD | BTNL3 | CD8 | DAP10 |
| GBD | BTNL3 | CD8 | DAP12 |
| GBD | BTNL3 | CD8 | CD32 |
| GBD | BTNL3 | CD8 | CD79a |
| GBD | BTNL3 | CD8 | CD79b |
| GBD | BTNL3 | CD4 | CD8 |
| GBD | BTNL3 | CD4 | CD3ζ |
| GBD | BTNL3 | CD4 | CD3δ |
| GBD | BTNL3 | CD4 | CD3γ |
| GBD | BTNL3 | CD4 | CD3ε |
| GBD | BTNL3 | CD4 | FcγRI-γ |
| GBD | BTNL3 | CD4 | FcγRIII-γ |
| GBD | BTNL3 | CD4 | FcεRIβ |
| GBD | BTNL3 | CD4 | FcεRIγ |
| GBD | BTNL3 | CD4 | DAP10 |
| GBD | BTNL3 | CD4 | DAP12 |
| GBD | BTNL3 | CD4 | CD32 |
| GBD | BTNL3 | CD4 | CD79a |
| GBD | BTNL3 | CD4 | CD79b |
| GBD | BTNL3 | b2c | CD8 |
| GBD | BTNL3 | b2c | CD3ζ |
| GBD | BTNL3 | b2c | CD3δ |
| GBD | BTNL3 | b2c | CD3γ |
| GBD | BTNL3 | b2c | CD3ε |
| GBD | BTNL3 | b2c | FcγRI-γ |
| GBD | BTNL3 | b2c | FcγRIII-γ |
| GBD | BTNL3 | b2c | FcεRIβ |
| GBD | BTNL3 | b2c | FcεRIγ |
| GBD | BTNL3 | b2c | DAP10 |
| GBD | BTNL3 | b2c | DAP12 |
| GBD | BTNL3 | b2c | CD32 |
| GBD | BTNL3 | b2c | CD79a |
| GBD | BTNL3 | b2c | CD79b |
| GBD | BTNL3 | CD137/41BB | CD8 |
| GBD | BTNL3 | CD137/41BB | CD3ζ |
| GBD | BTNL3 | CD137/41BB | CD3δ |
| GBD | BTNL3 | CD137/41BB | CD3γ |
| GBD | BTNL3 | CD137/41BB | CD3ε |
| GBD | BTNL3 | CD137/41BB | FcγRI-γ |
| GBD | BTNL3 | CD137/41BB | FcγRIII-γ |
| GBD | BTNL3 | CD137/41BB | FcεRIβ |
| GBD | BTNL3 | CD137/41BB | FcεRIγ |
| GBD | BTNL3 | CD137/41BB | DAP10 |
| GBD | BTNL3 | CD137/41BB | DAP12 |
| GBD | BTNL3 | CD137/41BB | CD32 |
| GBD | BTNL3 | CD137/41BB | CD79a |
| GBD | BTNL3 | CD137/41BB | CD79b |
| GBD | BTNL3 | ICOS | CD8 |
| GBD | BTNL3 | ICOS | CD3ζ |
| GBD | BTNL3 | ICOS | CD3δ |
| GBD | BTNL3 | ICOS | CD3γ |
| GBD | BTNL3 | ICOS | CD3ε |
| GBD | BTNL3 | ICOS | FcγRI-γ |
| GBD | BTNL3 | ICOS | FcγRIII-γ |
| GBD | BTNL3 | ICOS | FcεRIβ |
| GBD | BTNL3 | ICOS | FcεRIγ |
| GBD | BTNL3 | ICOS | DAP10 |
| GBD | BTNL3 | ICOS | DAP12 |
| GBD | BTNL3 | ICOS | CD32 |
| GBD | BTNL3 | ICOS | CD79a |
| GBD | BTNL3 | ICOS | CD79b |
| GBD | BTNL3 | CD27 | CD8 |
| GBD | BTNL3 | CD27 | CD3ζ |
| GBD | BTNL3 | CD27 | CD3δ |
| GBD | BTNL3 | CD27 | CD3γ |
| GBD | BTNL3 | CD27 | CD3ε |
| GBD | BTNL3 | CD27 | FcγRI-γ |
| GBD | BTNL3 | CD27 | FcγRIII-γ |
| GBD | BTNL3 | CD27 | FcεRIβ |
| GBD | BTNL3 | CD27 | FcεRIγ |
| GBD | BTNL3 | CD27 | DAP10 |
| GBD | BTNL3 | CD27 | DAP12 |
| GBD | BTNL3 | CD27 | CD32 |
| GBD | BTNL3 | CD27 | CD79a |
| GBD | BTNL3 | CD27 | CD79b |
| GBD | BTNL3 | CD28δ | CD8 |
| GBD | BTNL3 | CD28δ | CD3ζ |
| GBD | BTNL3 | CD28δ | CD3δ |
| GBD | BTNL3 | CD28δ | CD3γ |
| GBD | BTNL3 | CD28δ | CD3ε |
| GBD | BTNL3 | CD28δ | FcγRI-γ |
| GBD | BTNL3 | CD28δ | FcγRIII-γ |
| GBD | BTNL3 | CD28δ | FcεRIβ |
| GBD | BTNL3 | CD28δ | FcεRIγ |
| GBD | BTNL3 | CD28δ | DAP10 |
| GBD | BTNL3 | CD28δ | DAP12 |
| GBD | BTNL3 | CD28δ | CD32 |
| GBD | BTNL3 | CD28δ | CD79a |
| GBD | BTNL3 | CD28δ | CD79b |
| GBD | BTNL3 | CD80 | CD8 |
| GBD | BTNL3 | CD80 | CD3ζ |
| GBD | BTNL3 | CD80 | CD3δ |
| GBD | BTNL3 | CD80 | CD3γ |
| GBD | BTNL3 | CD80 | CD3ε |
| GBD | BTNL3 | CD80 | FcγRI-γ |
| GBD | BTNL3 | CD80 | FcγRIII-γ |
| GBD | BTNL3 | CD80 | FcεRIβ |
| GBD | BTNL3 | CD80 | FcεRIγ |
| GBD | BTNL3 | CD80 | DAP10 |
| GBD | BTNL3 | CD80 | DAP12 |
| GBD | BTNL3 | CD80 | CD32 |
| GBD | BTNL3 | CD80 | CD79a |
| GBD | BTNL3 | CD80 | CD79b |
| GBD | BTNL3 | CD86 | CD8 |
| GBD | BTNL3 | CD86 | CD3ζ |
| GBD | BTNL3 | CD86 | CD3δ |
| GBD | BTNL3 | CD86 | CD3γ |
| GBD | BTNL3 | CD86 | CD3ε |
| GBD | BTNL3 | CD86 | FcγRI-γ |
| GBD | BTNL3 | CD86 | FcγRIII-γ |
| GBD | BTNL3 | CD86 | FcεRIβ |
| GBD | BTNL3 | CD86 | FcεRIγ |
| GBD | BTNL3 | CD86 | DAP10 |
| GBD | BTNL3 | CD86 | DAP12 |
| GBD | BTNL3 | CD86 | CD32 |
| GBD | BTNL3 | CD86 | CD79a |
| GBD | BTNL3 | CD86 | CD79b |
| GBD | BTNL3 | OX40 | CD8 |
| GBD | BTNL3 | OX40 | CD3ζ |
| GBD | BTNL3 | OX40 | CD3δ |
| GBD | BTNL3 | OX40 | CD3γ |
| GBD | BTNL3 | OX40 | CD3ε |
| GBD | BTNL3 | OX40 | FcγRI-γ |
| GBD | BTNL3 | OX40 | FcγRIII-γ |
| GBD | BTNL3 | OX40 | FcεRIβ |

TABLE 3-continued

Third Generation CARs

| | Co-stimulatory Signal | Co-stimulatory Signal | Signal Domain |
|---|---|---|---|
| GBD | BTNL3 | OX40 | FcεRIγ |
| GBD | BTNL3 | OX40 | DAP10 |
| GBD | BTNL3 | OX40 | DAP12 |
| GBD | BTNL3 | OX40 | CD32 |
| GBD | BTNL3 | OX40 | CD79a |
| GBD | BTNL3 | OX40 | CD79b |
| GBD | BTNL3 | DAP10 | CD8 |
| GBD | BTNL3 | DAP10 | CD3ζ |
| GBD | BTNL3 | DAP10 | CD3δ |
| GBD | BTNL3 | DAP10 | CD3γ |
| GBD | BTNL3 | DAP10 | CD3ε |
| GBD | BTNL3 | DAP10 | FcγRI-γ |
| GBD | BTNL3 | DAP10 | FcγRIII-γ |
| GBD | BTNL3 | DAP10 | FcεRIβ |
| GBD | BTNL3 | DAP10 | FcεRIγ |
| GBD | BTNL3 | DAP10 | DAP10 |
| GBD | BTNL3 | DAP10 | DAP12 |
| GBD | BTNL3 | DAP10 | CD32 |
| GBD | BTNL3 | DAP10 | CD79a |
| GBD | BTNL3 | DAP10 | CD79b |
| GBD | BTNL3 | DAP12 | CD8 |
| GBD | BTNL3 | DAP12 | CD3ζ |
| GBD | BTNL3 | DAP12 | CD3δ |
| GBD | BTNL3 | DAP12 | CD3γ |
| GBD | BTNL3 | DAP12 | CD3ε |
| GBD | BTNL3 | DAP12 | FcγRI-γ |
| GBD | BTNL3 | DAP12 | FcγRIII-γ |
| GBD | BTNL3 | DAP12 | FcεRIβ |
| GBD | BTNL3 | DAP12 | FcεRIγ |
| GBD | BTNL3 | DAP12 | DAP10 |
| GBD | BTNL3 | DAP12 | DAP12 |
| GBD | BTNL3 | DAP12 | CD32 |
| GBD | BTNL3 | DAP12 | CD79a |
| GBD | BTNL3 | DAP12 | CD79b |
| GBD | BTNL3 | MyD88 | CD8 |
| GBD | BTNL3 | MyD88 | CD3ζ |
| GBD | BTNL3 | MyD88 | CD3δ |
| GBD | BTNL3 | MyD88 | CD3γ |
| GBD | BTNL3 | MyD88 | CD3ε |
| GBD | BTNL3 | MyD88 | FcγRI-γ |
| GBD | BTNL3 | MyD88 | FcγRIII-γ |
| GBD | BTNL3 | MyD88 | FcεRIβ |
| GBD | BTNL3 | MyD88 | FcεRIγ |
| GBD | BTNL3 | MyD88 | DAP10 |
| GBD | BTNL3 | MyD88 | DAP12 |
| GBD | BTNL3 | MyD88 | CD32 |
| GBD | BTNL3 | MyD88 | CD79a |
| GBD | BTNL3 | MyD88 | CD79b |
| GBD | BTNL3 | CD7 | CD8 |
| GBD | BTNL3 | CD7 | CD3ζ |
| GBD | BTNL3 | CD7 | CD3δ |
| GBD | BTNL3 | CD7 | CD3γ |
| GBD | BTNL3 | CD7 | CD3ε |
| GBD | BTNL3 | CD7 | FcγRI-γ |
| GBD | BTNL3 | CD7 | FcγRIII-γ |
| GBD | BTNL3 | CD7 | FcεRIβ |
| GBD | BTNL3 | CD7 | FcεRIγ |
| GBD | BTNL3 | CD7 | DAP10 |
| GBD | BTNL3 | CD7 | DAP12 |
| GBD | BTNL3 | CD7 | CD32 |
| GBD | BTNL3 | CD7 | CD79a |
| GBD | BTNL3 | CD7 | CD79b |
| GBD | BTNL3 | BTNL3 | CD8 |
| GBD | BTNL3 | BTNL3 | CD3ζ |
| GBD | BTNL3 | BTNL3 | CD3δ |
| GBD | BTNL3 | BTNL3 | CD3γ |
| GBD | BTNL3 | BTNL3 | CD3ε |
| GBD | BTNL3 | BTNL3 | FcγRI-γ |
| GBD | BTNL3 | BTNL3 | FcγRIII-γ |
| GBD | BTNL3 | BTNL3 | FcεRIβ |
| GBD | BTNL3 | BTNL3 | FcεRIγ |
| GBD | BTNL3 | BTNL3 | DAP10 |
| GBD | BTNL3 | BTNL3 | DAP12 |
| GBD | BTNL3 | BTNL3 | CD32 |
| GBD | BTNL3 | BTNL3 | CD79a |
| GBD | BTNL3 | BTNL3 | CD79b |
| GBD | BTNL3 | NKG2D | CD8 |
| GBD | BTNL3 | NKG2D | CD3ζ |
| GBD | BTNL3 | NKG2D | CD3δ |
| GBD | BTNL3 | NKG2D | CD3γ |
| GBD | BTNL3 | NKG2D | CD3ε |
| GBD | BTNL3 | NKG2D | FcγRI-γ |
| GBD | BTNL3 | NKG2D | FcγRIII-γ |
| GBD | BTNL3 | NKG2D | FcεRIβ |
| GBD | BTNL3 | NKG2D | FcεRIγ |
| GBD | BTNL3 | NKG2D | DAP10 |
| GBD | BTNL3 | NKG2D | DAP12 |
| GBD | BTNL3 | NKG2D | CD32 |
| GBD | BTNL3 | NKG2D | CD79a |
| GBD | BTNL3 | NKG2D | CD79b |
| GBD | NKG2D | CD28 | CD8 |
| GBD | NKG2D | CD28 | CD3ζ |
| GBD | NKG2D | CD28 | CD3δ |
| GBD | NKG2D | CD28 | CD3γ |
| GBD | NKG2D | CD28 | CD3ε |
| GBD | NKG2D | CD28 | FcγRI-γ |
| GBD | NKG2D | CD28 | FcγRIII-γ |
| GBD | NKG2D | CD28 | FcεRIβ |
| GBD | NKG2D | CD28 | FcεRIγ |
| GBD | NKG2D | CD28 | DAP10 |
| GBD | NKG2D | CD28 | DAP12 |
| GBD | NKG2D | CD28 | CD32 |
| GBD | NKG2D | CD28 | CD79a |
| GBD | NKG2D | CD28 | CD79b |
| GBD | NKG2D | CD8 | CD8 |
| GBD | NKG2D | CD8 | CD3ζ |
| GBD | NKG2D | CD8 | CD3δ |
| GBD | NKG2D | CD8 | CD3γ |
| GBD | NKG2D | CD8 | CD3ε |
| GBD | NKG2D | CD8 | FcγRI-γ |
| GBD | NKG2D | CD8 | FcγRIII-γ |
| GBD | NKG2D | CD8 | FcεRIβ |
| GBD | NKG2D | CD8 | FcεRIγ |
| GBD | NKG2D | CD8 | DAP10 |
| GBD | NKG2D | CD8 | DAP12 |
| GBD | NKG2D | CD8 | CD32 |
| GBD | NKG2D | CD8 | CD79a |
| GBD | NKG2D | CD8 | CD79b |
| GBD | NKG2D | CD4 | CD8 |
| GBD | NKG2D | CD4 | CD3ζ |
| GBD | NKG2D | CD4 | CD3δ |
| GBD | NKG2D | CD4 | CD3γ |
| GBD | NKG2D | CD4 | CD3ε |
| GBD | NKG2D | CD4 | FcγRI-γ |
| GBD | NKG2D | CD4 | FcγRIII-γ |
| GBD | NKG2D | CD4 | FcεRIβ |
| GBD | NKG2D | CD4 | FcεRIγ |
| GBD | NKG2D | CD4 | DAP10 |
| GBD | NKG2D | CD4 | DAP12 |
| GBD | NKG2D | CD4 | CD32 |
| GBD | NKG2D | CD4 | CD79a |
| GBD | NKG2D | CD4 | CD79b |
| GBD | NKG2D | b2c | CD8 |
| GBD | NKG2D | b2c | CD3ζ |
| GBD | NKG2D | b2c | CD3δ |
| GBD | NKG2D | b2c | CD3γ |
| GBD | NKG2D | b2c | CD3ε |
| GBD | NKG2D | b2c | FcγRI-γ |
| GBD | NKG2D | b2c | FcγRIII-γ |
| GBD | NKG2D | b2c | FcεRIβ |
| GBD | NKG2D | b2c | FcεRIγ |
| GBD | NKG2D | b2c | DAP10 |
| GBD | NKG2D | b2c | DAP12 |
| GBD | NKG2D | b2c | CD32 |
| GBD | NKG2D | b2c | CD79a |
| GBD | NKG2D | b2c | CD79b |
| GBD | NKG2D | CD137/41BB | CD8 |
| GBD | NKG2D | CD137/41BB | CD3ζ |
| GBD | NKG2D | CD137/41BB | CD3δ |
| GBD | NKG2D | CD137/41BB | CD3γ |

TABLE 3-continued

Third Generation CARs

| | Co-stimulatory Signal | Co-stimulatory Signal | Signal Domain |
|---|---|---|---|
| GBD | NKG2D | CD137/41BB | CD3ε |
| GBD | NKG2D | CD137/41BB | FcγRI-γ |
| GBD | NKG2D | CD137/41BB | FcγRIII-γ |
| GBD | NKG2D | CD137/41BB | FcεRIβ |
| GBD | NKG2D | CD137/41BB | FcεRIγ |
| GBD | NKG2D | CD137/41BB | DAP10 |
| GBD | NKG2D | CD137/41BB | DAP12 |
| GBD | NKG2D | CD137/41BB | CD32 |
| GBD | NKG2D | CD137/41BB | CD79a |
| GBD | NKG2D | CD137/41BB | CD79b |
| GBD | NKG2D | ICOS | CD8 |
| GBD | NKG2D | ICOS | CD3ζ |
| GBD | NKG2D | ICOS | CD3δ |
| GBD | NKG2D | ICOS | CD3γ |
| GBD | NKG2D | ICOS | CD3ε |
| GBD | NKG2D | ICOS | FcγRI-γ |
| GBD | NKG2D | ICOS | FcγRIII-γ |
| GBD | NKG2D | ICOS | FcεRIβ |
| GBD | NKG2D | ICOS | FcεRIγ |
| GBD | NKG2D | ICOS | DAP10 |
| GBD | NKG2D | ICOS | DAP12 |
| GBD | NKG2D | ICOS | CD32 |
| GBD | NKG2D | ICOS | CD79a |
| GBD | NKG2D | ICOS | CD79b |
| GBD | NKG2D | CD27 | CD8 |
| GBD | NKG2D | CD27 | CD3ζ |
| GBD | NKG2D | CD27 | CD3δ |
| GBD | NKG2D | CD27 | CD3γ |
| GBD | NKG2D | CD27 | CD3ε |
| GBD | NKG2D | CD27 | FcγRI-γ |
| GBD | NKG2D | CD27 | FcγRIII-γ |
| GBD | NKG2D | CD27 | FcεRIβ |
| GBD | NKG2D | CD27 | FcεRIγ |
| GBD | NKG2D | CD27 | DAP10 |
| GBD | NKG2D | CD27 | DAP12 |
| GBD | NKG2D | CD27 | CD32 |
| GBD | NKG2D | CD27 | CD79a |
| GBD | NKG2D | CD27 | CD79b |
| GBD | NKG2D | CD28δ | CD8 |
| GBD | NKG2D | CD28δ | CD3ζ |
| GBD | NKG2D | CD28δ | CD3δ |
| GBD | NKG2D | CD28δ | CD3γ |
| GBD | NKG2D | CD28δ | CD3ε |
| GBD | NKG2D | CD28δ | FcγRI-γ |
| GBD | NKG2D | CD28δ | FcγRIII-γ |
| GBD | NKG2D | CD28δ | FcεRIβ |
| GBD | NKG2D | CD28δ | FcεRIγ |
| GBD | NKG2D | CD28δ | DAP10 |
| GBD | NKG2D | CD28δ | DAP12 |
| GBD | NKG2D | CD28δ | CD32 |
| GBD | NKG2D | CD28δ | CD79a |
| GBD | NKG2D | CD28δ | CD79b |
| GBD | NKG2D | CD80 | CD8 |
| GBD | NKG2D | CD80 | CD3ζ |
| GBD | NKG2D | CD80 | CD3δ |
| GBD | NKG2D | CD80 | CD3γ |
| GBD | NKG2D | CD80 | CD3ε |
| GBD | NKG2D | CD80 | FcγRI-γ |
| GBD | NKG2D | CD80 | FcγRIII-γ |
| GBD | NKG2D | CD80 | FcεRIβ |
| GBD | NKG2D | CD80 | FcεRIγ |
| GBD | NKG2D | CD80 | DAP10 |
| GBD | NKG2D | CD80 | DAP12 |
| GBD | NKG2D | CD80 | CD32 |
| GBD | NKG2D | CD80 | CD79a |
| GBD | NKG2D | CD80 | CD79b |
| GBD | NKG2D | CD86 | CD8 |
| GBD | NKG2D | CD86 | CD3ζ |
| GBD | NKG2D | CD86 | CD3δ |
| GBD | NKG2D | CD86 | CD3γ |
| GBD | NKG2D | CD86 | CD3ε |
| GBD | NKG2D | CD86 | FcγRI-γ |
| GBD | NKG2D | CD86 | FcγRIII-γ |
| GBD | NKG2D | CD86 | FcεRIβ |
| GBD | NKG2D | CD86 | FcεRIγ |
| GBD | NKG2D | CD86 | DAP10 |
| GBD | NKG2D | CD86 | DAP12 |
| GBD | NKG2D | CD86 | CD32 |
| GBD | NKG2D | CD86 | CD79a |
| GBD | NKG2D | CD86 | CD79b |
| GBD | NKG2D | OX40 | CD8 |
| GBD | NKG2D | OX40 | CD3ζ |
| GBD | NKG2D | OX40 | CD3δ |
| GBD | NKG2D | OX40 | CD3γ |
| GBD | NKG2D | OX40 | CD3ε |
| GBD | NKG2D | OX40 | FcγRI-γ |
| GBD | NKG2D | OX40 | FcγRIII-γ |
| GBD | NKG2D | OX40 | FcεRIβ |
| GBD | NKG2D | OX40 | FcεRIγ |
| GBD | NKG2D | OX40 | DAP10 |
| GBD | NKG2D | OX40 | DAP12 |
| GBD | NKG2D | OX40 | CD32 |
| GBD | NKG2D | OX40 | CD79a |
| GBD | NKG2D | OX40 | CD79b |
| GBD | NKG2D | DAP10 | CD8 |
| GBD | NKG2D | DAP10 | CD3ζ |
| GBD | NKG2D | DAP10 | CD3δ |
| GBD | NKG2D | DAP10 | CD3γ |
| GBD | NKG2D | DAP10 | CD3ε |
| GBD | NKG2D | DAP10 | FcγRI-γ |
| GBD | NKG2D | DAP10 | FcγRIII-γ |
| GBD | NKG2D | DAP10 | FcεRIβ |
| GBD | NKG2D | DAP10 | FcεRIγ |
| GBD | NKG2D | DAP10 | DAP10 |
| GBD | NKG2D | DAP10 | DAP12 |
| GBD | NKG2D | DAP10 | CD32 |
| GBD | NKG2D | DAP10 | CD79a |
| GBD | NKG2D | DAP10 | CD79b |
| GBD | NKG2D | DAP12 | CD8 |
| GBD | NKG2D | DAP12 | CD3ζ |
| GBD | NKG2D | DAP12 | CD3δ |
| GBD | NKG2D | DAP12 | CD3γ |
| GBD | NKG2D | DAP12 | CD3ε |
| GBD | NKG2D | DAP12 | FcγRI-γ |
| GBD | NKG2D | DAP12 | FcγRIII-γ |
| GBD | NKG2D | DAP12 | FcεRIβ |
| GBD | NKG2D | DAP12 | FcεRIγ |
| GBD | NKG2D | DAP12 | DAP10 |
| GBD | NKG2D | DAP12 | DAP12 |
| GBD | NKG2D | DAP12 | CD32 |
| GBD | NKG2D | DAP12 | CD79a |
| GBD | NKG2D | DAP12 | CD79b |
| GBD | NKG2D | MyD88 | CD8 |
| GBD | NKG2D | MyD88 | CD3ζ |
| GBD | NKG2D | MyD88 | CD3δ |
| GBD | NKG2D | MyD88 | CD3γ |
| GBD | NKG2D | MyD88 | CD3ε |
| GBD | NKG2D | MyD88 | FcγRI-γ |
| GBD | NKG2D | MyD88 | FcγRIII-γ |
| GBD | NKG2D | MyD88 | FcεRIβ |
| GBD | NKG2D | MyD88 | FcεRIγ |
| GBD | NKG2D | MyD88 | DAP10 |
| GBD | NKG2D | MyD88 | DAP12 |
| GBD | NKG2D | MyD88 | CD32 |
| GBD | NKG2D | MyD88 | CD79a |
| GBD | NKG2D | MyD88 | CD79b |
| GBD | NKG2D | CD7 | CD8 |
| GBD | NKG2D | CD7 | CD3ζ |
| GBD | NKG2D | CD7 | CD3δ |
| GBD | NKG2D | CD7 | CD3γ |
| GBD | NKG2D | CD7 | CD3ε |
| GBD | NKG2D | CD7 | FcγRI-γ |
| GBD | NKG2D | CD7 | FcγRIII-γ |
| GBD | NKG2D | CD7 | FcεRIβ |
| GBD | NKG2D | CD7 | FcεRIγ |
| GBD | NKG2D | CD7 | DAP10 |
| GBD | NKG2D | CD7 | DAP12 |
| GBD | NKG2D | CD7 | CD32 |
| GBD | NKG2D | CD7 | CD79a |
| GBD | NKG2D | CD7 | CD79b |

TABLE 3-continued

Third Generation CARs

| | Co-stimulatory Signal | Co-stimulatory Signal | Signal Domain |
|---|---|---|---|
| GBD | NKG2D | BTNL3 | CD8 |
| GBD | NKG2D | BTNL3 | CD3ζ |
| GBD | NKG2D | BTNL3 | CD3δ |
| GBD | NKG2D | BTNL3 | CD3γ |
| GBD | NKG2D | BTNL3 | CD3ε |
| GBD | NKG2D | BTNL3 | FcγRI-γ |
| GBD | NKG2D | BTNL3 | FcγRIII-γ |
| GBD | NKG2D | BTNL3 | FcεRIβ |
| GBD | NKG2D | BTNL3 | FcεRIγ |
| GBD | NKG2D | BTNL3 | DAP10 |
| GBD | NKG2D | BTNL3 | DAP12 |
| GBD | NKG2D | BTNL3 | CD32 |
| GBD | NKG2D | BTNL3 | CD79a |
| GBD | NKG2D | BTNL3 | CD79b |
| GBD | NKG2D | NKG2D | CD8 |
| GBD | NKG2D | NKG2D | CD3ζ |
| GBD | NKG2D | NKG2D | CD3δ |
| GBD | NKG2D | NKG2D | CD3γ |
| GBD | NKG2D | NKG2D | CD3ε |
| GBD | NKG2D | NKG2D | FcγRI-γ |
| GBD | NKG2D | NKG2D | FcγRIII-γ |
| GBD | NKG2D | NKG2D | FcεRIβ |
| GBD | NKG2D | NKG2D | FcεRIγ |
| GBD | NKG2D | NKG2D | DAP10 |
| GBD | NKG2D | NKG2D | DAP12 |
| GBD | NKG2D | NKG2D | CD32 |
| GBD | NKG2D | NKG2D | CD79a |
| GBD | NKG2D | NKG2D | CD79b |

TABLE 4

CARs lacking Co-Simulatory Signal (for dual CAR approach)

| | Co-stimulatory Signal | Signal Domain |
|---|---|---|
| GBD | none | CD8 |
| GBD | none | CD3ζ |
| GBD | none | CD3δ |
| GBD | none | CD3γ |
| GBD | none | CD3ε |
| GBD | none | FcγRI-γ |
| GBD | none | FcγRIII-γ |
| GBD | none | FcεRiβ |
| GBD | none | FcεRIγ |
| GBD | none | DAP10 |
| GBD | none | DAP12 |
| GBD | none | CD32 |
| GBD | none | CD79a |
| GBD | none | CD8 |
| GBD | none | CD3ζ |
| GBD | none | CD3δ |
| GBD | none | CD3γ |
| GBD | none | CD3ε |
| GBD | none | FcγRI-γ |

TABLE 5

CARs lacking Signal Domain (for dual CAR approach)

| | Co-stimulatory Signal | Signal Domain |
|---|---|---|
| GBD | CD28 | none |
| GBD | CD8 | none |
| GBD | CD4 | none |
| GBD | b2c | none |
| GBD | CD137/41BB | none |
| GBD | ICOS | none |
| GBD | CD27 | none |
| GBD | CD28δ | none |
| GBD | CD80 | none |
| GBD | CD86 | none |
| GBD | OX40 | none |
| GBD | DAP10 | none |
| GBD | MyD88 | none |
| GBD | CD7 | none |
| GBD | DAP12 | none |
| GBD | MyD88 | none |
| GBD | CD7 | none |
| GBD | BTNL3 | none |
| GBD | NKG2D | none |

TABLE 6

Third Generation CARs lacking Signal Domain (for dual CAR approach)

| | Co-stimulatory Signal | Co-stimulatory Signal | Signal Domain |
|---|---|---|---|
| GBD | CD28 | CD28 | none |
| GBD | CD28 | CD8 | none |
| GBD | CD28 | CD4 | none |
| GBD | CD28 | b2c | none |
| GBD | CD28 | CD137/41BB | none |
| GBD | CD28 | ICOS | none |
| GBD | CD28 | CD27 | none |
| GBD | CD28 | CD28δ | none |
| GBD | CD28 | CD80 | none |
| GBD | CD28 | CD86 | none |
| GBD | CD28 | OX40 | none |
| GBD | CD28 | DAP10 | none |
| GBD | CD28 | MyD88 | none |
| GBD | CD28 | CD7 | none |
| GBD | CD28 | DAP12 | none |
| GBD | CD28 | MyD88 | none |
| GBD | CD28 | CD7 | none |
| GBD | CD8 | CD28 | none |
| GBD | CD8 | CD8 | none |
| GBD | CD8 | CD4 | none |
| GBD | CD8 | b2c | none |
| GBD | CD8 | CD137/41BB | none |
| GBD | CD8 | ICOS | none |
| GBD | CD8 | CD27 | none |
| GBD | CD8 | CD28δ | none |
| GBD | CD8 | CD80 | none |
| GBD | CD8 | CD86 | none |
| GBD | CD8 | OX40 | none |
| GBD | CD8 | DAP10 | none |
| GBD | CD8 | MyD88 | none |
| GBD | CD8 | CD7 | none |
| GBD | CD8 | DAP12 | none |
| GBD | CD8 | MyD88 | none |
| GBD | CD8 | CD7 | none |
| GBD | CD4 | CD28 | none |
| GBD | CD4 | CD8 | none |
| GBD | CD4 | CD4 | none |
| GBD | CD4 | b2c | none |
| GBD | CD4 | CD137/41BB | none |
| GBD | CD4 | ICOS | none |
| GBD | CD4 | CD27 | none |
| GBD | CD4 | CD28δ | none |
| GBD | CD4 | CD80 | none |
| GBD | CD4 | CD86 | none |
| GBD | CD4 | OX40 | none |
| GBD | CD4 | DAP10 | none |
| GBD | CD4 | MyD88 | none |
| GBD | CD4 | CD7 | none |
| GBD | CD4 | DAP12 | none |
| GBD | CD4 | MyD88 | none |
| GBD | CD4 | CD7 | none |
| GBD | b2c | CD28 | none |
| GBD | b2c | CD8 | none |
| GBD | b2c | CD4 | none |
| GBD | b2c | b2c | none |

TABLE 6-continued

Third Generation CARs lacking Signal Domain (for dual CAR approach)

| | Co-stimulatory Signal | Co-stimulatory Signal | Signal Domain |
|---|---|---|---|
| GBD | b2c | CD137/41BB | none |
| GBD | b2c | ICOS | none |
| GBD | b2c | CD27 | none |
| GBD | b2c | CD28δ | none |
| GBD | b2c | CD80 | none |
| GBD | b2c | CD86 | none |
| GBD | b2c | OX40 | none |
| GBD | b2c | DAP10 | none |
| GBD | b2c | MyD88 | none |
| GBD | b2c | CD7 | none |
| GBD | b2c | DAP12 | none |
| GBD | b2c | MyD88 | none |
| GBD | b2c | CD7 | none |
| GBD | CD137/41BB | CD28 | none |
| GBD | CD137/41BB | CD8 | none |
| GBD | CD137/41BB | CD4 | none |
| GBD | CD137/41 BB | b2c | none |
| GBD | CD137/41 BB | CD137/41BB | none |
| GBD | CD137/41 BB | ICOS | none |
| GBD | CD137/41 BB | CD27 | none |
| GBD | CD137/41 BB | CD28δ | none |
| GBD | CD137/41 BB | CD80 | none |
| GBD | CD137/41 BB | CD86 | none |
| GBD | CD137/41 BB | 0X40 | none |
| GBD | CD137/41 BB | DAP10 | none |
| GBD | CD137/41 BB | MyD88 | none |
| GBD | CD137/41 BB | CD7 | none |
| GBD | CD137/41 BB | DAP12 | none |
| GBD | CD137/41 BB | MyD88 | none |
| GBD | CD137/41 BB | CD7 | none |
| GBD | ICOS | CD28 | none |
| GBD | ICOS | CD8 | none |
| GBD | ICOS | CD4 | none |
| GBD | ICOS | b2c | none |
| GBD | ICOS | CD137/41BB | none |
| GBD | ICOS | ICOS | none |
| GBD | ICOS | CD27 | none |
| GBD | ICOS | CD28δ | none |
| GBD | ICOS | CD80 | none |
| GBD | ICOS | CD86 | none |
| GBD | ICOS | OX40 | none |
| GBD | ICOS | DAP10 | none |
| GBD | ICOS | MyD88 | none |
| GBD | ICOS | CD7 | none |
| GBD | ICOS | DAP12 | none |
| GBD | ICOS | MyD88 | none |
| GBD | ICOS | CD7 | none |
| GBD | ICOS | CD28 | none |
| GBD | ICOS | CD8 | none |
| GBD | ICOS | CD4 | none |
| GBD | ICOS | b2c | none |
| GBD | ICOS | CD137/41BB | none |
| GBD | ICOS | ICOS | none |
| GBD | ICOS | CD27 | none |
| GBD | ICOS | CD28δ | none |
| GBD | ICOS | CD80 | none |
| GBD | ICOS | CD86 | none |
| GBD | ICOS | 0X40 | none |
| GBD | ICOS | DAP10 | none |
| GBD | ICOS | MyD88 | none |
| GBD | ICOS | CD7 | none |
| GBD | ICOS | DAP12 | none |
| GBD | ICOS | MyD88 | none |
| GBD | ICOS | CD7 | none |
| GBD | CD27 | CD28 | none |
| GBD | CD27 | CD8 | none |
| GBD | CD27 | CD4 | none |
| GBD | CD27 | b2c | none |
| GBD | CD27 | CD137/41BB | none |
| GBD | CD27 | ICOS | none |
| GBD | CD27 | CD27 | none |
| GBD | CD27 | CD28δ | none |
| GBD | CD27 | CD80 | none |
| GBD | CD27 | CD86 | none |
| GBD | CD27 | 0X40 | none |
| GBD | CD27 | DAP10 | none |
| GBD | CD27 | MyD88 | none |
| GBD | CD27 | CD7 | none |
| GBD | CD27 | DAP12 | none |
| GBD | CD27 | MyD88 | none |
| GBD | CD27 | CD7 | none |
| GBD | CD28δ | CD28 | none |
| GBD | CD28δ | CD8 | none |
| GBD | CD28δ | CD4 | none |
| GBD | CD28δ | b2c | none |
| GBD | CD28δ | CD137/41BB | none |
| GBD | CD28δ | ICOS | none |
| GBD | CD28δ | CD27 | none |
| GBD | CD28δ | CD28δ | none |
| GBD | CD28δ | CD80 | none |
| GBD | CD28δ | CD86 | none |
| GBD | CD28δ | 0X40 | none |
| GBD | CD28δ | DAP10 | none |
| GBD | CD28δ | MyD88 | none |
| GBD | CD28δ | CD7 | none |
| GBD | CD28δ | DAP12 | none |
| GBD | CD28δ | MyD88 | none |
| GBD | CD28δ | CD7 | none |
| GBD | CD80 | CD28 | none |
| GBD | CD80 | CD8 | none |
| GBD | CD80 | CD4 | none |
| GBD | CD80 | b2c | none |
| GBD | CD80 | CD137/41BB | none |
| GBD | CD80 | ICOS | none |
| GBD | CD80 | CD27 | none |
| GBD | CD80 | CD28δ | none |
| GBD | CD80 | CD80 | none |
| GBD | CD80 | CD86 | none |
| GBD | CD80 | 0X40 | none |
| GBD | CD80 | DAP10 | none |
| GBD | CD80 | MyD88 | none |
| GBD | CD80 | CD7 | none |
| GBD | CD80 | DAP12 | none |
| GBD | CD80 | MyD88 | none |
| GBD | CD80 | CD7 | none |
| GBD | CD86 | CD28 | none |
| GBD | CD86 | CD8 | none |
| GBD | CD86 | CD4 | none |
| GBD | CD86 | b2c | none |
| GBD | CD86 | CD137/41BB | none |
| GBD | CD86 | ICOS | none |
| GBD | CD86 | CD27 | none |
| GBD | CD86 | CD28δ | none |
| GBD | CD86 | CD80 | none |
| GBD | CD86 | CD86 | none |
| GBD | CD86 | 0X40 | none |
| GBD | CD86 | DAP10 | none |
| GBD | CD86 | MyD88 | none |
| GBD | CD86 | CD7 | none |
| GBD | CD86 | DAP12 | none |
| GBD | CD86 | MyD88 | none |
| GBD | CD86 | CD7 | none |
| GBD | 0X40 | CD28 | none |
| GBD | 0X40 | CD8 | none |
| GBD | 0X40 | CD4 | none |
| GBD | 0X40 | b2c | none |
| GBD | 0X40 | CD137/41BB | none |
| GBD | 0X40 | ICOS | none |
| GBD | 0X40 | CD27 | none |
| GBD | 0X40 | CD28δ | none |
| GBD | 0X40 | CD80 | none |
| GBD | 0X40 | CD86 | none |
| GBD | 0X40 | 0X40 | none |
| GBD | 0X40 | DAP10 | none |
| GBD | 0X40 | MyD88 | none |
| GBD | 0X40 | CD7 | none |
| GBD | 0X40 | DAP12 | none |
| GBD | 0X40 | MyD88 | none |
| GBD | 0X40 | CD7 | none |
| GBD | DAP10 | CD28 | none |

TABLE 6-continued

Third Generation CARs lacking Signal Domain (for dual CAR approach)

| | Co-stimulatory Signal | Co-stimulatory Signal | Signal Domain |
|---|---|---|---|
| GBD | DAP10 | CD8 | none |
| GBD | DAP10 | CD4 | none |
| GBD | DAP10 | b2c | none |
| GBD | DAP10 | CD137/41BB | none |
| GBD | DAP10 | ICOS | none |
| GBD | DAP10 | CD27 | none |
| GBD | DAP10 | CD28δ | none |
| GBD | DAP10 | CD80 | none |
| GBD | DAP10 | CD86 | none |
| GBD | DAP10 | OX40 | none |
| GBD | DAP10 | DAP10 | none |
| GBD | DAP10 | MyD88 | none |
| GBD | DAP10 | CD7 | none |
| GBD | DAP10 | DAP12 | none |
| GBD | DAP10 | MyD88 | none |
| GBD | DAP10 | CD7 | none |
| GBD | DAP12 | CD28 | none |
| GBD | DAP12 | CD8 | none |
| GBD | DAP12 | CD4 | none |
| GBD | DAP12 | b2c | none |
| GBD | DAP12 | CD137/41BB | none |
| GBD | DAP12 | ICOS | none |
| GBD | DAP12 | CD27 | none |
| GBD | DAP12 | CD28δ | none |
| GBD | DAP12 | CD80 | none |
| GBD | DAP12 | CD86 | none |
| GBD | DAP12 | OX40 | none |
| GBD | DAP12 | DAP10 | none |
| GBD | DAP12 | MyD88 | none |
| GBD | DAP12 | CD7 | none |
| GBD | DAP12 | DAP12 | none |
| GBD | DAP12 | MyD88 | none |
| GBD | DAP12 | CD7 | none |
| GBD | MyD88 | CD28 | none |
| GBD | MyD88 | CD8 | none |
| GBD | MyD88 | CD4 | none |
| GBD | MyD88 | b2c | none |
| GBD | MyD88 | CD137/41BB | none |
| GBD | MyD88 | ICOS | none |
| GBD | MyD88 | CD27 | none |
| GBD | MyD88 | CD28δ | none |
| GBD | MyD88 | CD80 | none |
| GBD | MyD88 | CD86 | none |
| GBD | MyD88 | OX40 | none |
| GBD | MyD88 | DAP10 | none |
| GBD | MyD88 | MyD88 | none |
| GBD | MyD88 | CD7 | none |
| GBD | MyD88 | DAP12 | none |
| GBD | MyD88 | MyD88 | none |
| GBD | MyD88 | CD7 | none |
| GBD | CD7 | CD28 | none |
| GBD | CD7 | CD8 | none |
| GBD | CD7 | CD4 | none |
| GBD | CD7 | b2c | none |
| GBD | CD7 | CD137/41BB | none |
| GBD | CD7 | ICOS | none |
| GBD | CD7 | CD27 | none |
| GBD | CD7 | CD28δ | none |
| GBD | CD7 | CD80 | none |
| GBD | CD7 | CD86 | none |
| GBD | CD7 | OX40 | none |
| GBD | CD7 | DAP10 | none |
| GBD | CD7 | MyD88 | none |
| GBD | CD7 | CD7 | none |
| GBD | CD7 | DAP12 | none |
| GBD | CD7 | MyD88 | none |
| GBD | CD7 | CD7 | none |
| GBD | BTNL3 | CD28 | none |
| GBD | BTNL3 | CD8 | none |
| GBD | BTNL3 | CD4 | none |
| GBD | BTNL3 | b2c | none |
| GBD | BTNL3 | CD137/41BB | none |
| GBD | BTNL3 | ICOS | none |
| GBD | BTNL3 | CD27 | none |
| GBD | BTNL3 | CD28δ | none |
| GBD | BTNL3 | CD80 | none |
| GBD | BTNL3 | CD86 | none |
| GBD | BTNL3 | OX40 | none |
| GBD | BTNL3 | DAP10 | none |
| GBD | BTNL3 | MyD88 | none |
| GBD | BTNL3 | CD7 | none |
| GBD | BTNL3 | DAP12 | none |
| GBD | BTNL3 | MyD88 | none |
| GBD | BTNL3 | CD7 | none |
| GBD | NKG2D | CD28 | none |
| GBD | NKG2D | CD8 | none |
| GBD | NKG2D | CD4 | none |
| GBD | NKG2D | b2c | none |
| GBD | NKG2D | CD137/41BB | none |
| GBD | NKG2D | ICOS | none |
| GBD | NKG2D | CD27 | none |
| GBD | NKG2D | CD28δ | none |
| GBD | NKG2D | CD80 | none |
| GBD | NKG2D | CD86 | none |
| GBD | NKG2D | OX40 | none |
| GBD | NKG2D | DAP10 | none |
| GBD | NKG2D | MyD88 | none |
| GBD | NKG2D | CD7 | none |
| GBD | NKG2D | DAP12 | none |
| GBD | NKG2D | MyD88 | none |
| GBD | NKG2D | CD7 | none |

Also disclosed are bi-specific CARs. Also disclosed are CARs designed to work only in conjunction with another CAR that binds a different antigen, such as a tumor antigen. For example, in these embodiments, the endodomain of the disclosed CAR can contain only a signaling domain (SD) or a co-stimulatory signaling region (CSR), but not both. The second CAR (or endogenous T-cell) provides the missing signal if it is activated. For example, if the disclosed CAR contains an SD but not a CSR, then the immune effector cell containing this CAR is only activated if another CAR (or T-cell) containing a CSR binds its respective antigen. Likewise, if the disclosed CAR contains a CSR but not a SD, then the immune effector cell containing this CAR is only activated if another CAR (or T-cell) containing an SD binds its respective antigen.

Tumor antigens are proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated. Tumor antigens are well known in the art and include, for example, a glioma-associated antigen, carcinoembryonic antigen (CEA), EGFRvIII, IL-IIRa, IL-13Ra, EGFR, FAP, B7H3, Kit, CA LX, CS-1, MUC1, BCMA, bcr-abl, HER2, β-human chorionic gonadotropin, alphafetoprotein (AFP), ALK, CD19, TIM3, cyclin BI, lectin-reactive AFP, Fos-related antigen 1, ADRB3, thyroglobulin, EphA2, RAGE-1, RUI, RU2, SSX2, AKAP-4, LCK, OY-TESI, PAX5, SART3, CLL-1, fucosyl GM1, GloboH, MN-CA IX, EPCAM, EVT6-AML, TGS5, human telomerase reverse transcriptase, plysialic acid, PLAC1, RUI, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LAGE-la, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFRbeta, survivin and telomerase, legumain, HPV E6,E7, sperm protein 17, SSEA-4, tyrosinase, TARP, WT1, prostate-carcinoma tumor antigen-1 (PCTA-1), ML-IAP, MAGE, MAGE-A1,MAD-CT-1, MAD-CT-2, MelanA/MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, TIM3, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRC5D, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, SSTR2, CD19, TIM3, BCMA, GD2, CLL-1, CA-IX, MUCI, HER2, and any combination thereof.

Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, pl85erbB2, pl80erbB-3, c-met, nm-23H1, PSA, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3CA 27.29BCAA, CA 195, CA 242, CA-50, CAM43, CD68P1, CO-029, FGF-5, G250, Ga733EpCAM, HTgp-175, M344, MA-50, MG7-Ag, MOV18, NB/70K, NY-CO-1, RCASI, SDCCAG1 6, TA-90Mac-2 binding proteincyclophilm C-associated protein, TAAL6, TAG72, TLP, TPS, GPC3, MUC16, LMP1, EBMA-1, BARF-1, CS1, CD319, HER1, B7H6, L1CAM, IL6, and MET.

Nucleic Acids and Vectors

Also disclosed are polynucleotides and polynucleotide vectors encoding the disclosed GSC-specific CARs that allow expression of the GSC-specific CARs in the disclosed immune effector cells.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1a (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y); cholesterol ("Choi") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

Also disclosed are immune effector cells that are engineered to express the disclosed CARs (also referred to herein as "CAR-T cells." These cells are preferably obtained from the subject to be treated (i.e. are autologous). However, in some embodiments, immune effector cell lines or donor effector cells (allogeneic) are used. Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dentritic cells, mast cells, neutrophils, basophils, eosinophils, or any combinations thereof. For example, the immune effector cells can comprise T lymphocytes.

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate a different type of immune response.

Cytotoxic T cells (Tc cells, or CTLs) destroy virally infected cells and tumor cells, and are also implicated in transplant rejection. These cells are also known as $CD8^+$ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either $CD4^+$ or $CD8^+$. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of $CD4^+$ $T_{reg}$ cells have been described—naturally occurring $T_{reg}$ cells and adaptive $T_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4+ cells. In other embodiments, the T cells are enriched for one or more subsets based on cell surface expression. For example, in some cases, the T comprise are cytotoxic $CD8^+$ T lymphocytes. In some embodiments, the T cells comprise γδ T cells, which possess a distinct T-cell receptor (TCR) having one γ chain and one δ chain instead of a and β chains.

Natural-killer (NK) cells are CD56+CD3- large granular lymphocytes that can kill virally infected and transformed cells, and constitute a critical cellular subset of the innate immune system (Godfrey J, et al. Leuk Lymphoma 2012 53:1666-1676). Unlike cytotoxic $CD8^+$ T lymphocytes, NK cells launch cytotoxicity against tumor cells without the requirement for prior sensitization, and can also eradicate MHC-1-negative cells (Narni-Mancinelli E, et al. Int Immunol 2011 23:427-431). NK cells are safer effector cells, as they may avoid the potentially lethal complications of cytokine storms (Morgan RA, et al. Mol Ther 2010 18:843-851), tumor lysis syndrome (Porter DL, et al. N Engl J Med 2011 365:725-733), and on-target, off-tumor effects. Although NK cells have a well-known role as killers of cancer cells, and NK cell impairment has been extensively documented as crucial for progression of MM (Godfrey J, et al. Leuk Lymphoma 2012 53:1666-1676; Fauriat C, et al. Leukemia 2006 20:732-733), the means by which one might enhance NK cell-mediated anti-MM activity has been largely unexplored prior to the disclosed CARs.

Therapeutic Methods

Immune effector cells expressing the disclosed CARs can elicit an anti-tumor immune response against GSCs. The anti-tumor immune response elicited by the disclosed CAR-modified immune effector cells may be an active or a passive immune response. In addition, the CAR-mediated immune response may be part of an adoptive immunotherapy approach in which CAR-modified immune effector cells induce an immune response specific to GSCs.

Adoptive transfer of immune effector cells expressing chimeric antigen receptors is a promising anti-cancer therapeutic. Following the collection of a patient's immune effector cells, the cells may be genetically engineered to express the disclosed GSC-specific CARs, then infused back into the patient.

The disclosed CAR-modified immune effector cells may be administered either alone, or as a pharmaceutical composition in combination with diluents and/or with other components such as IL-2, IL-15, or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodiments formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an The disclosed CARs can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed CARs can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-Hi; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MED14736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed CARs can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbBI (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec ST1571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with a CARs for treating the disorders as described above may be an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-la from the human CXC and C-C chemokine families. Suitable cytokines include cytokine derivatives, cytokine variants, cytokine fragments, and cytokine fusion proteins.

In some embodiments, a therapeutic agent for use in combination with a CARs for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735; 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a CARs for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with an CARs for treating the disorders as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed CARs is administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed CARs is administered in combination with surgery.

CAR-T cells may be designed in several ways that enhance tumor cytotoxicity and specificity, evade tumor immunosuppression, avoid host rejection, and prolong their therapeutic half-life. TRUCK (T-cells Redirected for Universal Cytokine Killing) T cells for example, possess a CAR but are also engineered to release cytokines such as IL-12 that promote tumor killing. Because these cells are designed to release a molecular payload upon activation of the CAR once localized to the tumor environment, these CAR-T cells are sometimes also referred to as 'armored CARs'. Several cytokines as cancer therapies are being investigated both pre-clinically and clinically, and may also prove useful when similarly incorporated into a TRUCK form of CAR-T therapy. Among these include IL-2, IL-3. IL-4, IL-5, IL-6, IL-7, IL-10, IL-12, IL-13, IL-15, IL-18, M-CSF, GM-CSF, IFN-α, IFN-γ, TNF-α, TRAIL, FLT3 ligand, Lymphotactin, and TGF-β (Dranoff 2004). "Self-driving" or "homing" CAR-T cells are engineered to express a chemokine receptor in addition to their CAR. As certain chemokines can be upregulated in tumors, incorporation of a chemokine receptor aids in tumor trafficking to and infiltration by the adoptive T-cell, thereby enhancing both specificity and functionality of the CAR-T (Moon 2011). Universal CAR-T cells also possess a CAR, but are engineered such that they do not express endogenous TCR (T-cell receptor) or MHC (major histocompatibility complex) proteins. Removal of these two proteins from the signaling repertoire of the adoptive T-cell therapy prevents graft-versus-host-disease and rejection, respectively. Armored CAR-T cells are additionally so named for their ability to evade tumor immunosuppression and tumor-induced CAR-T hypofunction. These particular CAR-Ts possess a CAR, and may be engineered to not express checkpoint inhibitors. Alternatively, these CAR-Ts can be co-administered with a monoclonal antibody (mAb) that blocks checkpoint signaling. Administration of an anti-PDL1 antibody significantly restored the killing ability of CAR TILs (tumor infiltrating lymphocytes). While PD1-PDL1 and CTLA-4-CD80/CD86 signaling pathways have been investigated, it is possible to target other immune checkpoint signaling molecules in the design of an armored CAR-T including LAG-3, Tim-3, IDO-1, 2B4, and KIR. Other intracellular inhibitors of TILs include phosphatases (SHP1), ubiquitin-ligases (i.e., cbl-b), and kinases (i.e., diacylglycerol kinase). Armored CAR-Ts may also be engineered to express proteins or receptors that protect them against or make them resistant to the effects of tumor-secreted cytokines. For example, CTLs (cytotoxic T lymphocytes) transduced with the double negative form of the TGF-β receptor are resistant to the immunosuppression by lymphoma secreted TGF-β. These transduced cells showed notably increased antitumor activity in vivo when compared to their control counterparts.

A tandem CAR contains two sequential antigen binding domains facing the extracellular environment connected to the intracellular costimulatory and stimulatory domains. A dual CAR can be engineered such that one extracellular antigen binding domain is connected to the intracellular costimulatory domain and a second, distinct extracellular antigen binding domain is connected to the intracellular stimulatory domain. Because the stimulatory and costimulatory domains are split between two separate antigen binding domains, dual CARs are also referred to as "split CARs". In both tandem and dual CAR designs, binding of both antigen binding domains is necessary to allow signaling of the CAR circuit in the T-cell. Because these two CAR designs have binding affinities for different, distinct antigens, they are also referred to as "bi-specific" CARs.

One primary concern with CAR-T cells as a form of "living therapeutic" is their manipulability in vivo and their potential immune-stimulating side effects. To better control CAR-T therapy and prevent against unwanted side effects, a variety of features have been engineered including off-switches, safety mechanisms, and conditional control mechanisms. Both self-destruct and marked/tagged CAR-T cells for example, are engineered to have an "off-switch" that promotes clearance of the CAR-expressing T-cell. A self-destruct CAR-T contains a CAR, but is also engineered to express a pro-apoptotic suicide gene or "elimination gene" inducible upon administration of an exogenous molecule. A variety of suicide genes may be employed for this purpose, including HSV-TK (herpes simplex virus thymidine kinase), Fas, iCasp9 (inducible caspase 9), CD20, MYC TAG, and truncated EGFR (endothelial growth factor receptor). HSK for example, will convert the prodrug ganciclovir (GCV) into GCV-triphosphate that incorporates itself into replicating DNA, ultimately leading to cell death. iCasp9 is a chimeric protein containing components of FK506-binding protein that binds the small molecule AP1903, leading to caspase 9 dimerization and apoptosis. A marked/tagged CAR-T cell however, is one that possesses a CAR but also is engineered to express a selection marker. Administration of a mAb against this selection marker will promote clearance of the CAR-T cell. Truncated EGFR is one such targetable antigen by the anti-EGFR mAb, and administration of cetuximab works to promotes elimination of the CAR-T cell. CARs created to have these features are also referred to as sCARs for 'switchable CARs', and RCARs for 'regulatable CARs'. A "safety CAR", also known as an "inhibitory CAR" (iCAR), is engineered to express two antigen binding domains. One of these extracellular domains is directed against a tumor related antigen and bound to an intracellular costimulatory and stimulatory domain. The second extracellular antigen binding domain however is specific for normal tissue and bound to an intracellular checkpoint domain such as CTLA4, PD1, or CD45. Incorporation of multiple intracellular inhibitory domains to the iCAR is also possible. Some inhibitory molecules that may provide these inhibitory domains include B7-H1, B7-1, CD160, PIH, 2B4, CEACAM (CEACAM-1. CEACAM-3, and/or CEACAM-5), LAG-3, TIGIT, BTLA, LAIR1, and TGFP-R. In the presence of normal tissue, stimulation of this second antigen binding domain will work to inhibit the CAR. It should be noted that due to this dual antigen specificity, iCARs are also a form of bi-specific CAR-T cells. The safety CAR-T engineering enhances specificity of the CAR-T cell for tumor tissue, and is advantageous in situations where certain normal tissues may express very low levels of a tumor associated antigen that would lead to off target effects with a standard CAR (Morgan 2010). A conditional CAR-T cell expresses an extracellular antigen binding domain connected to an intracellular costimulatory domain and a separate, intracellular costimulator. The costimulatory and stimulatory domain sequences are engineered in such a way that upon administration of an exogenous molecule the resultant proteins will come together intracellularly to complete the CAR circuit. In this way, CAR-T activation can be modulated, and possibly even 'fine-tuned' or personalized to a specific patient. Similar to a dual CAR design, the stimulatory and costimulatory domains are physically separated when inactive in the conditional CAR; for this reason these too are also referred to as a "split CAR".

In some embodiments, two or more of these engineered features may be combined to create an enhanced, multifunctional CAR-T. For example, it is possible to create a CAR-T cell with either dual- or conditional-CAR design that also releases cytokines like a TRUCK. In some embodiments, a dual-conditional CAR-T cell could be made such that it expresses two CARs with two separate antigen binding domains against two distinct cancer antigens, each bound to their respective costimulatory domains. The costimulatory domain would only become functional with the stimulatory domain after the activating molecule is administered. For this CAR-T cell to be effective the cancer must express both cancer antigens and the activating molecule must be administered to the patient; this design thereby incorporating features of both dual and conditional CAR-T cells.

Typically, CAR-T cells are created using a-p T cells, however y-5 T cells may also be used. In some embodiments, the described CAR constructs, domains, and engineered features used to generate CAR-T cells could similarly be employed in the generation of other types of CAR-expressing immune cells including NK (natural killer) cells, B cells, mast cells, myeloid-derived phagocytes, and NKT cells. Alternatively, a CAR-expressing cell may be created to have properties of both T-cell and NK cells. In an additional embodiment, the transduced with CARs may be autologous or allogeneic.

Several different methods for CAR expression may be used including retroviral transduction (including y-retroviral), lentiviral transduction, transposon/transposases (Sleeping Beauty and PiggyBac systems), and messenger RNA transfer-mediated gene expression. Gene editing (gene insertion or gene deletion/disruption) has become of increasing importance with respect to the possibility for engineering CAR-T cells as well. CRISPR-Cas9, ZFN (zinc finger nuclease), and TALEN (transcription activator like effector nuclease) systems are three potential methods through which CAR-T cells may be generated.

Definitions

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "protein domain" refers to a portion of a protein, portions of a protein, or an entire protein showing structural integrity; this determination may be based on amino acid composition of a portion of a protein, portions of a protein, or the entire protein.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

A number of embodiments of the invention have been described. Nevertheless, it will be understood that various modifications may be made without departing from the spirit and scope of the invention. Accordingly, other embodiments are within the scope of the following claims.

EXAMPLES

Example 1: Phage Display Discovery of EYA1 as a Theranostic Target for Glioma Stem Cells Introduction Phage display is screening strategy that capitalizes on the unique properties of bacteriophages for the purposes of isolating short peptides specific for binding to a given receptor or cell type (Smith, G. P. Science 1985 228:1315-1317). In vivo phage display biopanning strategy was used to isolate GSC-specific binding peptides to elucidate new GSC regulators. Among the main obstacles in the development of targeted therapies against brain tumors is cell specificity and penetration of the BBB. To isolate peptides that circumvent these challenges in development of brain tumor targeting modalities, the in vivo biopanning strategy was modified to isolate peptides that target intracranially implanted xenografts. Using this strategy, both novel GSC maintenance targets were discovered and modalities for targeting GSCs in vivo were developed.

Results

Orthogonal In Vivo and In Vivo Biopanning Strategies Identify a GSC-Binding Peptide An in vivo biopanning strategy was previously leveraged with intravenous delivery of a phage library to an immunocompromised mouse bearing a glioma xenograft in the flank, followed by GSC enrichment using a previously validated marker, CD133. This strategy yielded several GSC binding peptides, leading to the identification of VAV3 as a GSC target (Liu, J. K. et al. Cell Death Differ 2014 21:1325-1339). While this strategy was promising, both the specificity and delivery of identified peptides was augmented through orthogonal screens in vitro with highly enriched GSCs for specificity and intracranial (IC) xenografts to select for peptides that penetrate the BBB. Due to low phage peptide recovery obtained from intracranial tumor dissociation, tumor cells could not undergo CD133 selection to isolate GSC specific binding peptides in vivo, yielding five phage peptides internalized in intracranial tumor cells. To compare the potential selectivity of these peptides for GSCs, a parallel in vitro biopanning strategy was performed to isolate peptides that specifically targeted GSCs, first using negative selection against extracellular matrix and non-stem glioma cells to eliminate non-GSC specific peptide sequences. Positive selection was repeated for three rounds to enrich for peptides with the greatest affinity for binding GSCs, yielding 53 phage peptides. Among the recovered phage peptides, there were several sequences recovered in multiple phage clones, indicating an enrichment for these sequences through successive rounds of biopanning. A single peptide sequence, AWEFYFP (SEQ ID NO:2) was shared between the two strategies (FIG. 1).

Using the National Center for Biotechnology Information (NCBI) Basic Local Alignment Search Tool (BLAST), the peptide sequence AWEFYFP (SEQ ID NO:2) returned EYA Transcriptional Coactivator and Phosphatase 1 (EYA1) as a possible match, with a 63% match with amino acids 6-11 in the EYA1 protein. Of note, amino acids 1-68 form the amino-terminal domain of human EYA1, containing the transcriptional co-activator domain (Rebay, I. Molecular and Cellular Biology. 2016 36:668-677).

GSCs Preferentially Express EYA1

Figure 5:
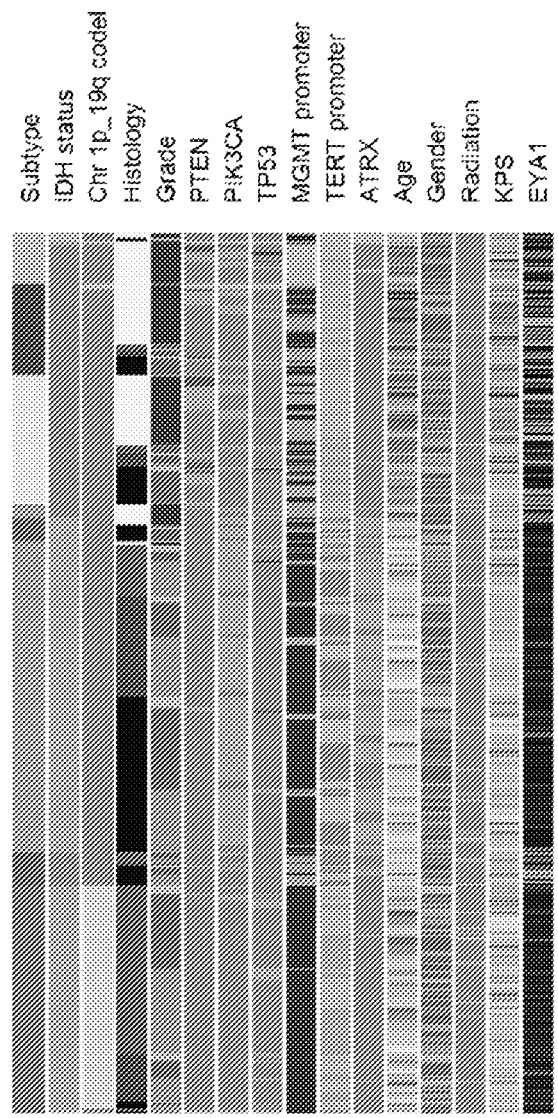
FIG. 5. TCGA analysis of EYA1. TCGA low grade and high grade analysis demonstrated EYA1 expression to correlate with IDH mutation, as well as MGMT promoter methylation. EYA1 also demonstrated a correlation with high G-CIMP phenotype.
Figure 5:
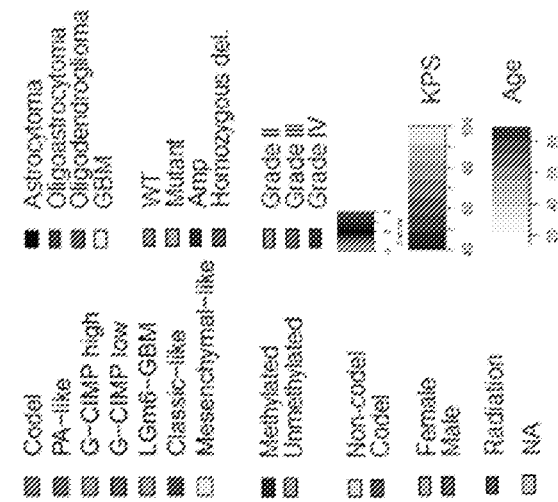

To interrogate a potential role of EYA1 in glioblastoma, the expression of EYA1 was investigated in The Cancer Genome Atlas (TCGA). Although there was not statistically significant difference in the expression of EYA1 between non-tumor and glioblastoma, EYA1 expression was significantly increased in the proneural subtype, which is histologically associated with increased tumor vasculature and glioma CpG island methylator phenotype (G-CIMP) in compared to other subtypes and non-G-CIMP (Jin, X. et al. Nat Med 2017 23:1352-1361; Kim, S. H. et al. Cell Death Differ 2015 22:1517-1525). Among glioblastoma patients with the more clinically aggressive non-G-CIMP status, higher expression of EYA1 correlated with decreased patient survival, indicating that EYA1 may play an important role in tumor progression amongst the more aggressive glioblastoma subtype. To further determine a potential function of EYA1 in glioblastoma, the Ivy Glioblastoma Atlas Project (Ivy GAP) database (Puchalski, R. B. et al. Science 2018 360:660-663) was used, which includes a panel of microdissected patient tumors with RNA sequencing, indicating increased EYA1 mRNA expression in the infiltrating microenvironment of glioblastomas, implicating a role in tumor proliferation and invasion. Finally, utilizing TCGA low grade and high grade dataset, EYA1 expression was found to be correlated to IDH mutants, MGMT promoter methylations, as well as G-CIMP high phenotype (FIG. 5).

Figure 6A:
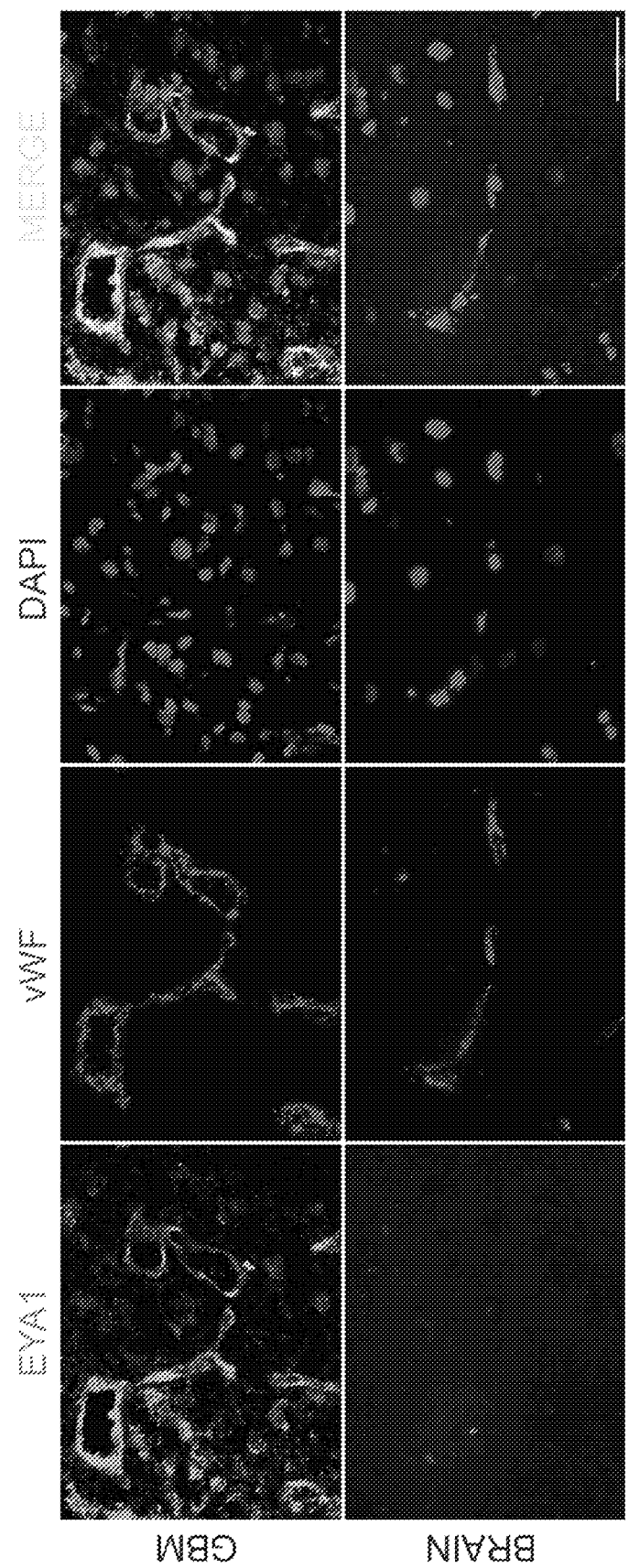
FIGS. 6A and 6B. EYA1 localization with endothelial cell markers. EYA1 demonstrates specificity within patient derived GBM tissue compared to normal brain and co-localization with von Willebrand Factor (vWF) (A) and CD31 (B).
Figure 6B:
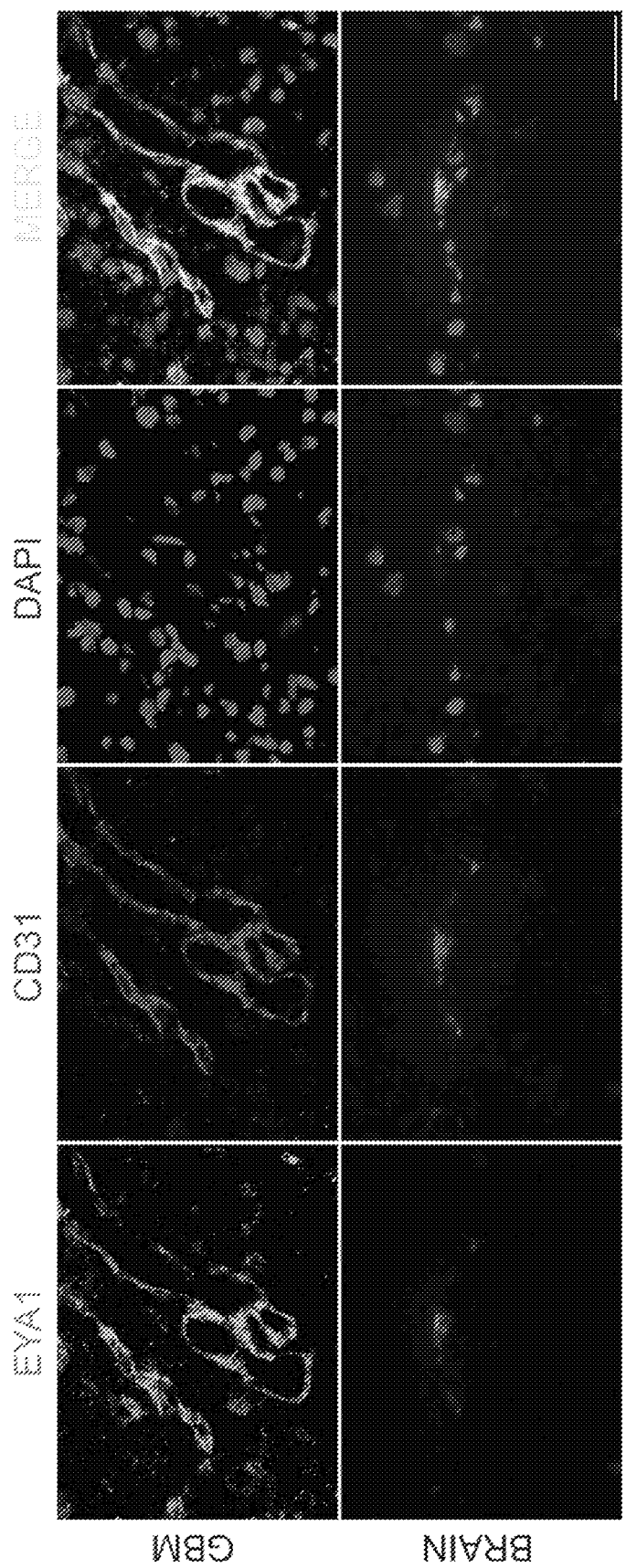

To determine EYA1 protein expression, immunohistochemistry was performed on a panel of surgically resected specimens from glioblastoma patients. EYA1 marked tumor cells coexpressing the GSC marker, SOX2, often in proximity to tumor vasculature, the perivascular niche, which is enriched within GSCs (Sarkar, A. et al. Cell stem cell 2013 12:15-30). Previous studies have suggested shared expression of antigens between GSCs and tumor endothelial cells potentially due to transdifferentiation towards an endothelial lineage (Ricci-Vitiani, L. et al. Nature 2010 468:824-828). Indeed, EYA1 co-stained cells lining tumor vasculature with von willenbrand Factor (vWF) and CD31, supporting EYA1 expression in tumor endothelial cells (FIG. 6). As a potential EYA1 peptide was isolated from GSCs, EYA1 expression was compared in a panel of matched GSCs and differentiated glioma cells (DGCs) that had been previously validated. EYA1 mRNA and protein levels were consistently elevated in GSCs, which also expressed SOX2. Further confirmation of the specificity of EYA1 was provided by the specific expression of SIX1, a known nuclear translocator of EYA1.

EYA1 Knockdown Suppresses GSC Growth, Self-Renewal and Invasion

To evaluate the role of EYA1 in GSCs, lentiviral transduction of short hairpin (shRNA) sequences was utilized to knockdown EYA1 (shEYA1) or a control shRNA sequence that does not target a mammalian genomic sequence (shCONT), with confirmation of successful EYA1 targeting at the mRNA and protein levels was confirmed using qRT-PCR and immunoblotting, respectively. The essential role of EYA1 in GSC maintenance was supported by attenuation of cellular growth in two GSC models starting between 2 and 3 days after transduction. One major limitation of conventional therapy is the invasion of glioblastoma cells into normal brain, precluding complete surgical resection. The EYA1 protein has distinct modules leading to a dual role as both a transcriptional co-activator and a tyrosine phosphatase. The contribution of these distinct functions remains to be defined, but through a combination of the two, EYA1 regulates cell migration and invasion in some cell types (Pandey, R. N. et al. Oncogene 2010 29:3715-3722). EYA1 served a similar role in GSCs as shRNA targeting of EYA1 decreased cell migration and invasion by >50%. Tumor sphere formation has been used as a surrogate for self-renewal, albeit with caveats. EYA1 targeting attenuated sphere formation using a limiting dilution assay study. Collectively, these results demonstrate that EYA1 contributes to multiple facets of tumor biology in GSCs.

EYA1 Knockdown Delays Tumor Formation and Prolongs Survival

The functional definition of cancer stem cells remains controversial, but the gold standard is tumor propagation in vivo. The EYA1 targeting approach was leveraged to investigate the contribution of EYA1 to in vivo tumor growth. GSC were transduced with either shEYA1 or shCONT then implanted into the right frontal lobes of immunocompromised mice. EYA1 knockdown increased tumor latency resulting in prolonged average survival of tumor-bearing mice (39 days vs. 32 days in 4121; 31 days vs. 24 days in 387). These results support EYA1 as a potential therapeutic target in glioblastoma.

EYA1 Regulates MYC in GSCs

Figure 2A:
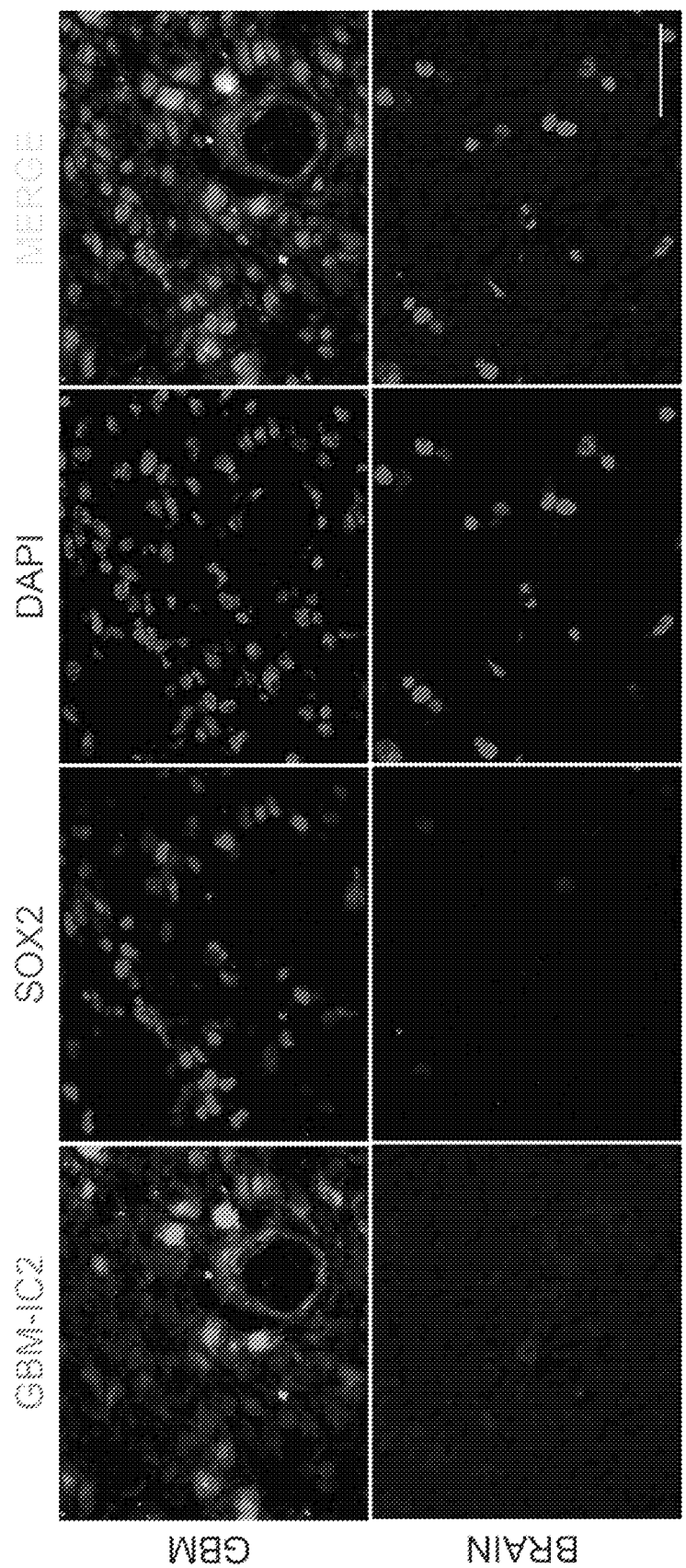
FIGS. 2A and 2B. GBM-IC2 preferentially binds to glioblastomas and GSCs. Fluorescently labeled GBM-IC2 demonstrates preferential binding to glioblastoma tissue, co-staining with SOX2 (A). GBM-IC2 conjugated with Cy5.5, demonstrates preferential binding to GSC tumor sphere (B).
Figure 2B:
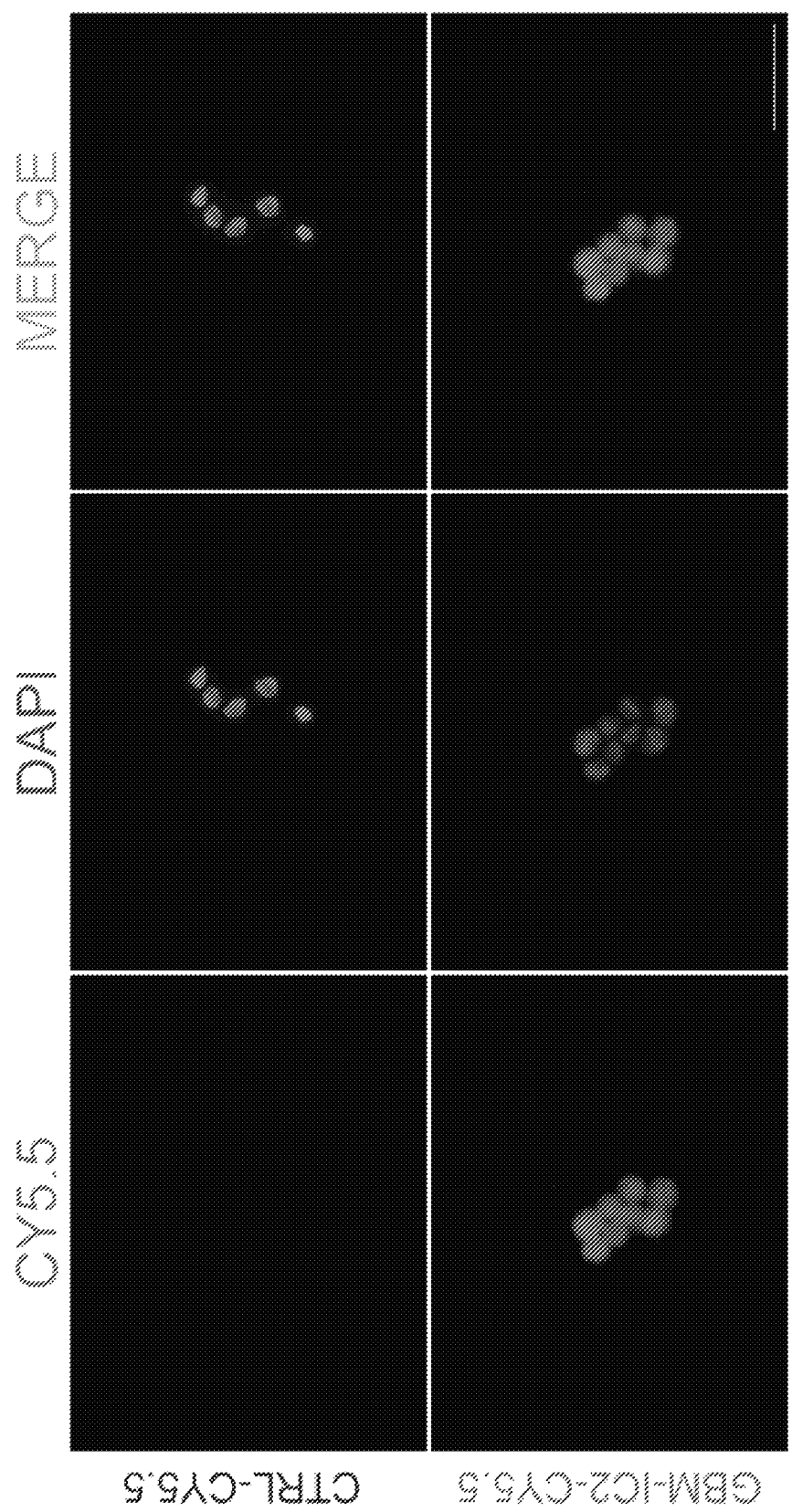

Canonically, EYA1 is localized to the cytoplasm, but also serves as a transcriptional co-activator, suggesting a nuclear localization, as well. Previous reports have linked EYA1 functionally to the SIX family, with SIX1 binding to EYA1 to induce EYA1 nuclear localization (Ohto, H. et al. Molecular and Cellular Biology. 1999 19:6815-6824). Further, EYA1 has been shown to be a regulator of MYC phosphorylation (J. Xu, et al. Developmental Cell. 2014 31:434-447). To understand the mechanisms through which EYA1 controls GSC proliferation, MYC levels were evaluated after EYA1 knockdown, revealing decreased MYC levels in mRNA expression and protein levels following EYA1 knockdown (FIG. 2A). To determine potential direct interaction, co-immunoprecipitation studies were performed with both EYA1 and MYC, revealing direct, physical interaction (FIG. 2B). These results indicate that EYA1 may exert effects on tumor cells through MYC regulation.

Phage Display-Identified Peptide Targets GSCs In Vitro and In Vivo

Phage display yields peptide sequences that inform target identification, like EYA1, but can also directly serve as ligands that may be used for cellular identification and/or targeting (i.e. theranostics). As the peptide AWEFYFP (SEQ ID NO:2) (GBM-IC2) was identified in both in vitro and in vivo biopanning for specific binding to GSCs, the potential utility of GBM-IC2 in the identification of GSCs was investigated. GBM-IC2 peptide conjugated with fluorescein specifically bound to glioblastoma tissue, relative to normal brain (FIG. 2). To determine the relative affinity of GBMIC2 for GSCs, co-staining with the GSC marker SOX2 was performed, revealing greater binding of GBM-IC2 to SOX2 expressing cells (FIG. 2).

Figure 3A:
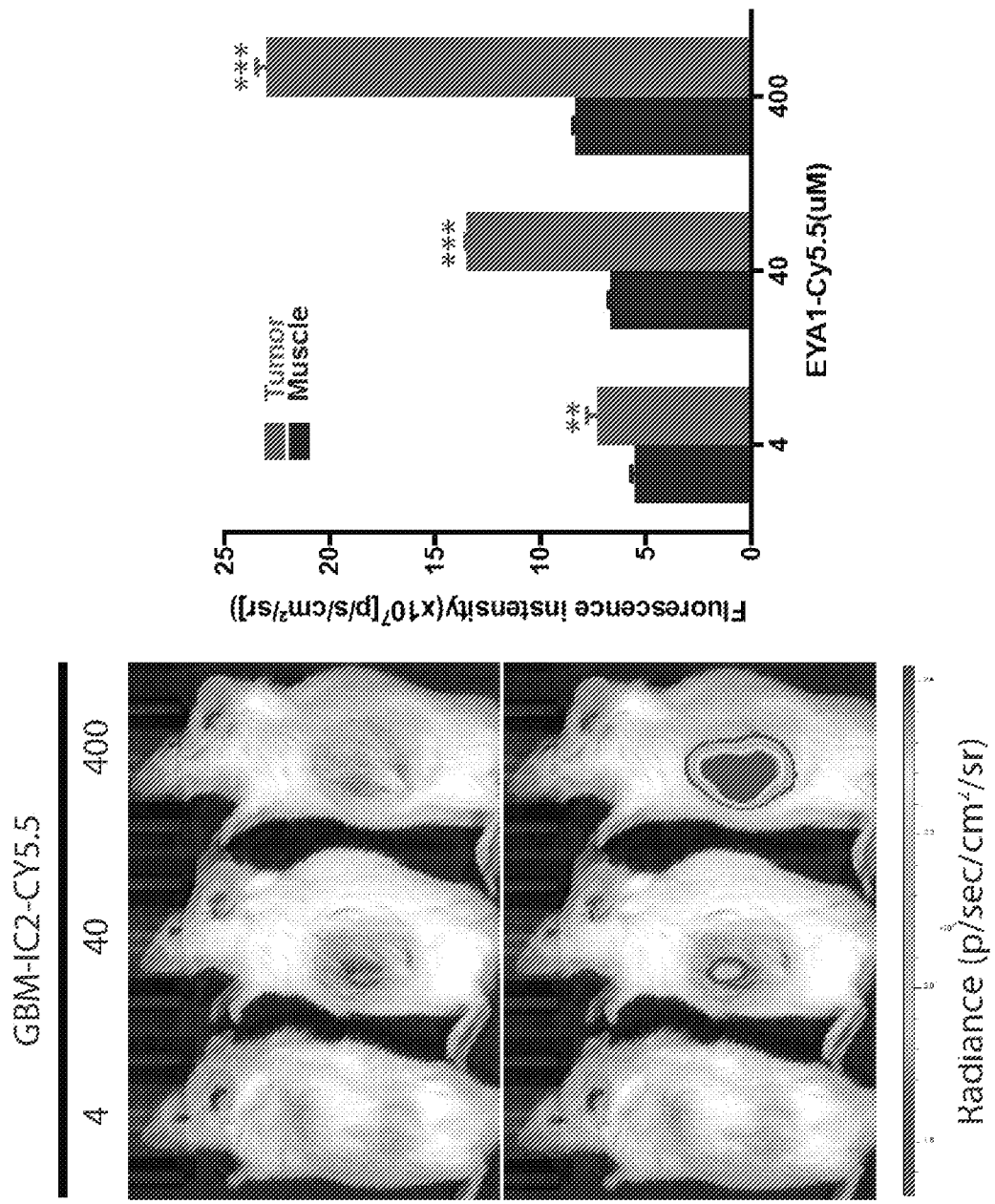
FIGS. 3A to 3C. GBM-IC2 targets glioblastoma xenografts following intravenous injection. GBM-IC2-Cy5.5 injected into the tail vein of NSG mice bearing glioblastoma xenografted into the subcutaneous flank demonstrates specific targeting of the tumor four hours after injection in a dose dependent manner in vivo (A) as well as ex vivo (B). Extended imaging of GBM-IC2-Cy5.5 injected into the tail vein demonstrates persistent tumor binding up 72 hours after peptide injection (C).
Figure 3B:
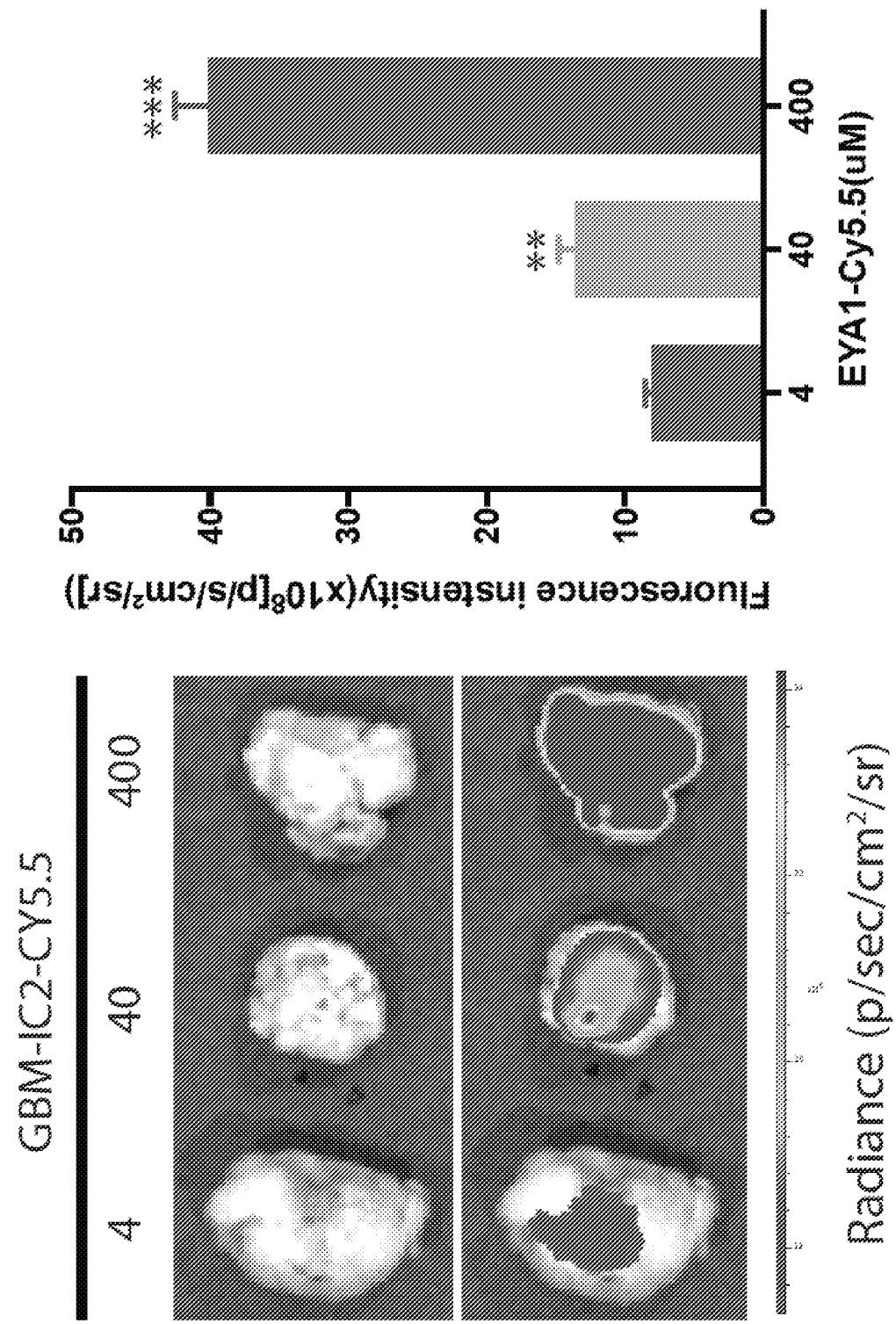
Figure 3C:
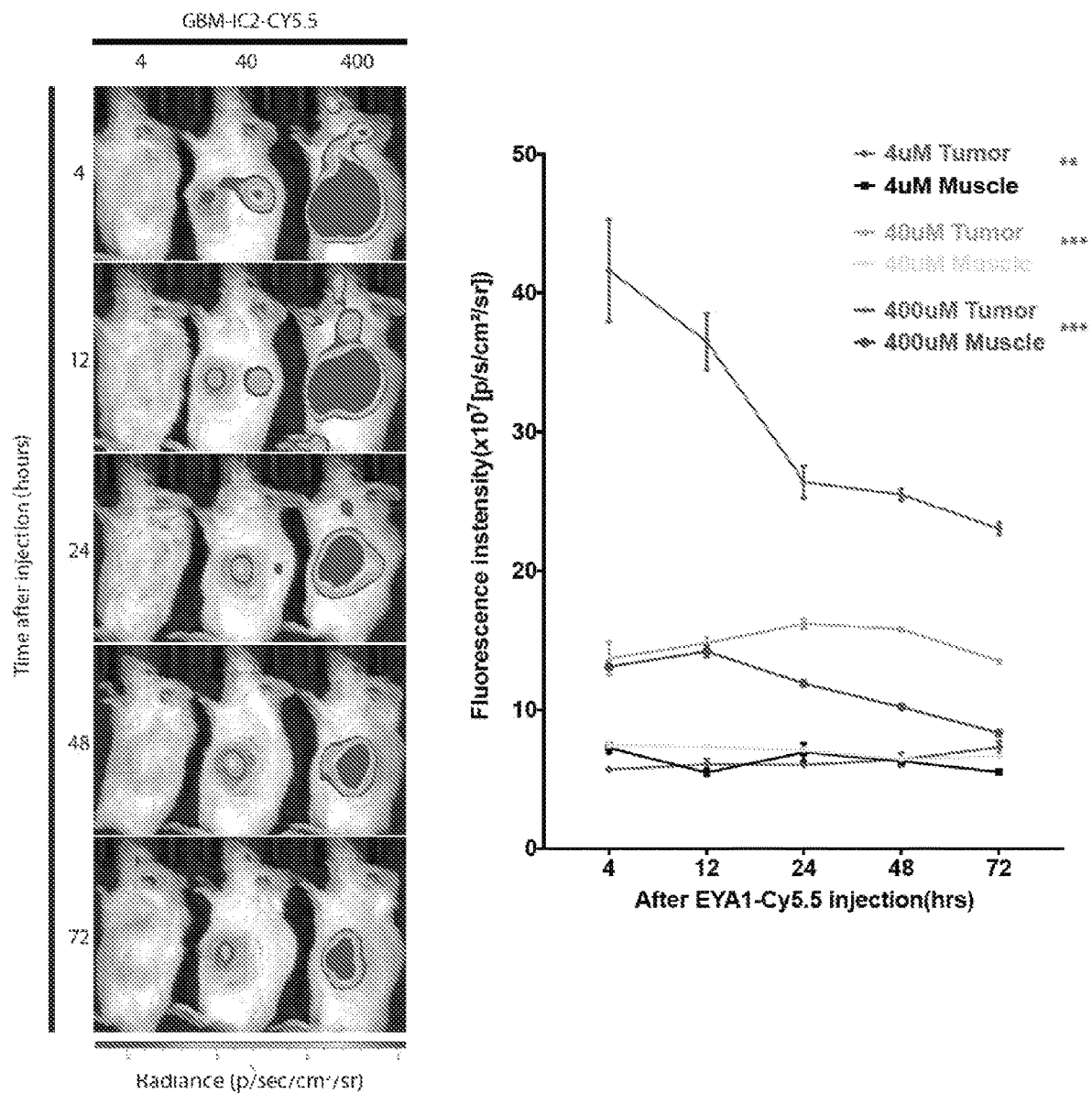

To lay the foundation for the translation of the GBM-IC2 into possible clinical applications, the peptide was conjugated with Cyanine 5.5, a near infrared marker, and targeting of GSCs was measured, revealing binding to GSCs in a concentration-dependent manner. To determine potential utility of the peptide in GSC detection in vivo, GBM-IC2-Cy5.5 was injected into the tail vein of mice bearing luciferase-labeled glioma xenografts in the flank to test peptide targeting without the limitations of the blood-brain barrier. Bioluminscent imaging demonstrated high specificity of binding to the tumor as early as 20 minutes after injection, lasting up to 72 hours post-injection with a gradual decrease in signal intensity (FIG. 3). As GBM-IC2 was recovered in an intracranial tumor screen, there was a potential utility of the peptide to be utilized in intracranial tumor detection. Therefore, vein injections of GBM-IC2-Cy5.5 were performed tail in mice bearing intracranial glioma patient-derived xenografts. Imaging performed 20 minutes post-injection demonstrated strong specificity of binding of tumor in the intracranial cavity, indicating the peptide was able to selectively travel through the vasculature and penetrate the BBB (FIG. 4).

Figure 4A:
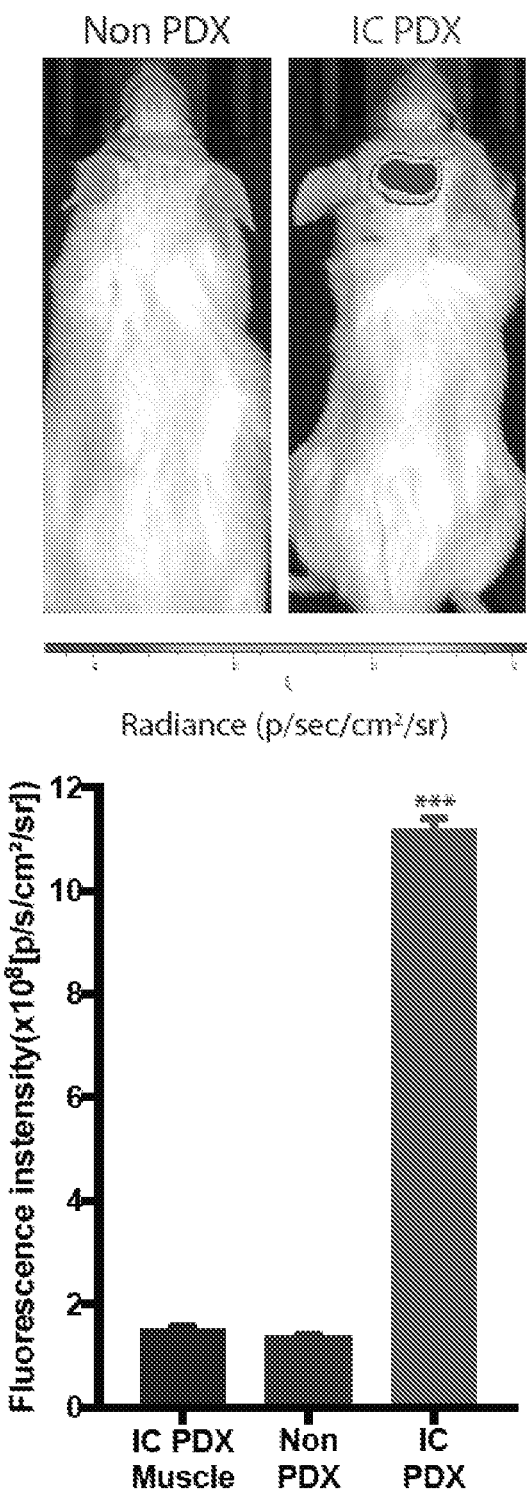
FIGS. 4A to 4C. GBM-IC2 targets intracranial glioblastoma xenografts. GBM-IC2-Cy5.5 injected into the tail vein of NSG mice bearing glioblastomas xenografted into the intracranial cavity demonstrates specific targeting of the intracranial tumor in vivo (A) and ex vivo (B). Histological analysis demonstrates positive fluorescent signal in the intracranial tumor samples (C).
Figure 4B:
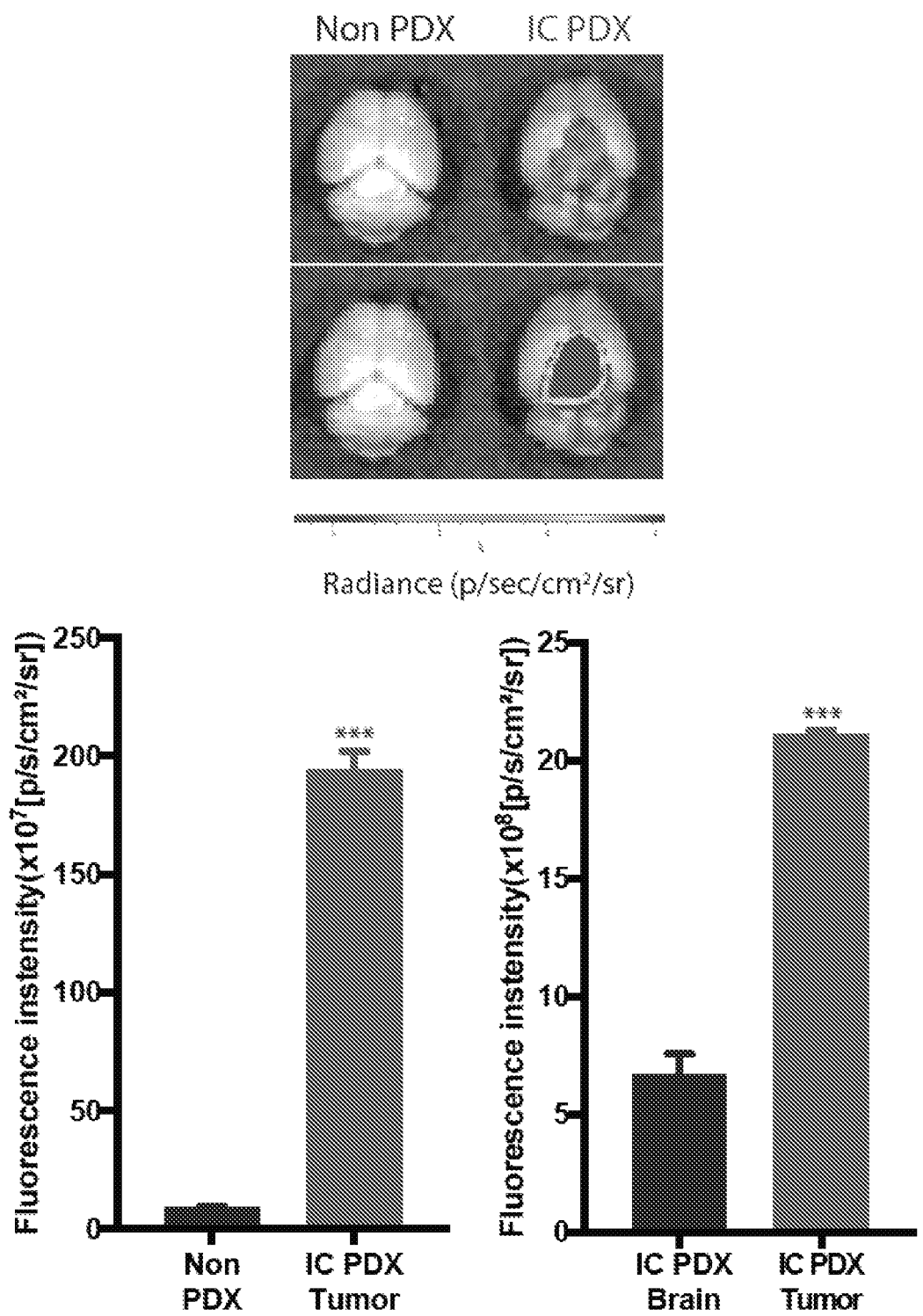
Figure 4C:
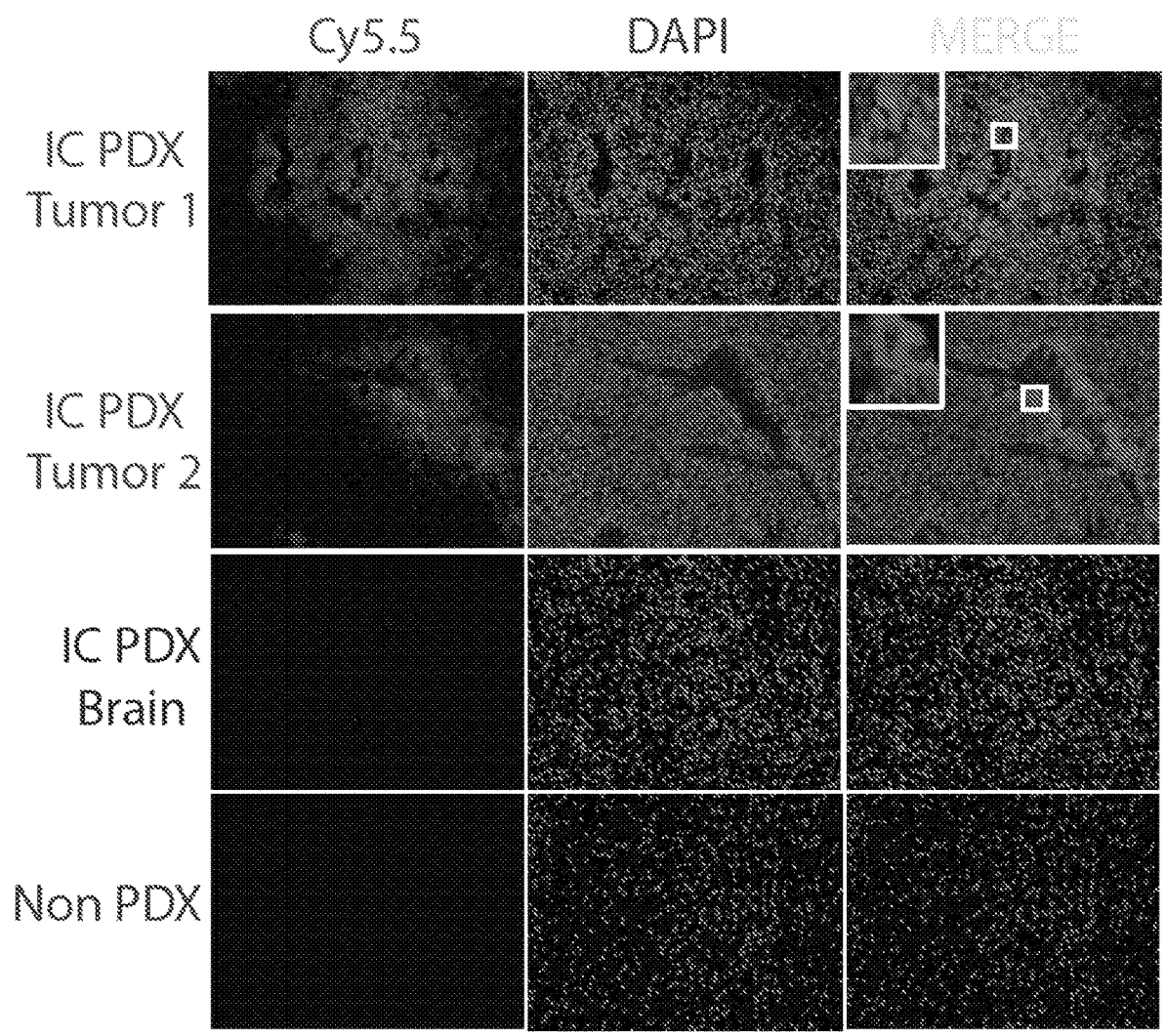

As further validation, animals bearing intracranial patient-derived xenografts were sacrificed and the brains were imaged and subsequently studied histologically, confirming specificity of peptide binding, with a strong congregation of peptide signal in the perivasculature areas (FIG. 4). Collectively, these results demonstrate that phage display can identify peptide sequences that specifically bind to gliomas, including in the intracranial compartment.

Discussion

Development of therapeutics that will more effectively target and treat glioblastoma will be depend on therapies that are able to overcome two major barriers. The first is to preferentially target glioblastoma cells without providing undue damage to the surrounding environment. The second is effectively reaching the neural environment and in doing so, being able to cross the BBB. These two barriers have long served as obstacles against the development of effective treatments against primary and metastatic brain tumors. Current treatment strategies against glioblastoma, consisting of maximal surgical resection followed by concurrent radiation and chemotherapy, have not proven to result in sustained relapse of tumor (Weller, M. et al. Lancet Oncol 2017 18:e315-e329). A possible explanation for the consistent recurrence of tumor growth may be due to GSCs, a subset population of tumors cells resistant to conventional therapy and capable of recapitulating tumor growth (Bao, S. et al. Nature 2006 444:756-760). Successful treatment of glioblastoma may depend upon development of therapeutics that will target these cells more effectively and with greater specificity.

Phage display biopanning is an effective tool for the development of targeted therapeutics through isolation of small peptides that have preferential binding capacity for a given receptor or cell type. Peptides can serve as effective targeting modalities as their small size allows for their use as fusion proteins or adjuncts to viral capsids or nanoparticles, without affecting the function of its cargo (Cui, Y. et al. ACS Appl Mater Interfaces 2016 8:32159-32169; Morshed, R. A. et al. Mol Pharm 2016 13:1843-1854). Ideally, biopanning is performed with the goal of isolating peptides that mimic a known ligand to replicate a specific ligand-receptor interaction. As definitive targets that identify GSCs remain elusive, a biopanning strategy consisting of a combination of negative and positive selection steps was employed to isolate peptides that possess a specific affinity for GSCs.

The biopanning results was the combination of two different strategies. The in vitro strategy selected for peptides that targeted GSCs by utilizing negative selection that eliminates peptides that bind to non-stem glioma cells. In vitro biopanning allows for more effective recovery of phage peptides but does not interrogate antigen expression in the native environment or assess delivery restrictions critical for translation into clinical use. Despite these shortcomings, the in vitro biopanning strategies allows for greater specificity in peptide selection because of the ability to select for peptides that bind a subpopulation of tumor cells, as defined by the CD133 surface marker. To select for peptides that have the capacity to target within the central nervous system, an in vivo biopanning strategy against intracranially xenografted glioma tumors was employed. Due to the smaller number of tumor cells that are recovered through an intracranial in vivo biopanning strategy, stem and non-stem tumor cells were not separated prior to collecting phage peptides. Through the in vitro biopanning strategy, 53 different phage clones were collected. Of these 53 clones, 6 different amino acid combinations appeared repeatedly, indicating that these combinations were isolated as a result of multiple rounds of enrichment against GSC binding. Although the in vivo biopanning strategy was able to isolate peptides with intracranial targeting potential, the low yield of peptide recovery through this method precluded enrichment through multiple rounds of biopanning. It was through combining the sequences isolated from both strategies that our peptide of interest was selected (GBM-IC2), as that particular peptide was both isolated repetitively in the in vitro screen as well as in the in vivo strategy, giving its potential for specificity for stem cell binding as well as in vivo targeting abilities.

To isolate novel targets that will allow better understanding of the mechanisms that drive GSC maintenance and identify possible therapeutic targets, the peptide sequence was used as a means to identify novel matching genes specific for GSCs. Among the genes recovered from a BLAST search, EYA1 became the focus of further study due it known role in cellular proliferation and carcinogenesis (Pandey, R. N. et al. Oncogene 2010 29:3715-3722; Tadjuidje, E. et al. Cell. Mol. Life Sci. 2012 70:1897-1913; Wu, K. et al. Cancer Research. 2013 73:4488-4499). EYA1 possesses multiple functions as a transcriptional co-activator and as a tyrosine and threonine phosphatases. Although previous studies have indicated the phosphatase functions of EYA1 are potentially involved in anti-apoptosis regulation and cellular migration, the transcriptional co-activator function is less well defined in those functions. BLAST search analysis matched the GBM-IC2 to the N-terminal domain of EYA1, which harbors the transcriptional co-activator component, suggesting that EYA1's role in GSC maintenance could depend on EYA1 ability to function as a transcriptional co-activator (Rayapureddi, J. P. et al. Nature. 2003 426:295-298). The findings indicate a relationship between EYA1 and MYC both by transcriptional regulation and function, suggesting that EYA1 may maintain GSCs through MYC.

The studies demonstrate that EYA1 plays a role in cellular proliferation and migration. Also noteworthy was EYA1's location in the perivascular niche, as well as its association with known endothelial markers. This provides support that EYA1 may play a particular role in glioblastoma angiogenesis. This is supported by TCGA analysis demonstrating EYA1 to be highly expressed in the proneural glioblastoma subtype, and may allow for an explanation as to why the proneural subtype may be susceptible to improvement in overall survival when administered antiangiogenic therapy (Sandmann, T. et al. J Clin Oncol 2015 33:2735-2744).

In addition to using phage display in target discovery, the use of the peptides as tumor homing mechanisms was explored. The EYA1-mimetic peptide (GBM-IC2) specifically binds to GSCs both in culture and in vivo. The ability of this peptide to target intracranial tumors at a cellular level carries significant implications for the peptides as vehicles for targeting glioblastoma. Cellular detection of tumor growth may supersede the current gold standard for imaging modalities to detect brain tumors, i.e. magnetic resonance imaging, which requires a certain threshold of tumor burden for the tumor to be visible. Cellular detection of tumor growth may allow for earlier diagnosis and confirmation of recurrence, as well as the ability to differentiate tumor recurrence from non-tumor radiographical progression, e.g. pseudo-progression or radiation necrosis. Peptide-based imaging modalities have been previously developed, but are limited to the specificity of the receptor on the targeted tumor cells (Cordier, D. et al. J Neurooncol 2010 100:129-136). Studies that GBMIC2, when conjugated with Cy5.5, is able to visualize tumor binding through live imaging were verified, confirming its effectiveness as an alternative to clinical imaging modalities. A potential limitation of fluorophore labeling is light penetration, which may be circumvented through peptide conjugation with radionuclides that will allow conventionally available PET/SPECT imaging (Chatalic, K. L. et al. J Nucl Med 2015 56:1809-1812).

Among the limitations of vectors that are currently being tested for enhancing therapeutic delivery to brain tumors is the need for direct implantation of the vector into the tumor bed following surgical resection (Ostertag, D. et al. Neuro Oncol 2012 14:145-159; Yin, D. et al. Cancer Gene Ther 2013 20:336-341). Even following implantation, distribution of vector into the adjacent brain parenchyma can be limited (Sampson, J. H. et al. J Neurosurg 2010 113:301-309). Peptide isolation through an in vivo biopanning strategies selects for peptides that are able to target tumor cells following intravenous injection, providing a systemic delivery with specific binding properties. In addition to developing peptide-based diagnostic imaging modalities, peptide tumor targeting can be utilized during surgical resection of tumors to augment intra-operative visualization of tumor tissue to improve extent of surgical resection (Stummer, W. et al. Clinical article. J Neurosurg 2011 114:613-623). Tumor targeting peptides can also be used to modify delivery vehicles, such as viral vectors or nanoparticles. These peptides are particularly attractive for modification of such vectors as their small size minimizes the possibility of steric interference.

The use of in vivo phage display biopanning to isolate peptides that can enter into the central nervous system and thereby penetrating the blood-brain-barrier does carry limitations. It is known that the BBB can be compromised in the setting of a neoplasm, and therefore access to the tumor may be due more to a breakdown of BBB and less due to transport across the barrier (Davies, D. C. J Anat 2002 200:639-646).

Materials and Methods

Isolation and Culture of Cells

Glioblastoma cells were harvest from patient samples at the Cleveland Clinic and Case Western Reserve University in accordance with an approved protocol by the Institutional Review Board. GSCs were isolated and maintained as previously described (Bao, S. et al. Nature 2006 444:756-760). For endothelial cell experiments, glioblastoma tissues or normal brain derived endothelial cells were obtained from Cleveland Clinic Tissue Bank and Cell Systems (Kirkland, Wash., USA) respectively. Endothelial cells were isolated and maintained as previously described (Huang, P. et al. Cancer Res 2012 72:1428-1437). Briefly, the fresh aliquots of GBM were placed in cold sterile saline, minced, digested with papain and DNase I (Worthington Biochemical Corporation) for 15-60 minutes at 37° C., filtered (40 μm), and the material trapped on the filter re-suspended and digested further in 2 mg/mL collagenase type II [Invitrogen (Gibco-BRL); 10 to 30 minutes. The suspension was filtered (70 μm), the cells in the filtrate pelleted (200 g, 5 minutes), resuspended in EGC-MV media (Lonza, Walkersville, Md., USA), and seeded onto laminin-coated wells. Confluent cells were detached with Accutase (Innovative Cell Technologies) and passaged into a 0.5% gelatin-coated flask in EC media. Pure EC populations were then obtained by magnetic bead separation using CD31-coupled MicroBeads (Miltenyi Biotec).

In Vitro and In Vivo Biopanning of Phage Library

The Ph.D.™-7 Phage Display Peptide Library Kit (New England BioLabs, Ipswich, Mass.) was used to complete these experiments. $5 \times 10^4$ glioblastoma cells were implanted into the brain hemisphere of 4 weeks old NOD.Cg-Prkdcscidll2rgtm1Wjl/SzJ (NSG) mouse under a Cleveland Clinic Foundation Institutional Animal Care and Use Committee approved protocol. After maximal tumor growth, the phage display library was injected via the tail vein of the mouse and allowed to circulate and bind to cellular targets for 24 hours. The tumor was then harvested and tumor cells were then lysed to allow for isolation and purification of bound phage peptides. Collected phages were transduced into E. coli for phage clone isolation and DNA sequencing to recover bound peptide sequences.

In parallel, in vitro biopanning was performed a previously described (Liu, J. K. et al. Cell Death Differ 2014 21:1325-1339). In brief, using the 7-amino acid length peptide library, negative selection was first performed against extracellular matrix coated plates and non-stem glioblastoma cells. The remaining phage library was applied to CD133(+) GSCs, and four rounds of positive selection were performed. Following the fourth round of selection, phage clones were isolated through bacterial infection and sequencing performed to isolate peptide sequences.

Immunostaining

Patient brain tissues were obtained from Cleveland Clinic Tissue Bank. Cells (GSC and DGC) or frozen-sectioned tissues (glioblastoma and normal brain) were fixed in 4% paraformaldehyde and permeabilized with 0.1% Triton X-100 and stained using following primary antibodies: EYA1 (Aviva System Biology, ARP32434_P050), SOX2 (R&D system, MAB2018), vWF (Abcam, ab68548), CD31 (Santa Cruz Biotechnology, sc-1506), MYC (Cell signaling, 5605), and SIX1 (Abcam, ab84329) primary antibodies were incubated overnight at 4° C., followed species appropriate secondary antibodies with incubation for 3.5 hours at room temperature. Nuclei were stained with DAPI, and slides were then mounted with FluorSave (Calbiochem, 345789). Images were taken using a Leica DM4000 uplight microscopy. For DAB staining, tissues were incubated with rabbit anti-EYA1 or anti-c-Myc antibody overnight at 4° C., followed goat anti-rabbit biotinylated secondary antibody with incubation for 3.5 hours at room temperature. After incubation with antibodies, tissues were stained using VECTASTAIN Elite ABC HRP Kit (VECTOR LABORATORIES, PK-6100) and DAB Peroxidase Substrate Kit (VECTOR LABORATORIES, SK-4100) according to the manufacturer's instructions. After counterstaining with 50% hematoxylin, images were taken.

Fluorescent Peptide Synthesis and Staining

5(6)-Carboxyfluorescein-conjugated peptide AWEFYFP that corresponds to the EYA1 protein was synthesized by Cleveland Clinic Molecular Biotechnology Core. 1 mg/ml of peptide was diluted in 1% BSA in PBS with 1 to 500 for single staining and 1 to 30 for double staining with anti-SOX2 antibody. Cells or tissues were fixed with 4% paraformaldehyde and permeabilized with 0.1% Triton X-100 and incubated with diluted peptides overnight at 4° C. Nuclei were stained with DAPI. Images were taken using a Leica DM4000 uplight microscopy or a Leica TCS-SP and SP-AOBS upright confocal microscopes.

Quantitative RT-PCR

Total tissue and cellular RNA were isolated using the RNeasy kit (Qiagen, Venlo, The Netherlands) and reverse transcribed into cDNA using the SuperScript III Reverse Transcription kit (Invitrogen, Carlsbad, Calif., USA). Quantitative reverse transcription PCR was performed per the manufacturer's protocol on Applied Biosystems 7900HT cycler using SYBR green Master mix (SA Bioscience, Valencia, Calif., USA) and gene-specific primers as follows:

```
EYA1 forward
(5'-GGAAGCCTGGCTGCAGTTGA-3' (SEQ ID NO: 34))
and

EYA1 reverse
(5'-CCGGGAGTGAATGAGCGAGA-3'
(SEQ ID NO: 35)),

SIX1 forward
(5'-CTCCTCCTCCAACAAGCAGA-3' (SEQ ID NO: 36))
and

SIX1 reverse
(5'-GGACTTTGGGGAGGTGAGAA-3' (SEQ ID NO: 37)).

Lentivirus-regulated gene expression
Lentiviral clones to express shRNA against EYA1:
TRCN0000369592:
                                        (SEQ ID NO: 38)
CCGGCAGCAACCAGTGCTAACTTATCTCGAGATA

AGTTAGCACTGGTTGCTGTTTTTG,

TRCN0000310704:
                                        (SEQ ID NO: 39)
CCGGTGCAGTTGAGGGCCGAAATTGCTCGAGCAAT

TTCGGCCCTCAACTGCATTTTTG,
and

TRCN0000303462:
                                        (SEQ ID NO: 40)
CCGGTCCCAATGGCACCGAAGTTAACTCGAGTTAA

CTTCGGTGCCATTGGGATTTTTG.

Lentiviral clones to express shRNA
against SIX1:
TRCN0000329879:
                                        (SEQ ID NO: 41)
CCGGCAATAACTCCTCCTCCAACAACTCGAGTTGT TGGAGGAGGAGTTATTGTTTTTG,
and TRCN0000329805:
                                        (SEQ ID NO: 42)
5'-CCGGAGCTTGTTTCTGGAGTTGTTTCTCGAGAA

ACAACTCCAGAAACAAGCTTTTTTG.

Lentiviral clones to express shRNA
against c-MYC:
TRCN0000039640:
                                        (SEQ ID NO: 43)
CCGGCAGTTGAAACACAAACTTGAACTCGAGTTCAA GTTTGTGTTTCAACTGTTTTTG
and TRCN0000039642:
                                        (SEQ ID NO: 44)
CCGGCCTGAGACAGATCAGCAACAACTCGAGTTGTT

GCTGATCTGTCTCAGGTTTTTG.
```

Lentiviral clones to express shRNA against Non-Target shRNA(SHC002) were purchased from Sigma-Aldrich(St. Louise, MO, USA). shRNA with non-overlapping sequences that had the best relative knockdown efficiency were used for all experiment. Lentivial particles were generated in 294FT cells in stem cell media with cotransfection with the packaging vectors pCMV-dR8.2 dvpr and pCMV-VSV-G (Addgene).

Western Blotting

Cells were collected and lysed in hypotonic buffer with nonionic detergent (50 mM Tris-HCl, pH 7.5, 150 mM NaCl, 0.5% NP-40, 50 mM NaF with protease inhibitors), incubated on ice for 15 min and cleared by centrifugation at 10,000 g at 4° C. for 10 min. Protein concentration was determined using the Bradford assay (Bio-Rad Laboratories, Hercules, Calif., USA). Equal amounts of protein were mixed with reducing Laemmli loading buffer, boiled and electrophoresed on NuPAGE Gels (Invitrogen), then transferred to polyvinylidene fluoride (PVDF) membranes (Millipore). Blocking was performed for 30 min with 5% nonfat dry milk in tris-buffered saline and Tween 20 and blotting performed with primary antibodies at 4° C. for 16 h. Following primary antibodies are used: EYA1 (Aviva System Biology, ARP32434_P050), SIX1 (Abcam, ab84329), SOX2 (R&D system, MAB2018), GFAP (DAKO, 20334), Actin (Santa Cruz Biotechnology, sc-1615), Cleaved PARP (Cell Signaling, 9541), cleaved Caspase-7 (Cell Signaling, 9491), c-Myc (EMD Millipore, OP10), p-MLC2 (Cell Signaling, 3674), t-MLC2 (Cell Signaling, 3672), c-Met (Cell Signaling, 8198), p-c-Met (Abcam, ab68141), CREB (Cell Signaling, 9197), p-CREB (Cell Signaling, 9198), p65 (Santa Cruz Biotechnology, sc-8008), and p-p65(BETHYL Laboratories, IHC-00524).

Co-Immunoprecipitation $1 \times 10^7$ cells were harvested and washed with pre-cold PBS twice. Cells were lysed in 1 ml of cold IP lysis buffer (Thermo Fisher Scientific, 87787) containing a 1× protease and phosphatase inhibitor cocktail (Roche, Germany) with an incubation at 4° C. for 30 minutes with a vortexing. Supernatants were collected and precleared with the protein A/G mixtures (Sigma). Precleared lysates were incubated with anti-EYA1 antibody at 4° C. for 2 hours with a rotation followed adding of 50 µl of protein A/G bead in pre-chilled lysis buffer. After the incubation at 4° C. for 2-4 hours, beads were collected and washed 3-5 times with a lysis buffer. NuPAGE LDS sample buffer (Novex, NP0007) were added to beads and heated at 95° C. for 10 minutes. Supernatant were collected and loaded in SDS-PAGE gels. After electrophoresis and transfer, signals were detected using primary antibodies against EYA1 (Aviva System Biology, ARP32434_P050), c-Myc (EMD Millipore, OP10), and SIX1 (Abcam, ab84329).

Cell Proliferation and Tumor Sphere Formation Assay

Cell proliferation assay using Cell-Titer Glow (Promega, Madison, Wis.) and tumor sphere formation were measured as per the manufacturer's protocol as previously described (38-40).

Flow Cytometric Analysis

Cells were dissociated to singles with TrypLE Express (Thermo Fisher Scientific) and recovered in Neurobasal medium at 37° C. for 1-2 hours. Before the incubation with primary antibodies, cells were blocked with 2% BSA in PBS for 30-50 minutes. Primary antibodies were treated at 4° C. for 40-90 minutes. Anti-EYA1 antibody (Aviva System Biology, ARP32434_P050), anti-IgG control antibody, 5(6)-carboxyfluorescein-conjugated peptide AWEFYFP, and cyanine 5.5-conjugated peptide AWEFYFP were used as primary antibodies. After washing with 1% BSA in PBS, cells were incubated with Alexa Fluor 488-conjugated goat anti-rabbit IgG antibody (Invitrogen, A11008) at 4° C. for 40 minutes. Unstained- or secondary antibody treated-cells without a primary antibody were used as negative controls. Labeled cells were analyzed by flow cytometry.

In Vitro Limiting Dilution Assay

For In vitro limiting dilution assays, decreasing numbers of cells per well (20, 10, 5, and 1) were plated in 96-well plates. Ten days after plating, the presence and number of neurospheres in each well was qualified. Extreme limiting dilution analysis was performed using software as previously described (Hu, Y. et al. J Immunol Methods 2009 347:70-78).

Tube Formation Assay $1\times10^5$ of endothelial cells were plated on a well of 6-well plate and transduced with lentivirus expressing EYA1 or Non-Target shRNA and grew in fresh EGM medium. Cells were detached from plates with an accutase and plated on the matrigel-coated 6-8 coverslips with the volume of 100 μl. After incubation for 1.5 hours, 700 μl of EGM medium was added into each well with coverslips. Cells were incubated for additional 3-8 hours and fixed with 4% paraformaldehyde and images were taken.

Wound Healing Assay

To assess cellular migration, monolayer wound-healing assay was performed. GSC cells were transfected with EYA1 shRNA1, EYA1 shRNA2 or non-targeting control shRNA. Cells were plated as a confluent monolayer in 24-well plate. The monolayer was scratched with 1 ml pipette tip across the center of the well. After scratching, well was washed twice with medium to remove the detached cells. After 24 hours, the photo of monolayer was taken on a microscope. The gap distance was quantitatively evaluated using ImageJ (NIH, Bethesda, Md., USA).

Invasion Assay

To determine the invasiveness of GSCs, we used BD BioCoat Matrigel invasion chambers (BD Biosciences, Franklin Lakes, N.J., USA). GSCs were transduced with EYA1 shRNA1, EYA1 shRNA2 or non-targeting control shRNA 48 hours before analysis. Before use, the invasion chambers were rehydrated using neurobasal media (without any growth factors) for 2 hours at 37° C. Cells were then transferred to the invasion chamber ($5\times10^4$ cells per well). Cells were allowed to invade through the Matrigel for 36-48 hours toward neurobasal media supplemented with growth factors (epidermal growth factor and fibroblast growth factor). Chambers were then fixed in 4% paraformaldehyde for 15 min, stained with crystal violet dye and washed in PBS. Cells were counted using an ImageJ (NIH, Bethesda, Md., USA).

Animal Survival and Intracranial Tumor Formation

GSCs were transduced with lentivirus expressing EYA1 or non-targeting shRNA. Following, $5\times10^4$ cells in 20ul of Neurobasal medium without any supplement were engrafted intracranially into 4 weeks old NSG mice under a protocol approved by the Cleveland Clinic Foundation Institutional Animal Care and Use Committee approval protocol. Animals were monitored until they developed neurological signs.

In Vivo Imaging

Cyanine 5.5-conjugated peptide AWEFYFP (SEQ ID NO:2) and control peptide GGGSGGG (SEQ ID NO:33) were synthesized by LifeTein, LCC. (Hillsborough, NJ, USA). GSCs were implanted into subcutaneously ($5\times10^5$ cells) or intracranially ($5\times10^4$ cells) into 4 weeks old NSG mice under a Cleveland Clinic Foundation Institutional Animal Care and Use Committee approved protocol. After 4 weeks, cyanine 5.5-conjugated peptides were delivered into the mice via intravenous injection. Signals from injected peptides were monitored by fluorescence channel of IVIS Spectrum CT In Vivo Imaging System (PerkinElmer, USA) for 72 hours.

Bioinformatics

Data were acquired from the TCGA glioblastoma dataset. For survival analysis, Kaplan-Meier plots were used to compare high versus low expression groups, cut at the median. G-CIMP tumors were excluded from analysis. Groups were compared using log-rank tests. Gene expression data in glioblastoma vs. non-tumor were compared using t-tests. For heatmap analysis, data were derived from the combined low grade glioma/glioblastoma TCGA dataset. Expression levels were extracted from RNA-sequencing data and analyzed using R.

Statistical Analysis

All grouped data are presented as mean±S.E. Differences between groups were assessed by Student's t-test or analysis of variance using GraphPadlnStat software (GraphPad Software, La Jolla, Calif., USA). *$P<0.05$; $P<0.01$; *$P<0.001$. Finally, utilizing TCGA low grade and high grade dataset, we found EYA1 expression to be correlated to IDH mutants, MGMT promoter methylations, as well as G-CIMP high phenotype (FIG. 5).

Example 2: GSC-Targeting CARs

The next goal was to test whether these peptides would be utilized as an antigen-binding domain of a chimeric antigen receptor (CAR), with the goal of designing a GSC-targeting cellular product. CARs are synthetic immune receptors designed to emulate the function of a conventional T-cell receptor, namely, to activate the cytolytic and cytokine secretion potential of T lymphocytes, upon recognition of a specific antigen (Abate-Daga D, et al. Mol Ther Oncolytics. 2016 3:16014). With this approach, readily available peripheral blood lymphocytes can be "trained" to recognize tumor-associated antigens, following ex vivo genetic manipulation to induce CAR expression.

Figure 7:
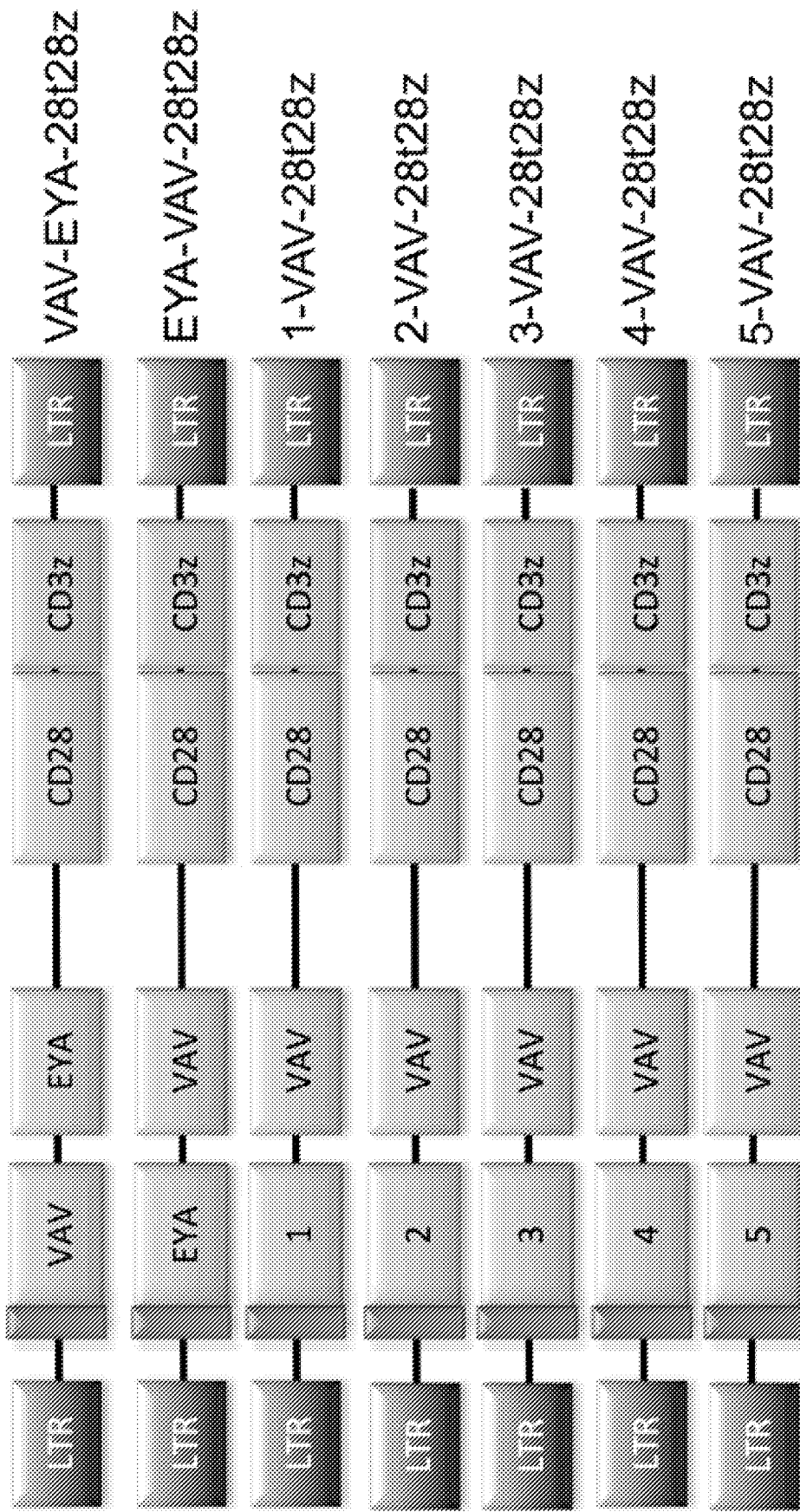
FIG. 7. Diagram of retroviral vectors for CAR expression. LTR: long terminal repeats, CD3z: CD3ζ domain.
Figure 8:
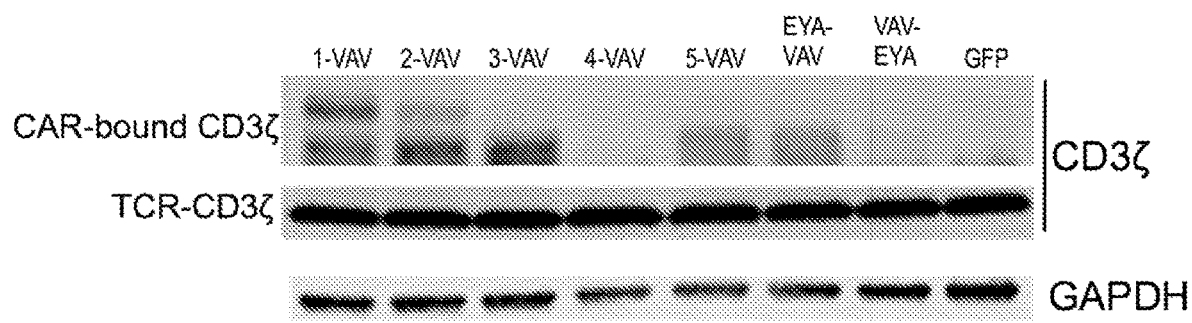
FIG. 8. CAR expression in gene-modified human primary T cells. Western blot of CD3ζ and GAPDH (house keeping) expression in whole cell extracts of primary T cells.
Figure 9:
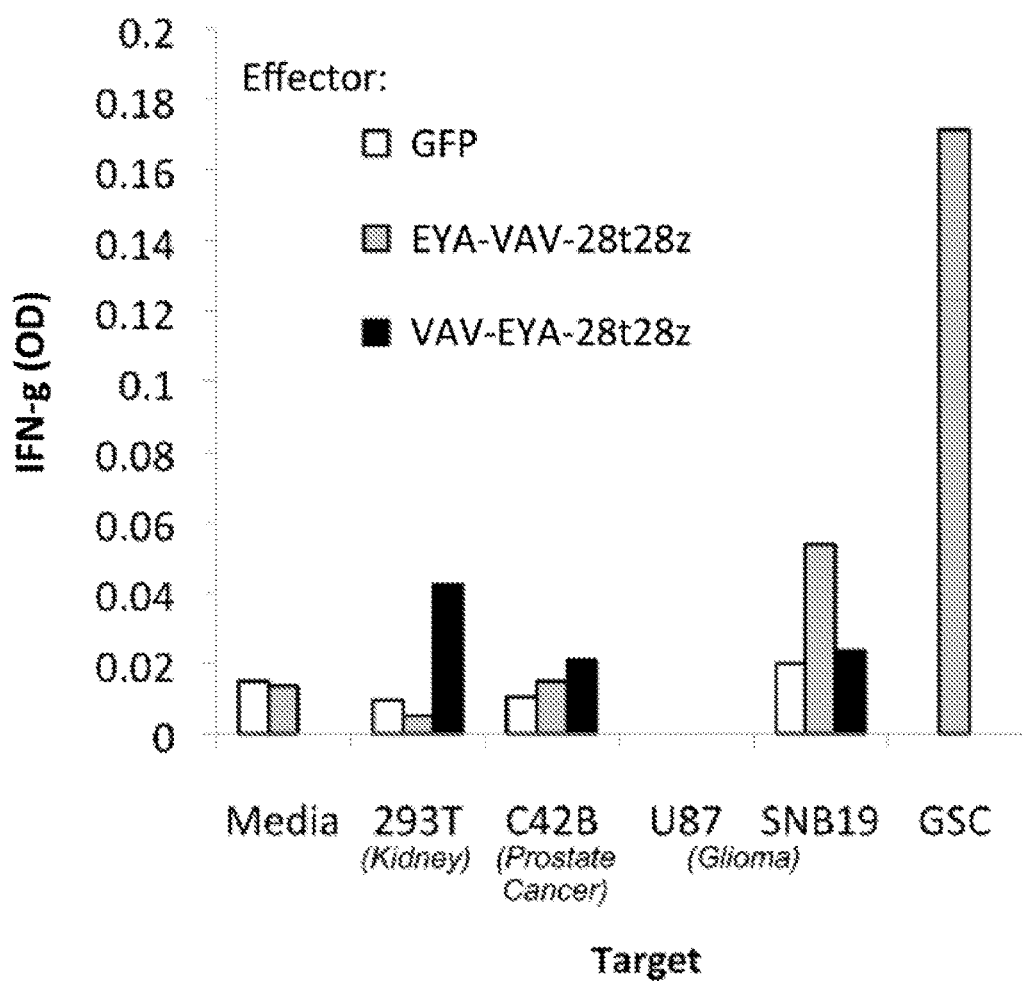
FIG. 9. EYA-VAV CAR recognizes patient-derived glioma stem cells in vitro. IFNG release assay following O/N co-culture.

Capitalizing on the unique ability of peptides EYA and VAV to bind to GSC, a series of chimeric antigen receptors (CARs) were designed that display a peptide derived from the EYA and VAV sequences, arranged in tandem, at the N-terminus of the CAR molecule. The role of the tandem peptides in the N-terminus of the CAR is to detect GSC, which in turn will activate the T cell through the CD3ζ domain in the C-terminus. Most CARs utilize antibody-derived molecules (Abate-Daga D, Let al. Hum Gene Ther. 2014 25(12):1003-12), or natural ligands (Brown CE, et al. N Engl J Med. 2016 375(26):2561-9; Brown CE, et al. Clin Cancer Res. 2012 18(8):2199-209) to receptors expressed by target cells to perform this function. Seven CAR constructs were generated based on combinations of peptides EYA and VAV (VAV-EYA and EYA-VAV), and of VAV plus five additional peptides (termed 1-VAV, 2-VAV, 3-VAV, 4-VAV, and 5-VAV) identified in the biopanning assays (FIG. 7). CAR cDNA was cloned into a retroviral expression vector used for clinical CAR-T cell manufacture, called pMSGV1, and the resulting constructs were used to transduce human primary T cells. The expression of the CAR molecules was first analyzed by Western blot against the CD3ζ chain of the CAR. Six of the seven CAR designs were expressed in transduced cells (FIG. 8). And at least one of them reacted specifically to GSC by secreting interferon-γ (IFNG), following an overnight coculture assay (FIG. 9).

Figure 10:
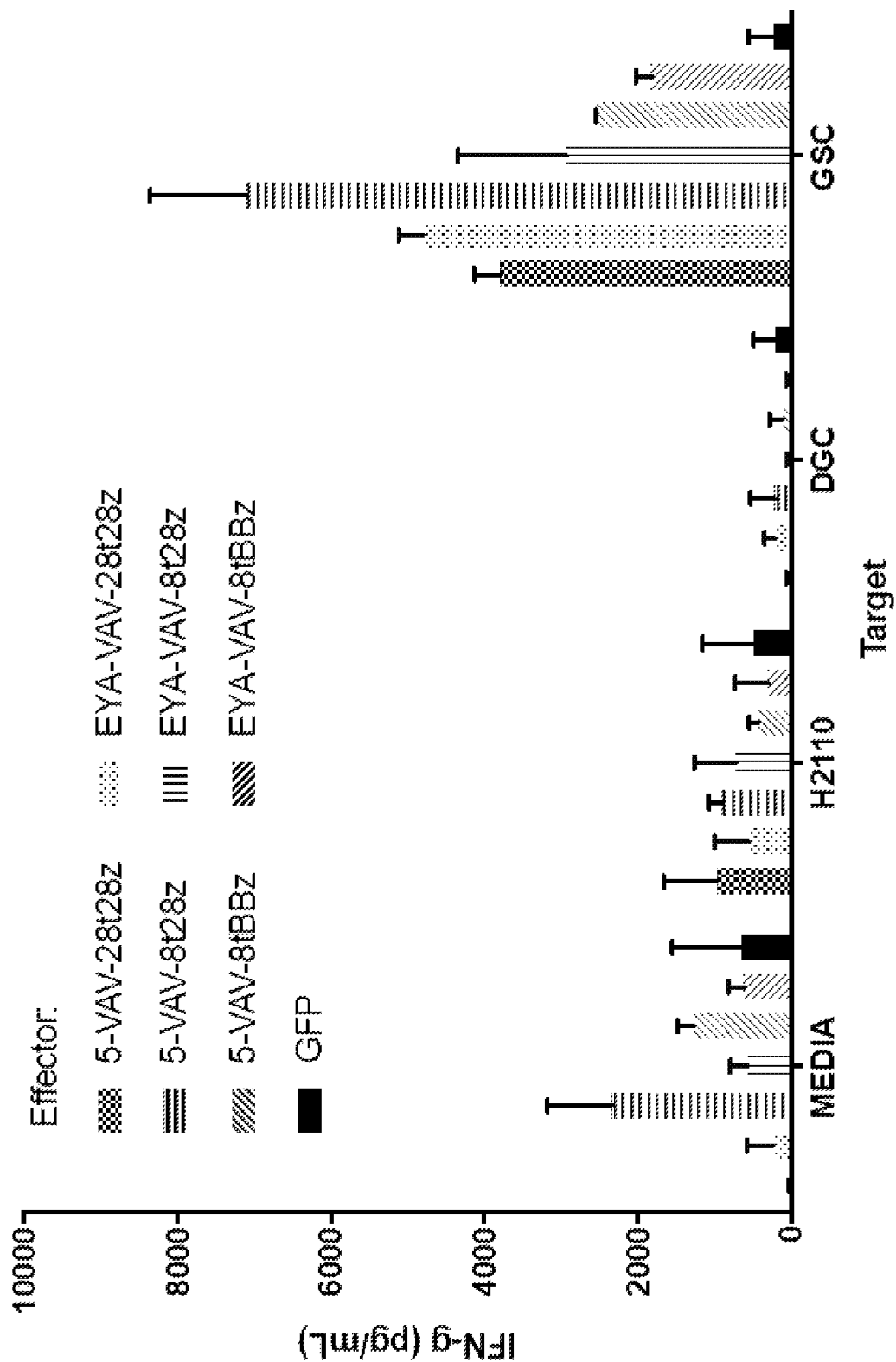
FIG. 10 depicts the results of interferon-gamma (IFN-g) release upon coculture of CAR-T cells with Glioma Stem Cells (GSC). CARs containing a target-binding domain derived from a peptide #5 (SEQ ID NO:7) linked to peptide VAV (SEQ ID NO: 1), or peptide EYA (SEQ ID NO:2) linked to peptide VAV (SEQ ID NO:1), induced of specific recognition of GSC (but not differentiated glioma cells, DGC, derived from the same patient). This was observed for CARs containing a CD28- or CD8-derived transmembrane domain (-28t, or -8t, respectively), and for CD28- or 4-1BB-derived costimulatory domains (28z, or BBz, respectively), albeit to varying degrees of strength. Lung cancer cells H2110 and culture media were used as negative controls.
Figure 11:
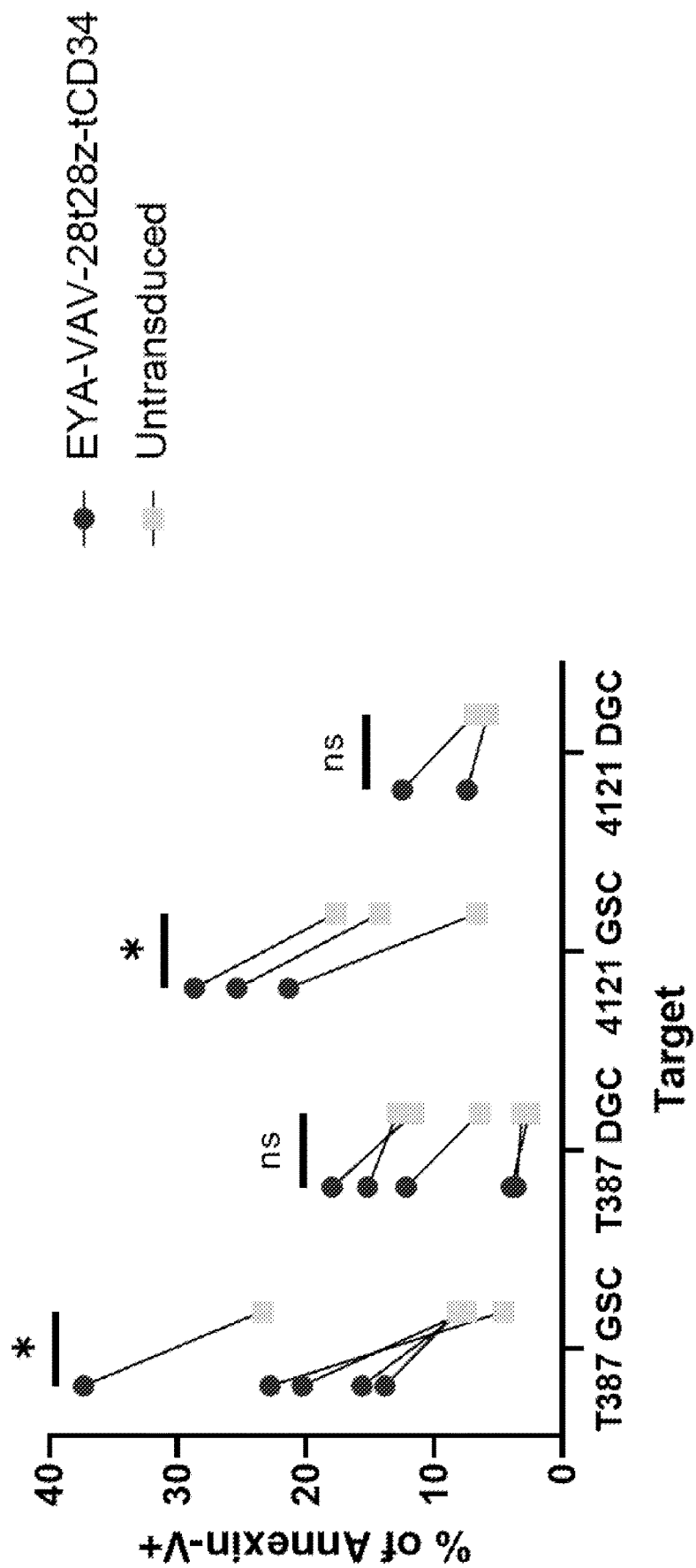
FIG. 11 shows EYA-VAV-28T28z CAR-T cells induce apoptosis of GSC cultures. Co-cultures of both T387 and 4121 glioma stem cells (GSC) and differentiated glioma cells (DGC) with CAR-transduced and untransduced T cells were run for 5 hours with a 2:1 effector-to-target ratio (4e5 tumor cells/well, 8e5 T cells/well) in 200 uL of GSC media. Cells for analysis were gated on CD3-/CSPG4+ singlets, and the percentages of Annexin-V+ tumor cells per condition were then plotted. *p<0.05; ns=not significant.
Figure 12A:
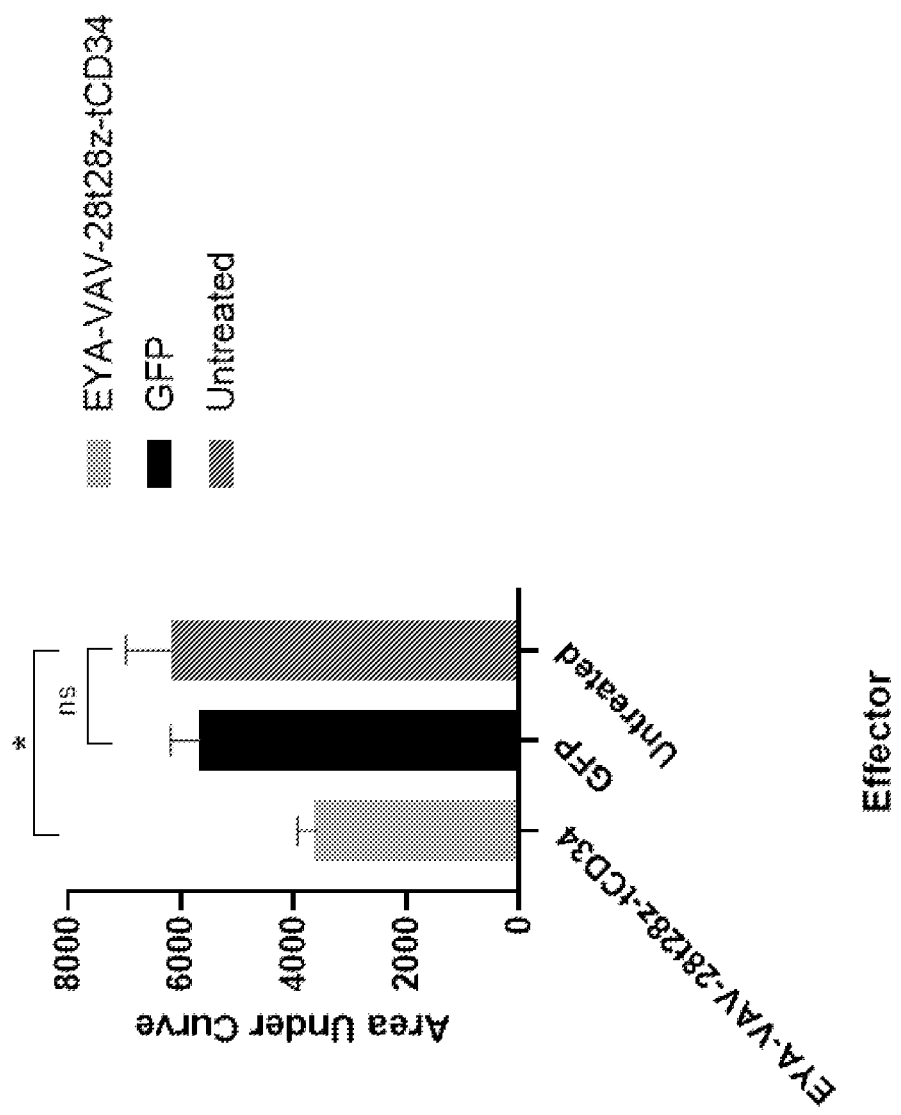
FIGS. 12A and 12B show EYA-VAV-28t28z CAR-T cells induce a delay tumor growth in vivo. 15 NSG mice were subcutaneously injected with 1e6 T387 glioma stem cells, and systemically injected 16 days later with 10e6 CAR-transduced T cells, mock-transduced T cells, or left untreated (5 mice/condition, with a standard deviation of 0.3 mm$^3$ in the average tumor volumes between each condition). All 15 mice received IP injections of 2.2e5 IU IL-2 on the day of the T cell injection, as well as the following two days. Measurements were taken by caliper three times per week. *p<0.05; **p<0.01.
Figure 12B:
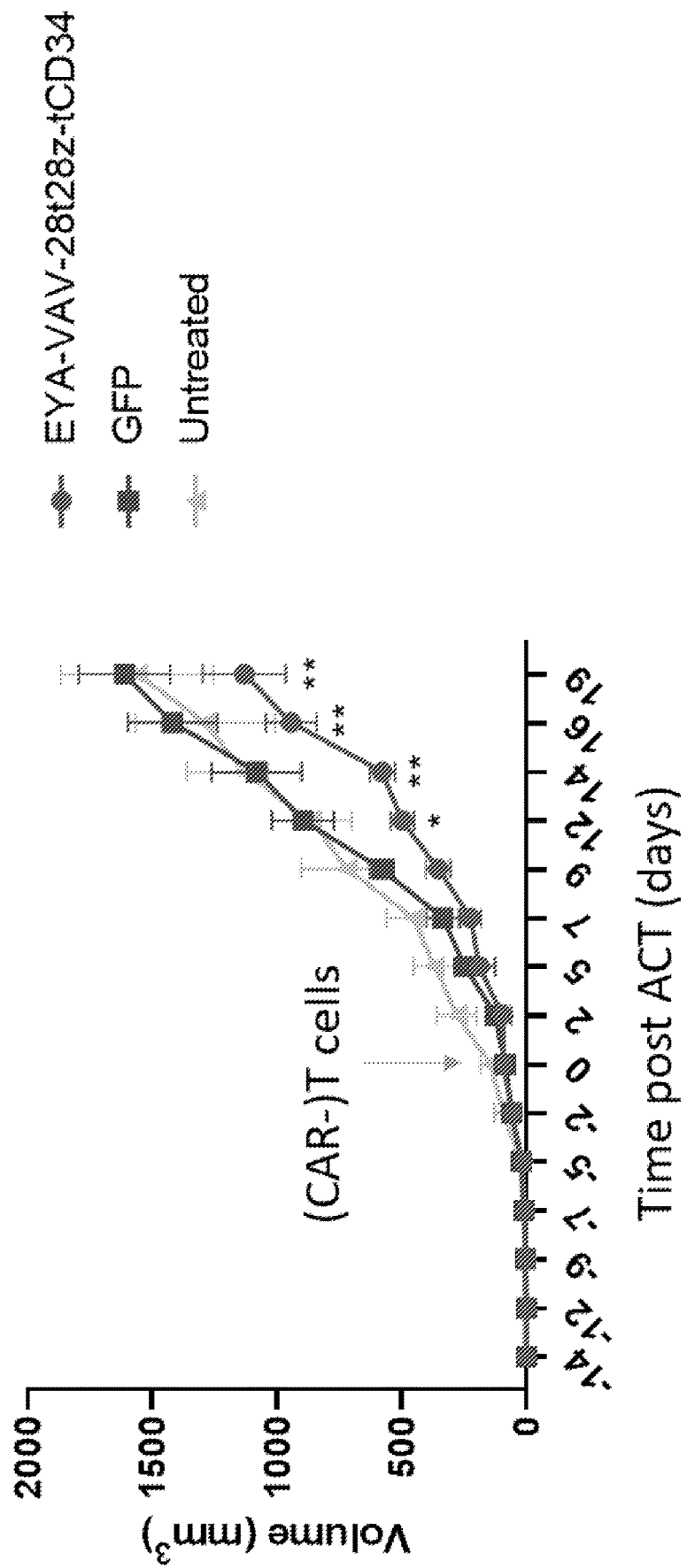

Next, further variations of these CARs were generated by including a different GSC-targeting domain (denoted as 5-VAV), and by substituting the transmembrane and/or costimulatory domains of the CARs. FIG. 10 depicts the results of Interferon-gamma (IFN-g) release upon coculture of CAR-T cells with Glioma Stem Cells (GSC). CARs containing a target-binding domain derived from a peptide #5 (SEQ ID NO:7) linked to peptide VAV (SEQ ID NO:1), or peptide EYA (SEQ ID NO:2) linked to peptide VAV (SEQ ID NO:1), induced of specific recognition of GSC (but not differentiated glioma cells, DGC, derived from the same patient). This was observed for CARs containing a CD28- or CD8-derived hinge/transmembrane domain (−28t, or −8t, respectively), and for CD28- or 4-1 BB-derived costimulatory domains (28z, or BBz, respectively), albeit to varying degrees of strength. Lung cancer cells H2110 and culture media were used as negative controls.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A polypeptide, comprising a Glioblastoma Stem Cells (GSC) antigen binding domain, a transmembrane domain, a co-stimulatory signaling region, and optionally an intracellular signaling domain, wherein the GSC antigen binding domain is a polypeptide selected from the group consisting of

SSQPFWS-GGGGSGGGGSGGGGS-AWEFYFP-GSTSGSGKPGSGEGSTKG (SEQ ID NO: 15)

AWEFYFP-GGGGSGGGGSGGGGS-SSQPFWS-GSTSGSGKPGSGEGSTKG (SEQ ID NO: 17)

AWTTTFP-GGGGSGGGGSGGGGS-SSQPFWS-GSTSGSGKPGSGEGSTKG. (SEQ ID NO: 19)

AWTWTLP-GGGGSGGGGSGGGGS-SSQPFWS-GSTSGSGKPGSGEGSTKG (SEQ ID NO: 21)

EWLFSMP-GGGGSGGGGSGGGGS-SSQPFWS-GSTSGSGKPGSGEGSTKG (SEQ ID NO: 23)

GWFYTFP-GGGGSGGGGSGGGGS-SSQPFWS-GSTSGSGKPGSGEGSTKG (SEQ ID NO: 25)

NWYWVYP-GGGGSGGGGSGGGGS-SSQPFWS-GSTSGSGKPGSGEGSTKG. (SEQ ID NO: 27)

2. The polypeptide of claim 1, wherein the costimulatory signaling region comprises the cytoplasmic domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

3. The polypeptide of claim 1, wherein the polypeptide is a chimeric antigen receptor (CAR) polypeptide defined by the formula:

SP—GBP—HG—TM—CSR—ISD; or

SP—GBP—HG—TM—ISD—CSR wherein "SP" represents a signal peptide,
wherein "GBP" represents a GSC-binding peptide,
wherein "HG" represents and optional hinge domain,
wherein "TM" represents a transmembrane domain,
wherein "CSR" represents a co-stimulatory signaling region,
wherein "ISD" represents an intracellular signaling domain, and
wherein "—" represents a bivalent linker.

4. The polypeptide of claim 1, wherein the intracellular signaling domain comprises a CD3 zeta (CD3) signaling domain.

5. The polypeptide of claim 1, wherein the polypeptide is a chimeric costimulatory receptor (CCR) polypeptide defined by the formula:

SP—GBP—HG—TM—ISD—CSR wherein "SP" represents a signal peptide,
wherein "GBP" represents a GSC-binding peptide,
wherein "HG" represents and optional hinge domain,
wherein "TM" represents a transmembrane domain,
wherein "CSR" represents a co-stimulatory signaling region, and
wherein "—" represents a bivalent linker.

6. An isolated nucleic acid sequence encoding the recombinant polypeptide of claim 1.

7. A vector comprising the isolated nucleic acid sequence of claim 6.

8. A cell comprising the vector of claim 7.

9. The cell of claim 8, wherein the cell is selected from the group consisting of an αβT cell, γδT cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, a regulatory T cell, or any combination thereof.

10. The cell of claim 9, wherein the cell exhibits an anti-tumor immunity when the antigen binding domain of the CAR binds to GSCs.

11. A method of providing an anti-cancer immunity in a subject with glioblastoma multiforme (GBM), the method comprising administering to the subject an effective amount of an immune effector cell genetically modified to express the polypeptide of claim 1, thereby providing an anti-tumor immunity in the subject.

12. The method of claim 11, wherein the immune effector cell is selected from the group consisting of a T cell, a Natural Killer (NK) cell, a cytotoxic T lymphocyte (CTL), and a regulatory T cell.

13. The method of claim 11, further comprising administering to the subject a checkpoint inhibitor.

14. The method of claim 13, wherein the checkpoint inhibitor comprises an anti-PD-1 antibody, anti-PD-L1 antibody, anti-CTLA-4 antibody, or a combination thereof.

* * * * *

```
                              SEQUENCE LISTING

Sequence total quantity: 44
SEQ ID NO: 1           moltype = AA  length = 7
FEATURE                Location/Qualifiers
REGION                 1..7
                       note = Synthetic Construct
source                 1..7
                       mol_type = protein
                       organism = synthetic construct
SEQUENCE: 1
SSQPFWS                                                                   7

SEQ ID NO: 2           moltype = AA  length = 7
FEATURE                Location/Qualifiers
REGION                 1..7
                       note = Synthetic Construct
source                 1..7
                       mol_type = protein
                       organism = synthetic construct
SEQUENCE: 2
AWEFYFP                                                                   7

SEQ ID NO: 3           moltype = AA  length = 7
FEATURE                Location/Qualifiers
REGION                 1..7
                       note = Synthetic Construct
source                 1..7
                       mol_type = protein
                       organism = synthetic construct
SEQUENCE: 3
AWTITFP                                                                   7

SEQ ID NO: 4           moltype = AA  length = 7
FEATURE                Location/Qualifiers
REGION                 1..7
                       note = Synthetic Construct
source                 1..7
                       mol_type = protein
                       organism = synthetic construct
SEQUENCE: 4
AWTWTLP                                                                   7

SEQ ID NO: 5           moltype = AA  length = 7
FEATURE                Location/Qualifiers
REGION                 1..7
                       note = Synthetic Construct
source                 1..7
                       mol_type = protein
                       organism = synthetic construct
SEQUENCE: 5
EWLFSMP                                                                   7

SEQ ID NO: 6           moltype = AA  length = 7
FEATURE                Location/Qualifiers
REGION                 1..7
                       note = Synthetic Construct
source                 1..7
                       mol_type = protein
                       organism = synthetic construct
SEQUENCE: 6
GWFYTFP                                                                   7
```

| | | |
|---|---|---|
| SEQ ID NO: 7<br>FEATURE<br>REGION<br><br>source | moltype = AA   length = 7<br>Location/Qualifiers<br>1..7<br>note = Synthetic Construct<br>1..7<br>mol_type = protein<br>organism = synthetic construct | |
| SEQUENCE: 7<br>NWYWVYP | | 7 |
| SEQ ID NO: 8<br>FEATURE<br>REGION<br><br>source | moltype = AA   length = 15<br>Location/Qualifiers<br>1..15<br>note = Synthetic Construct<br>1..15<br>mol_type = protein<br>organism = synthetic construct | |
| SEQUENCE: 8<br>GGGGSGGGGS GGGGS | | 15 |
| SEQ ID NO: 9<br>FEATURE<br>REGION<br><br>source | moltype = AA   length = 20<br>Location/Qualifiers<br>1..20<br>note = Synthetic Construct<br>1..20<br>mol_type = protein<br>organism = synthetic construct | |
| SEQUENCE: 9<br>GGGGSGGGGS GGGGSGGGGS | | 20 |
| SEQ ID NO: 10<br>FEATURE<br>REGION<br><br>source | moltype = AA   length = 18<br>Location/Qualifiers<br>1..18<br>note = Synthetic Construct<br>1..18<br>mol_type = protein<br>organism = synthetic construct | |
| SEQUENCE: 10<br>GSTSGSGKPG SGEGSTKG | | 18 |
| SEQ ID NO: 11<br>FEATURE<br>REGION<br><br>source | moltype = AA   length = 19<br>Location/Qualifiers<br>1..19<br>note = Synthetic Construct<br>1..19<br>mol_type = protein<br>organism = synthetic construct | |
| SEQUENCE: 11<br>PRGASKSGSA SQTGSAPGS | | 19 |
| SEQ ID NO: 12<br>FEATURE<br>REGION<br><br>source | moltype = AA   length = 19<br>Location/Qualifiers<br>1..19<br>note = Synthetic Construct<br>1..19<br>mol_type = protein<br>organism = synthetic construct | |
| SEQUENCE: 12<br>GTAAAGAGAA GGAAAGAAG | | 19 |
| SEQ ID NO: 13<br>FEATURE<br>REGION<br><br>source | moltype = AA   length = 19<br>Location/Qualifiers<br>1..19<br>note = Synthetic Construct<br>1..19<br>mol_type = protein<br>organism = synthetic construct | |
| SEQUENCE: 13<br>GTSGSSGSGS GGSGSGGGG | | 19 |
| SEQ ID NO: 14<br>FEATURE<br>REGION<br><br>source | moltype = AA   length = 20<br>Location/Qualifiers<br>1..20<br>note = Synthetic Construct<br>1..20<br>mol_type = protein<br>organism = synthetic construct | |
| SEQUENCE: 14<br>GKPGSGKPGS GKPGSGKPGS | | 20 |

| | | |
|---|---|---|
| SEQ ID NO: 15 | moltype = AA   length = 47 | |
| FEATURE | Location/Qualifiers | |
| REGION | 1..47 | |
| | note = Synthetic Construct | |
| source | 1..47 | |
| | mol_type = protein | |
| | organism = synthetic construct | |
| SEQUENCE: 15 | | |
| SSQPFWSGGG GSGGGGSGGG GSAWEFYFPG STSGSGKPGS GEGSTKG | | 47 |
| | | |
| SEQ ID NO: 16 | moltype = DNA   length = 253 | |
| FEATURE | Location/Qualifiers | |
| misc_feature | 1..253 | |
| | note = Synthetic Construct | |
| source | 1..253 | |
| | mol_type = other DNA | |
| | organism = synthetic construct | |
| SEQUENCE: 16 | | |
| tagactgctc gagccgccac catggttctg ctggtcacca gcctgctgct gtgcgagctg | | 60 |
| ccccaccccg cctttctgct gatccccagt agccagccat ctggagcgg tgggggggga | | 120 |
| tcaggcggcg gcgggagtgg ggggggtgga tcagcgtggg agttttactt tccaggctcc | | 180 |
| acatctggta gtggtaaacc cggatcaggt gagggaagca caaaaggtgc ggccgcattc | | 240 |
| gtgccggtct tcc | | 253 |
| | | |
| SEQ ID NO: 17 | moltype = AA   length = 47 | |
| FEATURE | Location/Qualifiers | |
| REGION | 1..47 | |
| | note = Synthetic Construct | |
| source | 1..47 | |
| | mol_type = protein | |
| | organism = synthetic construct | |
| SEQUENCE: 17 | | |
| AWEFYFPGGG GSGGGGSGGG GSSSQPFWSG STSGSGKPGS GEGSTKG | | 47 |
| | | |
| SEQ ID NO: 18 | moltype = DNA   length = 253 | |
| FEATURE | Location/Qualifiers | |
| misc_feature | 1..253 | |
| | note = Synthetic Construct | |
| source | 1..253 | |
| | mol_type = other DNA | |
| | organism = synthetic construct | |
| SEQUENCE: 18 | | |
| tagactgctc gagccgccac catggttctg ctggtcacca gcctgctgct gtgcgagctg | | 60 |
| ccccaccccg cctttctgct gatccccgca tgggagtttt actttcccgg tggaggtggg | | 120 |
| tctggtgggg ggggaagcgg tggaggtggt agctctagcc aaccttttctg gagtgggagt | | 180 |
| acgagtgggt ccggcaagcc aggtctggc aaggatcaa ctaaaggtgc ggccgcattc | | 240 |
| gtgccggtct tcc | | 253 |
| | | |
| SEQ ID NO: 19 | moltype = AA   length = 47 | |
| FEATURE | Location/Qualifiers | |
| REGION | 1..47 | |
| | note = Synthetic Construct | |
| source | 1..47 | |
| | mol_type = protein | |
| | organism = synthetic construct | |
| SEQUENCE: 19 | | |
| AWTITFPGGG GSGGGGSGGG GSSSQPFWSG STSGSGKPGS GEGSTKG | | 47 |
| | | |
| SEQ ID NO: 20 | moltype = DNA   length = 253 | |
| FEATURE | Location/Qualifiers | |
| misc_feature | 1..253 | |
| | note = Synthetic Construct | |
| source | 1..253 | |
| | mol_type = other DNA | |
| | organism = synthetic construct | |
| SEQUENCE: 20 | | |
| tagactgctc gagccgccac catggttctg ctggtcacca gcctgctgct gtgcgagctg | | 60 |
| ccccaccccg cctttctgct gatccccgcc tggacgatta cgttcccctgg tggcggaggt | | 120 |
| tctggcggtg gaggaagtgg tggtggcggc agcagttccc aacctttctg gtcaggttcc | | 180 |
| acgagtggaa gcggcaaacc gggcagtggc gaagggagta cgaagggagc ggccgcattc | | 240 |
| gtgccggtct tcc | | 253 |
| | | |
| SEQ ID NO: 21 | moltype = AA   length = 47 | |
| FEATURE | Location/Qualifiers | |
| REGION | 1..47 | |
| | note = Synthetic Construct | |
| source | 1..47 | |
| | mol_type = protein | |
| | organism = synthetic construct | |

```
SEQUENCE: 21
AWTWTLPGGG GSGGGGSGGG GSSSQPFWSG STSGSGKPGS GEGSTKG                47

SEQ ID NO: 22           moltype = DNA   length = 253
FEATURE                 Location/Qualifiers
misc_feature            1..253
                        note = Synthetic Construct
source                  1..253
                        mol_type = other DNA
                        organism = synthetic construct
SEQUENCE: 22
tagactgctc gagccgccac catggttctg ctggtcacca gcctgctgct gtgcgagctg    60
ccccaccccg cctttctgct gatccccgct tggacatgga cccttcccgg aggtggtggc   120
tctgggggg gcgggtcagg tggaggcggt tctagtagtc aaccgttttg gtccggcagt   180
acctccggga gtggcaaacc cggcagtggt gaaggttcca cgaaaggagc ggccgcattc   240
gtgccggtct tcc                                                      253

SEQ ID NO: 23           moltype = AA    length = 47
FEATURE                 Location/Qualifiers
REGION                  1..47
                        note = Synthetic Construct
source                  1..47
                        mol_type = protein
                        organism = synthetic construct
SEQUENCE: 23
EWLFSMPGGG GSGGGGSGGG GSSSQPFWSG STSGSGKPGS GEGSTKG                47

SEQ ID NO: 24           moltype = DNA   length = 253
FEATURE                 Location/Qualifiers
misc_feature            1..253
                        note = Synthetic Construct
source                  1..253
                        mol_type = other DNA
                        organism = synthetic construct
SEQUENCE: 24
tagactgctc gagccgccac catggttctg ctggtcacca gcctgctgct gtgcgagctg    60
ccccaccccg cctttctgct gatccccgag tggctgtttt ccatgccagg cggagggggc   120
agcggagggg cgcagtgg cggagggggc tcatcctcac aaccttttg gagtggatca   180
acatctgggt ctgggaagcc tggatctggt gagggatcaa ccaagggggc ggccgcattc   240
gtgccggtct tcc                                                      253

SEQ ID NO: 25           moltype = AA    length = 47
FEATURE                 Location/Qualifiers
REGION                  1..47
                        note = Synthetic Construct
source                  1..47
                        mol_type = protein
                        organism = synthetic construct
SEQUENCE: 25
GWFYTFPGGG GSGGGGSGGG GSSSQPFWSG STSGSGKPGS GEGSTKG                47

SEQ ID NO: 26           moltype = DNA   length = 253
FEATURE                 Location/Qualifiers
misc_feature            1..253
                        note = Synthetic Construct
source                  1..253
                        mol_type = other DNA
                        organism = synthetic construct
SEQUENCE: 26
tagactgctc gagccgccac catggttctg ctggtcacca gcctgctgct gtgcgagctg    60
ccccaccccg cctttctgct gatccccggt tggttttaca ccttccctgg tggaggaggc   120
tccggcgggg gcggttctgg tggcggggc tcctctagtc aaccattctg gtcaggaagc   180
acgtcaggga gcgaaaaacc gggaagcggg gaggggtcca ccaaggggc ggccgcattc    240
gtgccggtct tcc                                                      253

SEQ ID NO: 27           moltype = AA    length = 47
FEATURE                 Location/Qualifiers
REGION                  1..47
                        note = Synthetic Construct
source                  1..47
                        mol_type = protein
                        organism = synthetic construct
SEQUENCE: 27
NWYWVYPGGG GSGGGGSGGG GSSSQPFWSG STSGSGKPGS GEGSTKG                47

SEQ ID NO: 28           moltype = DNA   length = 253
FEATURE                 Location/Qualifiers
misc_feature            1..253
                        note = Synthetic Construct
```

```
                        source             1..253
                                           mol_type = other DNA
                                           organism = synthetic construct
SEQUENCE: 28
tagactgctc gagccgccac catggttctg ctggtcacca gcctgctgct gtgcgagctg    60
ccccacccccg cctttctgct gatccccaac tggtattggg tctacccccgg cggtggcggc  120
tctggtggcg gtggctcagg tggaggcggt agctcttcac aaccattctg gagcgggtct   180
acgtctggta gcggtaaacc agggtccggt gaggggagta cgaaggggggc ggccgcattc  240
gtgccggtct tcc                                                      253

SEQ ID NO: 29          moltype = AA   length = 7
FEATURE                Location/Qualifiers
REGION                 1..7
                       note = Synthetic Construct
source                 1..7
                       mol_type = protein
                       organism = synthetic construct
SEQUENCE: 29
QYRPTHS                                                               7

SEQ ID NO: 30          moltype = AA   length = 7
FEATURE                Location/Qualifiers
REGION                 1..7
                       note = Synthetic Construct
source                 1..7
                       mol_type = protein
                       organism = synthetic construct
SEQUENCE: 30
LSKKLPV                                                               7

SEQ ID NO: 31          moltype = AA   length = 7
FEATURE                Location/Qualifiers
REGION                 1..7
                       note = Synthetic Construct
source                 1..7
                       mol_type = protein
                       organism = synthetic construct
SEQUENCE: 31
EPFTIGR                                                               7

SEQ ID NO: 32          moltype = AA   length = 7
FEATURE                Location/Qualifiers
REGION                 1..7
                       note = Synthetic Construct
source                 1..7
                       mol_type = protein
                       organism = synthetic construct
SEQUENCE: 32
NTQPPTT                                                               7

SEQ ID NO: 33          moltype = AA   length = 7
FEATURE                Location/Qualifiers
REGION                 1..7
                       note = Synthetic Construct
source                 1..7
                       mol_type = protein
                       organism = synthetic construct
SEQUENCE: 33
GGGSGGG                                                               7

SEQ ID NO: 34          moltype = DNA   length = 20
FEATURE                Location/Qualifiers
misc_feature           1..20
                       note = Synthetic Construct
source                 1..20
                       mol_type = other DNA
                       organism = synthetic construct
SEQUENCE: 34
ggaagcctgg ctgcagttga                                                20

SEQ ID NO: 35          moltype = DNA   length = 20
FEATURE                Location/Qualifiers
misc_feature           1..20
                       note = Synthetic Construct
source                 1..20
                       mol_type = other DNA
                       organism = synthetic construct
SEQUENCE: 35
ccgggagtga atgagcgaga                                                20
```

```
SEQ ID NO: 36              moltype = DNA   length = 20
FEATURE                    Location/Qualifiers
misc_feature               1..20
                           note = Synthetic Construct
source                     1..20
                           mol_type = other DNA
                           organism = synthetic construct
SEQUENCE: 36
ctcctcctcc aacaagcaga                                              20

SEQ ID NO: 37              moltype = DNA   length = 20
FEATURE                    Location/Qualifiers
misc_feature               1..20
                           note = Synthetic Construct
source                     1..20
                           mol_type = other DNA
                           organism = synthetic construct
SEQUENCE: 37
ggactttggg gaggtgagaa                                              20

SEQ ID NO: 38              moltype = DNA   length = 58
FEATURE                    Location/Qualifiers
misc_feature               1..58
                           note = Synthetic Construct
source                     1..58
                           mol_type = other DNA
                           organism = synthetic construct
SEQUENCE: 38
ccggcagcaa ccagtgctaa cttatctcga gataagttag cactggttgc tgtttttg    58

SEQ ID NO: 39              moltype = DNA   length = 58
FEATURE                    Location/Qualifiers
misc_feature               1..58
                           note = Synthetic Construct
source                     1..58
                           mol_type = other DNA
                           organism = synthetic construct
SEQUENCE: 39
ccggtgcagt tgagggccga aattgctcga gcaatttcgg ccctcaactg cattttg    58

SEQ ID NO: 40              moltype = DNA   length = 58
FEATURE                    Location/Qualifiers
misc_feature               1..58
                           note = Synthetic Construct
source                     1..58
                           mol_type = other DNA
                           organism = synthetic construct
SEQUENCE: 40
ccggtcccaa tggcaccgaa gttaactcga gttaacttcg gtgccattgg gattttg    58

SEQ ID NO: 41              moltype = DNA   length = 58
FEATURE                    Location/Qualifiers
misc_feature               1..58
                           note = Synthetic Construct
source                     1..58
                           mol_type = other DNA
                           organism = synthetic construct
SEQUENCE: 41
ccggcaataa ctcctcctcc aacaactcga gttgttggag gaggagttat tgtttttg    58

SEQ ID NO: 42              moltype = DNA   length = 58
FEATURE                    Location/Qualifiers
misc_feature               1..58
                           note = Synthetic Construct
source                     1..58
                           mol_type = other DNA
                           organism = synthetic construct
SEQUENCE: 42
ccggagcttg tttctggagt tgtttctcga gaaacaactc cagaaacaag cttttttg    58

SEQ ID NO: 43              moltype = DNA   length = 58
FEATURE                    Location/Qualifiers
misc_feature               1..58
                           note = Synthetic Construct
source                     1..58
                           mol_type = other DNA
                           organism = synthetic construct
SEQUENCE: 43
ccggcagttg aaacacaaac ttgaactcga gttcaagttt gtgtttcaac tgtttttg    58
```

```
SEQ ID NO: 44          moltype = DNA  length = 58
FEATURE                Location/Qualifiers
misc_feature           1..58
                       note = Synthetic Construct
source                 1..58
                       mol_type = other DNA
                       organism = synthetic construct
SEQUENCE: 44
ccggcctgag acagatcagc aacaactcga gttgttgctg atctgtctca ggtttttg    58
```